(12) United States Patent
Zollinger et al.

(10) Patent No.: US 11,318,242 B2
(45) Date of Patent: May 3, 2022

(54) MANIFOLD FOR A MEDICAL WASTE COLLECTION SYSTEM

(71) Applicant: Stryker Corporation, Kalamazoo, MI (US)

(72) Inventors: Michael Zollinger, Chelsea, MI (US); Peter LaDuke, Holland, MI (US)

(73) Assignee: Stryker Corporation, Kalamazoo, MI (US)

( * ) Notice: Subject to any disclaimer, the term of this patent is extended or adjusted under 35 U.S.C. 154(b) by 350 days.

(21) Appl. No.: 16/679,922

(22) Filed: Nov. 11, 2019

(65) Prior Publication Data

US 2020/0324028 A1    Oct. 15, 2020

Related U.S. Application Data

(63) Continuation-in-part of application No. 16/522,066, filed on Jul. 25, 2019, now Pat. No. 10,603,416.

(Continued)

(51) Int. Cl.
*A61M 1/00* (2006.01)
*A61B 50/10* (2016.01)
*A61B 50/13* (2016.01)

(52) U.S. Cl.
CPC ............ *A61M 1/79* (2021.05); *A61B 50/10* (2016.02); *A61B 50/13* (2016.02);
(Continued)

(58) Field of Classification Search
CPC ... A61B 2217/005; A61B 50/10; A61B 50/13; A61M 1/0023; A61M 1/79; A61M 1/86;
(Continued)

(56) References Cited

U.S. PATENT DOCUMENTS

| 2,784,717 A | 3/1957 | Thompson |
| 2,854,027 A | 9/1958 | Kaiser et al. |

(Continued)

FOREIGN PATENT DOCUMENTS

| CH | 391963 A | 5/1965 |
| CN | 107951576 A | 4/2018 |

(Continued)

OTHER PUBLICATIONS

U.S. Appl. No. 16/399,026, filed Apr. 30, 2019.

(Continued)

*Primary Examiner* — Kai H Weng
(74) *Attorney, Agent, or Firm* — Howard & Howard Attorneys PLLC

(57) ABSTRACT

A medical waste collection system for collecting medical waste material, and a manifold for filtering the waste material and/or coupling a suction tube to the system. The system may include a receiver in which the manifold is configured to be inserted in a proximal direction to facilitate an inlet mechanism moving correspondingly in the distal direction. The manifold may include an arm, a spine, a lock element, and/or a catch each having a surface with a relative position in the proximal-to-distal direction. The rim and the catch may be spaced apart by a void, and the rim may be positioned below the catch. The housing may include a body portion, a first leg extending proximally from the body portion, and a second leg spaced apart from the first leg to define the void. The rim may be on the first leg, and the catch may be on the second leg.

15 Claims, 98 Drawing Sheets

Related U.S. Application Data which is a continuation of application No. 16/383,218, filed on Apr. 12, 2019, now Pat. No. 10,471,188.

(60) Provisional application No. 62/876,229, filed on Jul. 19, 2019.

(52) U.S. Cl.
CPC .......... *A61B 2217/005* (2013.01); *A61M 1/60* (2021.05); *A61M 1/63* (2021.05); *A61M 1/631* (2021.05); *A61M 1/71* (2021.05); *A61M 1/74* (2021.05); *A61M 1/743* (2021.05); *A61M 1/78* (2021.05); *A61M 1/782* (2021.05); *A61M 1/784* (2021.05); *A61M 2209/082* (2013.01)

(58) Field of Classification Search
CPC ...... A61M 2205/125; A61M 2209/084; A61M 1/0001; A61M 1/63; A61M 1/784; A61M 1/0058; A61M 1/78; A61M 1/782; A61M 1/74; A61M 1/743; A61M 1/631; A61M 1/71; A61M 1/60; A61M 2209/082
See application file for complete search history.

(56) References Cited

U.S. PATENT DOCUMENTS

| | | |
|---|---|---|
| 3,044,491 A | 7/1962 | Sangster |
| 3,085,689 A | 4/1963 | Hering et al. |
| 3,415,086 A | 12/1968 | Trainer |
| 3,540,062 A | 11/1970 | Leone |
| 3,612,089 A | 10/1971 | Beguiristain |
| 3,844,407 A | 10/1974 | Buie |
| 3,936,031 A | 2/1976 | Berman et al. |
| 4,014,329 A | 3/1977 | Welch et al. |
| 4,063,556 A | 12/1977 | Thomas et al. |
| 4,291,706 A | 9/1981 | Voges et al. |
| 4,376,053 A | 3/1983 | Bullock et al. |
| 4,475,904 A | 10/1984 | Wang |
| 4,643,197 A | 2/1987 | Greene et al. |
| 4,653,493 A | 3/1987 | Hoppough |
| 4,658,707 A | 4/1987 | Hawkins et al. |
| 4,728,006 A | 3/1988 | Drobish et al. |
| 4,729,764 A | 3/1988 | Gualtier |
| 4,735,610 A | 4/1988 | Akkas et al. |
| 4,737,148 A | 4/1988 | Blake |
| 4,744,785 A | 5/1988 | Rosenthal et al. |
| 4,857,063 A | 8/1989 | Glenn |
| 4,863,446 A | 9/1989 | Parker |
| 4,870,975 A | 10/1989 | Cronk et al. |
| 4,915,688 A | 4/1990 | Bischof et al. |
| 4,941,975 A | 7/1990 | Schewe |
| 4,990,137 A | 2/1991 | Graham |
| 5,074,334 A | 12/1991 | Onodera |
| 5,108,381 A | 4/1992 | Kolozsi |
| 5,112,019 A | 5/1992 | Metzler et al. |
| 5,115,842 A | 5/1992 | Crafts et al. |
| 5,182,542 A | 1/1993 | Adelman et al. |
| 5,195,961 A | 3/1993 | Takahashi et al. |
| 5,201,417 A | 4/1993 | Outlaw, III |
| 5,223,151 A | 6/1993 | Rojas |
| 5,242,434 A | 9/1993 | Terry |
| 5,242,474 A | 9/1993 | Herbst et al. |
| 5,284,621 A | 2/1994 | Kaufman |
| 5,308,583 A | 5/1994 | Sanuki |
| 5,312,377 A | 5/1994 | Dalton |
| 5,312,479 A | 5/1994 | Weinstein et al. |
| 5,363,860 A | 11/1994 | Nakao et al. |
| 5,383,234 A | 1/1995 | Russell |
| 5,419,687 A | 5/1995 | Adahan |
| 5,458,138 A | 10/1995 | Gajo |
| 5,464,042 A | 11/1995 | Haunhorst |
| 5,476,447 A | 12/1995 | Noda et al. |
| 5,575,293 A | 11/1996 | Miller et al. |
| 5,601,712 A | 2/1997 | Adams et al. |
| 5,613,966 A | 3/1997 | Makower et al. |
| 5,624,417 A | 4/1997 | Cook et al. |
| 5,624,418 A | 4/1997 | Shepard |
| 5,637,103 A | 6/1997 | Kerwin et al. |
| 5,681,742 A | 10/1997 | MersKelly et al. |
| 5,725,516 A | 3/1998 | Cook et al. |
| 5,736,098 A | 4/1998 | Kerwin et al. |
| 5,792,126 A | 8/1998 | Tribastone et al. |
| 5,807,359 A | 9/1998 | Bemis et al. |
| 5,817,068 A | 10/1998 | Urrutia |
| 5,830,199 A | 11/1998 | Chaffringeon |
| 5,863,443 A | 1/1999 | Mainwaring |
| 5,871,476 A | 2/1999 | Hand |
| 5,885,240 A | 3/1999 | Bradbury et al. |
| 5,901,717 A | 5/1999 | Dunn et al. |
| 5,911,786 A | 6/1999 | Nielsen et al. |
| 5,914,047 A | 6/1999 | Griffiths |
| 5,922,196 A | 7/1999 | Baumann |
| 5,928,935 A | 7/1999 | Reuss, Jr. et al. |
| 5,947,954 A | 9/1999 | Bonaldo |
| 5,968,032 A | 10/1999 | Sleister |
| 5,997,733 A | 12/1999 | Wilbur et al. |
| 6,024,720 A | 2/2000 | Chandler et al. |
| 6,027,490 A | 2/2000 | Radford et al. |
| 6,045,596 A | 4/2000 | Holland, Jr. et al. |
| 6,056,731 A | 5/2000 | Koetke et al. |
| 6,058,731 A | 5/2000 | Byczynski et al. |
| 6,070,751 A | 6/2000 | Mejias |
| 6,180,000 B1 | 1/2001 | Wilbur et al. |
| 6,187,188 B1 | 2/2001 | Janik et al. |
| 6,222,283 B1 | 4/2001 | Regia |
| 6,244,311 B1 | 6/2001 | Hand et al. |
| 6,273,296 B1 | 8/2001 | Brown |
| 6,331,246 B1 | 12/2001 | Beckham et al. |
| 6,375,625 B1 | 4/2002 | French et al. |
| 6,391,102 B1 | 5/2002 | Bodden et al. |
| 6,400,141 B1 | 6/2002 | Apel et al. |
| 6,488,675 B1 | 12/2002 | Radford et al. |
| 6,506,168 B1 | 1/2003 | Fathallah et al. |
| 6,562,233 B1 | 5/2003 | Schilling et al. |
| 6,579,455 B1 | 6/2003 | Muzik et al. |
| 6,673,055 B2 | 1/2004 | Bemis et al. |
| 6,695,891 B2 | 2/2004 | Reid |
| 6,749,319 B1 | 6/2004 | Muse |
| 6,770,061 B2 | 8/2004 | Wildman |
| 6,788,211 B2 | 9/2004 | Kouznetsov et al. |
| 6,837,267 B2 | 1/2005 | Weis et al. |
| 6,875,193 B1 | 4/2005 | Bonnette et al. |
| 6,893,056 B2 | 5/2005 | Guala |
| 6,893,425 B2 | 5/2005 | Dunn et al. |
| 6,902,673 B2 | 6/2005 | Smit et al. |
| 6,918,893 B2 | 7/2005 | Houde et al. |
| 6,935,459 B2 | 8/2005 | Austin et al. |
| 6,951,228 B2 | 10/2005 | Steigerwalt et al. |
| 7,090,663 B2 | 8/2006 | Dunn et al. |
| 7,153,294 B1 | 12/2006 | Farrow |
| 7,244,236 B2 | 7/2007 | Merkle |
| 7,258,711 B2 | 8/2007 | Dunn et al. |
| 7,294,256 B2 | 11/2007 | Happel et al. |
| 7,347,828 B2 | 3/2008 | Francese et al. |
| 7,459,078 B2 | 12/2008 | Klein et al. |
| 7,497,340 B2 | 3/2009 | Hershberger et al. |
| 7,615,037 B2 | 11/2009 | Murray et al. |
| 7,621,898 B2 | 11/2009 | Lalomia et al. |
| 7,758,556 B2 | 7/2010 | Perez-Cruet et al. |
| 7,981,049 B2 | 7/2011 | Ritchie et al. |
| 8,088,079 B2 | 1/2012 | Kaye et al. |
| 8,137,329 B2 | 3/2012 | Romano et al. |
| 8,216,199 B2 | 7/2012 | Murray et al. |
| 8,382,660 B2 | 2/2013 | Okada |
| 8,485,987 B2 | 7/2013 | Videbaek et al. |
| 8,509,736 B2 | 8/2013 | Hodge |
| 8,518,002 B2 | 8/2013 | Murray et al. |
| 8,696,674 B2 | 4/2014 | Howard et al. |
| RE44,920 E | 6/2014 | Dunn et al. |
| 8,740,866 B2 | 6/2014 | Reasoner et al. |
| 8,801,682 B2 | 8/2014 | Kensy |
| 8,858,518 B2 | 10/2014 | Schafer et al. |
| 8,877,146 B2 | 11/2014 | Williamson, IV et al. |

(56) References Cited

U.S. PATENT DOCUMENTS

| | | |
|---|---|---|
| 8,915,897 B2 | 12/2014 | Murray et al. |
| 8,974,399 B2 | 3/2015 | Teixeira et al. |
| 9,089,801 B1 | 7/2015 | Gavlak et al. |
| 9,143,610 B2 | 9/2015 | Hodge |
| 9,272,127 B2 | 3/2016 | Rada et al. |
| 9,457,135 B2 | 10/2016 | Neatrour et al. |
| 9,579,428 B1 | 2/2017 | Reasoner et al. |
| 9,671,318 B1 | 6/2017 | Bedoe et al. |
| 9,782,524 B2 | 10/2017 | Reasoner et al. |
| 9,788,818 B2 | 10/2017 | Parks |
| 9,795,723 B2 | 10/2017 | Gavlak et al. |
| 9,909,103 B2 | 3/2018 | Howard et al. |
| 9,943,291 B2 | 4/2018 | VanderWoude et al. |
| 10,105,470 B2 | 10/2018 | Reasoner et al. |
| 10,471,188 B1 | 11/2019 | Zollinger et al. |
| 2001/0040123 A1 | 11/2001 | Beckham |
| 2002/0026160 A1 | 2/2002 | Takahashi et al. |
| 2003/0073928 A1 | 4/2003 | Kortenbach et al. |
| 2003/0125639 A1 | 7/2003 | Fisher et al. |
| 2003/0164600 A1 | 9/2003 | Dunn et al. |
| 2003/0213733 A1 | 11/2003 | Beckham et al. |
| 2004/0016691 A1 | 1/2004 | Smit et al. |
| 2004/0055470 A1 | 3/2004 | Strauser et al. |
| 2004/0079418 A1 | 4/2004 | Weis et al. |
| 2004/0102743 A1 | 5/2004 | Walker |
| 2004/0138632 A1 | 7/2004 | Bemis et al. |
| 2004/0143227 A1 | 7/2004 | Rollin et al. |
| 2004/0163884 A1 | 8/2004 | Austin et al. |
| 2004/0261525 A1 | 12/2004 | Chen |
| 2005/0004537 A1 | 1/2005 | Dunn et al. |
| 2005/0010179 A1 | 1/2005 | Dunn et al. |
| 2005/0127212 A1 | 6/2005 | Kassanits |
| 2005/0139532 A1 | 6/2005 | Hershberger et al. |
| 2005/0171495 A1 | 8/2005 | Austin et al. |
| 2005/0173638 A1 | 8/2005 | Powell |
| 2005/0183780 A1 | 8/2005 | Michaels et al. |
| 2005/0187529 A1 | 8/2005 | Reasoner et al. |
| 2005/0189288 A1 | 9/2005 | Hershberger et al. |
| 2005/0209585 A1 | 9/2005 | Nord et al. |
| 2006/0189950 A1 | 8/2006 | Rogers et al. |
| 2006/0231508 A1 | 10/2006 | Marzett et al. |
| 2007/0135778 A1 | 6/2007 | Murray et al. |
| 2007/0135779 A1 | 6/2007 | Lalomia et al. |
| 2007/0191731 A1 | 8/2007 | Kaye |
| 2009/0234192 A1 | 9/2009 | Okada |
| 2010/0030132 A1 | 2/2010 | Niezgoda et al. |
| 2011/0106029 A1 | 5/2011 | Garren et al. |
| 2014/0323914 A1 | 10/2014 | VanderWoude et al. |
| 2014/0336599 A1 | 11/2014 | Patel et al. |
| 2014/0338529 A1 | 11/2014 | Reasoner et al. |
| 2017/0028110 A1 | 2/2017 | Smith et al. |
| 2017/0043064 A1 | 2/2017 | Reasoner et al. |
| 2017/0160169 A1 | 6/2017 | Bedoe et al. |
| 2017/0304511 A1 | 10/2017 | Harpham et al. |
| 2018/0221804 A1 | 8/2018 | Reasoner et al. |
| 2018/0235583 A1 | 8/2018 | VanderWoude et al. |
| 2018/0243487 A1 | 8/2018 | Murray et al. |
| 2018/0256790 A1 | 9/2018 | Murray et al. |
| 2018/0333520 A1 | 11/2018 | Mills et al. |
| 2019/0001029 A1* | 1/2019 | Davie ................. A61M 1/0023 |
| 2019/0038195 A1 | 2/2019 | Peterson et al. |

FOREIGN PATENT DOCUMENTS

| | | | |
|---|---|---|---|
| EP | 0184629 | A2 | 6/1986 |
| EP | 0691279 | A2 | 1/1996 |
| EP | 0882440 | A2 | 12/1998 |
| EP | 1166805 | A2 | 1/2002 |
| EP | 1099854 | B1 | 5/2002 |
| EP | 1380316 | A1 | 1/2004 |
| EP | 2100550 | A1 | 9/2009 |
| EP | 2359878 | A2 | 8/2011 |
| EP | 2359879 | A2 | 8/2011 |
| EP | 2364736 | A2 | 9/2011 |
| EP | 2384776 | A1 | 11/2011 |
| EP | 2384777 | A1 | 11/2011 |
| EP | 2388024 | A1 | 11/2011 |
| EP | 2388025 | A1 | 11/2011 |
| FR | 2744359 | A1 | 8/1997 |
| GB | 2058227 | A | 4/1981 |
| JP | S5539296 | A | 3/1980 |
| JP | H02145393 | U | 12/1990 |
| JP | H06178780 | A | 6/1994 |
| JP | H08500763 | A | 1/1996 |
| JP | H10501145 | A | 2/1998 |
| JP | H10503391 | A | 3/1998 |
| JP | H11000392 | A | 1/1999 |
| JP | 2001017489 | A | 1/2001 |
| JP | 2003325658 | A | 11/2003 |
| JP | 2003534088 | A | 11/2003 |
| JP | 2007209764 | A | 8/2007 |
| JP | 2009519776 | A | 5/2009 |
| WO | 9308897 | A1 | 5/1993 |
| WO | 9626750 | A1 | 9/1996 |
| WO | 9900154 | A1 | 1/1999 |
| WO | 03075821 | A2 | 9/2003 |
| WO | 2004075740 | A1 | 9/2004 |
| WO | 2005042061 | A1 | 5/2005 |
| WO | 2005079947 | A2 | 9/2005 |
| WO | 2007070570 | A2 | 6/2007 |
| WO | 2007079319 | A2 | 7/2007 |
| WO | 2007103842 | A2 | 9/2007 |
| WO | 2008118397 | A1 | 10/2008 |
| WO | 2013090579 | A1 | 6/2013 |
| WO | 2014066337 | A2 | 5/2014 |
| WO | 2017112684 | A1 | 6/2017 |
| WO | 2017127541 | A1 | 7/2017 |
| WO | 2018170233 | A1 | 9/2018 |
| WO | 2018175389 | A1 | 9/2018 |
| WO | 2019222655 | A2 | 11/2019 |

OTHER PUBLICATIONS

ASTM, "Designation: F 960-86, Standard Spefication for Medical and Surgical Suction and Drainage Systems", 2000, 8 pages.

English language abstract for JP 2003-534088 extracted from espacenet.com database on Feb. 26, 2018, 2 pages.

English language abstract and machine-assisted English translation for EP 1 380 316 extracted from espacenet.com database on Feb. 26, 2018, 21 pages.

English language abstract and machine-assisted English translation for FR 2 744 359 extracted from espacenet.com database on Feb. 26, 2018, 6 pages.

English language abstract and machine-assisted English translation for JP 2001-017489 extracted from espacenet.com database on Feb. 26, 2018, 27 pages.

English language abstract and machine-assisted English translation for JP 2003-325658 extracted from espacenet.com database on Feb. 26, 2018, 20 pages.

English language abstract and machine-assisted English translation for JPH 02-145393 extracted from PAJ database on Feb. 26, 2018, 2 pages.

English language abstract and machine-assisted English translation for JPH 06-178780 extracted from espacenet.com database on Feb. 26, 2018, 28 pages.

English language abstract for EP 0 882 440 extracted from espacenet.com database on Feb. 26, 2018, 1 page.

English language abstract for JP 2007-209764 extracted from espacenet.com database on Nov. 13, 2017, 2 pages.

English language abstract for JPH 08-500763 extracted from espacenet.com database on Feb. 26, 2018, 2 pages.

English language abstract for JPH 10-501145 extracted from espacenet.com database on Feb. 26, 2018, 1 page.

English language abstract for JPH 10-503391 extracted from espacenet.com database on Feb. 26, 2018, 2 pages.

English language abstract for JPH 11392 extracted from espacenet.com database on Feb. 26, 2018, 1 page.

English language abstract for WO 2004/075740 extracted from espacenet.com database on Nov. 13, 2017, 2 pages.

(56) References Cited

OTHER PUBLICATIONS

English language abstract not found for JP 2009-519776; however, see English language equivalent U.S. Pat. No. 9,782,524. Original document extracted from espacenet.com database on Nov. 13, 2017, 5 pages.

International Search Report for Application No. PCT/US2007/063253 dated Dec. 5, 2007, 5 pages.

International Search Report for PCT/US2006/047531 dated Aug. 23, 2007, 6 pages.

International Search Report for PCT/US2006/061791 dated Jan. 23, 2008, 5 pages.

International Search Report for PCT/US2012/069516 dated Apr. 5, 2013, 3 pages.

International Search Report for PCT/US2017/014128 dated Jun. 13, 2017, 3 pages.

Invitation to Pay Additional Fees and Communication Relating to the Results of the Partial International Search for PCT/US2006/061791 dated Sep. 9, 2007, 3 pages.

LMS, "Medi-Flo Valves Specification Sheets", Nov. 2005, 7 pages.

LMS, "V33 SureFlo Valve", 2005, 1 page.

Machine-assisted English translation for CH 391963 extracted from espacenet.com database on Feb. 26, 2018, 11 pages.

Machine-assisted English translation for JPS 55-39296 extracted from espacenet.com database on Nov. 13, 2017, 7 pages.

Portable Suction Sources, Health Devices, vol. 7, No. 5, Mar. 1978, pp. 119-141.

*Stryker Corporation et al.* v. *Poseidon Surgical, LLC*, "Defendants/Counterclaimants Initial Invalidity and Unenforceability Contentions", United States District Court, Western District of Michigan, Southern Division, Civil Action No. 1:16-cv-01199, Mar. 29, 2017, 40 pages.

Stryker Instruments, "Neptune Waste Management System, Instructions for Use, Neptune Gold Rover, REF 700-2, Neptune Docking Station, REF 700-6", Sep. 2005, 20 pages.

The Merriam-Webster Dictionary, "Definition of Disk or Disc", Eleventh Edition, p. 206, 2 pages.

Vernay Laboratories, "Valve Specification Sheets", Nov. 2005, 6 pages.

U.S. Appl. No. 16/383,218, filed Apr. 12, 2019.

U.S. Appl. No. 16/522,066, filed Jul. 25, 2019.

English language abstract and machine-assisted English translation for CN 107951576 extracted from espacenet.com database on Aug. 19, 2020, 9 pages.

International Search Report for Application No. PCT/US2019/060732 dated Mar. 12, 2020, 3 pages.

\* cited by examiner

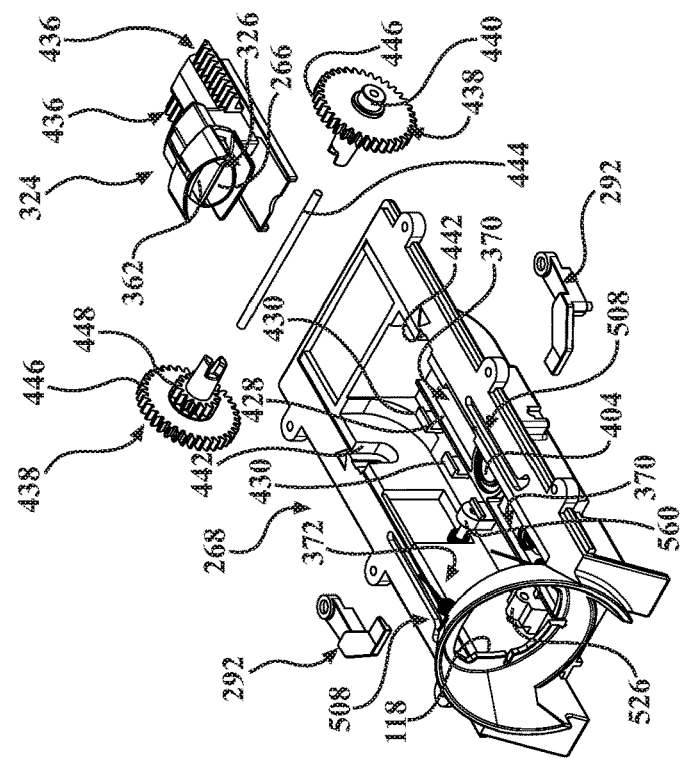
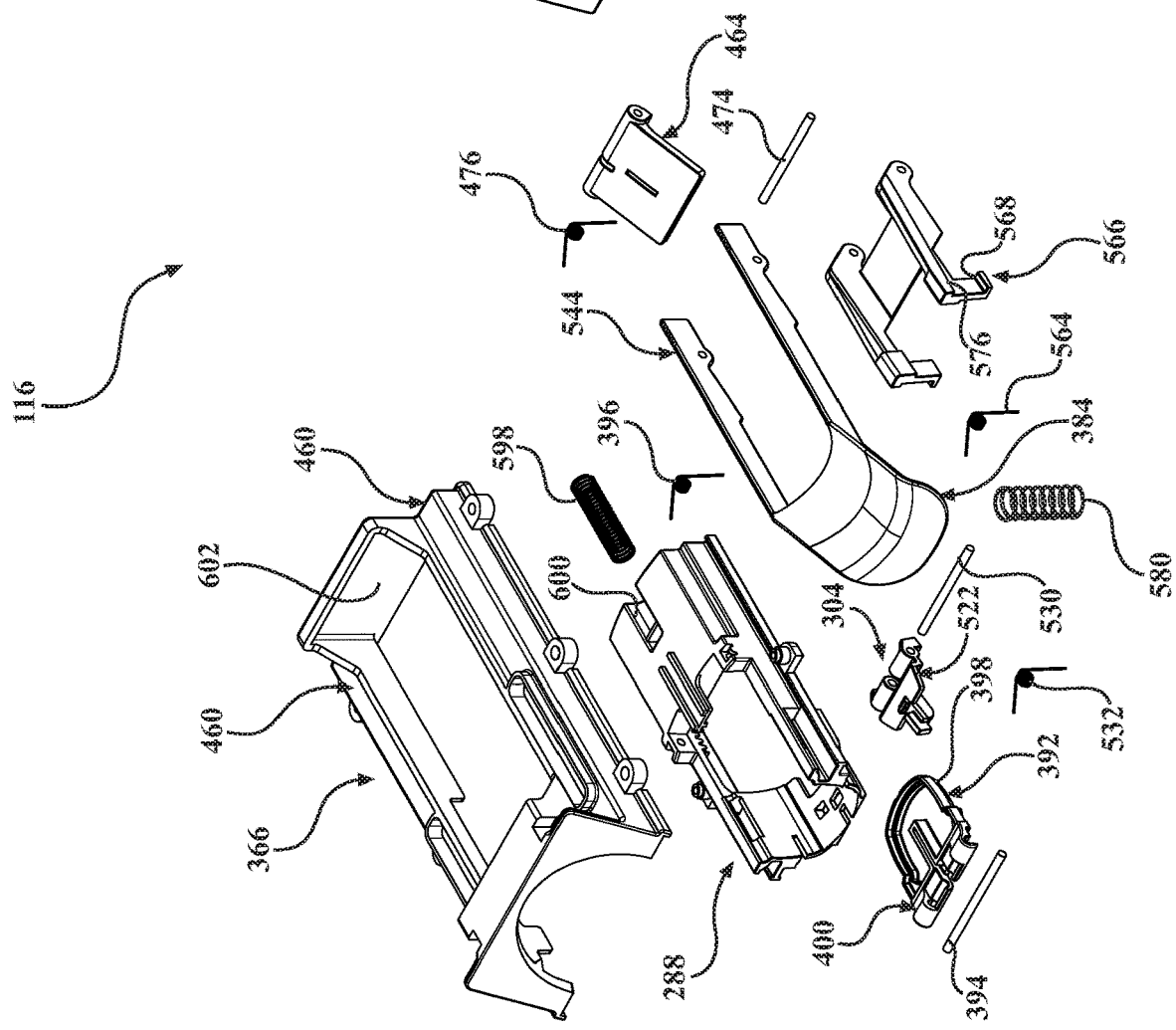
FIG. 28

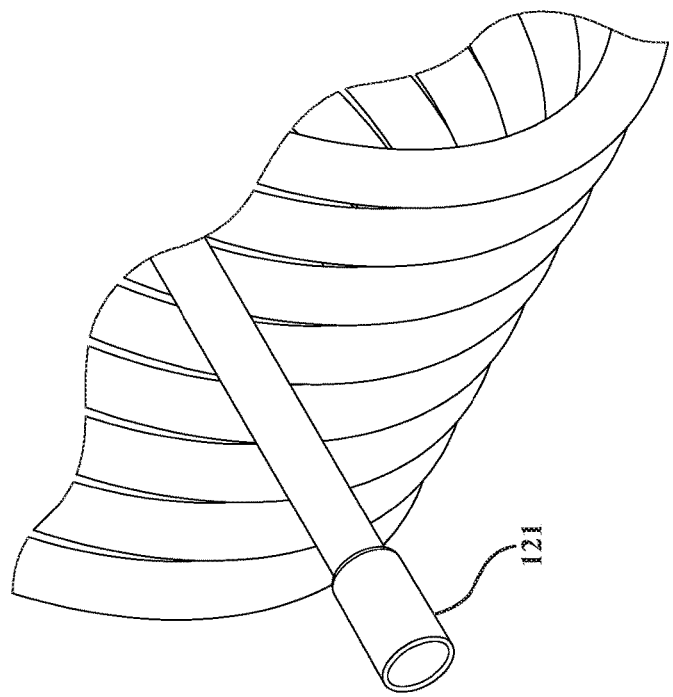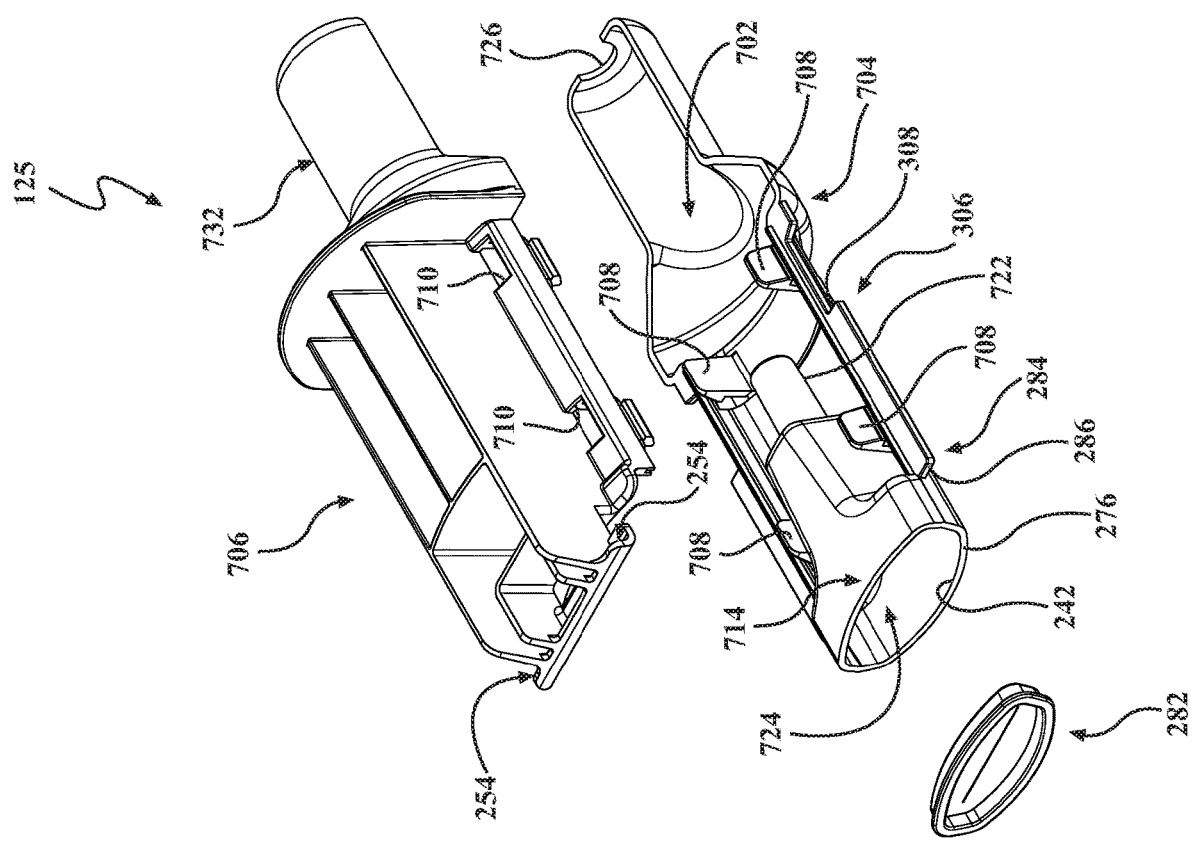
FIG. 88

MANIFOLD FOR A MEDICAL WASTE COLLECTION SYSTEM

REFERENCE TO RELATED APPLICATIONS

This is a continuation-in-part of copending U.S. application Ser. No. 16/522,066, filed Jul. 25, 2019, which is a continuation of U.S. application Ser. No. 16/383,218, filed Apr. 12, 2019. This application also claims priority to and all the benefits of U.S. Provisional Application No. 62/876,229, filed Jul. 19, 2019. The entire contents of each of the above applications are hereby incorporated by reference.

BACKGROUND

A byproduct of some surgical procedures is the generation of liquid, semisolid, and/or solid waste material. The liquid waste material may include bodily fluids and irrigating solution(s) at the surgical site, and the solid and semisolid waste material may include bits of tissue and pieces of surgical material(s). The medical waste, regardless of its phase, is preferably collected so it neither fouls the surgical site nor becomes a biohazard in the medical suite in which the procedure is being performed.

The medical waste may be removed from the surgical site through a suction tube under the influence of a vacuum provided by a suction source. One exemplary medical waste collection system is sold under the tradename NEPTUNE by Stryker Corporation (Kalamazoo, Mich.) with certain versions of the medical waste collection system disclosed in commonly owned United States Patent Publication No. 2005/0171495, published Aug. 4, 2005, International Publication No. WO 2007/070570, published Jun. 21, 2007, and International Publication No. WO 2014/066337, published May 1, 2014, the entire contents of each are incorporated herein by reference.

A manifold may be provided that facilitates interfacing the suction tube with the medical waste collection system. Additionally or alternatively, the manifold may include a filter element for filtering the waste material to avoid clogging or compromise of components of the medical waste collection system. An unused manifold may be operably coupled with the medical waste collection system before or during the procedure, and the used manifold may be operably decoupled from the medical waste collection system during or after the procedure. Facilitating safe and efficient repeated coupling and decoupling of manifolds with the medical waste collection system requires a robust interface, which remains an area of particular interest and development. Moreover, in instances where the manifold configured to filter the waste material, the manifold, including its components having intricate geometries, may become contaminated. Efforts to reprocess a previously used manifold—in which it is attempted to remove the contamination—may be unsatisfactory and result in a reprocessed article of questionable quality relative to an unused, genuine manifold. Thus, it may be desirable to ensure that the manifold is single use and disposable.

SUMMARY

With the scope of the invention defined by the claims and clauses included herein without limiting effect of the Summary, the present disclosure is directed to a manifold for a medical waste collection system. The manifold may be for filtering medical waste and/or for coupling a suction tube to the medical waste collection system. The medical waste collection system includes a receiver defining an opening into which the manifold is configured to be inserted in a proximal direction and removed in a distal direction opposite the proximal direction. The manifold includes a housing. The housing may define a manifold volume and an outlet opening in fluid communication with the manifold volume. The housing may include a rim defining the outlet opening. A filter element may be disposed within the manifold volume. The housing includes an arm, a lock element, a spine, and/or a catch. The arm may include a proximally-directed surface, and the lock element may include a distally-directed surface positioned distal to the proximally-directed surface of the arm. The spine may include a proximally-directed surface positioned proximal to the distally-directed surface of the lock element and distal to the proximally-directed surface of the arm. The proximally-directed surface of the spine may include an incline, for example, a ramped, curved, or stepped surface. The catch may include a distally-directed surface positioned proximal to the proximally-directed surface of the arm. The rim and the catch may be spaced apart by a void. The rim may be positioned below the catch when the manifold is oriented for insertion into the opening of the receiver.

The housing may include a body portion, a first leg extending proximally from the body portion, and a second leg spaced apart from the first leg by the void. The second leg may extend proximally from the body portion. The arm, the lock element, and/or the spine may be disposed on the body portion and/or the first leg. The catch may be disposed on the second leg. The arm, the lock element, and/or the catch may be at least a pair of arms, a pair of lock elements, and a pair of catches, respectively. The proximally-directed surface of the arm is configured to engage a sled assembly of the receiver during insertion of the manifold to facilitate moving the sled assembly in the proximal direction. The distally-directed surface of the lock element is configured to engage (or be engaged by) a locking assembly of the receiver after insertion of the manifold into the receiver. The proximally-directed surface of the spine is configured engage a sled lock assembly of the receiver to permit movement of the sled assembly in the proximal direction. The distally-directed surface of the catch is configured to engage (or be engaged by) a claw of the receiver and facilitate movement of the sled assembly in the distal direction during removal of the manifold from the receiver.

The sled assembly is configured to be moved in the proximal direction during insertion of the manifold into the receiver to facilitate the inlet mechanism moving correspondingly in the distal direction to establish fluid communication between the suction outlet and the receiver outlet as the manifold assumes the fully inserted operative position, and further establish fluid communication between the waste container and the manifold. The sled assembly is further configured to be moved in the distal direction during removal of the manifold from the receiver to facilitate the inlet mechanism moving correspondingly in the proximal direction to break fluid communication between the suction outlet and the receiver outlet. The locking assembly may include a biasing element biasing the locking assembly to a locked configuration in which an engagement surface engages the manifold in a fully inserted operative position to prevent distal movement of the manifold and the sled assembly. An actuator coupled to a release member may be configured to receive an input from a user to move the locking assembly from the locked configuration to an unlocked configuration in which the engagement surface disengages from the manifold to permit the movement of the manifold and the sled assembly in the distal direction. The sled lock assembly may include a biasing element configured to bias a latch to a locked configuration in which the latch engages the sled assembly to prevent movement of the sled assembly in the proximal direction. Insertion of the manifold into the receiver to a first operative position moves the sled lock assembly from the locked configuration to an unlocked configuration in which the latch disengages from the sled assembly to permit movement of the sled assembly in the proximal direction. The claw may be movably coupled to the housing and pivotably coupled to the sled assembly, wherein the claw is configured to engage the manifold in the fully inserted operative position and facilitate the movement of the sled assembly in the distal direction in response to the manifold being moved in the distal direction during removal of the manifold from the receiver.

A seal may be coupled to the rim. The seal includes a seal body shaped to cover the outlet opening. The outlet opening may have a width greater than a height so as to be non-circular in shape. The seal body may be shaped to cover the non-circular outlet opening. The seal may include an inner seal rim coupled to the seal body, and an outer seal rim spaced apart from the inner seal rim to define a groove sized to receive the rim such that the seal is coupled to the housing with interference engagement with the seal body covering the non-circular outlet opening. The filter element may include a basket, and a seal retaining element coupled to the basket. The seal retaining element of the filter element supports the seal in sealing engagement with the rim. The filter element of the manifold may include a plurality of apertures configured to filter the medical waste, and a keyway separate from the apertures. A projection may extend from an inner surface of the housing and through the keyway of the filter element. The projection is joined to the filter element, for example, through thermoplastic staking, such that removing the filter element from the housing requires mutilation of the manifold. The filter element may further include a rib fused to a slot of the housing, for example, through laser welding, such that removing the filter element from the housing requires mutilation of the manifold. A use indicator may be disposed within the manifold volume and configured to absorb liquid and/or solid from the medical waste. The use indicator may be supported on a tray of the filter element. The use indicator may be disposed within the second leg of the housing.

The manifold may lack the aforementioned manifold volume through the medical waste is directed. In certain implementations, a device for coupling a suction tube to the medical waste collection system includes a void space through which a portion of the suction tube is configured to be disposed. The device may include a first housing portion and a second housing portion coupled to the first housing portion. The first and second housing portions may be configured to move the device between an open configuration in which the void space is accessible, and a closed configuration in which the void space is inaccessible. A tube adapter may be coupled to the housing such that an inlet port is disposed within the void space.

The manifold may include a radiofrequency identification (RFID) tag coupled to the housing. The RFID tag may include memory storing data for determining whether the manifold is usable with the medical waste collection system with the RFID tag adapted to be in electronic communication with a data reader of the receiver when the manifold is coupled with the manifold receiver. The receiver may include a sensor in communication with the controller and configured to output a signal indicative of a position of the sled assembly in the proximal-to-distal direction, wherein the controller is configured to control the vacuum source based on the signal from the sensor. The medical waste collection system may include a docking station having an off-load pump and a docking controller to operate the off-load pump to transfer waste material to the docking station. The sensor may be configured to output a signal based on a presence of the manifold in the receiver, and the controller may be configured to generate an off-load signal to the docking controller based on whether the chassis is coupled to the docking station and the signal output by the sensor. The off-load signal may be operative to cause the docking controller to operate the off-load pump of the docking station to draw waste from the waste container to the docking station. The output signal may be further indicative of a position of the sled assembly. The output signal may be further indicative of whether the manifold is inserted into the receiver to a fully inserted operative position. The controller may be further configured to prevent operation of the off-load pump based on the output signal when the manifold is not inserted into the receiver to the full inserted operative position.

BRIEF DESCRIPTION OF THE DRAWINGS

Advantages of the present disclosure will be readily appreciated as the same becomes better understood by reference to the following detailed description when considered in connection with the accompanying drawings.

FIG. 28 is an exploded view of the receiver.

FIG. 88 is an exploded view of a device with the suction tube decoupled from the device.

DETAILED DESCRIPTION

Figure 1:
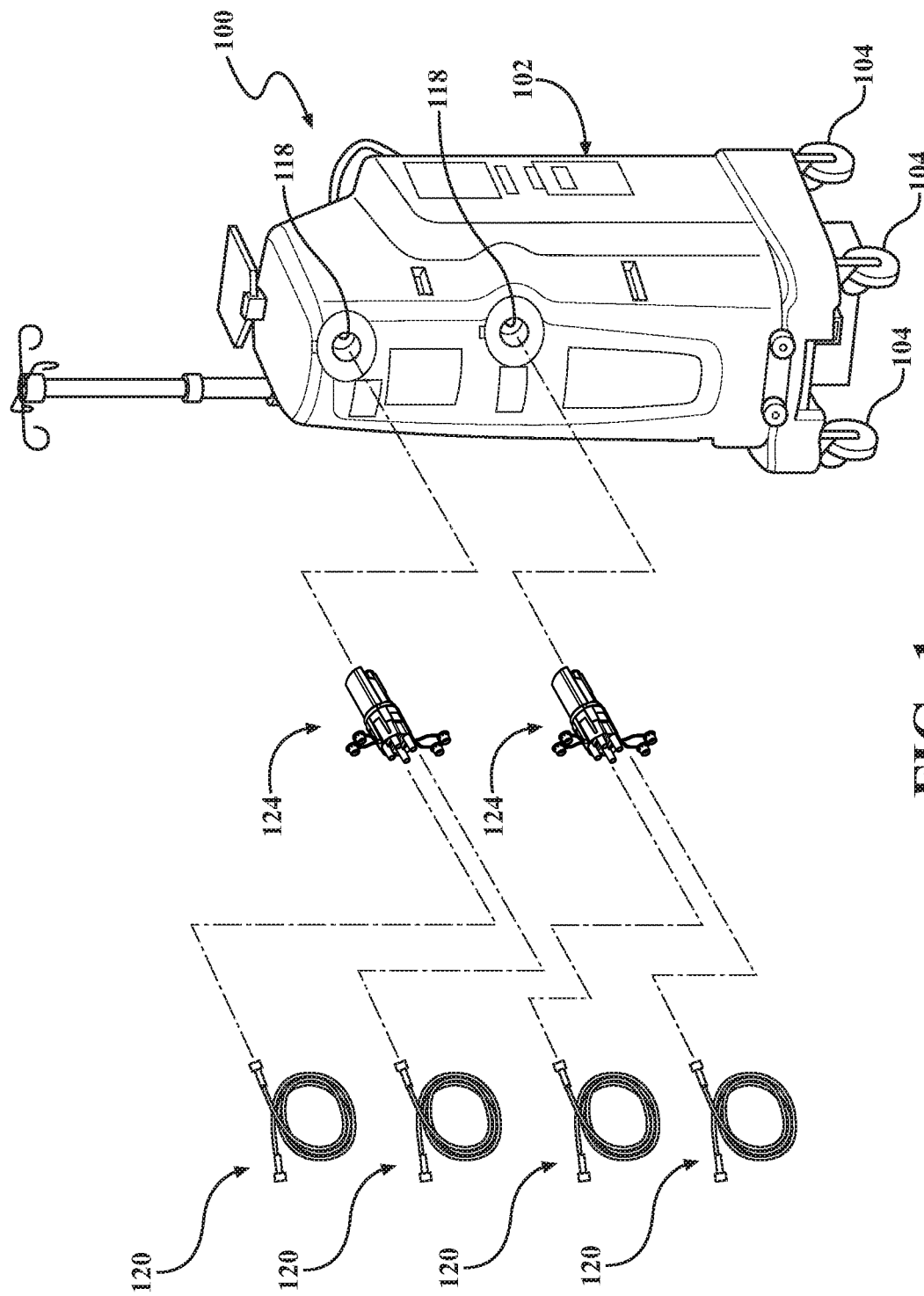
FIG. 1 is a perspective view of a medical waste collection system with each of two manifolds configured to be removably inserted into a respective one of two receivers of the medical waste collection system. Two suction tubes are shown and configured to be removably coupled to each of the two manifolds.
Figure 2:
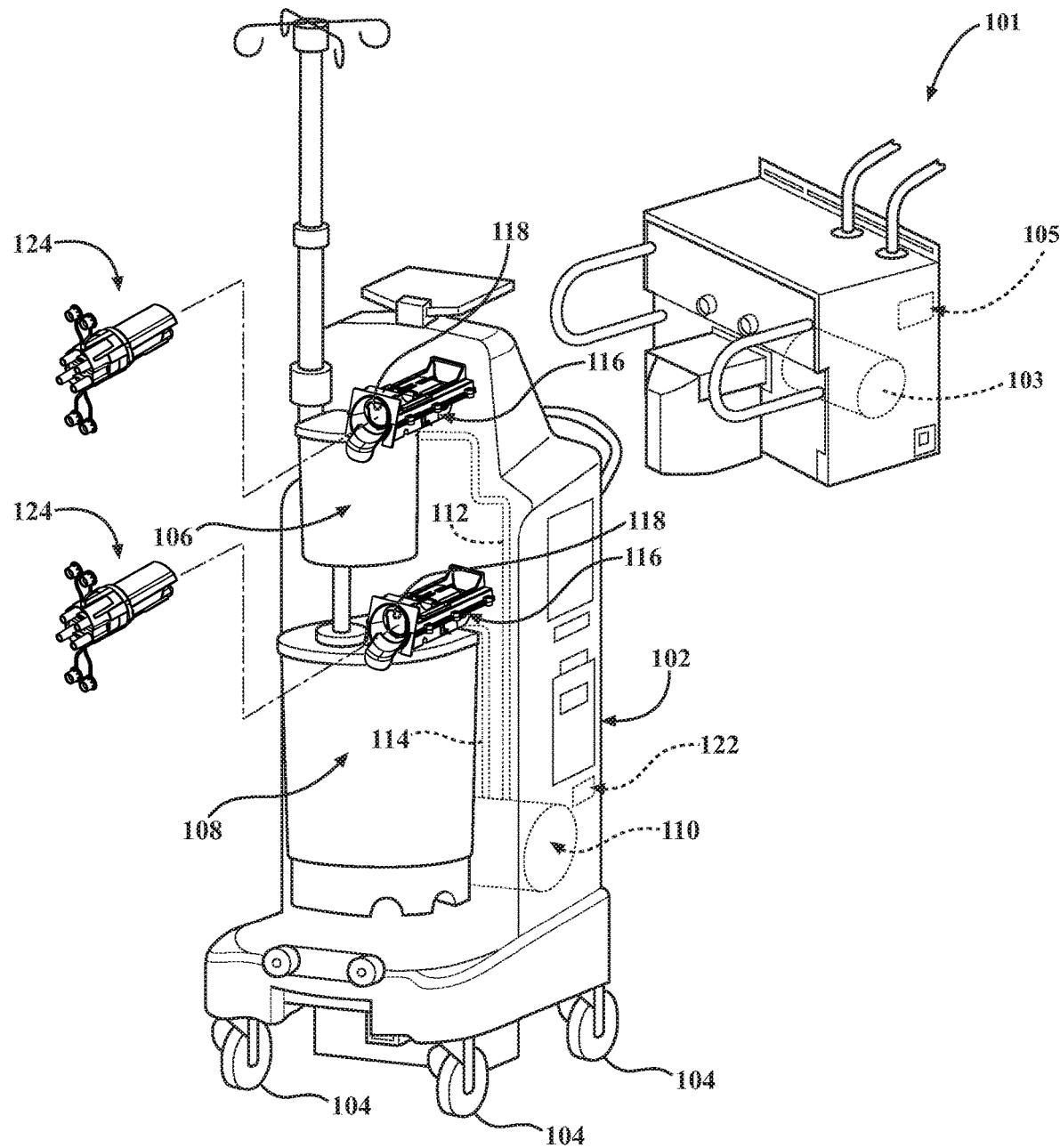
FIG. 2 is a perspective view of the medical waste collection system and the manifolds of FIG. 1 with a front cover of the medical waste collection system removed to show the receivers coupled to a respective one of two waste containers of the medical waste collection system.

FIGS. 1 and 2 show a medical waste collection system 100 for collecting the waste material generated during medical procedures, and more particularly surgical procedures. The medical waste collection system 100 collects the waste material and/or stores the waste material until it is necessary or desired to off-load and dispose of the waste material. The medical waste collection system 100 may be transported to and operably coupled with a docking station 101 through which the waste material is emptied. The docking station 101 includes an off-load pump 103 and a docking controller 105 operatively coupled to the off-load pump 103. The docking station 101 may otherwise assume any suitable form, for example, that disclosed in commonly owned U.S. Pat. No. 7,621,898 issued Nov. 24, 2009, the entire contents of which are hereby incorporated by reference.

The medical waste collection system 100 may include a chassis 102 and wheels 104 for moving the system 100 along a floor surface within a medical facility. The medical waste collection system 100 includes at least one waste container 106, 108 defining a waste volume for collecting and storing the waste material. FIG. 2 shows a first waste container 106 arranged above a second waste container 108 having a relatively greater or larger volume than the first waste container 106. A vacuum pump 110 (in phantom) is supported on the chassis 102 and configured to draw suction on one or both of the first and second waste containers 106, 108 through one or more vacuum lines 112, 114. At least one vacuum regulator (not shown) may also be supported on the chassis 102 and in fluid communication with the vacuum pump 110 and the waste container(s) 106, 108. The vacuum regulator(s) are configured to regulate a level of the suction drawn on the waste container(s) 106, 108. Suitable construction and operation of several subsystems of the medical waste collection system 100 are disclosed in aforementioned commonly owned United States Patent Publication No. 2005/0171495, International Publication No. WO 2007/070570, and International Publication No. WO 2014/066337. Suitable construction and operation of several subsystems of the medical waste collection system 100 may also be disclosed in commonly owned International Publication No. WO 2017/112684, published Jun. 29, 2017, the entire contents of which are hereby incorporated by reference. A single waste container system is contemplated.

The medical waste collection system 100 includes at least one receiver 116 supported on the chassis 102. In a most general sense, the receiver(s) 116 define an opening 118 sized to removably receive at least a portion of a manifold 124 in a manner to be described throughout the present disclosure. FIG. 2 shows two receivers 116 with each of the receivers 116 associated with a respective one of the first and second waste containers 106, 108. Alternatively, a single receiver and/or a single manifold may be provided. The receiver(s) 116 include a suction inlet 266 (see FIGS. 33-36) configured to be arranged in fluid communication with the respective one of the waste containers 106, 108. A suction path may be established from suction tube(s) 120 to the waste containers 106, 108 through the manifold(s) 124 removably inserted into the receivers 116. The vacuum generated by the vacuum pump 110 is drawn on the suction tube(s) 120, and the waste material at the surgical site is drawn through the manifold(s) 124, through the suction inlet 266, through a suction outlet 410 of the receiver 116, and into the waste container(s) 106, 108.

Figure 3:
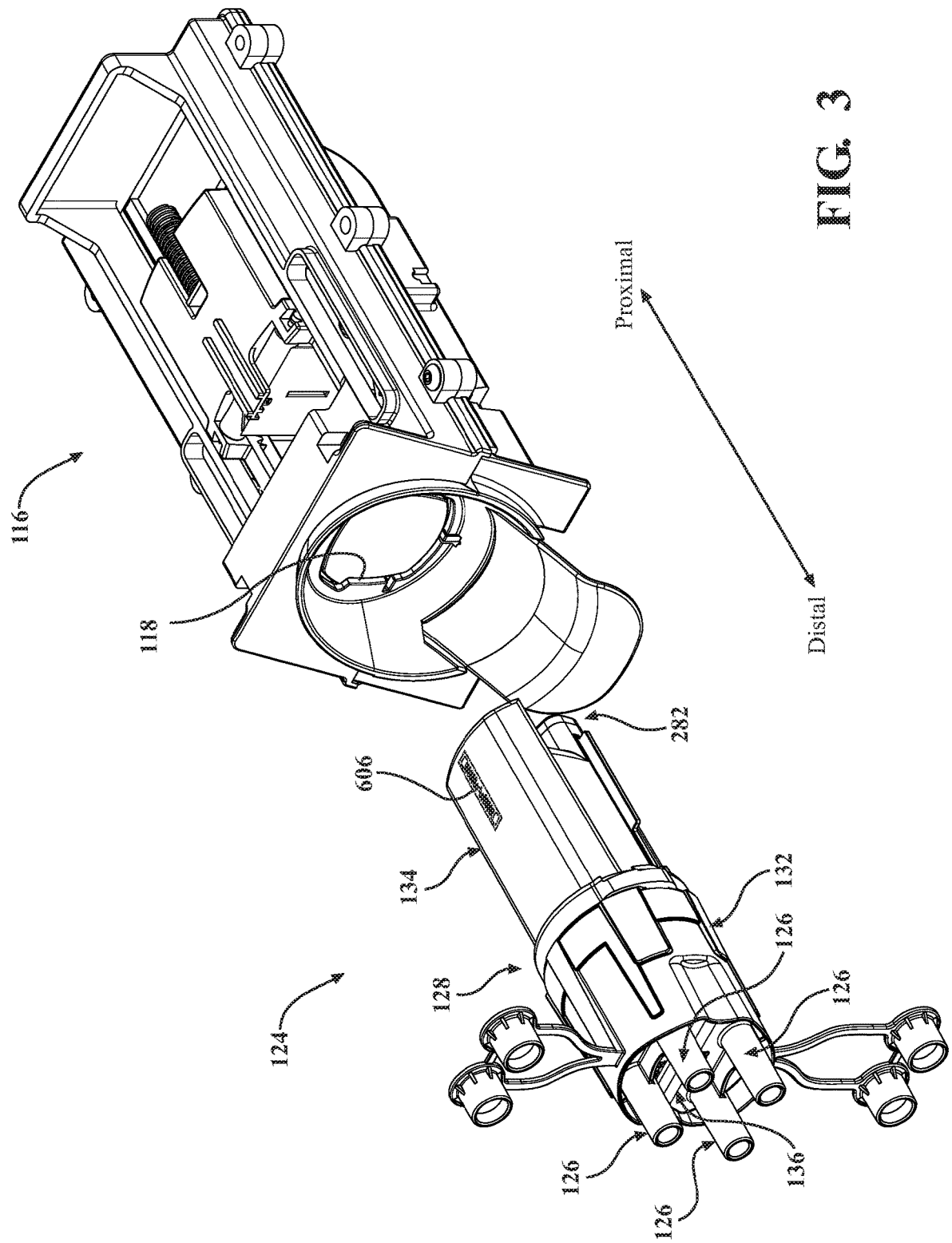
FIG. 3 is a perspective view of the manifold and the receiver with the manifold oriented for insertion into an opening of the receiver.

Referring to FIG. 3, the manifold 124 is shown in a decoupled operative position in which the manifold 124 is separate or spaced apart from the receiver 116. FIG. 3 may be representative of the manifold 124 prior to insertion into the receiver 116 and/or after removal of the manifold 124 from the receiver 116. The manifold 124 is configured to be inserted into the receiver 116 through the opening 118, and the suction tube(s) 120 are coupled to inlet fitting(s) 126 of the manifold 124. The resulting arrangement is schematically reflected in FIG. 1 in which two suction tubes 120 are coupled to two of four inlet fittings 126 of each of the manifolds 124. Any number of inlet fitting(s) are contemplated, and it is further contemplated that the suction tube(s) 120 may be integral with the housing 128. The aforementioned suction path is established, and an instrument (not shown) coupled to an end of the suction tube(s) 120 opposite the manifold(s) 124 may be directed to the surgical site to collect the waste material under the influence of the vacuum provided by the vacuum pump 110.

Figure 4:
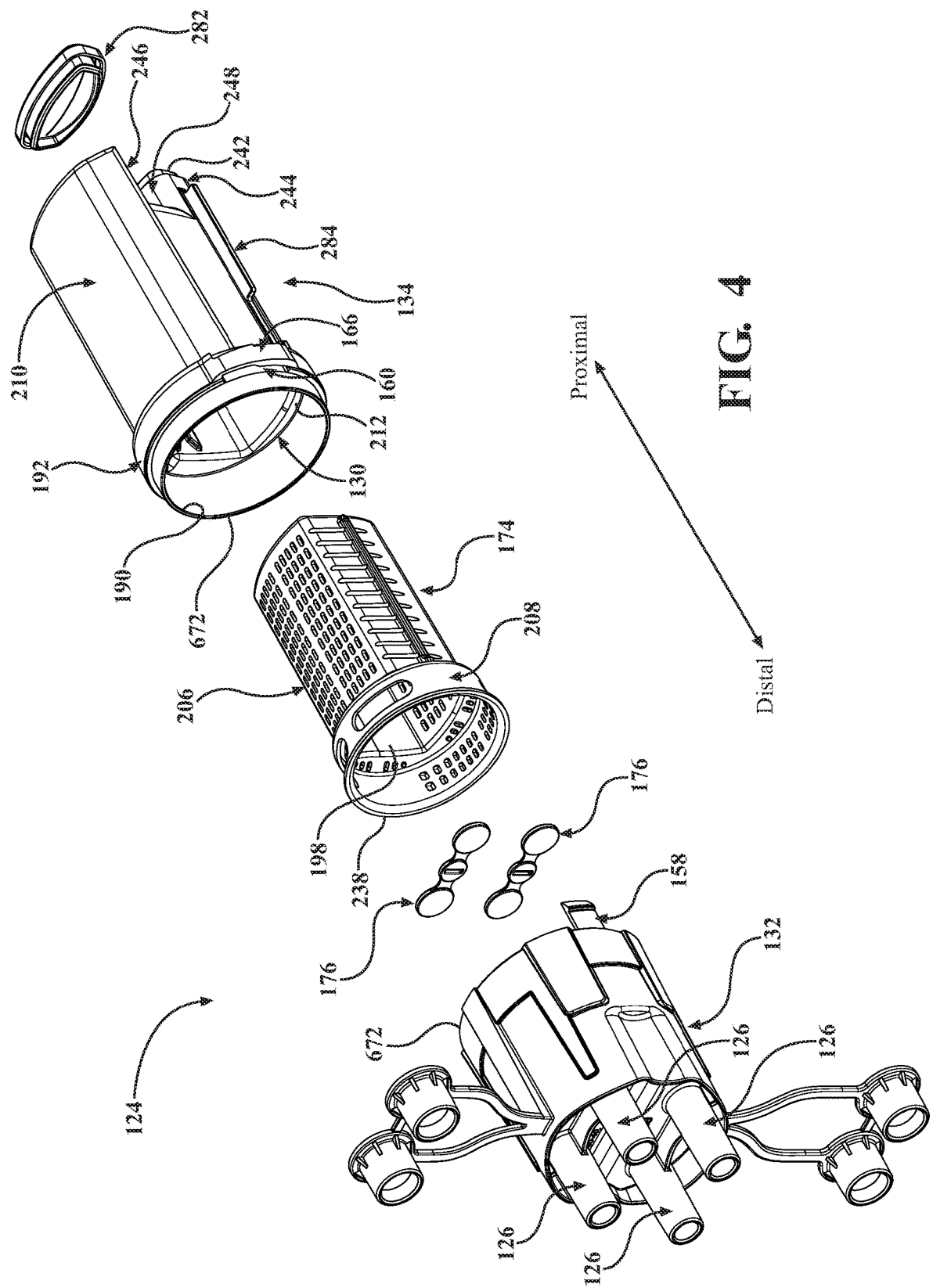
FIG. 4 is an exploded view of the manifold.

With further reference to FIG. 4, the manifold 124 includes a housing 128. The housing 128 may define a manifold volume 130 in certain configurations. The housing 128 may be considered any external structure or component of the manifold 124. FIG. 4 shows the manifold 124 including a head 132 coupled to a trunk 134 to at least partially form the housing 128. The head 132 is positioned distal to the trunk 134 when the manifold 124 is oriented for insertion into the opening 118 of the receiver 116, as shown in FIG. 3. As used throughout the present disclosure, the terms "distal" and "proximal" may refer to the respective directions identified in arrows of FIG. 3 and additional figures throughout the present disclosure. In another convention, the term "distal" may refer to a direction generally away from a rear barrier 602 of the receiver 116 (see FIG. 27), and the term "proximal" may refer to a direction generally towards the rear barrier 602 of the receiver 116. In still another convention, the term "distal" may refer to a direction generally towards a front of the manifold 124 and towards the surgical site, and the term "proximal" refers to a direction generally towards a rear of the manifold 124 (when the manifold 124 is inserted into the receiver 116) and away from the surgical site. In an alternative to the multi-piece construction including the head 132 and the trunk 134, the housing 128 of the manifold 124 may be of unitary or monolithic construction (see, e.g., FIGS. 89-92).

The head 132 (or any other portion of the housing 128) may include the inlet fitting(s) 126. The inlet fitting(s) 126 may extend distally from a crown 136 to define a distal end of the manifold 124. Alternatively, the inlet fitting(s) 126 may be coupled to a structure that is separate from the housing 128 (i.e., not directly coupled to the head 132) with the inlet fitting(s) 126 being in fluid communication with an outlet opening 242 to be described to establish the suction path (see, e.g., FIGS. 85-102). It is further contemplated that any features described as being a part of the head 132 may alternatively be a part of the trunk 134, and any features described as being a part of the trunk 134 may alternatively be a part of the head 132. In certain implementations, the housing 128 may merely provide the structural support for the certain various components without defining the outlet opening 242 (see, e.g., FIGS. 85-102). In other words, the housing 128 may not define the manifold volume 130 but instead support certain structures described below, including but not limited to arm(s) 284, catch(es) 254, a spine 300, and/or locking element(s) 306. For another example, arrangements in which the outlet opening 242 is defined by a structure separate from a housing is shown in FIGS. 81-98 and those described in U.S. Patent Publication No. 2018/0333520, published Nov. 22, 2018, the entire contents of which is hereby incorporated by reference.

Figure 5:
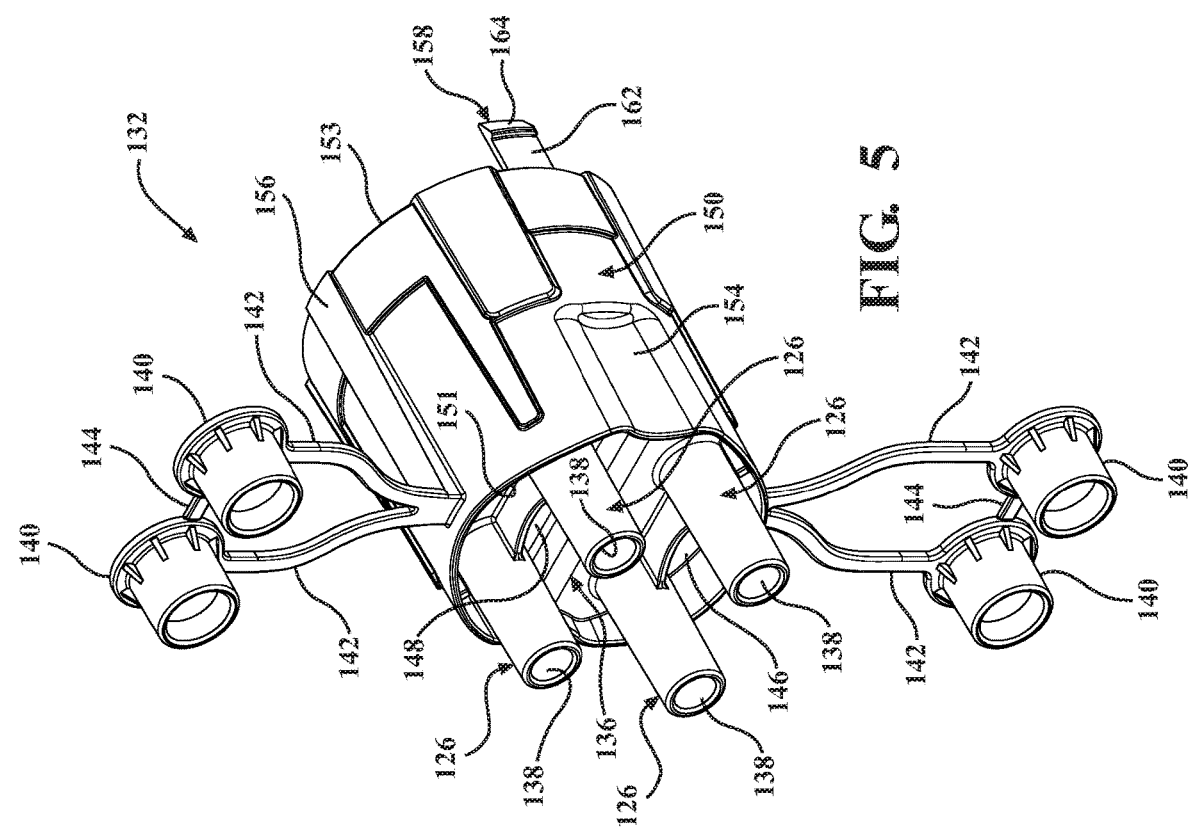
FIG. 5 is a perspective view of a head of the manifold.

Each of the inlet fittings 126 may define an inlet bore 138. FIGS. 3-5 show four of the inlet fittings 126 extending distally from the crown 136 in a parallel arrangement according to one implementation. The manifold 124, therefore, is configured to be removably coupled with four of the suction tubes 120 to be simultaneously operable with operation of the medical waste collection system 100. Should one or more of the inlet fittings 126 not be removably coupled with the suction tube 120, a cap 140 may be removably coupled with a distal portion of the inlet fitting(s) 126 to seal a respective one of the inlet bores 138 from fluid communication with the ambient. The resulting arrangement prevents ambient air from being drawn into the inlet bores 138 under the influence of the vacuum when the respective inlet fitting(s) 126 are not intended for use for at least a portion of the surgical procedure. The vacuum may be directed through the inlet fitting(s) 126 to which the suction tube(s) 120 are coupled without compromise, thereby providing improved control of the vacuum level at the surgical site. The cap(s) 140 may be coupled to the housing 128 with one or more tethers 142 extending outwardly from the head 132, and pairs of the caps 140 may be coupled to one another with webbing 144 such that the pairs of the caps 140 may be coupled to and decoupled from respective pairs of the inlet fittings 126 in tandem. Alternatively, the caps 140 may be provided separately, and/or the tether(s) 142 may be removably coupled to the head 132.

The crown 136 shown in FIG. 5 may include a lower face 146 and an upper face 148 each from which a pair of the inlet fittings 126 extend distally. The lower face 146 is positioned below the upper face 148 when the manifold 124 is oriented for insertion within the opening 118 of the receiver 116. The lower face 146 may be positioned more distal to the upper face 148 such that, owing to a length of the inlet fittings 126 being equal, a lower pair of the inlet fittings 126 extend more distally than an upper pair of the inlet fittings 126. The resulting arrangement is generally shown in the elevation view of FIG. 7, and the axial staggering between the upper and lower pairs of the inlet fittings 126 may provide additional clearance for a user's hand to confidently couple and decouple the suction tube(s) 120 and/or the cap(s) 140 with the inlet fitting(s) 126. It is contemplated that the inlet fittings 126 may be positioned in other suitable arrangements to achieve its desired function.

Figure 6:
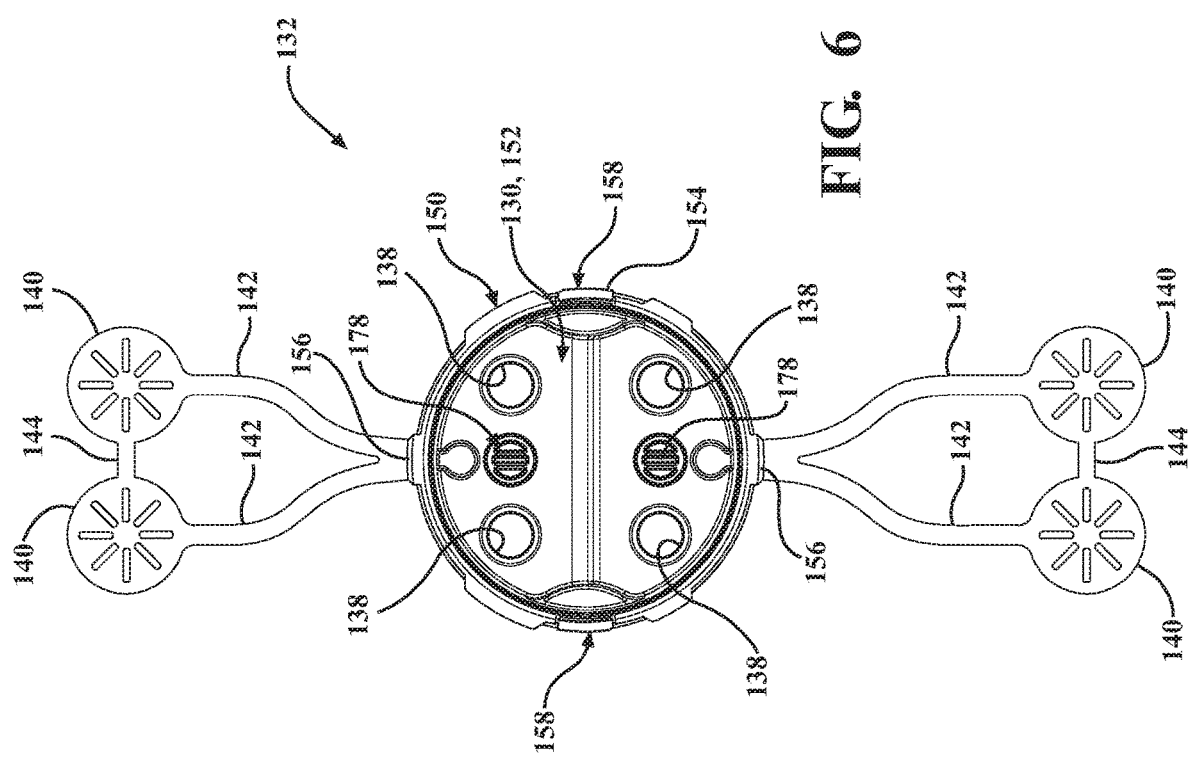
FIG. 6 is a rear elevation view of the head.
Figure 7:
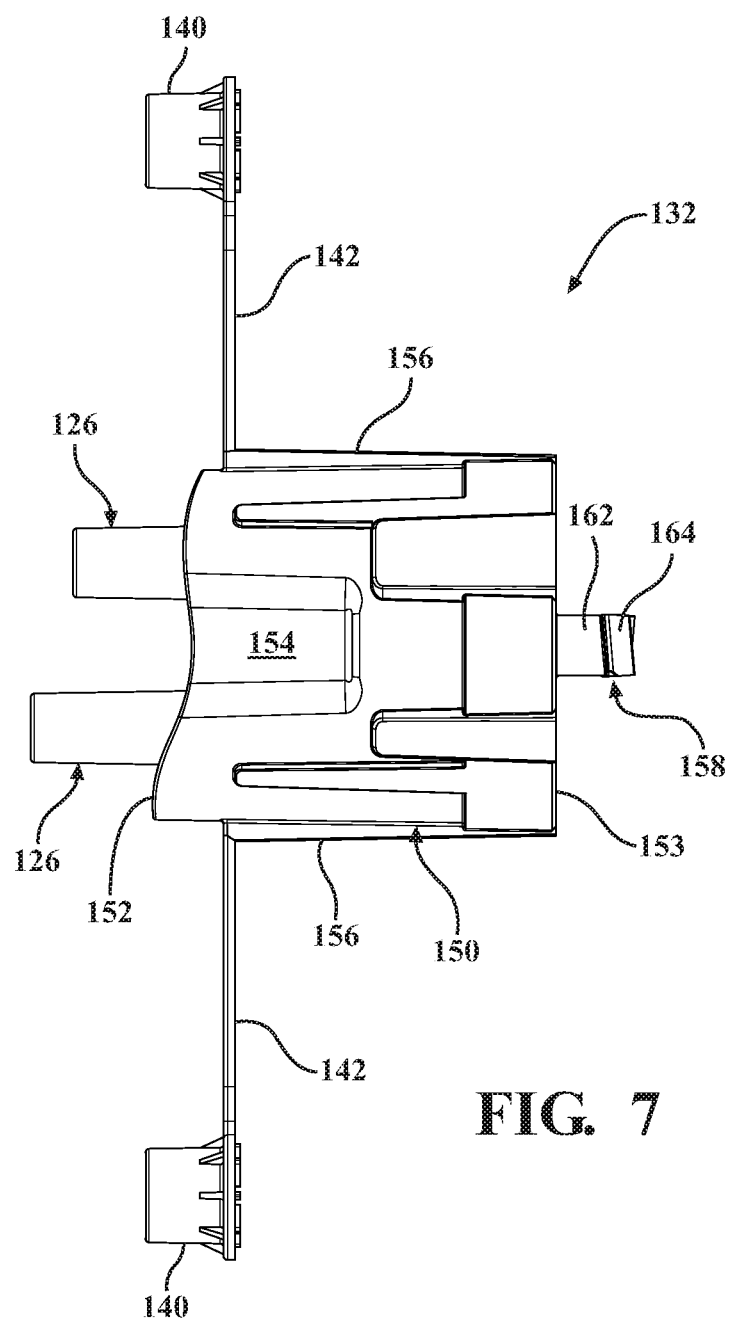
FIG. 7 is a side elevation view of the head.

The head 132 may include at least one side 150. The side 150 may extend between a distal rim 151 opposite a proximal rim 153. The distal rim 151 may be positioned slightly distal to the crown 136 such that the crown 136 is recessed. The side 150 may be considered a singular surface that is cylindrical in shape, as shown in FIGS. 5 and 6, or plural surfaces arranged in any suitable geometry. An inner or proximal surface of the crown 136 and an inner surface of the side 150 may cooperate to define a cavity 152, best shown in FIG. 6, that may define at least a portion of the manifold volume 130. In such an arrangement, the inlet bore(s) 138 are in fluid communication with the cavity 152, and thus the manifold volume 130. The side 150 may include at least one control surface 154 configured to be manipulated by the user to facilitate inserting the manifold 124 into the opening 118 of the receiver 116. The control surface(s) 154 may include a depression formed within the side 150 and positioned diametrically opposite one another (one shown in FIGS. 5 and 7), or other suitable geometric features or materials configured to enhance handling of the manifold 124. The side 150 may include at least one orienting indicia 156 configured to provide a visual indication of the proper orientation of the manifold 124 to be inserted within the opening 118 of the receiver 116. FIGS. 5-7 show the orienting indicia 156 as ridges diametrically opposed to one another and extending proximally-to-distally along upper and lower aspects of the side 150. The orienting indicia 156 may include other geometric features or indicia, for example, color contrasting with adjacent portions of the head 132.

In certain implementations, the head 132 and the trunk 134 are removably coupled to one another. Referring to FIGS. 4-9, the head 132 includes at least one key 158 or head coupler configured to be removably coupled with at least one keyway 160 or trunk coupler of the trunk 134. The key 158 may be two keys 158 diametrically opposed to one another and extending proximally from the proximal rim 153 of the head 132. The keyway 160 may be two keyways 160 diametrically opposed to one another and defined between at least one lip 166 extending radially outwardly from a collar 168 of the trunk 134. The keyway(s) 160 may include an insertion portion 170 and a locking portion 172 in communication with the insertion portion 170. As best shown in FIG. 9, the insertion portion 170 may be wider than the locking portion 172. In other words, a portion of the lip 166 defining the locking portion 172 may be thinner than a portion of the lip 166 defining the insertion portion 170. The key 158 may include a shank 162, and a barb 164 extending from the shank 162. The barb 164 may be thicker than the shank 162. The width of the insertion portion 170 is greater or larger than a thickness of the barb 164 and greater or larger than a thickness of the shank 162, and the width of the locking portion 172 is less than the thickness of the barb 164 and greater or larger than the thickness of the shank 162. Further, a length of the shank 162 may be at least equal to a length of the lip 166. More particularly, the length of the shank 162 may be greater or larger than the length of the portion of the lip 166 defining the insertion portion 170, and the length of the shank 162 may be approximately equal to the length of the portion of the lip 166 defining the locking portion 172. As a result, during assembly of the manifold 124 or when it is desired to couple the head 132 with the trunk 134, the head 132 is oriented relative to the trunk 134 such that the barb(s) 164 are rotationally aligned with the insertion portion(s) 170. The head 132 is moved towards the trunk 134 such that the barb(s) 164 extend through the insertion portion(s) 170 to pass the lip 166, and the shank 162 is positioned within the insertion portion(s) 170. The head 132 is rotated relative to the trunk 134, for example, clockwise in the view of FIG. 9, to move the key(s) 158 within the keyway(s) 160. The shank(s) 162 move from within the insertion portion(s) 170 to within the locking portion(s) 172 with the barb(s) 164 positioned in an interference arrangement with the portion of the lip(s) 166 defining the locking portion(s) 172. The interference prevents axial movement of the head 132 relative to the trunk 134, and the head 132 may be considered secured to the trunk 134 to form the housing 128 of the manifold 124.

The removable coupling between the head 132 and the trunk 134 may provide access to the manifold volume 130 within which a filter element 174 is disposed. Among other advantages, accessing the filter element 174 may allow the user to retrieve waste material collected within the filter element 174, most notably a polyp or tissue sample, for further examination and processing during certain surgical procedures. Commonly-owned International Publication No. WO 2013/090579, published Jun. 20, 2013, the entire contents of which is hereby incorporated by reference, discloses a manifold including a tissue trap for collecting the polyp or the tissue sample. In certain implementations, the manifold 124, including the head 132, may include further features to facilitate collection of tissue sample(s). One such implementation is disclosed in commonly-owned International Publication No. PCT/US2019/032911, filed May 17, 2019, the entire contents of which is hereby incorporated by reference.

When it is desired to decouple the head 132 from the trunk 134, the aforementioned method steps are reversed. The head 132 is rotated relative to the trunk 134, counterclockwise in the view of FIG. 9, to move the key(s) 158 within the keyway(s) 160. The shank(s) 162 move from within the locking portion(s) 172 to within the insertion portion(s) 170 with the barb(s) 164 removed from the interference arrangement with the portion of the lip(s) 166 defining the locking portion(s) 172. The head 132 moves away from the trunk 134 such that the barb(s) 164 pass the lip(s) 166, and the keys(s) 158 may be considered disengaged from the keyway(s) 160. The cavity 152 of the head 132 may be accessible, and/or the manifold volume 130 of the trunk 134 may be accessed through a distal opening 190 at least partially defined by a neck 192 of the trunk 134, as shown in FIG. 4.

In certain implementations, the head 132 and the trunk 134 are rigidly connected through a suitable joining process, for example, spin welding, solvent bonding, adhesives, mechanical fastening, and the like. As previously mentioned, the housing 128 may be of unitary or monolithic construction such that there is no discrete head and trunk. Suitable manufacturing processes for forming the housing 128 may include injection molding, three-dimensional printing, computer numerical control (CNC) machining, polymer casting, vacuum forming, blow molding, among others. Suitable materials for forming the housing 128 may include polymers, composites, metals, ceramics, and combinations thereof. The materials include sufficient anticorrosive properties to avoid degradation when exposed to the waste material and sufficient mechanical properties to maintain integrity under the vacuum levels to be provided by the medical waste collection system 100. The polymers of polyethylene, polypropylene, polyvinyl chloride, polyethylene terephthalate (PET, PETE), polystyrene, polycarbonate, and poly(methyl methacrylate) may be particularly well suited for the manifold 124 in low-cost and disposable implementations.

Referring again to FIG. 4, the manifold 124 may include at least one valve 176 configured to prevent backflow from the manifold volume 130 to the inlet bore(s) 138. With further reference to FIG. 6, the valve(s) 176 may be coupled to the head 132 and disposed within the cavity 152 of the head 132 that may define at least a portion of the manifold volume 130. In particular, the inner or proximal surface of the crown 136 may include a coupler 178, such as a protrusion extending proximally. The valve 176, shown in FIG. 15, includes a coupler 180 complementary to the coupler 178 of the head 132. The coupler 180 may be a slot disposed within a central hub 182 of the valve 176 and sized to engage the protrusion with an interference arrangement. The slot may be cruciform in shape. Additionally or alternatively, a suitable joining process such as adhesives, mechanical fastening, and the like, may be used to couple the valve(s) 176 with the head 132.

Figure 15:
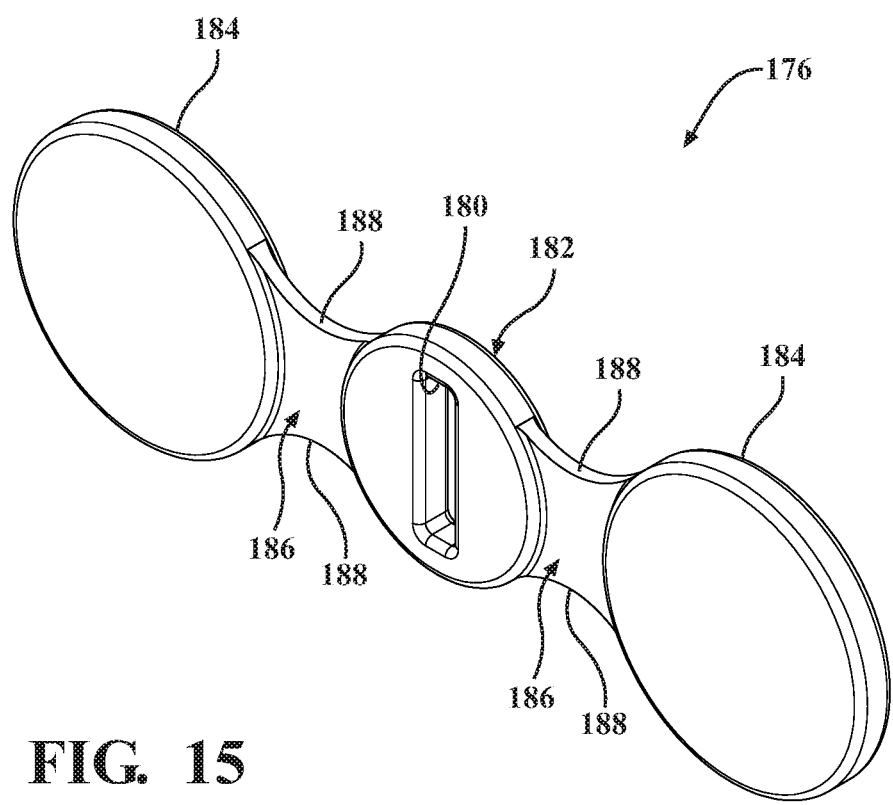
FIG. 15 is a perspective view of a valve.

The valve 176 may include a pair of flappers 184 coupled to the central hub 182 with flexible wings 186. The flexible wings 186 include a length sufficient to space each of the pair of flappers 184 from the central hub 182 by a distance equal to a distance between the coupler 178 of the head 132 and a corresponding pair of the inlet bores 138. The flappers 184 are sized to cover the inlet bores 138 with the flappers 184 being optionally circular in shape as shown in FIG. 15. The valve 176 may be dimensioned to have a thickness significantly less than a width and a length of the valve 176, and the valve 176 may be formed with elastic material(s) such as a rubber or other polymers with suitable viscoelasticity. The dimensions and material(s) of the valve 176 are configured to facilitate resilient deformation about an axis transverse to the length of the valve 176. In other words, the dimensions and material(s) of the valve 176 are configured to facilitate the wings 186 resiliently deforming to permit movement of the flappers 184 in the proximal-to-distal direction. FIG. 15 shows the valve 176 in its natural or unstressed state. The flexible wings 186 may include at least one cutout 188 along the length with the cutout 188 configured to impart a living hinge about the aforementioned axis. FIG. 15 shows two of the cutouts 188 on opposing widthwise sides of the wings 186 with the axis considered to extend through apexes of the cutouts 188. The size and shape of the cutout(s) 188 may be designed to tune the flexural properties to the wings 186 based on a desired magnitude of movement of the flapper 184 under anticipated levels of vacuum provided by the vacuum pump 110.

During assembly of the manifold 124, the valve(s) 176 may be coupled to the housing 128, and more particularly to the head 132. The complementary couplers 178, 180 are engaged, and the valve(s) 176 are positioned directly adjacent or abutting the inner or proximal surface of the head 132. In particular, with the valve(s) 176 in the natural or unstressed state, the flappers 184 are abutting the inner or proximal surface of the head 132 and covering the inlet bores 138. With the manifold 124 inserted into the receiver 116 and with operation of the medical waste collection system 100, the vacuum is drawn on or through the manifold(s) 124 in fluid communication with the waste container(s) 106, 108. Should no cap 140 be sealing a respective one of the inlet bores 138 from fluid communication with the ambient, the vacuum drawn on or through the manifold 124 is sufficient to resiliently deform the wings 186 to permit movement of the flappers 184 in the proximal direction. In other words, the dimensions, the material(s), and/or the cutout(s) 188 of the valve(s) 176 facilitate flexing of the wings 186 and movement of the flappers 184 away from a proximal end of the inlet bore 138. The movement of the flappers 184 away from the proximal end of the inlet bore 138 establishes the suction path from the inlet bore 138 to the manifold volume 130, and thus to the waste container(s) 106, 108. Upon cessation of the vacuum drawn on or through the manifold 124, the valve(s) 176 return to the natural or unstressed state in which the wings 186 resiliently move the flappers 184 into abutment with the inner or proximal surface of the head 132 to cover and seal the proximal end of the inlet bores 138. The sealing of the proximal end of the inlet bores 138 prevent backflow from the manifold volume 130 to the inlet bores 138, and thus possible egress of the waste material through the inlet bores 138.

Referring now to FIGS. 4 and 16-18, the filter element 174 may be optionally disposed within the manifold volume 130. The filter element 174, in a broadest sense, includes structures configured to capture or collect the semisolid or solid waste material entrained within the liquid waste material being drawn through the manifold 124 under the influence of the vacuum provided by the medical waste collection system 100. The filter element 174 may include a basket 206 including a base wall 194 and least one side 196 extending distally from the base wall 194 to define a mouth 198 opposite the base wall 194. Owing to geometry of the trunk 134 to be described within which the filter element 174 is at least partially disposed, the filter element 174 may correspondingly include an upper wall 200, a lower wall 202, and opposing sides 204 when the manifold 124 is oriented for insertion into the opening 118 of the receiver 116. The opposing sides 204 may extend between the upper and lower walls 200, 202, and each of the upper wall 200, the lower wall 202, and the opposing sides 204 may extend distally from the base wall 194. The resulting arrangement may be considered the aforementioned basket 206 that is substantially square or rectangular in section. In certain implementations, the basket 206 may be substantially cylindrical in section, and other suitable shapes are contemplated. Further, the filter element 174 may be implemented as a foam or composite member configured to allow air to pass therethrough while capturing or collecting the semisolid or solid waste material. It should be appreciated that not all configurations of the manifold require use of the filter element 174, and manifold designs that do not include a filter element are contemplated. Further, the filter element 174 may be disposed in a location separate from the manifold volume 130 that is in fluid communication with the outlet opening 242 of the manifold 124.

The filter element 174 may include a brim 208 coupled to the basket 206. The brim 208 extends distally from the basket 206, and may extend radially outwardly from the mouth 198 of the basket 206. The brim 208 may include an outer diameter or dimension greater or larger than an outer diameter or dimension of the basket 206. With further reference to FIG. 4, a length of the basket 206 may be such that the basket 206 is disposed within a body portion 210 of the trunk 134, and a length of the brim 208 may be such that the brim 208 is disposed within the neck 192 of the trunk 134. A step 212 extends radially inward from an inner surface of the neck 192 and/or radially outward from an inner surface of the body portion 210 to define a transition between the neck 192 and the body portion 210. The neck 192 may include an inner diameter or inner dimension greater or larger than an inner diameter or inner dimension of the body portion 210. A flared wall 214 of the filter element 174 defining a transition between the basket 206 and is configured to be positioned adjacent to or in abutment with the step 212 of the trunk 134. The resulting arrangement includes the basket 206 being disposed within a portion of the manifold volume 130 defined by the body portion 210, and the brim 208 being disposed within a portion of the manifold volume 130 defined by the neck 192. Other suitable configurations are contemplated, for example, the basket 206 and/or the brim 208 may be disposed within the cavity 152 of the head 132 that may define a portion of the manifold volume 130. The brim 208 of the filter element 174 may be considered optional, and further shapes and configurations of the filter element 174 suitable for certain implementations of the manifold 124 are disclosed in commonly-owned International Publication No. WO 2018/170233, filed Mar. 15, 2018, the entire contents of which are hereby incorporated by reference.

Figure 16:
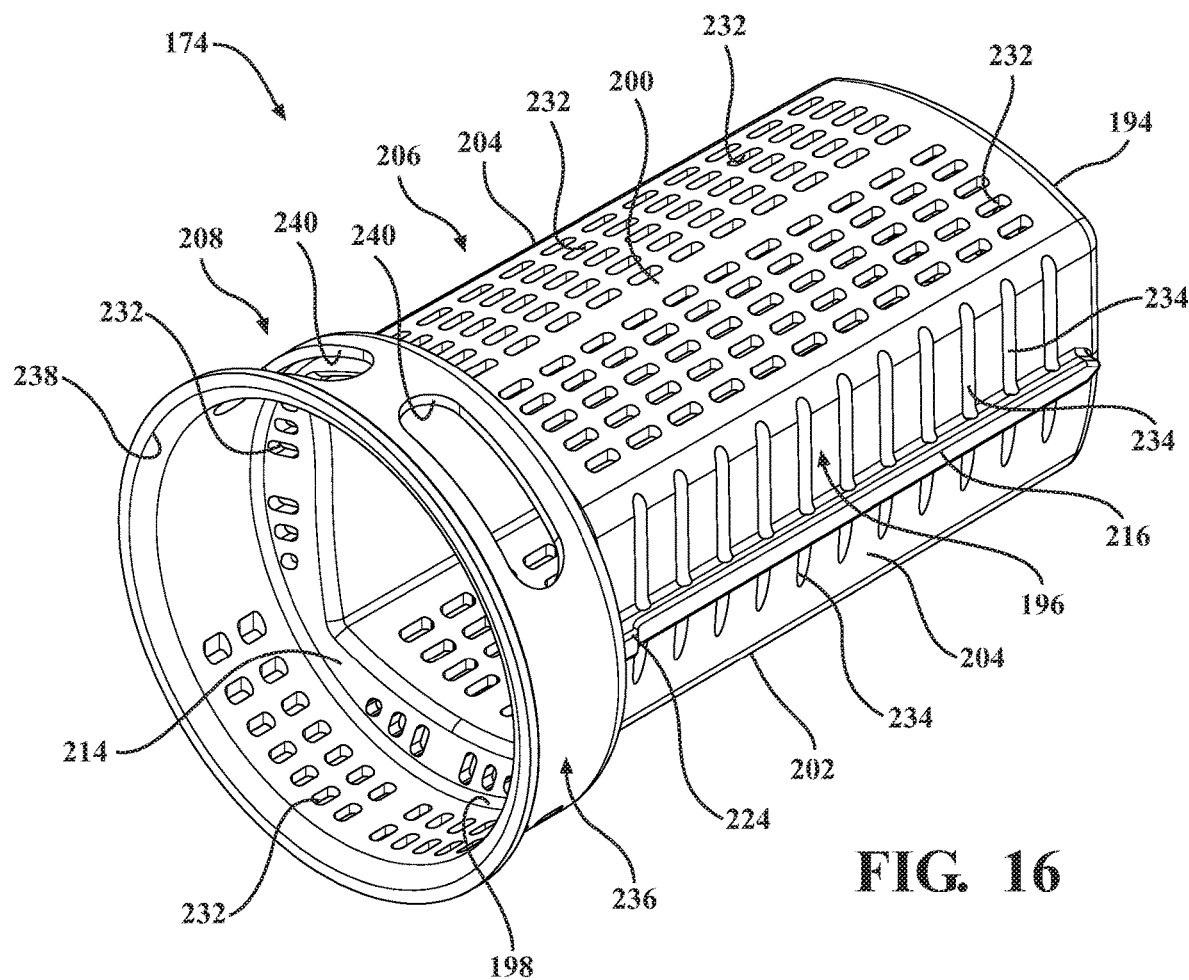
FIG. 16 is a front perspective view of a filter element.
Figure 17:
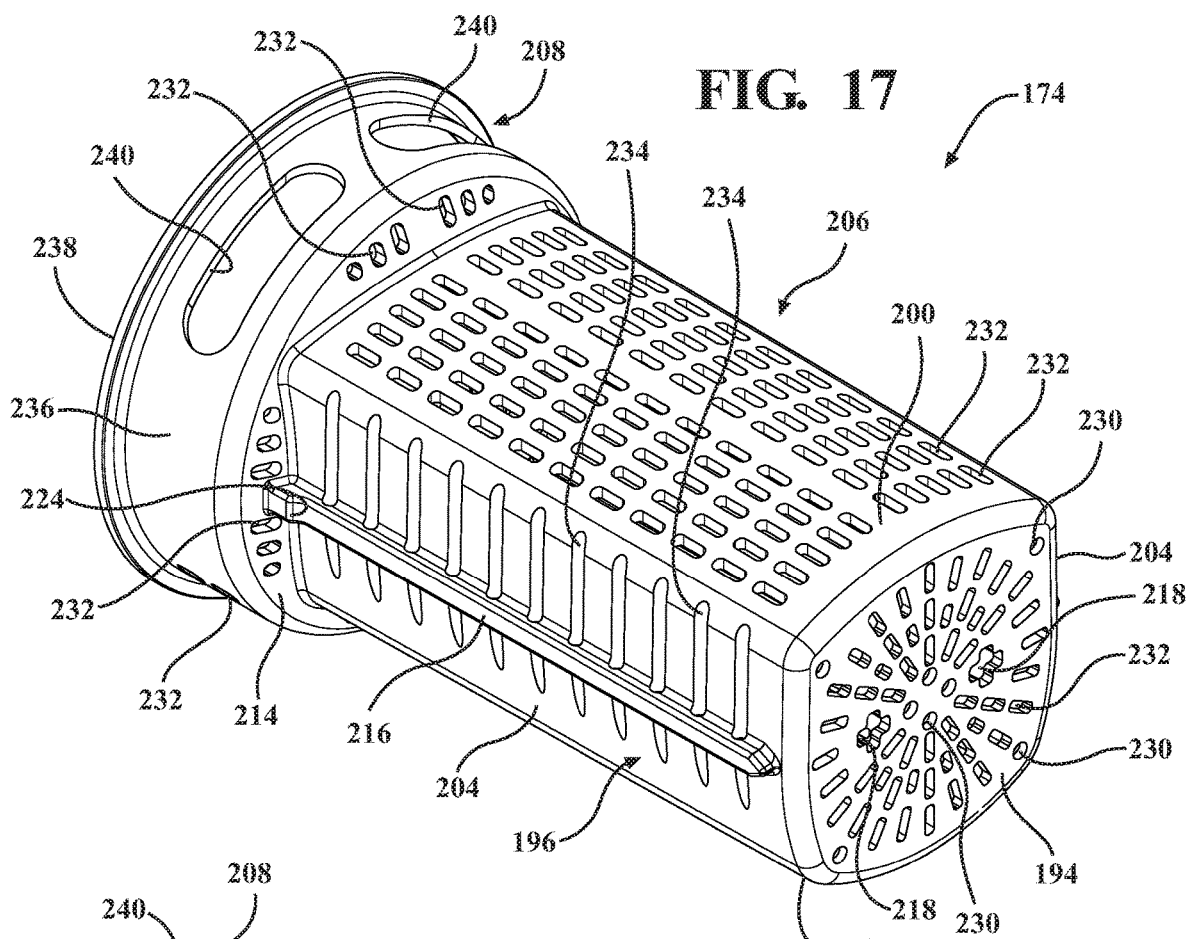
FIG. 17 is a rear perspective view of the filter element.

To facilitate coupling and locating the filter element 174 within the trunk 134, the filter element 174 may include at least one guide 216 and at least one centering hole 218. With continued reference to FIGS. 16-18 and further reference to FIG. 9, the guide(s) 216 may include a rail extending laterally outward from one of the opposing sides 204 of the basket 206 and oriented in the proximal-to-distal direction. The rail may be sized and oriented to be slidably inserted within a complementary slot 220 defined between parallel railings 222 extending laterally inward from the inner surface of the body portion 210 of the trunk 134. FIGS. 9 and 17 show two rails extending laterally outward from the opposing sides 204, and two complementary slots 220 extending laterally inward from opposing inner surfaces of the body portion 210. The guide(s) 216 include a proximal end near the base wall 194 of the basket 206, and a distal end adjacent or on the flared wall 214 of the brim 208. A laterally-outward taper 224 near the distal end of the guide(s) 216 may be configured to be in an interference arrangement with a complementary structure of the trunk 134 when the filter element 174 is fully seated within the manifold volume 130. The centering hole(s) 218 may be defined within the base wall 194 of the basket 206, as best shown in FIG. 17. The centering hole(s) 218 of FIG. 17 include two centering holes 218 that are cruciform in shape to function as a keyway for cruciform-shaped protrusions 226 extending distally from an inner surface of a proximal wall 228 of the trunk 134, as shown in FIG. 9. The cruciform shape is but one example, and other geometries are contemplated. It is further contemplated that the two centering holes 218 may have different shapes, and less or more than two centering holes 218 may be utilized in any suitable position on the base wall 194 of the basket 206. The two centering holes 218 are spaced apart from one another by a distance equal to a distance separating the two protrusions 226. The guide(s) 216 and the centering hole(s) 218 cooperate to ensure the filter element 174 is fully seated within the manifold volume 130 with minimal "play" (e.g., inadvertent proximal, distal, lateral, and/or rotational movement from component tolerances or the like). Further, the guide(s) 216 and the centering hole(s) 218, in view of their relative shapes, dimensions, and/or positions, may cooperate to prevent an unauthorized filter element from being coupled with the trunk 134, for example, during attempted reprocessing of the manifold 124. For example, the specific shape(s) of the centering hole(s) 218 may ensure that only genuine filter elements 174 are compatible, otherwise the protrusion(s) 226 prevent the unauthorized filter element from being fully seated within the trunk 134, and thereby further preventing the head 132 from being properly coupled to the trunk 134.

Figure 18:
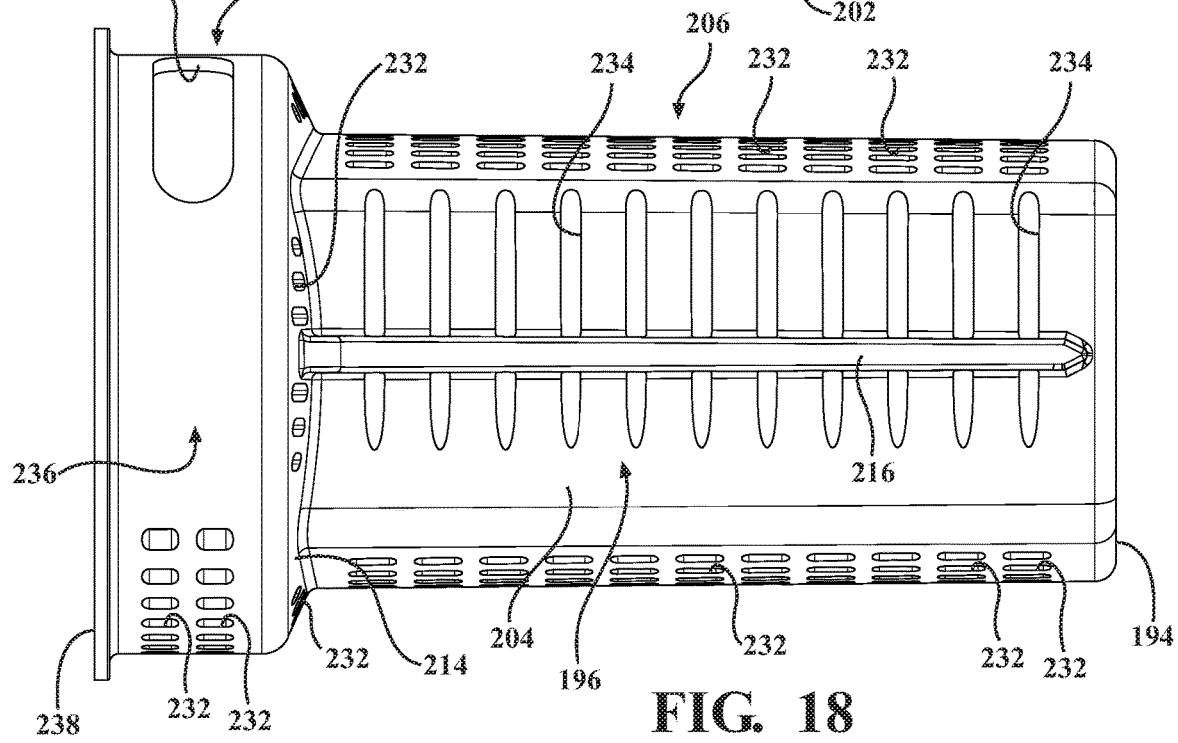
FIG. 18 is a side elevation view of the filter element.

The apertures of the filter element 174 may be shaped as holes 230, pores 232, and/or slots 234, among others. The holes 230, the pores 232, and/or the slots 234 may be defined within any one or more of the base wall 194, the upper wall 200, the lower wall 202, the opposing sides 204, the flared wall 214, and the brim 208. FIGS. 16-18 show the holes 230 defined within the base wall 194, the pores 232 defined within the upper wall 200, the lower wall 202, the flared wall 214, and the brim 208, and the slots 234 defined within the opposing sides 204. The apertures—in type and position—are arranged in a manner to minimize clogging of the filter element 174. For example, the slots 234 defined within the opposing sides 204 are positioned closer to the upper wall 200 than to the lower wall 202. As the semisolid or solid waste material is collected, it will accumulate on bottom of the basket 206 under the influence of gravity with subsequent flow of the waste material passing above the accumulation. Upon accumulation of sufficient amounts of the semisolid or solid waste material, it may be desirable for the waste material to encounter the slots 234, which have a smallest dimension approximately equal to the pores 232 (to capture the semisolid or solid waste material of the same size as the pores 232) with a greater or larger area of opening to permit greater volume flow through the slots 234. Further, the vertical arrangement of the slots 234 is transverse to the suction path and parallel to gravity. Thus, with further accumulation of the semisolid or solid waste material, at least a portion of the slots 234 remain unobstructed until substantially an entirety of the basket 206 is consumed with the waste material, thereby maximizing the operational lifecycle of the manifold 124.

The brim 208 may include at least one sidewall 236 extending between the flared wall 214 and a distal rim 238 of the filter element 174. The sidewall 236 may be considered a singular side that is cylindrical in shape, or plural sides arranged in any suitable geometry. A length of the sidewall 236 may be less than the basket 206, and the sidewall 236 may include the outer diameter or dimension greater or larger than the outer diameter or dimension of the basket 206. The sidewall 236 may include the pores 232, particularly by a lower portion of the sidewall 236 as show in FIG. 16. The sidewall 236 may further define at least one overfill opening 240 positioned on an upper portion of the sidewall 236. The overfill opening(s) 240 are configured to maximize the operational cycle of the manifold 124. As previously explained, as the semisolid or solid waste material is collected, it will accumulate on bottom of the basket 206 under the influence of gravity. Owing to the direction of the suction path (i.e., in the proximal direction), as the semisolid or solid waste material will accumulate on the base wall 194 of the basket 206. Should a sufficient amount of the semisolid or solid waste material be generated over the course of the surgical procedure, an entirety of the basket 206 may become consumed with the accumulated semisolid or solid waste material. In other words, most or all of the holes 230, the pores 232, and/or the slots 234 of the filter element 174 may become clogged with the semisolid or solid waste material. The overfill opening(s) 240 are sized and positioned to permit the suction path to be routed through the overfill opening(s) 240 and external to the basket 206. In other words, owing to understood principles of fluid dynamics where fluid assumes the path of least resistance, the suction path in the aforementioned scenario extends from the inlet bore(s) 138, through the head 132, through the overfill opening(s) 240, within the trunk 134 between the basket 206 and the inner surface of the trunk 134, and to the outlet opening 242 to be described. Further, the cavity 152 of the head 132 defining a portion of the manifold volume 130 may afford additional volume distal to the filter element 174 for the accumulation of additional semisolid or solid waste material as the suction path is directed through the overfill opening(s) 240.

Certain features of the manifold 124 will now be introduced with reference to FIGS. 4, 8 and 10-14, and further described later in relation to complementary components of the receiver 116. The several views of FIGS. 4, 8, 11 and 12 show the manifold 124 oriented for insertion into the opening 118 of the receiver 116 (see also FIG. 3), and for convention the directional references (e.g., proximal, distal, upper, lower, above, below, etc.) are made with the manifold 124 in the insertion orientation. Further, the directional references made with the manifold 124 in the insertion orientation may be considered as being viewed in side elevation (e.g., FIGS. 11 and 12), and/or in view of the respective directional arrows identified.

The manifold 124 includes the housing 128. The housing 128 may define the manifold volume 130 and the outlet opening 242. The outlet opening 242 may be in fluid communication with the manifold volume 130. The outlet opening 242 may be defined by the trunk 134 of the housing 128. The housing 128 may include the body portion 210, a first leg 244, and/or a second leg 246. The first leg 244 and/or the second leg 246 may extend from the body portion 210, and more particularly one or both of the first and second legs 244, 246 may extend proximally from the body portion 210. Alternatively, the first leg 244 and/or the second leg 246 may extend proximally from the collar 168 positioned distal to the body portion 210, the first leg 244 may extend from the second leg 246, and/or the second leg 246 may extend from at least a portion of the first leg 244. The first leg 244 may be positioned above or below the second leg 246 when the manifold 124 is oriented for insertion into the opening 118 of the receiver 116.

Figure 8:
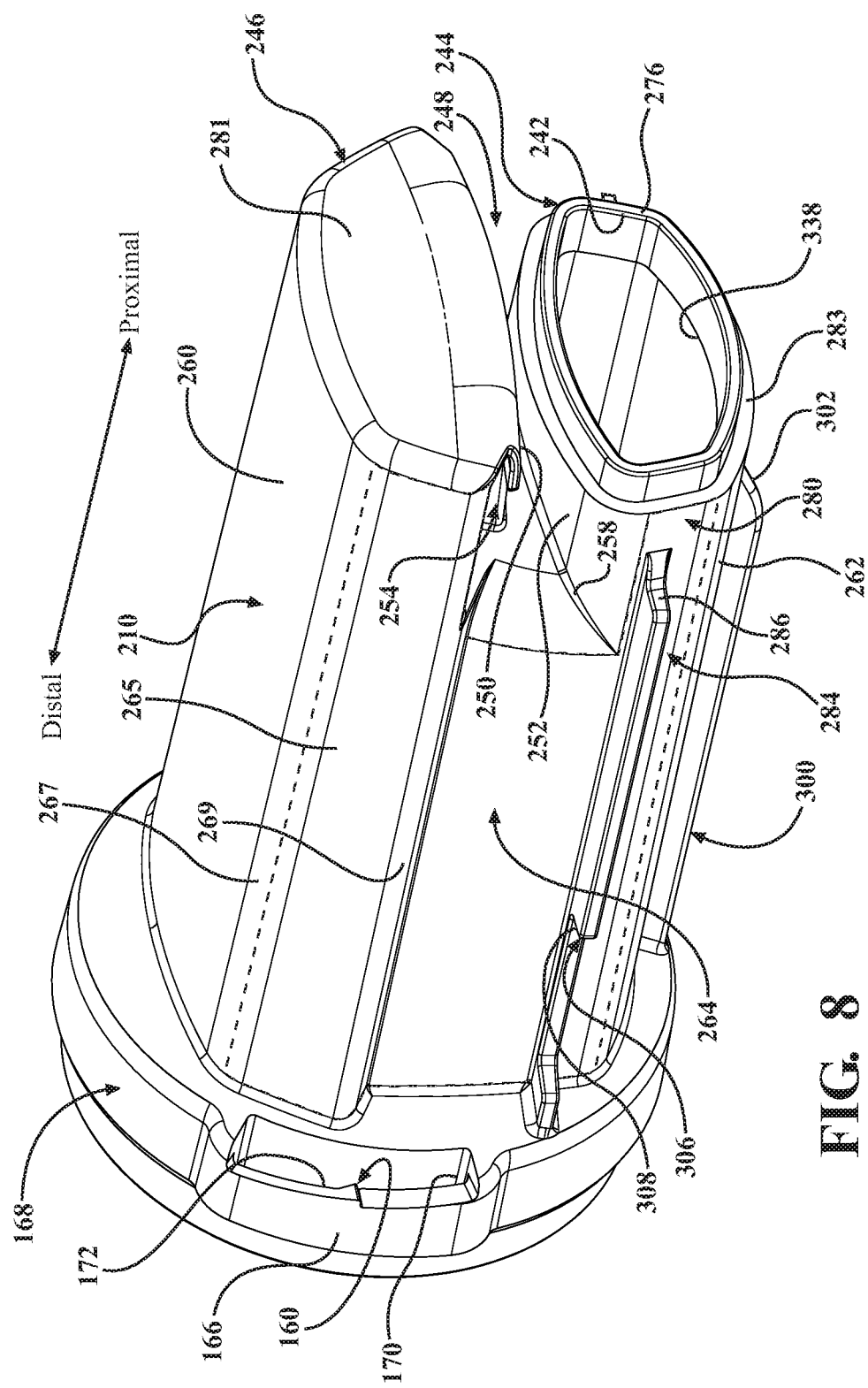
FIG. 8 is a rear perspective view of a trunk of the manifold. A seal of the manifold has been removed to show an outlet opening of the trunk.
Figure 9:
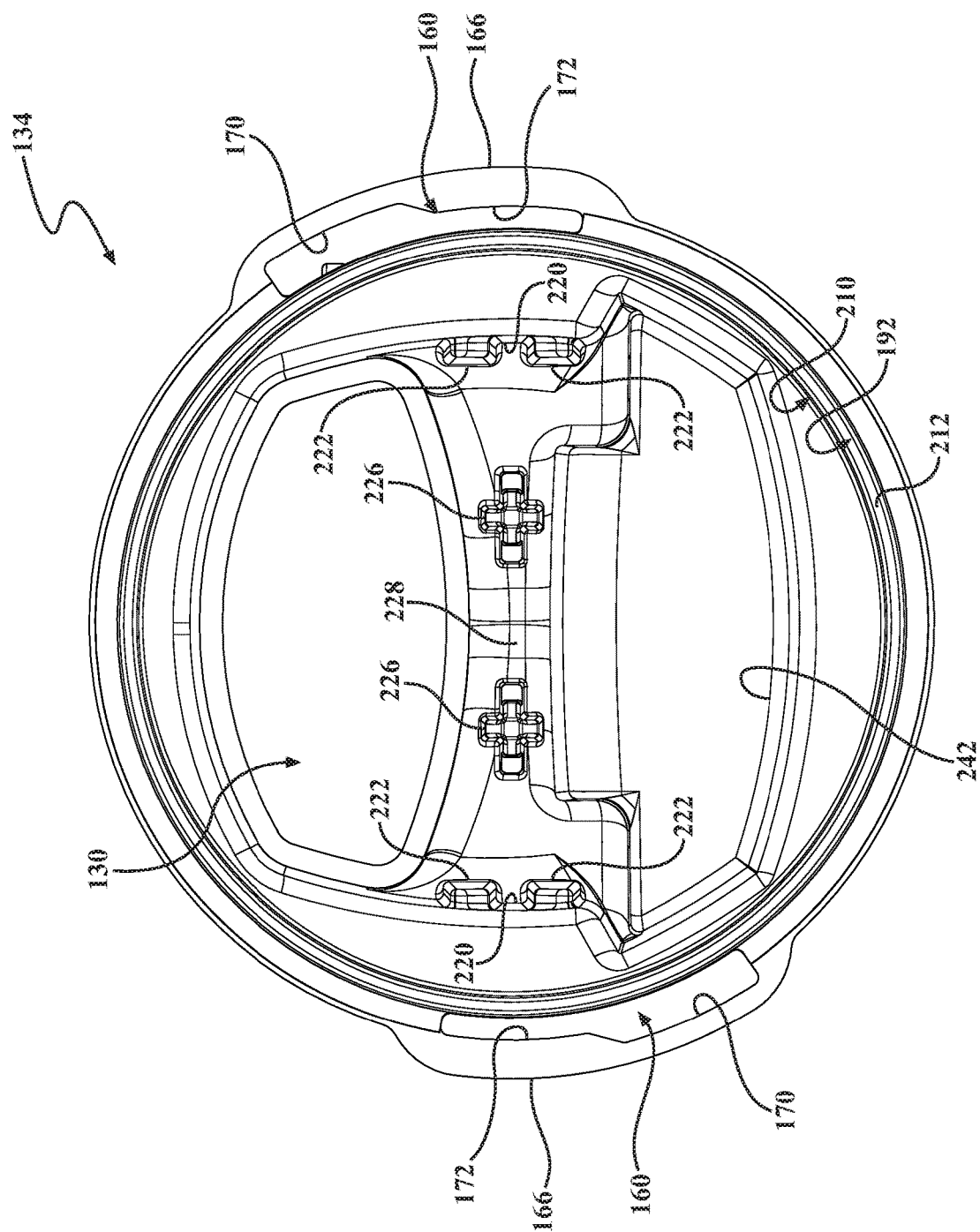
FIG. 9 is front elevation view of the trunk.
Figure 11:
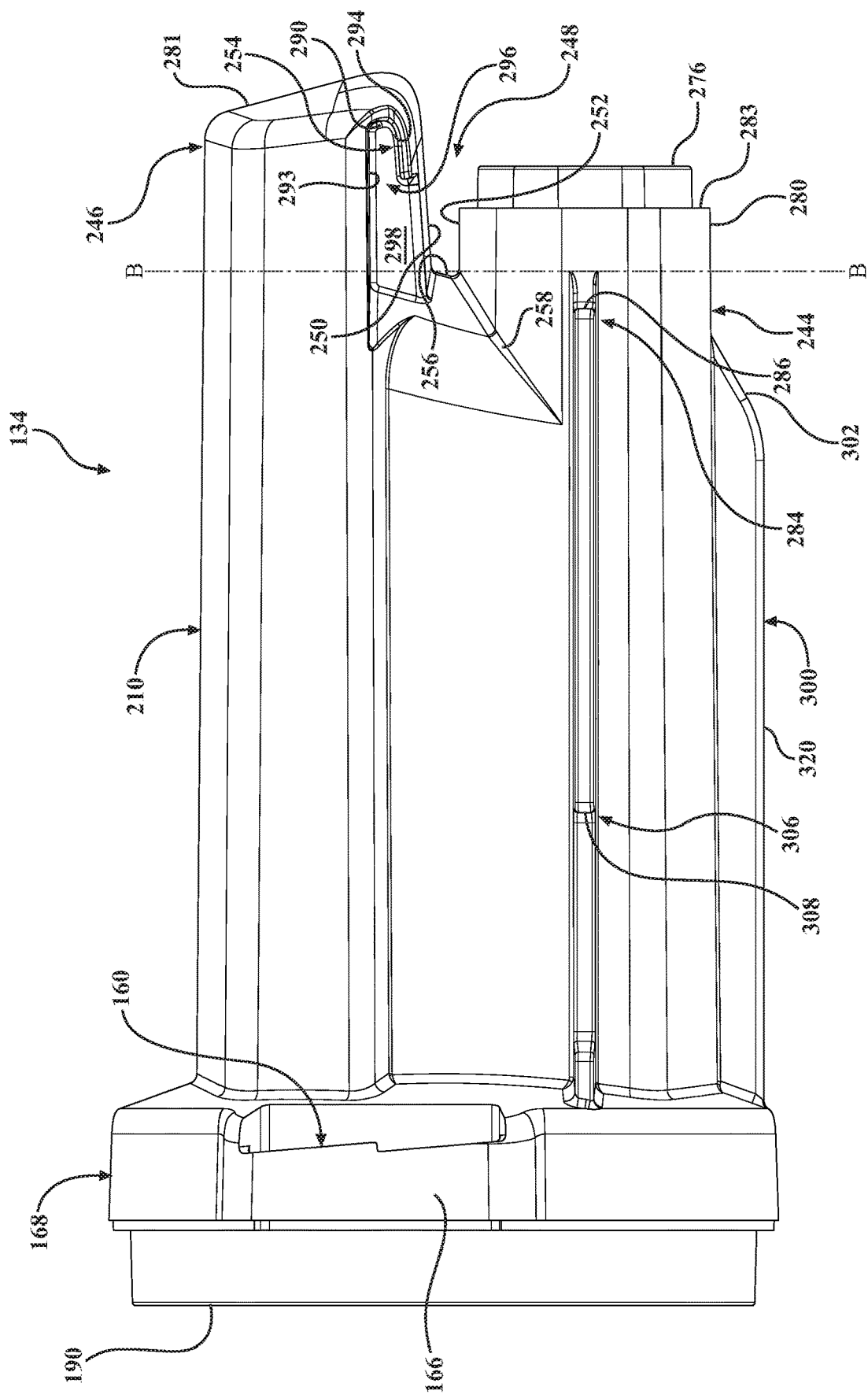
FIG. 11 is a side elevation view of the trunk.
Figure 12:
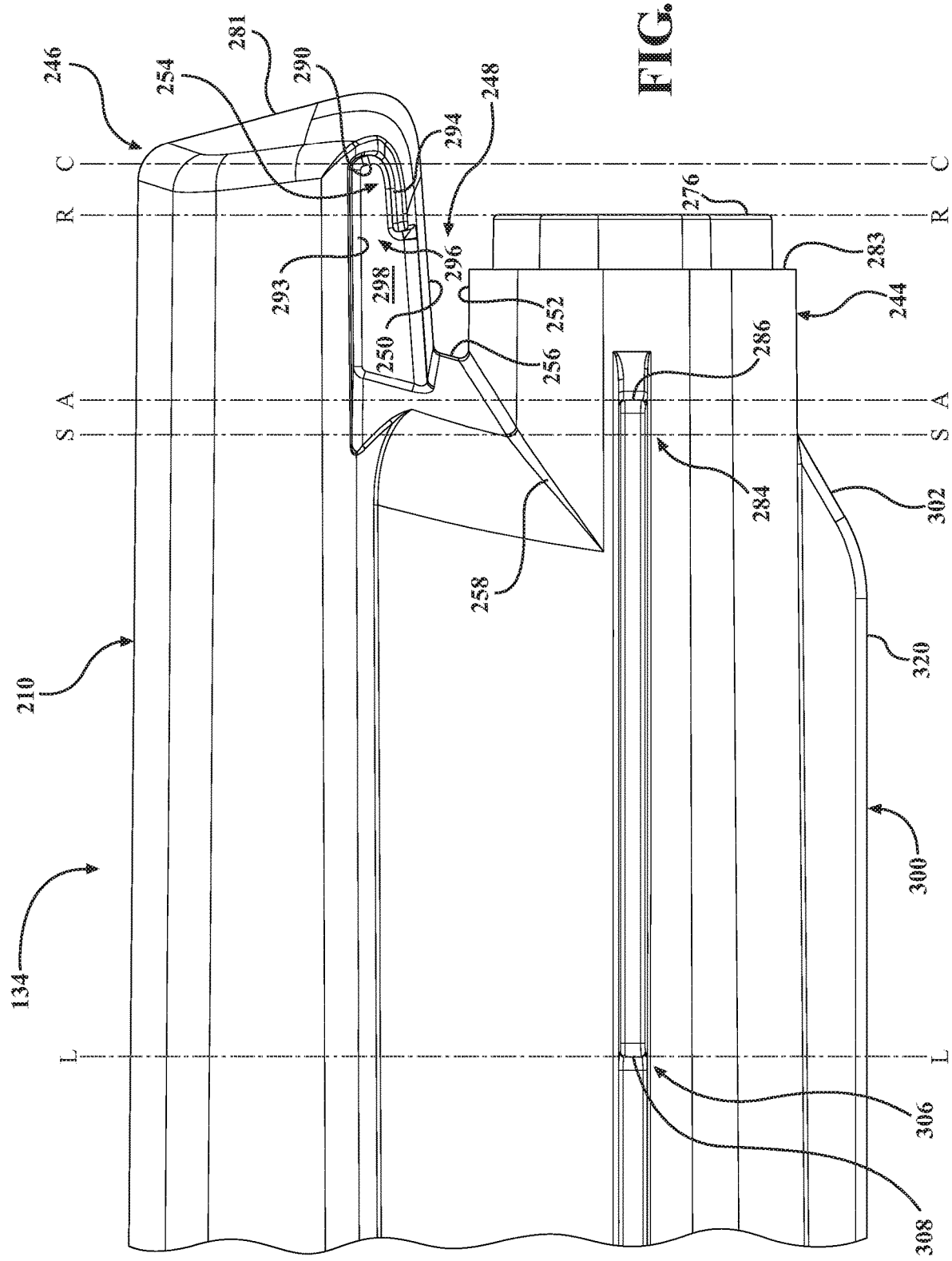
FIG. 12 is a detailed side elevation view of a portion of the trunk.

The first and second legs 244, 246 may be spaced apart from one another to at least partially define a void 248, as best shown in the perspective view of FIG. 8 and the side elevation views of FIGS. 11 and 12. The void 248 may be at least partially defined between a lower aspect 250 of the second leg 246 and an upper aspect 252 of the first leg 244. The lower aspect 250 of the second leg 246 is shown as a wall generally extending between opposing sides of the second leg 246. In certain implementations, the lower aspect 250 may extend laterally by a lesser extent than shown, for example, where slots or other geometric features extend through the second leg 246. In certain implementations, a catch 254 to be further described may be a generally standalone structure (see, e.g., FIG. 68) such that the catch 254 and the first leg 244 define the void 248. For example, the second leg 246 with the catch 254 may be a narrower than shown in FIG. 6 and extend proximally from the body portion 210 and/or the first leg 244.

The body portion 210 may include a distal aspect 256, and the void 248 may be further defined by the distal aspect 256. The distal aspect 256 may extend between the first and second legs 244, 246 to define an extent of separation between the first and second legs 244, 246. More particularly, the distal aspect 256 may extend between the upper and lower aspects 250, 252 to define three sides of the void 248 that is slot-shaped. For example, FIG. 12 shows the distal aspect 256 as a generally vertically-oriented surface distally bounding the void 248 and generally defining a height of the void 248. The upper and lower aspects 250, 252 may be generally horizontally-oriented surfaces bounding the void 248 from above and below, respectively, and generally defining a depth of the void 248. Other sizes and/or shapes of the void 248 are contemplated. The first and/or second legs 244, 246 may be considered to extend from the distal aspect 256.

For convention, a vertical plane perpendicular to the proximal-to-distal direction and extending through a proximal-most point of the distal aspect 256 may be considered a boundary (B) separating the body portion 210 and the first and/or second legs 244, 246, as identified in FIG. 11. A portion of the housing 128, and more particularly the trunk 134, distal to the boundary (B) may be considered the body portion 210, and upper and lower portions of the housing 128, and more particularly the trunk 134, proximal to the boundary (B) may be considered the second and first legs 246, 244, respectively. It is understood that the distal aspect 256 may include curvature in the proximal-to-distal direction, and/or the upper aspect 252 of the first leg 244 may include curvature in the upper-to-lower direction to result in the geometry best shown in FIGS. 8 and 12. An interface 258 may extend between adjacent surfaces at least partially defining the body portion 210 and/or the first leg 244. The first and second legs 244, 246 may include a cross-sectional area less than a cross-sectional area of the body portion 210 with the respective cross-sectional areas being in vertical planes perpendicular to the proximal-to-distal direction.

Figure 31:
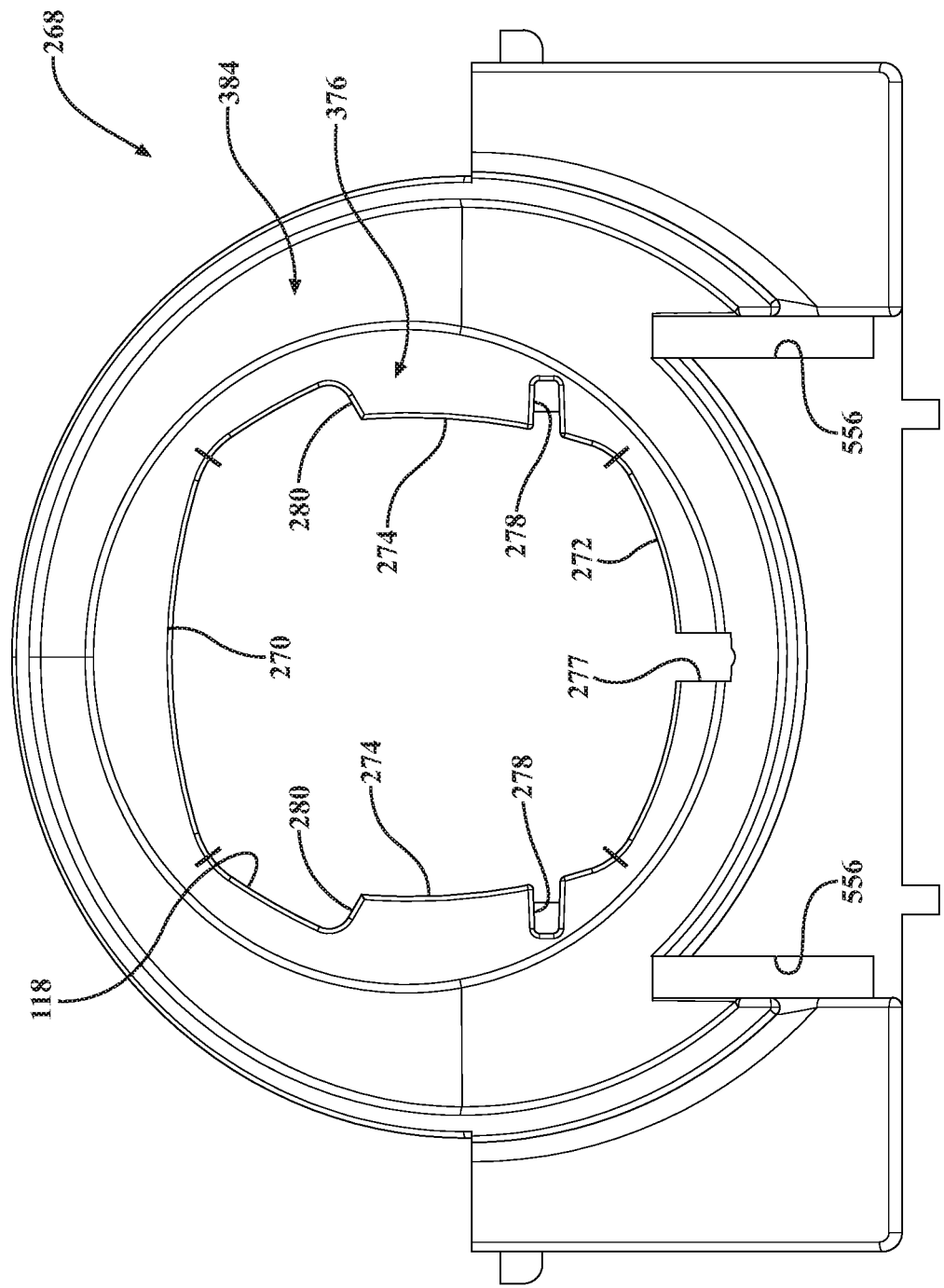
FIG. 31 is a front elevation view of the lower housing.

The housing 128 may include an upper wall 260, a lower wall 262, and opposing sides 264 extending between the upper and lower walls 260, 262. FIG. 8 includes a convention for delineating the upper wall 260, the lower wall 262, and the opposing sides 264. In particular, a boundary is shown in phantom to identify one of the opposing sides 264, and a same boundary on the other one of the opposing sides 264 may be assumed. An upper portion of the trunk 134 between the opposing sides 264 may be considered the upper wall 260, and a lower portion of the trunk 134 between the opposing sides 264 may be considered the lower wall 262. Likewise, the opposing sides 264 may extend between the upper and lower walls 260, 262. Another convention may include the opposing sides 264 being the exterior side surface(s) being generally vertically-oriented, the upper wall 260 being the exterior upper surface(s) being generally horizontally-oriented, and the lower wall 262 being the exterior lower surface(s) being generally horizontally-oriented. Still another convention for delineating the upper wall 260, the lower wall 262, and the opposing sides 264 of the housing 128 may be in relation to a complementary shape of the opening 118 of the receiver 116. FIG. 31 shows a lower housing 268 of the receiver 116 including a front elevation view of the opening 118 with four annotated markings intersecting the opening 118. The four annotated markings may be positioned at approximately the four corners of the opening 118 being generally square or rectangular in shape. The opening 118 may include and/or be defined by an upper segment 270 between an upper pair of the annotated markings, a lower segment 272 between a lower pair of the annotated markings (excluding a spine slot 277), and opposing side segments 274 between respective lateral pairs of the annotated markings (excluding arm slots 278 and recesses 279). The upper wall 260 of the housing 128 may be considered any surface(s) that are positioned towards, near, or adjacent the upper segment 270 when the manifold 124 is inserted within the opening 118, lower wall 262 of the housing 128 may be considered any surface(s) that are positioned towards, near, or adjacent the lower segment 272 when the manifold 124 is inserted within the opening 118, and sides 264 of the housing 128 may be considered any surface(s) that are positioned towards, near, or adjacent the side segments 274 when the manifold 124 is inserted within the opening 118. Other conventions are contemplated, and it is to be appreciated that owing to the shape and features of the manifold 124, the shape of the opening 118, and the features of the receiver 116, manifolds compatible with the receiver 116 may include discernable upper and lower walls and sides. It is understood that potentially trivial changes in the illustrated geometries may be included without deviating from the above conventions.

Returning to FIG. 8, the opposing sides 264 and the lower wall 262 may cooperate to form at least a portion of the first leg 244, and the opposing sides 264 and the upper wall 260 may cooperate to form at least a portion of the second leg 246. A tubulate wall 280 at least partially defining the first leg 244 may include the upper aspect 252, the opposing sides 264, and the lower wall 262. The second leg 246 may include the lower aspect 250, the opposing sides 264, the upper wall 260, and a base wall 281. An interior of the second leg 246 formed by the lower aspect 250, the opposing sides 264, the upper wall 260, and the base wall 281 may define a cavity (not identified) such that the second leg 246 is hollow, as generally appreciated from FIG. 9. The cavity may define at least a portion of the manifold volume 130, and thus may be in fluid communication with the outlet opening 242. In certain implementations, the second leg 246 is at least substantially solid, or closed to a remainder of the manifold volume 130. In such an arrangement, the second leg 246 may not define a portion of the manifold volume 130. The base wall 281 may define a proximal end of the manifold 124. It is contemplated that, in certain implementations, the housing 128 may include a third leg, a fourth leg, a fifth leg, or more legs extending from the collar 168 and/or the body portion 210.

The housing 128 may include a rim 276 defining the outlet opening 242. The rim 276 may be disposed on the first leg 244, and more particularly at or near a proximal end of the first leg 244. In one convention, the rim 276 may be considered a proximally-directed surface at the proximal end of the first leg 244. In another convention, the rim 276 may be a three-dimensional structure including a depth extending from the proximal end of the first leg 244. For example, FIGS. 8 and 11 show a step 283 extending radially inward from a tubulate wall 280 at least partially defining the first leg 244 with the rim 276 extending proximally from the step 283. FIG. 12 includes a vertical plane perpendicular to the proximal-to-distal direction and extending through the rim 276, identified as (R), indicative of a proximal-to-distal location of the rim 276 to be further referenced. The rim 276 may include a width greater or larger than a height such that the outlet opening 242 is non-circular. The tubulate wall 280 may also include a width greater or larger than a height, and the dimensions of the rim 276 may be approximately equal to the dimensions of the tubulate wall 280 such that the outlet opening 242 is complementarily shaped to approximate a cross section of the first leg 244. Alternatively, the rim 276 may have a cross sectional area different than that of the first leg 244. The rim 276 may be configured to be coupled with a seal 282 to be described.

The manifold 124 includes at least one arm 284 extending outwardly from the housing 128. A pair of arms 284 are referenced throughout the present disclosure, but it is appreciated that a singular arm may be provided. FIGS. 8 and 11-13 show the arms 284 as elongate rib-like structures in the proximal-to-distal direction and including a width greater or larger than a thickness. In certain implementations, the arms 284 may not be elongate in the proximal-to-distal direction but rather, for example, a square- or cylindrical-shaped post extending outwardly from the housing 128. The arm(s) 284 may be integrally formed with the housing 128, formed separately and fixed directly to the housing 128, or coupled to the housing 128 through an intermediate structure.

The arms 284 may extend outwardly from at least one of the body portion 210 and the first leg 244. In other words, the arms 284 may extend away from the manifold volume 130. With particular reference to FIG. 11, at least a portion of the arms 284 (one shown) extend outwardly from the body portion 210, with a proximal end of the arms 284 optionally near the boundary (B) between the body portion 210 and the first leg 244. Alternatively, the proximal end of the arms 284 may not adjacent or near the boundary between the body portion 210 and the first leg 244. With the interface 258 between the body portion 210 and the first leg 244 being distally-sloping, it may be considered that a portion of the arms 284 extend outwardly from the body portion 210, and another portion of the arms 284 extend outwardly from the first leg 244. Further, the arms 284 may extend outwardly from the opposing sides 264 of the housing 128, and more particularly extend laterally outward from the opposing sides 264. As used herein, the term "lateral" or "laterally" may refer to a direction perpendicular to the proximal-to-distal direction, and/or a direction towards or away from the opposing sides 264 of the manifold 124. Alternatively, the arms 284 may extend from the housing 128 in other manners, and not necessarily in the outward direction. The arms 284 may be sized and shaped to movably be inserted through arm slots 278 at least partially defining the opening 118 of the receiver 116 (see FIGS. 29-31). A width of the arms 284 may be less than a width of the arm slots 278, and the arms 284 may be angled relative to an adjacent aspect of the housing 128 so as to be substantially horizontal when the manifold 124 is oriented for insertion into the opening of the receiver 116. The arms 284 may be of any suitable length, and it is understood that the arms 284 may extend from the body portion 210 and/or the first leg 244. It should be appreciated that not all configurations of the manifold 124 require use of the arm(s) 284, and manifold designs that do not include arms are contemplated.

The arms 284 each include a proximally-directed surface 286. The proximally-directed surface 286 is configured to engage a sled assembly 288 of the receiver 116 (see FIGS. 38 and 39) during insertion of the manifold 124 into the receiver 116 to facilitate moving the receiver 116, and components thereof, between operative positions to be described. The proximally-directed surfaces 286 may be positioned distal to the boundary (B) of FIG. 11, and hence in such a convention, the arms 284 are extending laterally outward from only the body portion 210. FIG. 12 includes a vertical plane perpendicular to the proximal-to-distal direction and extending through the proximally-directed surfaces 286, identified as (A), indicative of a proximal-to-distal location of the proximally-directed surfaces 286 of the arms 284. The proximally-directed surfaces 286 of the arms 284 may be positioned distal to the rim 276, and thus the rim 276 may be positioned proximal to the proximally-directed surfaces 286 (i.e., plane A is distal to plane R, and plane R is proximal to plane A).

The manifold 124 includes the catch 254 previously introduced with a pair of catches 254 to be described. It should be appreciated that a singular catch may be provided, and manifold designs that do not include the catch(es) are contemplated. The catches 254 may be defined by the housing 128, and more particularly by the trunk 134. The catches 254 may be disposed on the second leg 246, as best shown in FIGS. 8 and 10-12. The catches 254 may be positioned adjacent or within the portions of the opposing sides 264 defining the second leg 246, and/or the catches 254 may be laterally spaced apart from one another by the lower aspect 250 of the second leg 246. The catches 254 may be integrally formed with the housing 128, formed separately and fixed directly to the housing 128, or coupled to the housing 128 through an intermediate structure.

The rim 276 and at least one of the catches 254 may be spaced apart from one another by the void 248. More particularly, the rim 276 on the first leg 244 may be spaced apart from the catches 254 on the second leg 246 by the void 248. In other words, the rim 276 may be on a first or lower side of the void 248, and the catches 254 may be on a second or upper side of the void 248 opposite the first or upper side. Further, the rim 276 is positioned below the catches 254 when the manifold 124 is oriented for insertion into the opening 118 of the receiver 116, as best shown in FIGS. 11 and 12.

Figure 40:
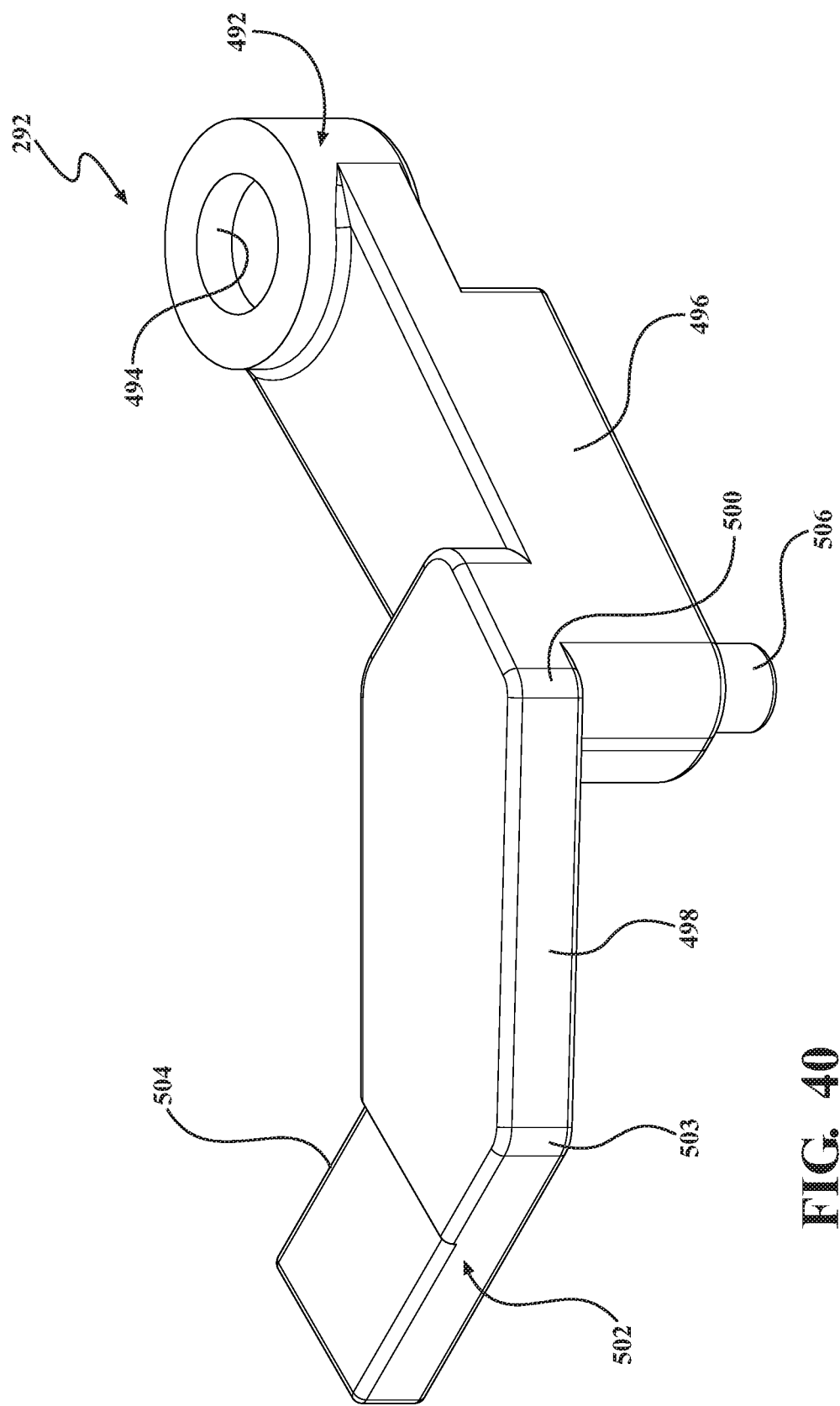
FIG. 40 is a perspective view of one of the claws.

Each of the catches 254 includes a distally-directed surface 290. The distally-directed surfaces 290 of the catches 254 are configured to be engaged by claws 292 of the sled assembly 288 of the receiver 116 (see FIG. 40) during insertion and removal of the manifold 124 into the receiver 116 to facilitate moving the receiver 116 between operative positions to be described. The distally-directed surfaces 290 may be positioned proximal to the boundary (B) of FIG. 11. FIG. 12 includes a vertical plane perpendicular to the proximal-to-distal direction and extending through the distally-directed surfaces 290, identified as (C), indicative of a proximal-to-distal location of catches 254. The distally-directed surfaces 290 of the catches 254 may be positioned proximal to the rim 276, and thus the rim 276 may be positioned distal to the distally-directed surfaces 290 (i.e., plane C is proximal to plane R, and plane R is distal to plane C). Further, the distally-directed surfaces 290 of the catches 254 may be positioned proximal to the proximally-directed surfaces 286 of the arms 284, and thus the proximally-directed surfaces 286 of the arms 284 may be positioned distal to the distally-directed surfaces 290 (i.e., plane C is proximal to plane A, and plane A is distal to plane C).

In certain implementations, the catch(es) 254 may be a hook-like structure including the distally-directed surface 290 along a bend of the hook-like structure, and further include opposing upper and lower aspects 293, 294 separated by a gap 296. The upper and lower aspects 293, 294 may generally be horizontally-oriented surfaces bounding the gap 296 from above and below, respectively, and generally defining a width of the gap 296. The width of the gap 296 may be at least equal to a thickness of the claws 292. In certain implementations, the catch(es) 254 may further include a laterally-directed surface 298 such that the catches 254 are shaped as a recess within the housing 128. The laterally-directed surfaces 298 may generally be vertically-oriented surfaces and further bounding the gap 296. Other constructions of the catches 254 are contemplated, namely any suitable structure disposed on the body portion 210 and/or the second leg 246 that includes the distally-directed surfaces 290 suitable to be engaged by claws 292 of the sled assembly 288. For example, each of the catches may be configured as a protrusion extending from the collar 168, the body portion 210, the first leg 244, and/or the second leg 246, with the protrusion having the distally-directed surface 290 positioned as described above. If more than one catch 254 is included, the catches 254 may vary in design from one another, including variance in shape and/or position. In other words, the catches 254 need not assume the aforementioned hook-like structure, but rather may be any suitable structure having the distally-directed surfaces 290.

The manifold 124 may include a spine 300 extending outwardly from the housing 128. FIGS. 8 and 11-13 show the spine 300 as an elongate structure in the proximal-to-distal direction and including a width greater or larger than a thickness. In certain implementations, the spine 300 may not be elongate in the proximal-to-distal direction but rather, for example, a square- or a cylindrical-shaped post extending outwardly from the housing 128. The spine 300 may be integrally formed with the housing 128, formed separately and fixed directly to the housing 128, or coupled to the housing 128 through an intermediate structure.

Figure 13:
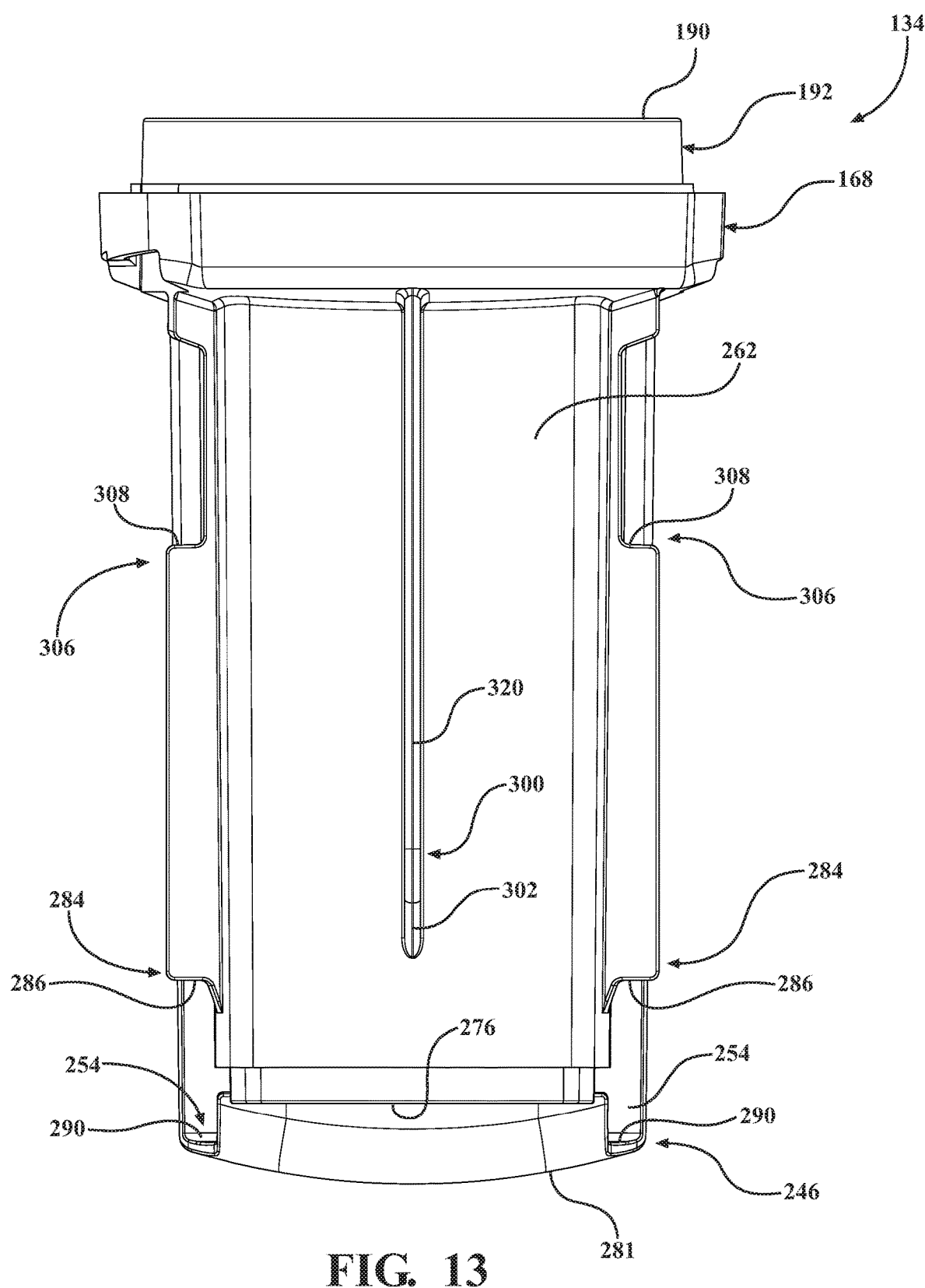
FIG. 13 is a bottom plan view of the trunk.
Figure 14:
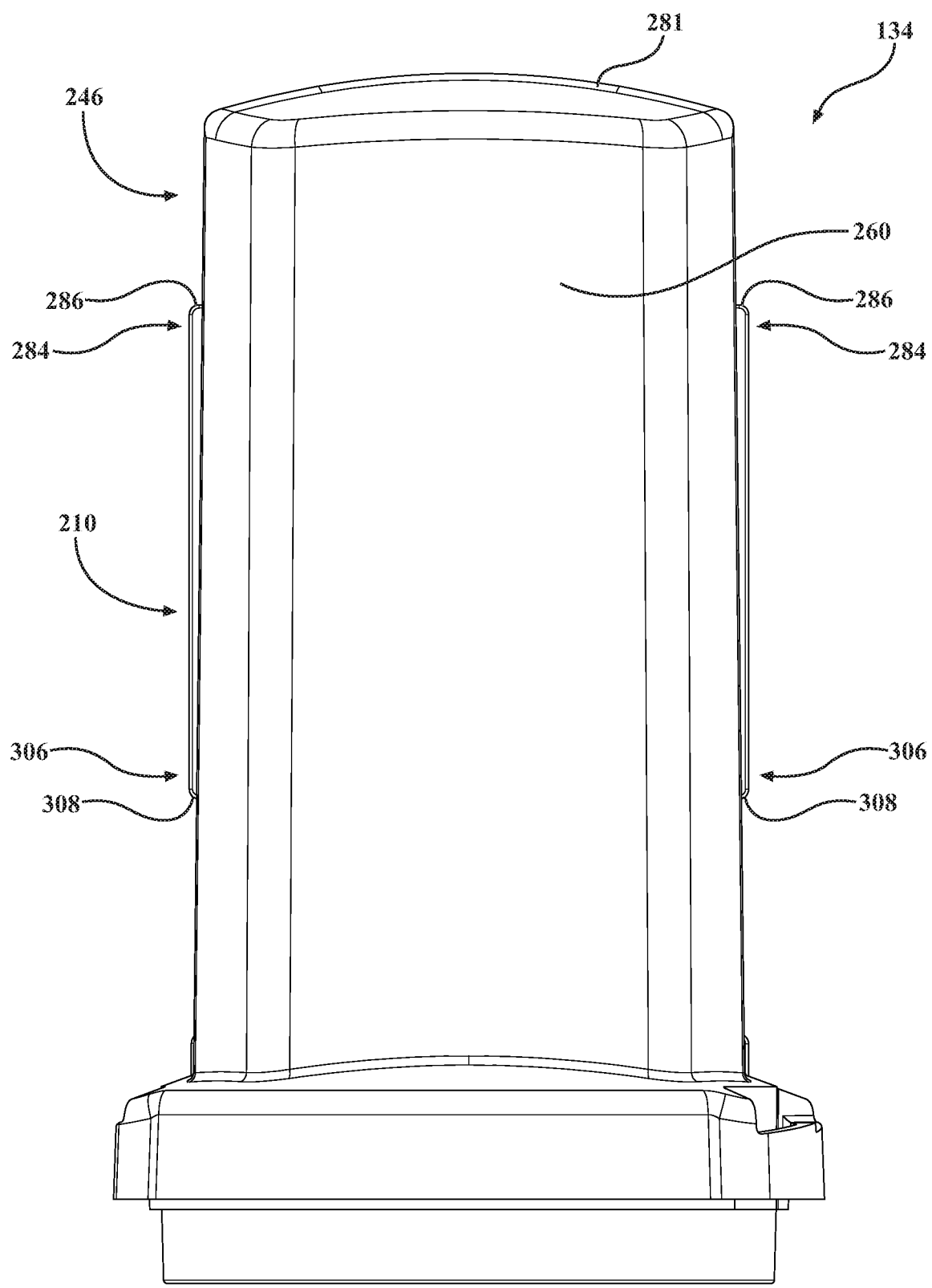
FIG. 14 is a top plan view of the trunk.

The spine 300 may extend outwardly from at least one of the body portion 210, the first leg 244, and/or the second leg 246. In other words, the spine 300 may extend away from the manifold volume 130. With particular reference to FIG. 11, the spine 300 extends outwardly from the housing 128 distal to the boundary (B) such that the spine 300 extends outwardly from the body portion 210. Further, the spine 300 may extend outwardly from the bottom wall 262 of the trunk 134, and more particularly extend downwardly from the bottom wall 262. Alternatively, the spine 300 may extend from the housing 128 in other manners, and not necessarily in the outward direction. A width of the spine 300 may be less than a width of the spine slot 277 (see FIGS. 29-31), and the spine 300 may be oriented substantially vertically when the manifold 124 is oriented for insertion into the opening of the receiver 116. The spine 300 may extend distally to a position adjacent the collar 168, as best shown in FIG. 13, or to a distal position spaced apart from the collar 168. In other words, various lengths of the spine 300 are contemplated. It should be appreciated that not all configurations of the manifold require use of the spine 300, and manifold designs that do not include a spine are contemplated.

The spine 300 includes a proximally-directed surface 302. FIG. 12 includes a vertical plane perpendicular to the proximal-to-distal direction and extending through a proximal end of the proximally-directed surface 302, identified as (S), indicative of a proximal-to-distal location of the proximally-directed surface 302 of the spine 300. The proximally-directed surface 302 of the spine 300 may be positioned distal to the rim 276, and thus the rim 276 may be positioned proximal to the proximally-directed surface 302 (i.e., plane S is distal to plane R, and plane R is proximal to plane S). Further, the proximally-directed surface 302 of the spine 300 may be positioned distal to the distally-directed surfaces 290 of the catches 254, and thus the distally-directed surfaces 290 of the catches 254 may be positioned proximal to the proximally-directed surface 302 (i.e., plane S is distal to plane C, and plane C is proximal to plane S).

Still further, the proximally-directed surface 302 of the spine 300 may be positioned distal to the proximally-directed surfaces 286 of the arms 284, and thus the proximally-directed surfaces 286 of the arms 284 may be positioned proximal to the proximally-directed surface 302 (i.e., plane S is distal to plane A, and plane A is proximal to plane S). In certain implementations, the proximally-directed surface 302 is inclined towards the lower wall 262 of the housing 128 in the proximal direction to define a proximal end of the spine 300. The incline may include a ramped surface, a curved surface, or a series of surfaces in a stepwise manner. Alternatively, the proximally-directed surface 302 may assume other shapes, for example, having a surface orthogonal to the trunk 134. The spine 300 is configured to engage a sled lock assembly 304 of the receiver 116 (see FIG. 39) during insertion and removal of the manifold 124 into the receiver 116 to facilitate moving the receiver 116, and components thereof, between the operative positions to be described.

The manifold 124 includes at least one lock element 306 extending outwardly from the housing 128. A pair of lock elements 306 are referenced throughout the present disclosure, but it is appreciated that a singular lock element may be provided, and manifold designs that do not include a lock element are contemplated. FIGS. 8 and 11-13 show each of the lock elements 306 as sharing the elongate structure as a respective one of the arms 284. In particular, the lock elements 306 each may include a distally-directed surface 308 at a distal end of the elongate structure opposite the proximally-directed surface 286 of the arms 284. The lock elements 306 may be at least substantially coplanar with the arms 284 in the proximal-to-distal direction. In certain implementations, the distally-directed surfaces 308 of the lock elements 306 may be disposed on a separate structure than the proximally-directed surfaces 286 of the arms 284. For example, a second elongate structure may be provided in the proximal-to-distal direction and including a width greater or larger than a thickness. In other words, a slot or void may separate the lock elements 306 from the arms 284. In certain implementations, the lock elements 306 may not be elongate in the proximal-to-distal direction but rather, for example, a square- or cylindrical-shaped post extending outwardly from the housing 128 to define the distally-directed surface 308 described above. The lock elements 306 may be integrally formed with the housing 128, formed separately and fixed directly to the housing 128, or coupled to the housing 128 through an intermediate structure.

The lock elements 306 may extend outwardly from at least one of the body portion 210 and the first leg 244. In other words, the lock elements 306 may extend away from the manifold volume 130. The lock elements 306 may be positioned distal to the boundary (B) of FIG. 11, and hence in the introduced convention the lock elements 306 extend laterally outward from only the body portion 210. The lock elements 306 may extend outwardly from the opposing sides 264 of the housing 128, and more particularly extend laterally outward from the opposing sides 264. Alternatively, the lock elements 306 may extend from the housing 128 in other manners, and not necessarily in the outward direction. The lock elements 306 may be sized and shaped to movably be inserted through the arm slots 278 at least partially defining the opening 118 of the receiver 116 (see FIGS. 29-31). A width of the lock elements 306 may be less than a width of the arm slots 278, and the lock elements 306 may be angled relative to an adjacent aspect of the housing 128 so as to be substantially horizontal when the manifold 124 is oriented for insertion into the opening of the receiver 116. Other constructions of the lock elements 306 are contemplated, for example, any suitable structure disposed on the body portion 210, the first leg 244, and/or the second leg 246 that includes the distally-directed surfaces 308. For example, a prong that is separate from the body portion 210 and/or the first and second legs 244, 246, and extending from the collar 168 may define the distally-directed surfaces 308.

The distally-directed surfaces 308 are configured to engage a locking assembly 310 of the receiver 116 (see FIGS. 43 and 44) after insertion of the manifold 124 into the receiver 116 to selectively prevent distal movement of the manifold 124 relative to the receiver 116. FIG. 12 includes a vertical plane perpendicular to the proximal-to-distal direction and extending through the distally-directed surfaces 308, identified as (L), indicative of a proximal-to-distal location of the lock elements 306. The distally-directed surfaces 308 of the lock elements 306 may be positioned distal to the rim 276, and thus the rim 276 may be positioned proximal to the distally-directed surfaces 308 (i.e., plane L is distal to plane R, and plane R is proximal to plane L). Further, the distally-directed surfaces 308 of the lock elements 306 may be positioned distal to the distally-directed surfaces 290 of the catches 254, and thus the distally-directed surfaces 290 of the catches 254 may be positioned proximal to the distally-directed surfaces 308 (i.e., plane L is distal to plane C, and plane C is proximal to plane L). Still further, the distally-directed surfaces 308 of the lock elements 306 may be positioned distal to the proximally-directed surfaces 286 of the arms 284, and thus the proximally-directed surfaces 286 of the arms 284 may be positioned proximal to the distally-directed surfaces 308 (i.e., plane L is distal to plane A, and plane A is proximal to plane L). Still yet further, the distally-directed surfaces 308 of the lock elements 306 may be positioned distal to the proximally-directed surface 302 of the spine 300, and thus the proximally-directed surface 302 of the spine 300 may be positioned proximal to the distally-directed surfaces 308 (i.e., plane L is distal to plane S, and plane S is proximal to plane L). The relative positioning in the proximal-to-distal direction of each of the rim 276, the proximally-directed surfaces 286 of the arms 284, the distally-directed surfaces 290 of the catches 254, the proximally-directed surface 302 of the spine 300, and/or the distally-directed surfaces 308 of the lock elements 306 are advantageously tuned to facilitate precise operative timing of complementary components of the receiver 116 as the manifold 124 is inserted within the receiver 116.

Referring again to FIG. 10, the shape and/or radial position of the outlet opening 242 is configured to, among other advantages, maximize volume flow of the waste material through the manifold 124 in view of gravity and the insertion orientation of the manifold 124 into the receiver 116. As previously mentioned, the rim 276 may include a width greater or larger than a height such that the outlet opening 242 is non-circular. In certain implementations, the outlet opening 242 may be oblong and defined by the rim 276 including an upper segment 312, a lower segment 314 opposite the upper segment 312, and opposing side segments 316 extending between the upper and lower segments 312, 314. The upper segment 312, the lower segment 314, and/or the opposing side segments 316 may be arcuate or planar in shape. Alternatively, the outlet opening 242 may have a shape that is at least substantially circular, for example, as described in commonly owned U.S. Pat. No. 7,615,037, issued Nov. 10, 2009, the entire contents of which is incorporated herein by reference.

Figure 10:
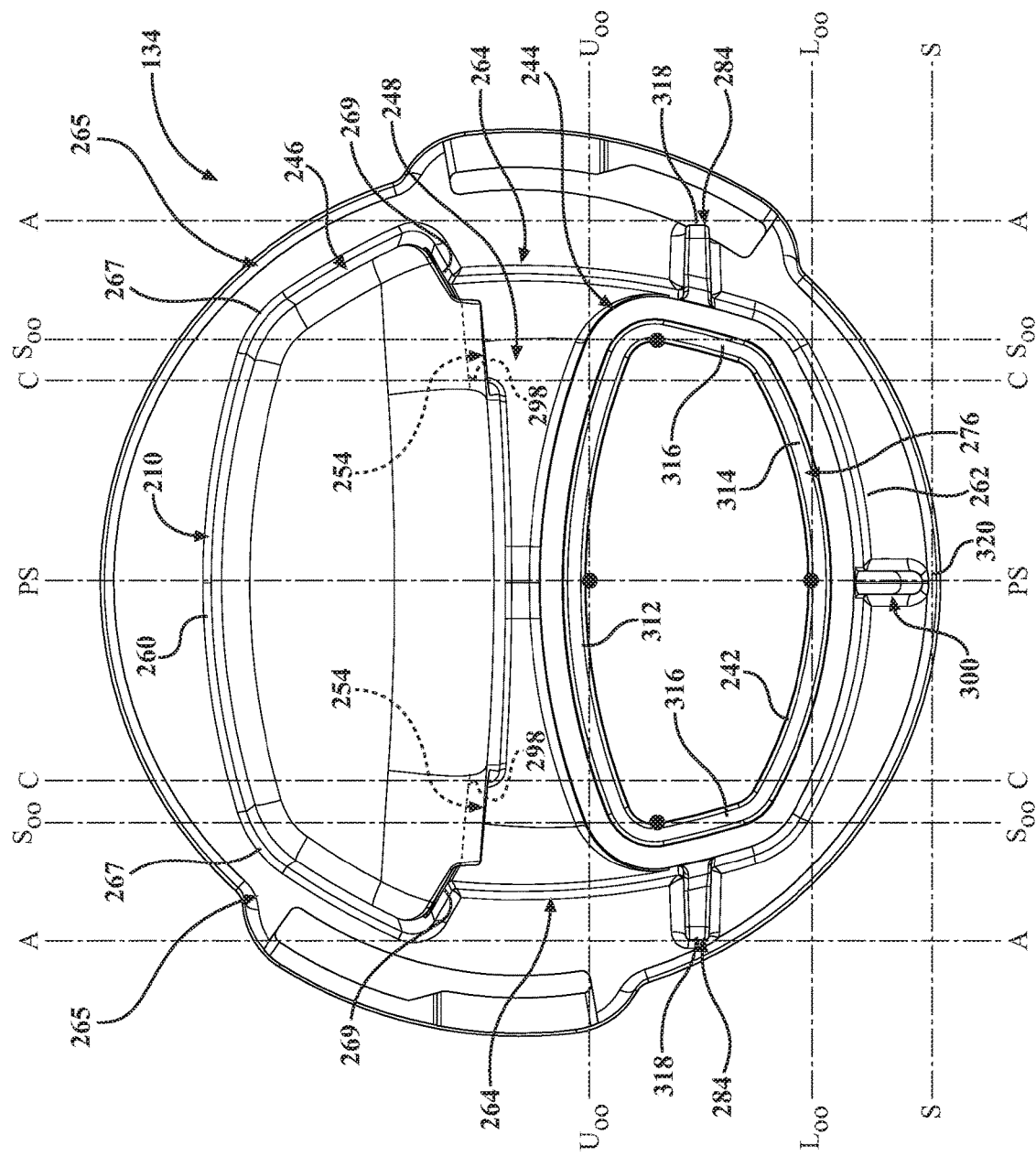
FIG. 10 is a rear elevation view of the trunk.

The width of the outlet opening 242 may be defined between opposing lateral-most points, and the height of the outlet opening 242 may be defined between an uppermost point opposite a lowermost point with the points annotated in FIG. 10. Vertical and horizontal planes in the proximal-to-distal direction and extending through each of the opposing lateral-most points, the uppermost point, and the lowermost point of the outlet opening 242, respectively, are labelled ($S_{oo}$), ($U_{oo}$), and ($L_{oo}$), respectively. The opposing side segments 316 may be oriented such that the opposing lateral-most points of the outlet opening 242 are at intersections between the upper segment 312 and each of the opposing side segments 316. The intersections between the lower segment 314 and each of the opposing side segments 316 may be spaced laterally inward relative to the intersections between the upper segment 312 and each of the opposing side segments 316, resulting in the shape at least similar to that shown in FIG. 10. With the upper and lower segments 312 being arcuate in shape and defining concave surfaces oriented towards one another, the uppermost point and the lowermost point may be at midpoints of the upper and lower segments 312, respectively. The vertical plane in the proximal-to-distal direction and bifurcating the outlet opening 242 may be a plane of symmetry (PS). The plane of symmetry (PS) may be equidistant from each of the opposing lateral-most points, and further may intersect the uppermost and lowermost points. The outlet opening 242 may be symmetrical about the plane of symmetry (PS), but not symmetrical about a horizontal plane in the proximal-to-distal direction and perpendicular to the plane of symmetry (PS).

FIG. 10 shows the outlet opening 242 positioned entirely within a lower half of the manifold 124 when the manifold 124 is oriented for insertion within the opening 118 of the receiver 116. During operation of the medical waste collection system 100, the waste material may descend towards the outlet opening 242 under the influence of gravity. Yet, relative to, for example, a circular opening positioned entirely within the lower half, the volume flow achievable through the outlet opening 242 at a given vacuum level may be sufficiently enhanced. Similarly, a circular opening capable of achieving the volume flow at a given vacuum level on par with the outlet opening 242 of the manifold 124 would otherwise require the circular opening assume nearly an entirety of the proximal end of the manifold. The outlet opening 242 of the manifold 124 addresses the aforementioned technical challenges.

In certain implementations previously described, the arms 284 extend outwardly from the trunk 134 of the housing 128, extend laterally outward from the opposing sides 264 of the housing 128, and/or extend from the housing 128 more generally, such as from the collar 168. With continued reference to FIG. 10, the arms 284 may be disposed on a horizontal plane in the proximal-to-distal direction that intersects the outlet opening 242. The arms 284 each may include a laterally-directed surface 318 that cooperate to define a width that is greater or larger than the width of the rim 276 and the outlet opening 242. FIG. 10 shows vertical planes in the proximal-to-distal direction and extending through the laterally-directed surfaces 318, identified as (A), indicative of lateral positions of the arms 284. In other words, in the illustrated configuration, the laterally-directed surfaces 318 of the arms 284 are positioned farther from the plane of symmetry (PS) than the respective lateral-most points of the outlet opening 242 (i.e., the planes (A) are at a greater distance from the plane of symmetry (PS) than the planes $S_{oo}$). Likewise, the lock elements 306 may extend outwardly from the trunk 134 of the housing 128, and/or extend laterally outward from the opposing sides 264 of the housing 128. The lock elements 306 may also be disposed on a horizontal plane in the proximal-to-distal direction that intersects the outlet opening 242. The lock elements 306 each may include a laterally-directed surface that cooperate to define a width that is greater or larger than the width of the rim 276 and the outlet opening 242. In the illustration of FIG. 10, the laterally-directed surfaces of the lock elements 306 may be coplanar with the laterally-directed surfaces 318 of the arms 284 (i.e., plane A). Alternatively, the lock elements 306 may extend outwardly from the trunk 134 of the housing 128, and/or extend laterally outward from the opposing sides 264 of the housing 128 to a greater or lesser extent than the arms 284.

The catches 254 (identified in phantom in FIG. 10) may be positioned in an upper half of the manifold 124 when the manifold 124 is oriented for insertion within the opening 118 of the receiver 116. The catches 254 may be positioned above the uppermost point of the outlet opening 242. Further, the laterally-directed surfaces 298 of the catches 254 may cooperate to define a width that is less than the width of the rim 276 and the outlet opening 242. FIG. 10 shows vertical planes in the proximal-to-distal direction and extending through the laterally-directed surfaces 298, identified as (C), indicative of lateral positions of the catches 254. In other words, the laterally-directed surfaces 298 of the catches 254 are positioned nearer to the plane of symmetry (PS) than the respective lateral-most points of the outlet opening 242 (i.e., the planes C are at a lesser distance from the plane of symmetry (PS) than the planes $S_{oo}$).

The spine 300 may be positioned in the lower half of the manifold 124 when the manifold 124 is oriented for insertion within the opening 118 of the receiver 116. The spine 300 may be positioned below the lowermost point of the outlet opening 242. Further, the spine 300 may be coplanar with the plane of symmetry (PS). FIG. 10 shows a horizontal plane in the proximal-to-distal direction and extending through a downwardly-directed surface 320 of the spine 300, identified as (S), indicative of a downward position of the spine 300. In other words, the downwardly-directed surface 320 of the spine 300 is positioned below the lowermost point of the outlet opening 242 (i.e., the plane S is below the plane $L_{oo}$).

The rim 276 is configured to be coupled with the seal 282 of the manifold 124. As to be described, the seal 282 may provide a face seal with a complementary sealing surface 322 of an inlet mechanism 324 including the suction inlet 266, and/or may provide a radial seal with a suction fitting 326 defining the suction inlet 266 (see FIGS. 33 and 60-64). The seal(s) may be considered an interface between the manifold 124 and the receiver 116 to preserve suction across the interface. In certain implementations, with the suction fitting 326 configured to extend through the seal 282 to within the manifold volume 130, the radial seal may reduce or prevent egress of the waste material around the suction fitting 326 penetrating the seal 282. The seal 282 may be of unitary or monolithic construction, or a multi-piece component. The seal 282 may be formed of a polymeric material with suitable hardness and resiliency, for example, a rubber or plastic having a Shore A Hardness within the range of approximately 20 to 90 durometers, and more particularly within the range of approximately 35 to 75 durometers, and even more particularly within the range of approximately 50 to 60 durometers.

Referring now to FIGS. 19-22, the seal 282 may include an outer seal rim 328 and an inner seal rim 330 spaced apart from the outer seal rim 328 to define a groove 332. The groove 332 is shaped complementary to the shape of the rim 276, and the groove 332 is sized to snugly receive the rim 276 such that the seal 282 and the trunk 134 are coupled to one another via interference engagement. Among other advantages, the interference engagement may permit external coupling of the seal 282 for ease during assembly of the manifold 124, and further may provide improved retention of the seal 282 on the rim 276 as the suction fitting 326 penetrates the seal 282 in a manner to be described. The aforementioned advantages may be realized in a single-piece seal of unitary or monolithic construction without additional components such as retention rings, clips, and the like. It is contemplated that solvent bonding, adhesive, or the like, may be utilized to supplement the interference engagement. The seal 282 may also be secured to the rim 276 without including the groove 332.

Figure 19:
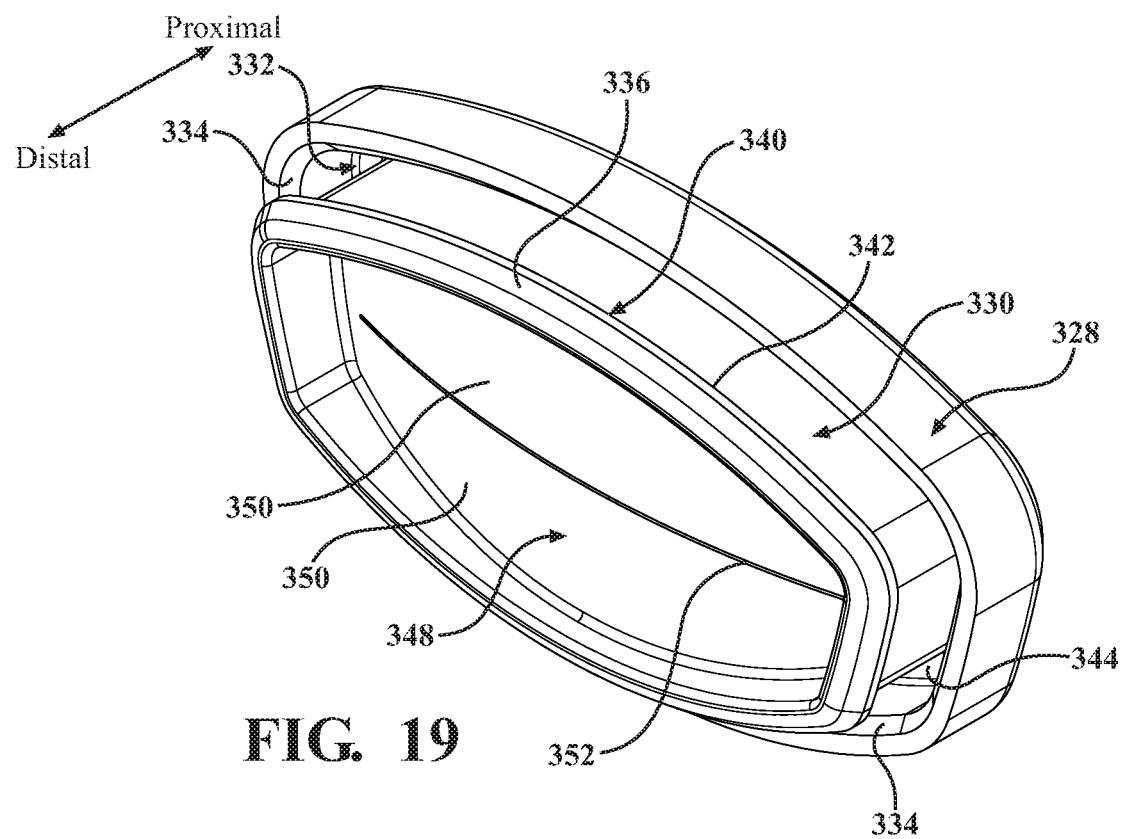
FIG. 19 is a front perspective view of the seal.

The outer seal rim 328 may include an inwardly tapered surface 334, and the inner seal rim 330 may include an outwardly tapered surface 336. Owing to the resiliency of the seal 282, the tapered surfaces 334, 336 cooperate to guide the rim 276 of the housing 128 into the groove 332 during assembly. As best shown in FIG. 19, a proximal end or edge of the inner seal rim 330 is positioned distal to a proximal end or edge of the outer seal rim 328. A depth of the outer seal rim 328 in the proximal-to-distal direction may be approximately equal to a depth of the first leg 244 proximal to the step 283 (see FIGS. 8 and 11). A thickness of the outer seal rim 328 may be approximately equal to a size of the step 283. With the seal 282 coupled to the rim 276, an outer surface of the outer seal rim 328 is substantially flush with the tubulate wall 280 at least partially defining the first leg 244. The arrangement may include an upper aspect of the outer seal rim 328 spaced apart from the second leg 246 and at least partially defining the void 248.

The inner seal rim 330 may include a lip 340 extending radially outwardly. The lip 340 may include the outwardly tapered surface 336 previously introduced, and a retention surface 342 that is proximally-directed. A depth of the inner seal rim 330 in the proximal-to-distal direction may be defined between a proximal face 344 at least partially defining the groove 332 and the retention surface 342 with the depth of the inner seal rim 330 approximately equal to a distance between the rim 276 and an interior step 338 within the first leg 244, as shown in FIG. 8. With the seal 282 coupled to the rim 276, the retention surface 342 may flex outwardly to be positioned distal and adjacent to the interior step 338 of the housing 128. The interference engagement between the retention surface 342 and the interior step 338 may facilitate the improved retention of the seal 282 on the rim 276, particularly as the suction fitting 326 is removed from within the seal 282 in a manner to be described.

Figure 20:
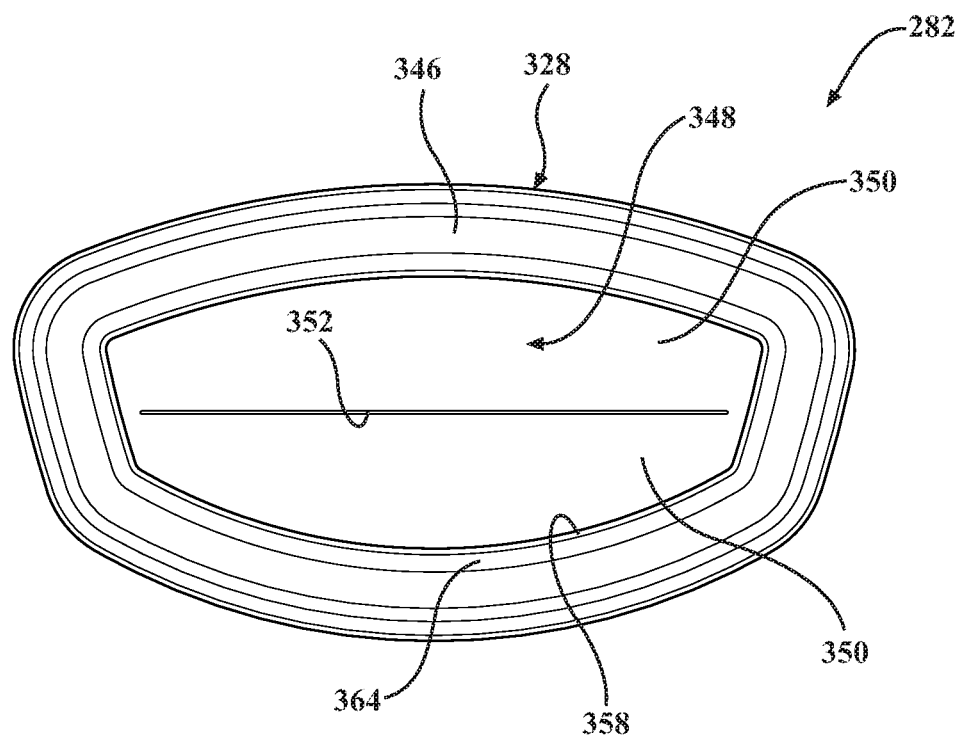
FIG. 20 is a rear elevation view of the seal.
Figure 21:
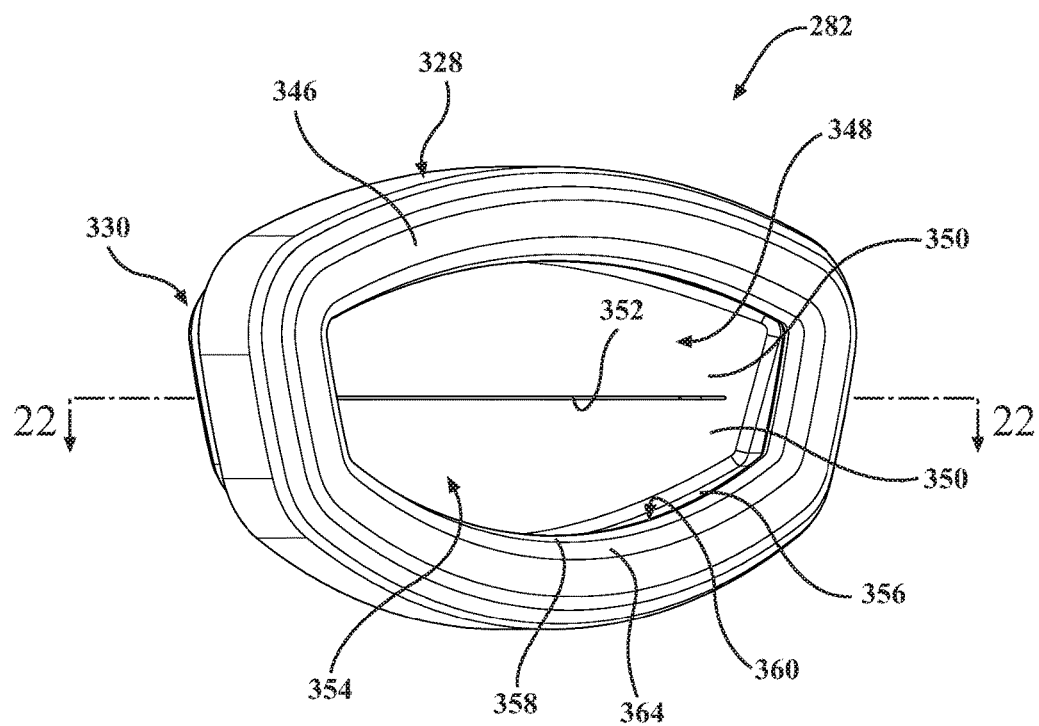
FIG. 21 is a rear perspective view of the seal.
Figure 22:
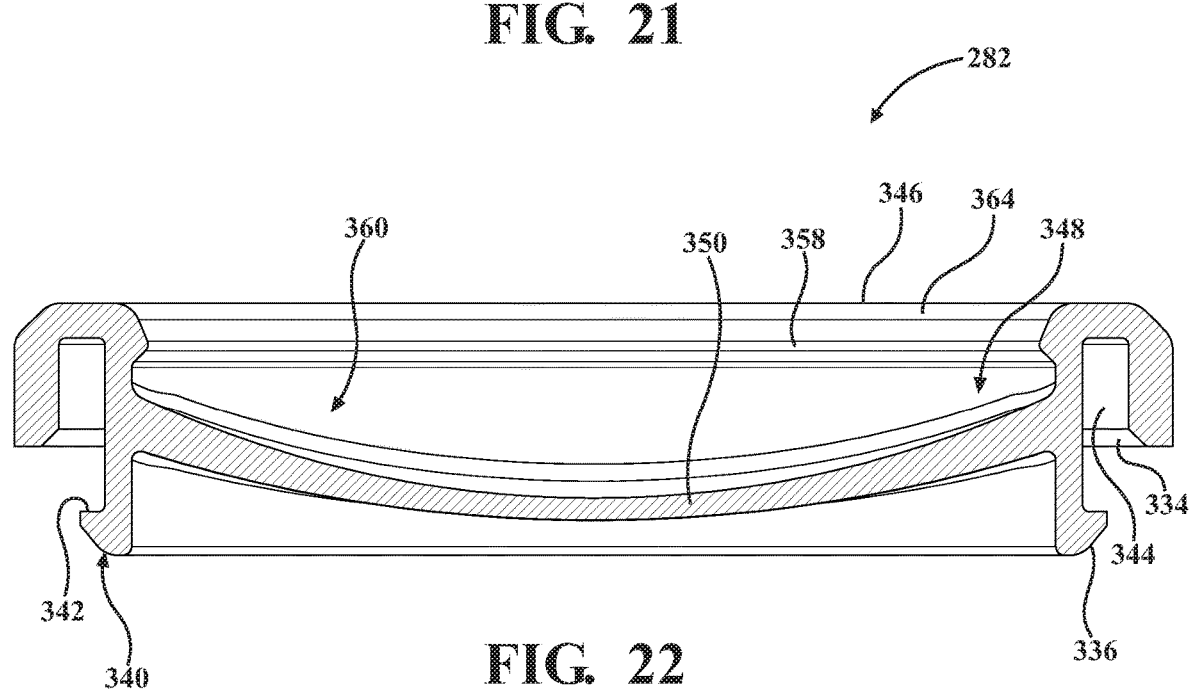
FIG. 22 is a sectional plan view of the seal of FIG. 21 taken along section lines 22-22.

The seal 282 may include a sealing surface 346. The sealing surface 346 may be disposed on the outer seal rim 328 and define a proximal-most surface of the seal 282. The sealing surface 346 is configured to provide the aforementioned face seal with the sealing surface 322 of the inlet mechanism 324 (see FIG. 62). The seal 282 may include a seal body 348 shaped to cover the outlet opening 242, and more particularly the non-circular outlet opening 242. The seal body 348 may include a width greater or larger than a height with the width and height generally corresponding to the width and height of the outlet opening 242, respectively. The seal body 348 may include at least one flap 350 configured to deflect with insertion of the suction fitting 326 through an aperture 352 at least partially defining the flap 350. FIGS. 19-21 show the aperture 352 as a slit extending laterally through the seal body 348 to define a pair of flaps 350. With insertion of the suction fitting 326 through the slit, the suction fitting 326 urges an upper one of the flaps 350 to deflect upwardly, and a lower one of the flaps 350 to deflect downwardly. Other suitable configurations are contemplated, for example, two slits in a cruciform arrangement to define four flaps that are generally triangular in shape.

With continued reference to FIGS. 20 and 21, the outer seal rim 328 may at least partially define a cavity 354. The cavity 354 may be at least partially defined by an inner surface 356 of the outer seal rim 328. The inner surface 356 may be positioned distal to the sealing surface 346 such that the seal body 348 may be considered recessed within the seal 282 relative to the sealing surface 346. The cavity 354 may be further defined by a radial sealing surface 358. The radial sealing surface 358 may be oriented in the proximal-to-distal direction and sized to slidably and snugly receive the suction fitting 326 of the inlet mechanism 324. The radial sealing surface 358 may be positioned radially inwardly from the inner surface 356 such that the cavity 354 may include an annular pocket 360. The flaps 350, the annular pocket 360, the radial sealing surface 358, and the sealing surface 346 individually or collectively may reduce or prevent the egress of the waste material from the manifold volume 130 when the suction fitting 326 is penetrating the seal body 348 and a vacuum is being drawn through the manifold volume 130 during operation of the medical waste collection system 100. Owing to the resiliency of the flaps 350, the flaps 350 generally conform to an outer surface 362 of the suction fitting 326 (see FIG. 62). The flaps 350 may reduce or prevent the egress of the waste material through the aperture 352. Should any waste material egress between the aperture 352 and the outer surface 362 of the suction fitting 326, the waste material, no longer influenced by the vacuum, may descend under the influence of gravity to be collected in the annular pocket 360. The radial sealing surface 358 may prevent the egress of the waste material collected in the annular pocket 360, or otherwise prevent egress of the waste material between the outer surface 362 of the suction fitting 326 and the seal 282. The sealing surface 346 may be in abutment with the sealing surface 322 of the inlet mechanism 324, and the aforementioned face seal may further prevent egress of the waste material. The seal 282 may advantageously provide at least four mechanisms by which the egress of the waste material is reduced or prevented.

The seal 282 may include a tapered surface 364 extending between the sealing surface 346 and the radial sealing surface 358. Owing to the relatively close tolerances between the radial sealing surface 358 and the outer surface 362 of the suction fitting 326, the tapered surface 364 may guide the suction fitting 326 into the cavity 354 during insertion of the manifold 124 into the receiver 116.

Figure 23:
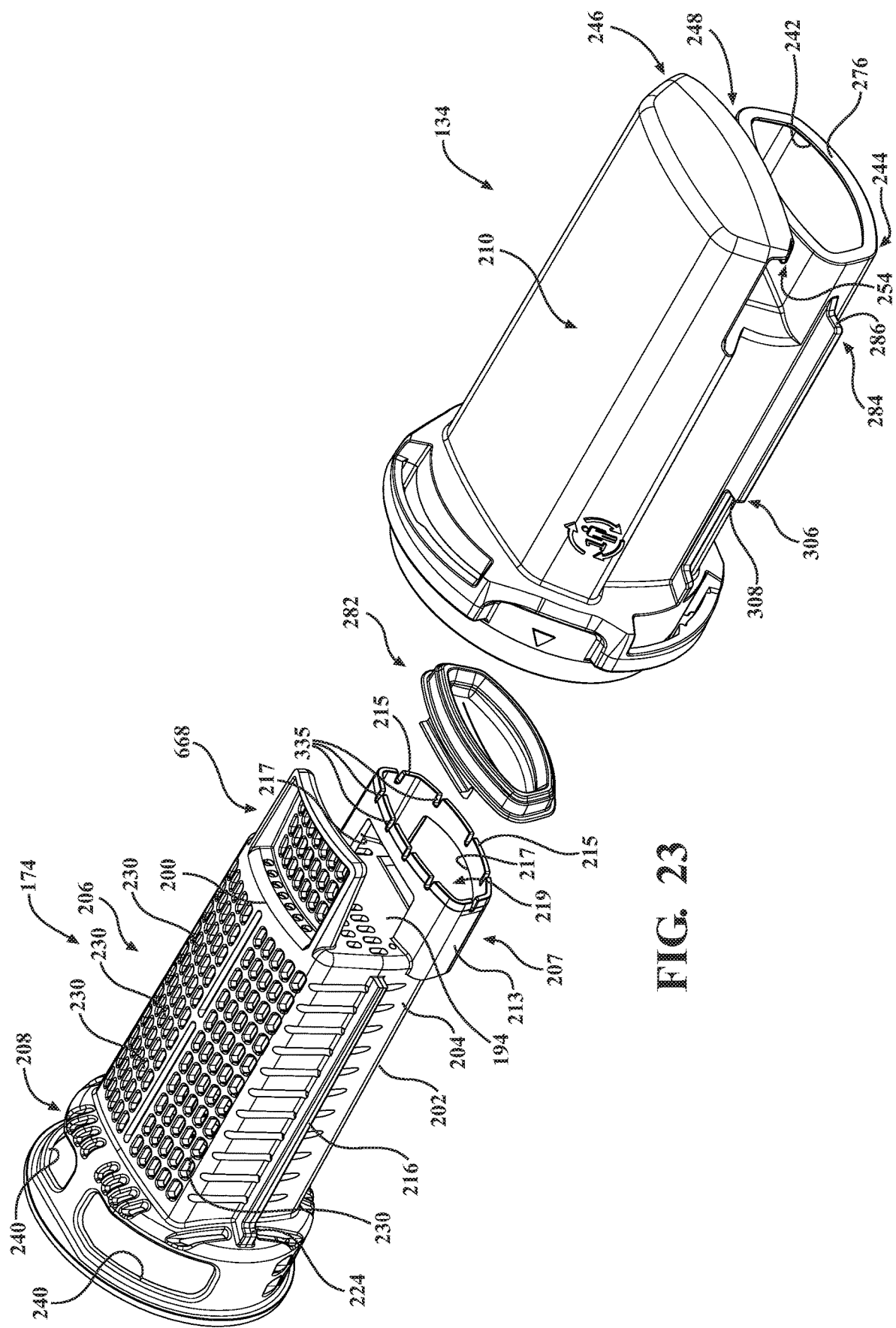
FIG. 23 is an exploded view of a portion of the manifold including the trunk, the filter element, and the seal.
Figure 26:
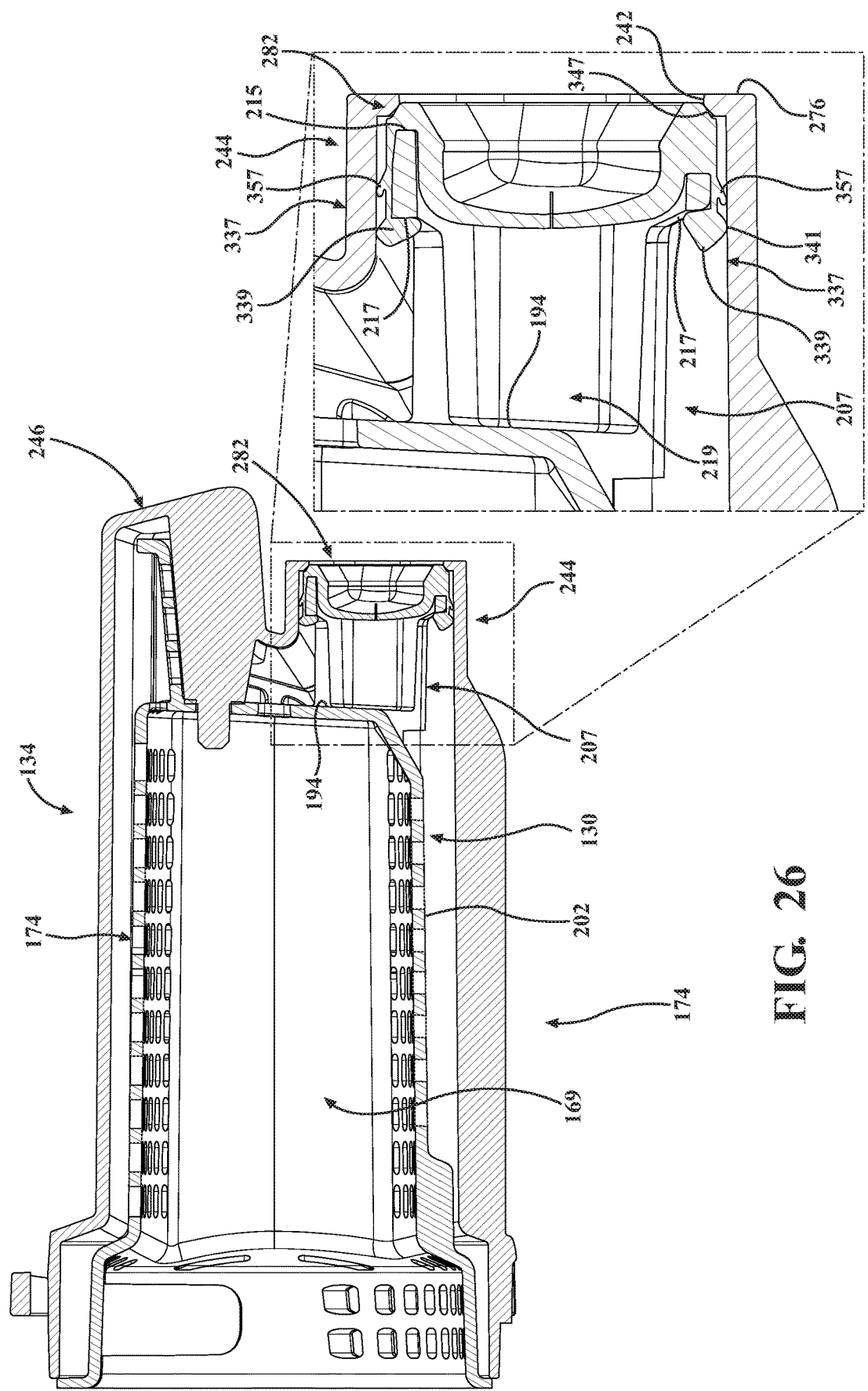
FIG. 26 is a sectional view of the portion of the manifold of FIG. 23 including a detailed view showing the filter element retaining the seal.

In certain implementations, the filter element 174 may be utilized to position the seal 282 to block egress of fluid through the outlet opening 242. Referring now to FIGS. 23 and 26, the filter element 174 may include a seal retaining element 207 coupled to the basket 206. In particular, the seal retaining element 207 may extend proximally from the base wall 194 of the basket 206. The seal retaining element 207 may include an upper aspect 209, a lower aspect 211, and opposing lateral aspects 213 cooperatively forming a structure that is tubular in shape and defining a void space 219. Each of the upper, lower, and opposing lateral aspects 209, 211, 213 terminate at a rim 215. The seal retaining element 207 may have an axial profile generally shaped to the first leg 244 of the housing 128. In other words, the seal retaining element 207 may be non-circular in shape and shaped in a manner generally corresponding to the shape of the outlet opening 242. The upper aspect 209 and/or the lower aspect 211 of the seal retaining element 207 may define an aperture 217 in communication with the void space 219. In implementations where an adjacent portion of the base wall 194 does not include the holes 230 or pores 232, as shown in FIG. 23, the suction path is established from the filter volume 169 through the upper wall 200, lower wall 202, and/or the base wall 194, through the apertures 217, and into the void space 219 to the outlet opening 242.

Figure 24:
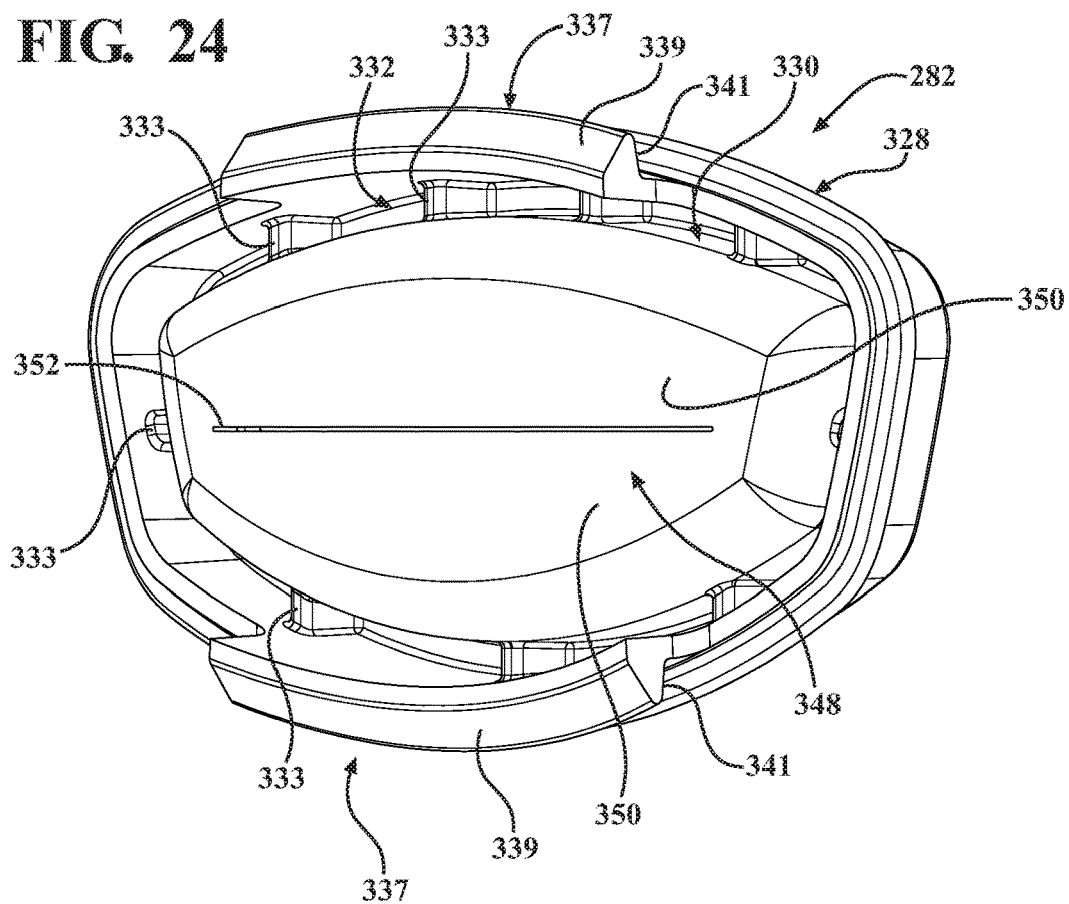
FIG. 24 is a rear perspective view of the seal.
Figure 25:
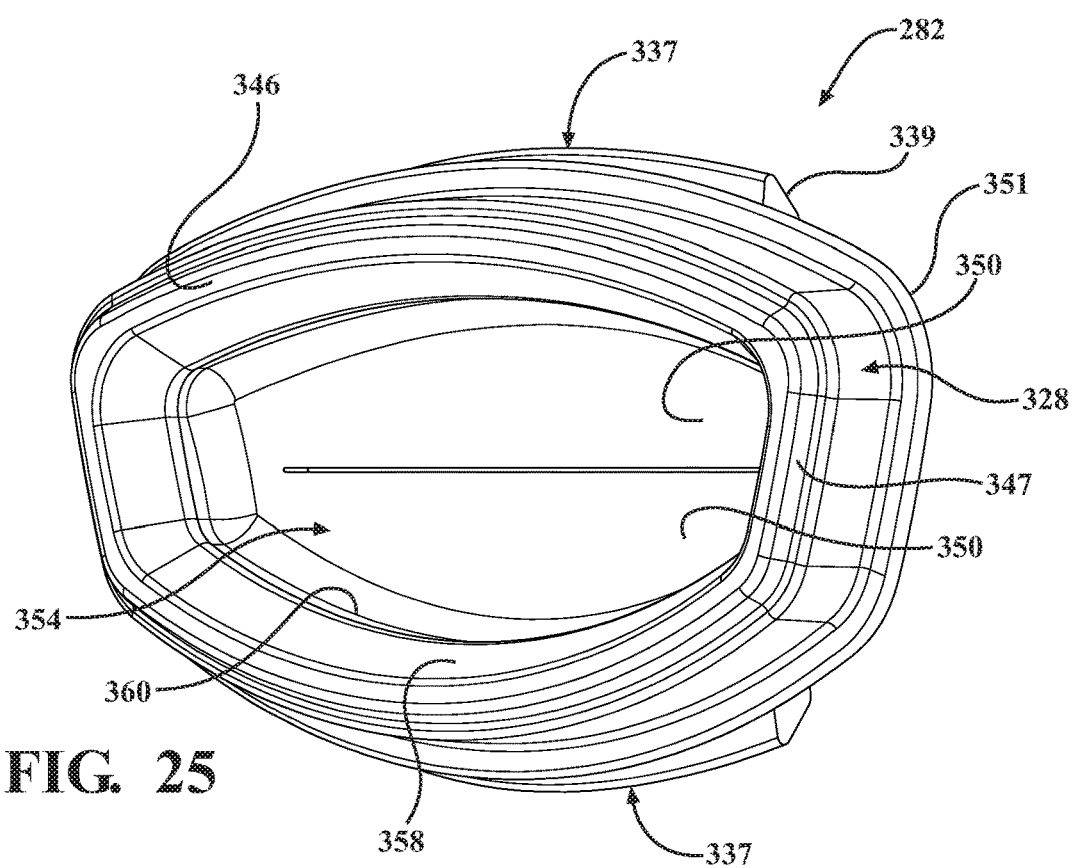
FIG. 25 is a front perspective view of the seal.

FIGS. 24 and 25 show an implementation of the seal 282 configured to be positioned by the seal retaining element 207. More particularly, the seal 282 may be coupled to the seal retaining element 207, for example, compressed between the rim 215 of the seal retaining element 207 and the rim 276 defining the outlet opening 242 in a manner to be described. The seal 282 includes the outer seal rim 328 and the inner seal rim 330 spaced apart from the outer seal rim 328 to define the groove 332. The groove 332 is shaped complementary to the shape of the rim 215 of the seal retaining element 207, and the groove 332 is sized to snugly receive the rim 215 such that the seal 282 and the trunk 134 are coupled to one another via interference engagement. The seal 282 may also be secured to the rim 215 without including the groove 332. The interference engagement between the rim 215 of the seal retaining element 207 and the groove 332 of the seal 282 may be further provided with ribs 333 configured to engage slots 335 defined by the seal retaining element 207. The slots 335 may be defined vertically and horizontally within the seal retaining element 207, and correspondingly the ribs 333 may be arranged vertically and horizontally within with groove 332 of the seal 282. It is appreciated that, alternatively, the ribs 333 and the slots 335 may be oriented in a complementary radial arrangement.

The seal 282 may include at least one tongue 337 configured to resiliently deflect when the seal 282 is positioned within the first leg 244 of the trunk 134. FIG. 24 shows two tongues 337 positioned opposite one another relative to the seal body 348. The tongues 337 may extend distally from the outer seal rim 328 and include a flange 339. The flanges 339 extends outwardly (i.e., away from the seal body 348) to a distance to interfere with the first leg 244. In other words, a thickness of the tongues 337, including the flanges 339, is greater than the gaps between the seal retaining element 207 and the inner surface of the first leg 244. Thus, as the seal 282 is assembled within the first leg 244, for example, from the distal direction, the flanges 339 urges the tongues 337 to resiliently flex inwardly. In one example, the flange 339 includes a taper surface and a locking surface 341 to form a generally triangular-shaped flange when viewed in side elevation. Other suitable shapes are contemplated, such as circular and square, so long as the flange 339 provides for inward flexing within the seal retaining element 207. In particular, FIG. 26 includes a detailed sectional view showing the seal retaining element 207 of the filter element 174 retaining the seal 282 in a position suitable to block egress of fluid through the outlet opening 242. During assembly, the seal 282 may be coupled to the seal retaining element 207 such that the rim 215 is disposed within the groove 332 with interference engagement. The tongues 337 may include a length in the proximal-to-distal direction greater than a distance between the rim 215 and the apertures 217 of the seal retaining element 207. In other words, when the seal 282 is coupled to the rim 215, the tongues 337 are axially positioned adjacent the apertures 217. As a result, as the filter element 174 and the seal 282 are inserted into the manifold volume 130, the flanges 339 engages the inner surface of the first leg 244 and causes the tongues 337 to resiliently flex inwardly within the apertures 217, as shown in the detailed view of FIG. 26. The locking surface 341 engages the inner surface of the first leg 244 such that the tongues 337 prevent axial movement of the seal 282 relative to the housing 128. In particular, with the axial position of the filter element 174 maintained by the head 132 being coupled to the trunk 134, the stack up of components maintains the axial position of the seal 282, particularly as the inlet mechanism 324 is inserted through the seal 282 with a distally-directed force on the seal 282. Further sealing may be provided with a lip 351 extending outwardly from the outer seal rim 328 by a distance greater than the gap between the seal retaining element 207 and the inner surface of the first leg 244. The lip 351 may be resiliently compressed and/or deflected to effectively seal the outlet opening 242 from the manifold volume 130 to block egress of fluid through the outlet opening 242.

The seal 282 may further include a stepped surface 347 is positioned in abutment with an interior surface of the rim 276. FIG. 26 shows the stepped surface 347 engaging the rim 276 in a manner to prevent proximal movement of the seal 282 relative to the rim 276. It is appreciated that the proximal-most surface of the seal 282 (e.g., the stepped surface 347) may be at least slightly recessed within the first leg 244, as shown in FIG. 26. In such an arrangement, there may not be a face seal provided, as the previously described sealing mechanisms prevent egress of fluid through the outlet opening 242. It is contemplated that, in certain implementations, the seal 282 may extend proximally beyond the rim 276 such that a sealing surface is provided (e.g., the sealing surface 346 of FIG. 21).

The basket 206 may be disposed in the body portion 210 and the seal retaining element 207 disposed in the first leg 244. The seal 282 may include the seal body 348 shaped to cover the outlet opening 242, and more particularly the non-circular outlet opening 242. The seal body 348 may include at least one flap 350 configured to deflect with insertion of the suction fitting 326 through the aperture 352 at least partially defining the flaps 350. With insertion of the suction fitting 326 through the slit, the suction fitting 326 urges an upper one of the flaps 350 to deflect upwardly, and a lower one of the flaps 350 to deflect downwardly. The outer seal rim 328 may at least partially define the cavity 354. The cavity 354 may be further defined by a radial sealing surface 358. The radial sealing surface 358 may be oriented in the proximal-to-distal direction and sized to slidably and snugly receive the suction fitting 326 of the inlet mechanism 324.

Figure 27:
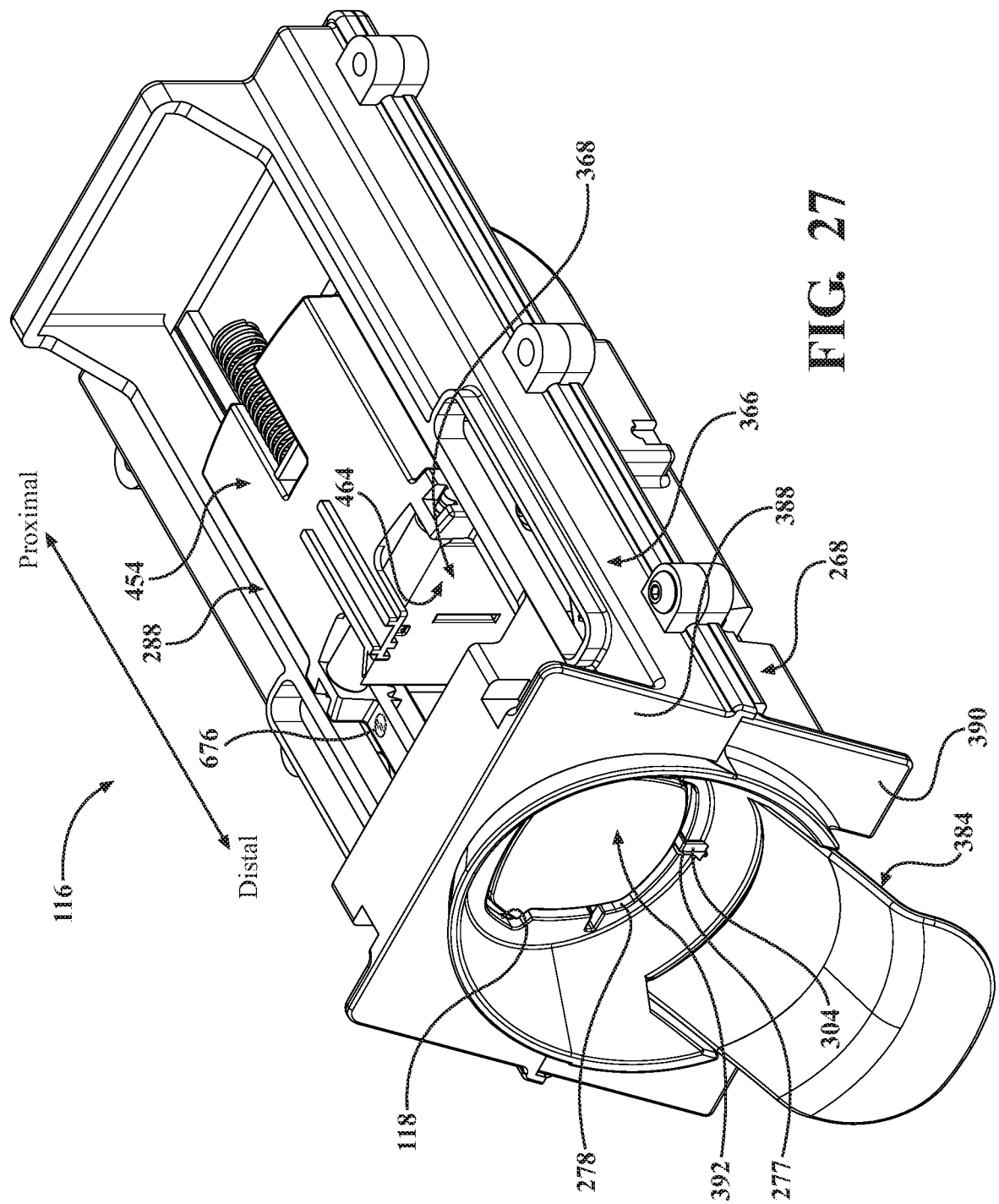
FIG. 27 is a perspective view of the receiver.
Figure 29:
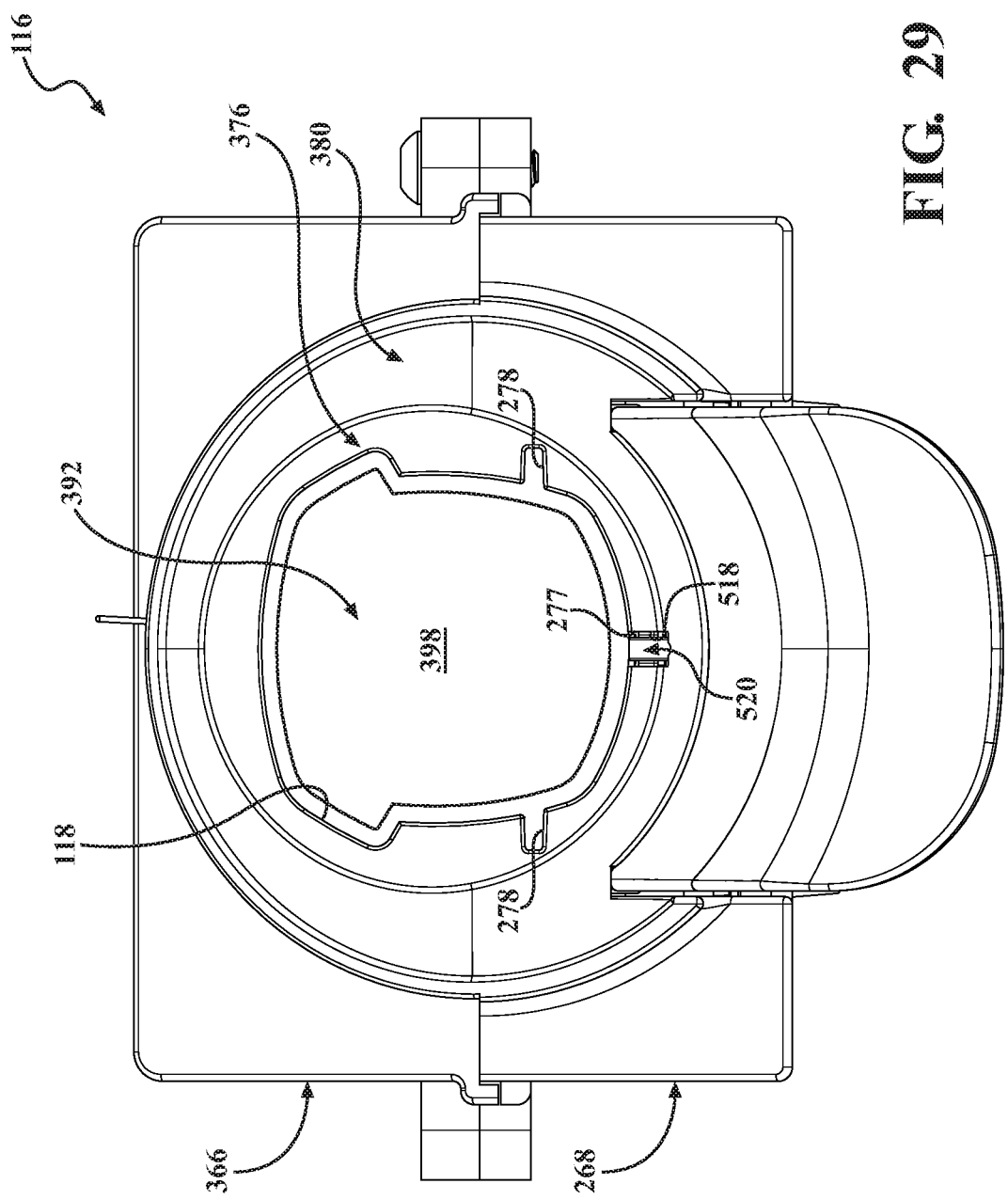
FIG. 29 is a front elevation view of the receiver.

Referring now to FIGS. 27-29, the receiver 116 may include the lower housing 268 previously introduced, and an upper housing 366 coupled to the lower housing 268. The lower and upper housings 268, 366 cooperate to define a receiver volume 368 in fluid communication with the opening 118. The receiver volume 368 is sized to removably receive at least a portion of the manifold 124. The lower housing 268 may include a base 370, opposing sides 372 extending upwardly from the base 370, and a rear wall 374 extending upwardly from the base 370 and extending between the opposing sides 372. The lower housing 268 may further define the opening 118. A crown 376 opposite the rear wall 374 may be coupled to the opposing sides 372 and/or the base 370 opposite the rear wall 374 to collectively define a cavity 378 that is box-shaped. The crown 376 defines the opening 118 that is in fluid communication with the cavity 378, and the cavity 378 may be considered a portion of the receiver volume 368. The crown 376 may include a brim 380 flaring radially outwardly in the distal direction. The brim 380 may be positioned external the medical waste collection system 100 so as to be visible to the user. The brim 380 may be shaped at least similar to a frustum of a cone and configured to guide the proximal end of the manifold 124 towards the opening 118 as the manifold 124 is readied to be inserted into the receiver 116. The brim 380 may define a recess 382 shaped to accommodate at least a portion of a tongue 384 of the locking assembly 310 to be described.

Figure 45:
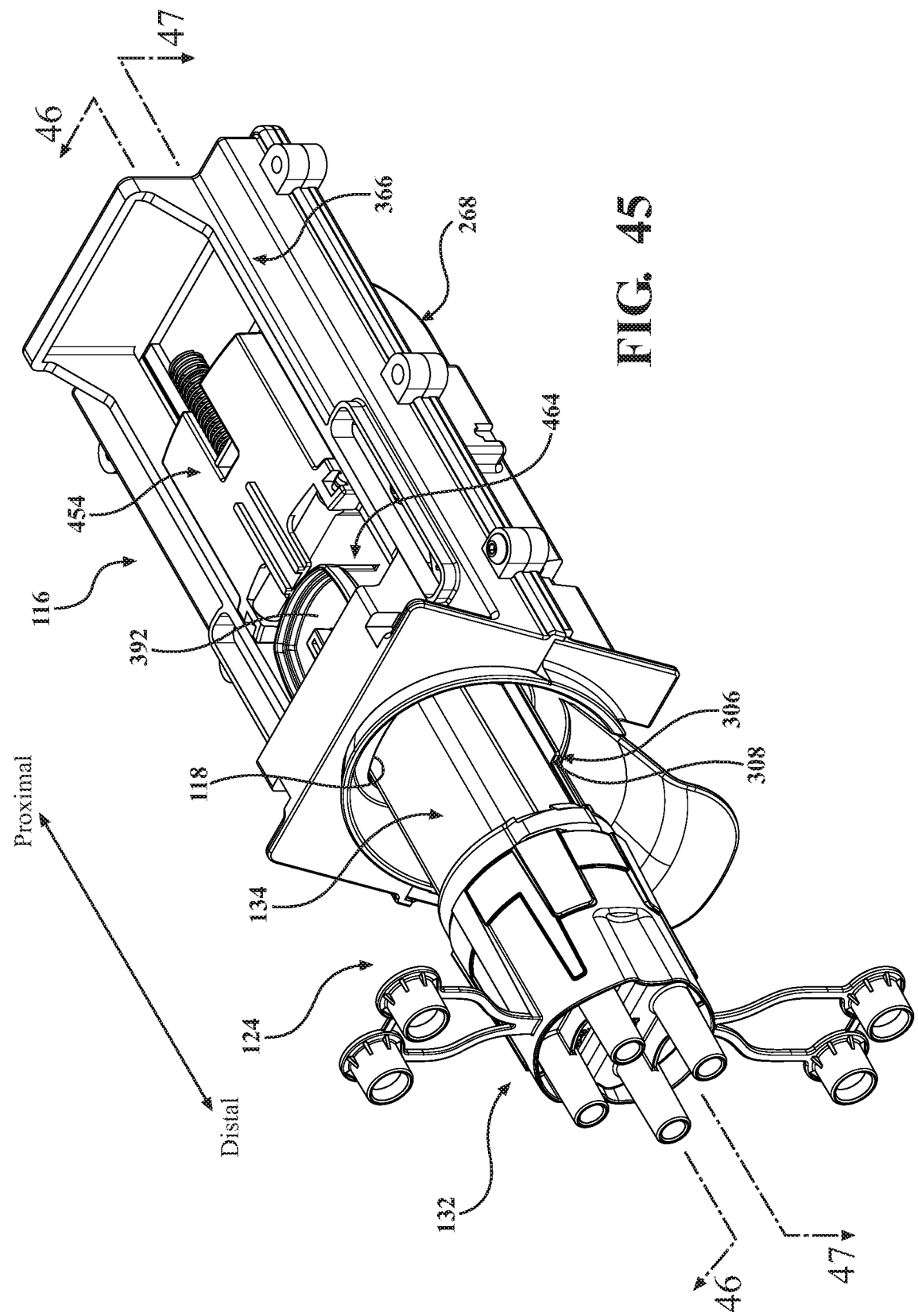
FIG. 45 is a perspective view of the manifold and the receiver in a first operative position.

With continued reference to FIG. 27, the upper housing 366 may include a faceplate 388 defining a semicircular cutout contoured to an upper portion of the brim 380. With the upper housing 366 coupled to the lower housing 268, the faceplate 388 of the upper housing 366 and a faceplate 390 of the lower housing 268 are in a planar arrangement so as to be flush with one another. The faceplates 388, 390 may be arranged at an angle relative to vertical, for example, oriented proximally in the proximal direction, so as to be contoured to a complementary exterior surface of the medical waste collection system 100. Alternatively, the faceplates 388, 390 may be vertical or in any other suitable orientation. A first barrier 392 may be coupled to the upper housing 366 and configured to selectively cover at least most of the opening 118 when the manifold 124 is in the decoupled configuration. Alternatively, the first barrier 392 may be pivotably coupled to another suitable structure of the receiver 116, for example, the lower housing 268. Referring to FIGS. 27 and 28, the first barrier 392 may be pivotably coupled to the upper housing 366 with a pin 394 extending through an upper coupler 400 of the first barrier 392, and extending laterally between opposing recesses within an underside of the upper housing 366. A biasing element 396, for example, a torsion spring, may be coupled to the first barrier 392 and the upper housing 366 with the biasing element 396 configured to urge the first barrier 392 to a closed configuration in which a front surface 398 of the first barrier 392 is substantially flush with the crown 376 defining the opening 118. A front surface 402 of the upper coupler 400 may be positioned proximal to the front surface 398 of the first barrier 392 such that, in the closed configuration, the front surface 402 abuts an inner surface of the crown 376 with the front surface 398 of the first barrier 392 substantially flush with an outer surface of the crown 376. The first barrier 392 is configured to move from the closed configuration to an open configuration in which the first barrier 392 is pivoted about the pin 394 against the biasing element 396. For example, during insertion of the manifold 124 into the receiver 116, the base wall 281 of the manifold 124 contacts and urges the front surface 398 in a proximal direction to impart pivoting of the first barrier 392 about the pin 394 (see FIGS. 45-47). With the manifold 124 at least partially inserted into the receiver 116, the first barrier 392 may be disposed adjacent the upper wall 200 of the trunk 134. It is readily appreciated from FIG. 29 that a slight gap may exist between the first barrier 392 and the opening 118, and thus the first barrier 392 may not be configured to meaningfully prevent egress of the waste material. The first barrier 392 may provide a visual obstruction to the manifold volume 130, which may include residual amounts of the waste material from a previous medical procedure. The first barrier 392 may or may not be locked in the closed configuration prior to insertion of the manifold 124 into the receiver 116.

The receiver 116 may define a receiver outlet 404. The receiver outlet 404 may be defined within the base 370 of the lower housing 268. The receiver outlet 404 may be in fluid communication with a respective one of the waste containers 106, 108 to which the receiver 116 is coupled. In a manner to be described in greater detail, the inlet mechanism 324 previously introduced may prevent fluid communication between the receiver outlet 404 and the receiver volume 368 until the manifold 124 is in the fully inserted operative position, after which the receiver outlet 404 is in fluid communication with the manifold volume 130 of the manifold 124 (via the inlet mechanism 324).

FIGS. 33-36 show the inlet mechanism 324 including the suction fitting 326 defining the suction inlet 266. The inlet mechanism 324 may include a housing 406 defining a passageway 408 between the suction inlet 266 and a suction outlet 410 defined within a base 412 of the inlet mechanism 324. The suction fitting 326 extends distally from the housing 406 adjacent to the sealing surface 322. The passageway 408 may include a first portion extending through the suction fitting 326 and at least a portion the housing 406, and a second portion extending from the first portion to the suction outlet 410. The first and second portions of the passageway 408 may be arranged at least substantially perpendicular to one another, in particular with the first portion arranged in the proximal-to-distal direction and the second portion arranged in the upper-to-lower direction. The inlet mechanism 324 is movably disposed within the cavity 378 of the lower housing 268, and movement of the inlet mechanism 324 selectively provides or prevents fluid communication between the suction outlet 410 and the receiver outlet 404.

In certain implementations, the suction fitting 326 is configured to penetrate the seal 282 to be at least partially positioned within the first leg 244 of the manifold 124. The suction fitting 326 may include the outer surface 362 tapering radially outward in the proximal direction away from the suction inlet 266. The outward taper may facilitate improved sealing between the suction inlet 266 and the seal 282, and more particularly, between outer surface 362 and the flaps 350 and the radial sealing surface 358. With the suction fitting 326 penetrating the seal 282, fluid communication is provided between the manifold volume 130 and the suction outlet 410.

The inlet mechanism 324 includes a first support element 414 and/or a second support element 416 each configured to facilitate positioning the manifold 124 within the receiver 116 in the fully inserted operative position, and/or support the manifold 124 in the fully inserted operative position. The first support element 414 may be coupled to the housing 406 and extend distally from the housing 406. The first support element 414 may include a lower surface 418 opposite an upper surface 420. With concurrent reference to FIGS. 10 and 11, the lower surface 418 may be arcuate in shape and contoured to the upper aspect 252 of the first leg 244. Further, the lower surface 418 may be spaced apart from the outer surface 362 of the suction fitting 326 by a distance at least equal to a thickness of the upper aspect 252 of the tubulate wall 280 at least partially defining the first leg 244. Additionally or alternatively, the lower surface 418 may be spaced apart from the outer surface 362 of the suction fitting 326 by a distance at least equal to a thickness of the outer seal rim 328 of the seal 282. A thickness of the first support element 414 defined between the lower and upper surfaces 418, 420 may be less than a thickness of the void 248 defined between the first and second legs 244, 246, and more particularly the distance between the upper aspect 252 of the first leg 244 and the lower aspect 250 of the second leg 246. Still further, a depth of the first support element 414 may be defined between a distal edge 422 and the sealing surface 322, and the depth may be less than or equal to a depth of the void 248 defined between the length of the upper and lower aspects 250, 252 bounding the void 248 from above and below, respectively. Still yet further, the distal edge 422 of the first support element 414 may be arcuate in shape in the proximal-to-distal direction and contoured to the distal aspect 256 extending between the first and second legs 244, 246 and at least partially defining the void 248. When the manifold 124 is inserted into the receiver 116 in the fully inserted operative positive, the above arrangement results in the first support element 414 being seated or nestled within the void 248 with the seal 282 in engagement with at least one of the sealing surfaces 322, 362 of the inlet mechanism 324. In other words, the first support element 414 facilitates ensuring that the manifold 124 is inserted to a proper insertion depth within the receiver 116 in the fully inserted operative position. The first support element 414 may further support the manifold 124 to minimize movement of the manifold 124 relative to the receiver 116 when in the fully inserted operative position.

The second support element 416 may be coupled to the housing 406 and extend distally from the housing 406. The second support element 416 may be positioned opposite the first support element 414 relative to the suction fitting 326. The second support element 416 may include a lower surface 424 opposite an upper surface 426. At least the upper surface 426 may be arcuate in shape and contoured to the first leg 244. The upper surface 426 may be spaced apart from the outer surface 362 of the suction fitting 326 by a distance at least equal to a thickness of a lower aspect of the tubulate wall 280 at least partially defining the first leg 244. Additionally or alternatively, the upper surface 426 may be spaced apart from the outer surface 362 of the suction fitting 326 by a distance at least equal to a thickness of the outer seal rim 328 of the seal 282. Further, a thickness of the second support element 416 defined between the lower and upper surfaces 424, 426 may be less than a thickness of the spine 300, and more particularly a distance between the lower aspect of the tubulate wall 280 and the downwardly-directed surface 320 of the spine 300 (see FIG. 11). When the manifold 124 is inserted into the receiver 116 in the fully inserted operative position, the above arrangement results in the second support element 416 being adjacent to the lower aspect of the first leg 244 and positioned in the proximal-to-distal direction between the proximally-directed surface 302 of the spine 300 and the rim 276. The second support element 416 may cooperate with the first support element 414 to facilitate ensuring that the manifold 124 is inserted to a proper insertion depth within the receiver 116 in the fully inserted operative position. The second support element 416 may further support the manifold 124 to minimize movement of the manifold 124 relative to the receiver 116 when in the fully inserted operative position.

Figure 30:
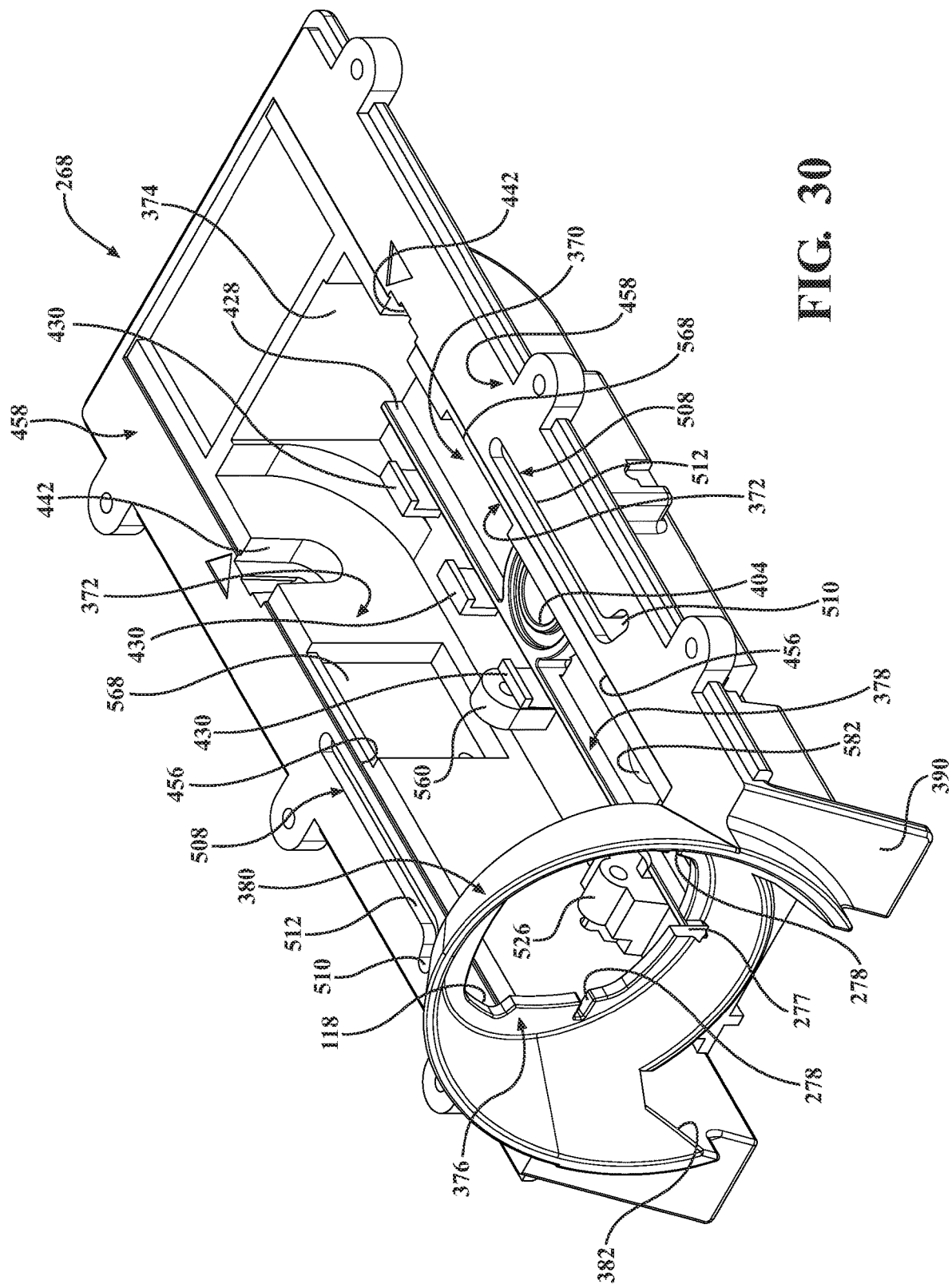
FIG. 30 is a perspective view of a lower housing of the receiver.
Figure 32:
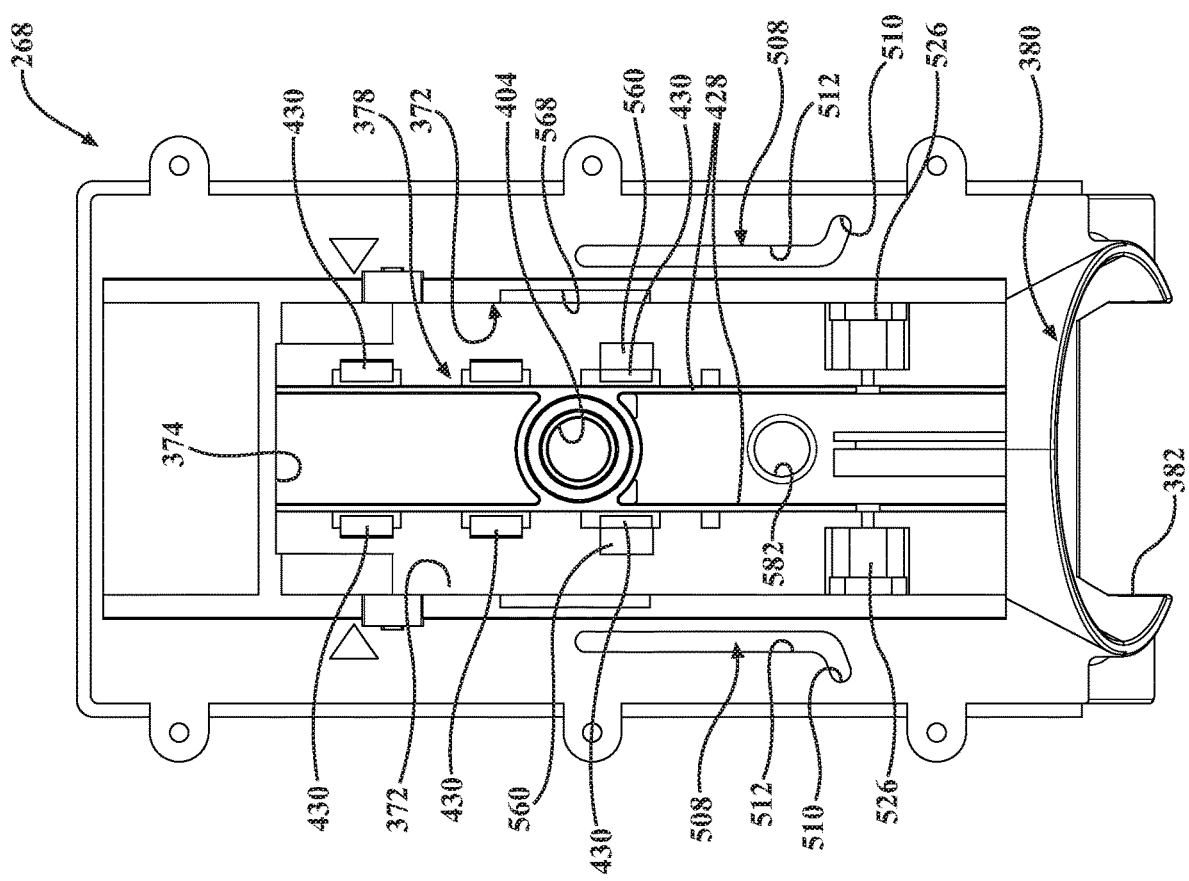
FIG. 32 is a top plan view of the lower housing.

As mentioned, the inlet mechanism 324 is movably disposed within the cavity 378 of the lower housing 268. With further reference to FIGS. 28, 30 and 32, the lower housing 268 includes railings 428 extending upwardly from the base 370. The railings 428 may extend between the rear wall 374 and the crown 376. The railings 428 may include a pair of railings 428 oriented parallel to one another and oriented in the proximal-to-distal direction. The receiver outlet 404 may be defined within the base 370 between the railings 428. The lower housing 268 may include at least one retention element 430 positioned near the railings 428. The retention element(s) 430 may include pairs of L-shaped tabs extending upwardly from the base 370 adjacent to the railings 428. The railings 428 and the retention elements 430 may cooperate to couple the inlet mechanism 324 to the lower housing 268 in a manner that permits slidable movement of the inlet mechanism 324 relative to the lower housing 268 in the proximal-to-distal direction. The base 412 of the inlet mechanism 324 includes a base plate 432, and at least one foot 434 coupled to opposing edges of the base plate 432. The feet 434 may extend along the opposing edge of the base plate 432 in the proximal-to-distal direction. The feet 434 extend downwardly from the base plate 432 by a distance equal to or less than a distance by which the railings 428 extend upwardly from the base 370 of the lower housing 268. Further, the feet 434 may be spaced apart from one another by a distance at least equal to a distance between the railings 428. The base plate 432 may be supported on the railings 428 with the feet 434 positioned adjacent the railings 428 in a gap defined between the railings 428 and the retention elements 430. The retention elements 430 may include a height at least equal to a thickness of the feet 434 such that, when the base plate 432 may be supported on the railings 428, an inwardly extending flange of the retention elements 430 extends over at least a portion of the feet 434. The retention elements 430 may prevent movement of the inlet mechanism 324 relative to the lower housing 268 in all degrees of freedom other than translation in the proximal-to-distal direction.

Figure 33:
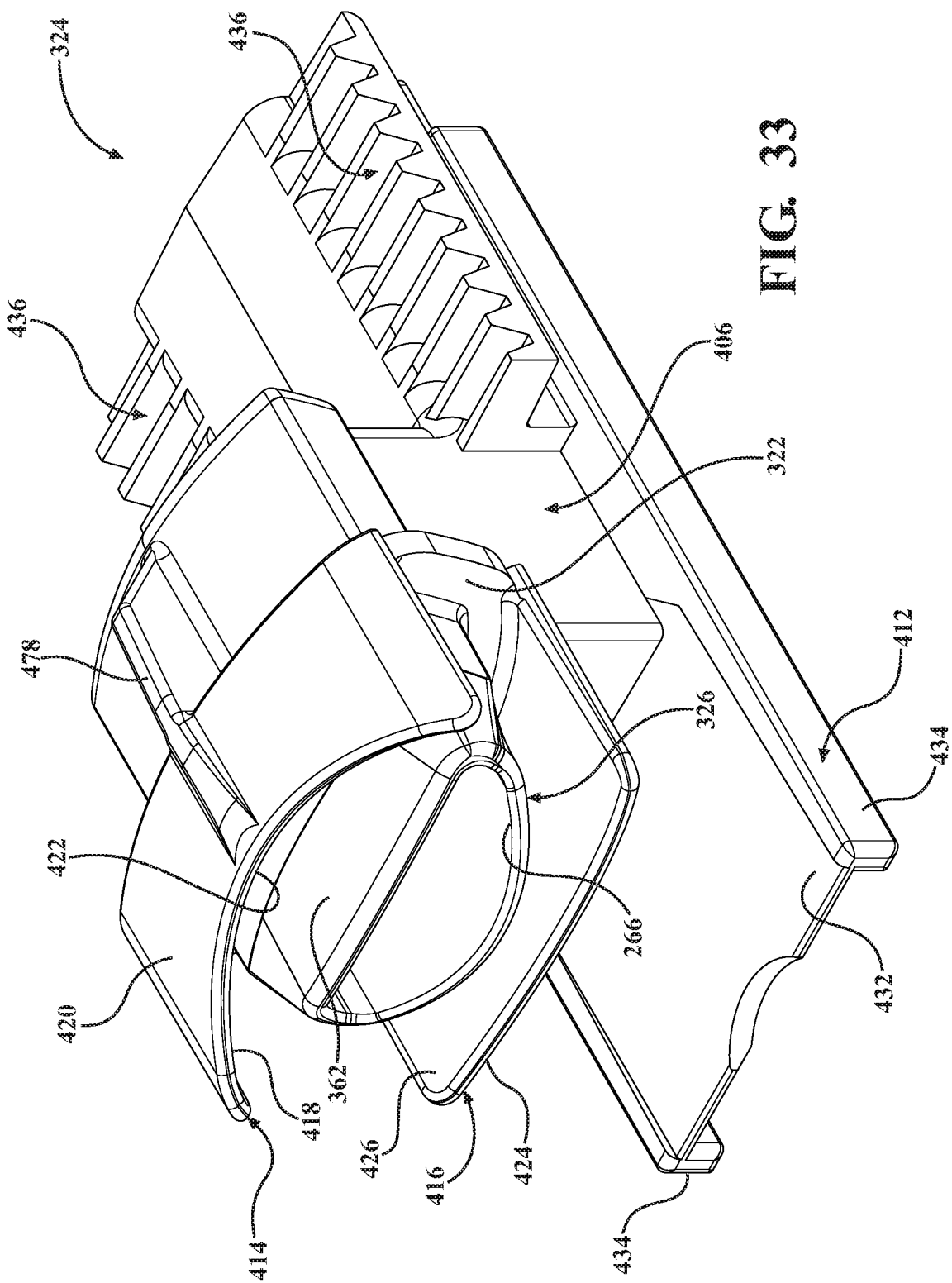
FIG. 33 is a top perspective view of an inlet mechanism of the receiver.

The inlet mechanism 324 may include at least one rack gear 436. FIGS. 28 and 33 show two of the rack gears 436 arranged parallel to one another and oriented in the proximal-to-distal direction. The rack gear(s) 436 are configured to receive an input from at least one transfer gear 438 to facilitate translation of the inlet mechanism 324 relative to the lower housing 268 in the proximal-to-distal direction. As mentioned, when the manifold 124 is not in the fully inserted operative position, the inlet mechanism 324 is positioned such that no fluid communication is provided between the suction outlet 410 and the receiver outlet 404. In particular, when the manifold 124 is not in the fully inserted operative position, the base plate 432 is positioned above the receiver outlet 404 to at least substantially seal the receiver volume 368 from the receiver outlet 404. As the manifold 124 is being moved towards the fully inserted operative position, the inlet mechanism 324 translates relative to the lower housing 268 such that the suction outlet 410 moves towards alignment with the receiver outlet 404. As the manifold 124 is being moved away from the fully inserted operative position, for example, during removal of the manifold 124, the inlet mechanism 324 translates relative to the lower housing 268 such that the suction outlet 410 moves away from alignment with the receiver outlet 404. Finally, when the manifold 124 is in the fully inserted operative position, the suction outlet 410 and the receiver outlet 404 are aligned to provide fluid communication between the receiver volume 368 and the waste container(s) 106, 108 (see FIGS. 61 and 62). The arrangement advantageously prevents suction through the suction inlet 266 without the manifold 124 being inserted into the receiver 116 in the fully inserted operative position. Otherwise, even if the medical waste collection system 100 is operating and a vacuum is being drawn on the waste container(s) 106, 108, the suction path is broken at an interface between the suction outlet 410 and the receiver outlet 404.

Figure 37:
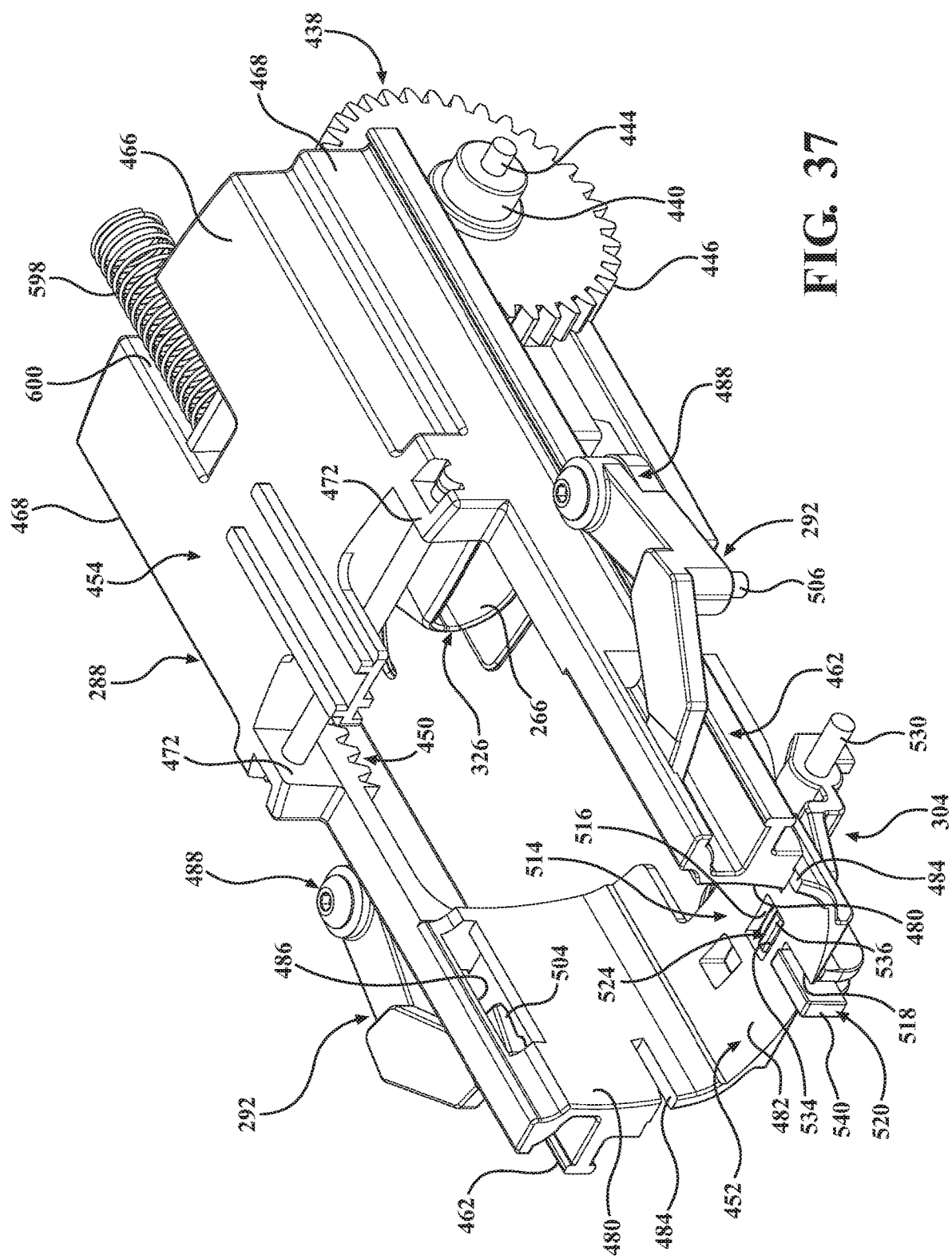
FIG. 37 is a top perspective view of a sled assembly of the receiver. The inlet mechanism, a sled lock assembly, and claws of the receiver are shown engaging the sled assembly in respective positions. The lower housing—to which the inlet mechanism, the sled lock assembly, and the claws are coupled—is not shown for clarity.

With continued reference to FIG. 28, and further reference to FIG. 37, the transfer gear(s) 438 each may include a hub 440 disposed within a respective one of recesses 442 defined within a respective one of the opposing sides 372 of the lower housing 268. An axle 444 extends through the transfer gear(s) 438. The transfer gear(s) 438 are configured to rotate about the axle 444. Two transfer gears 438 are shown with the transfer gears 438 coupled to one another in a tongue-in-groove arrangement such that the transfer gears 438 rotate in unison about the axle 444. The transfer gears 438 each may include an input spur gear 446, and an output spur gear 448. The input spur gears 446 engage a respective rack gear 450 of the sled assembly 288 (see FIG. 39), and the output spur gears 448 engage a respective one of the rack gears 436 of the inlet mechanism 324. The insertion of the manifold 124 into the receiver 116 moves the sled assembly 288 in the proximal direction, and the transfer gears 438 causes translation of the inlet mechanism 324 in the distal direction. Likewise, the removal of the manifold 124 from the receiver 116 moves the sled assembly 288 in the distal direction, and the transfer gears 438 causes translation of the inlet mechanism 324 in the proximal direction. The transfer gears 438 may be configured to improve the mechanical advantage between the forces provided to the sled assembly 288 (via the manifold 124) and the resulting forces on the inlet mechanism 324. In other words, the transfer gears 438 may be designed to require less force provided to the manifold 124 to move the inlet mechanism 324. The mechanical advantage may be greater than one-to-one, and two-, three-, or four-to-one (or more).

The sled assembly 288 is movably coupled to the lower housing 268 and/or the upper housing 366. In certain implementations, complementary surfaces of the lower and upper housings 268, 366 cooperate to define slots 456 extending the proximal-to-distal direction. The lower housing 268, best shown in FIG. 30, includes the slots 456 at or near upper aspects of the opposing sides 372. More particularly, the slots 456 of the lower housing 268 may be defined between the opposing sides 372 and the mating flanges 458 extending laterally outward from the opposing sides 372. A complementary arrangement may be provided on an underside of mating flanges 460 of the upper housing 366 to define a thickness at least equal to a thickness of rails 462 of the sled assembly 288 extending in the proximal-to-distal direction. The rails 462 may extend laterally outward from opposing sides of each of a cradle 452, and a roof 454 coupled to the cradle 452. In certain implementations, the rails 462 extend along a length of the sled assembly 288. With the mating flanges 458, 460 of the lower and upper housings 268, 366 coupled to one another, the rails 462 are configured to translate within the slots 456 in the proximal-to-distal direction. Thus, the sled assembly 288 is configured to translate relative to the lower and upper housings 268, 366 in the proximal-to-distal direction.

Figure 38:
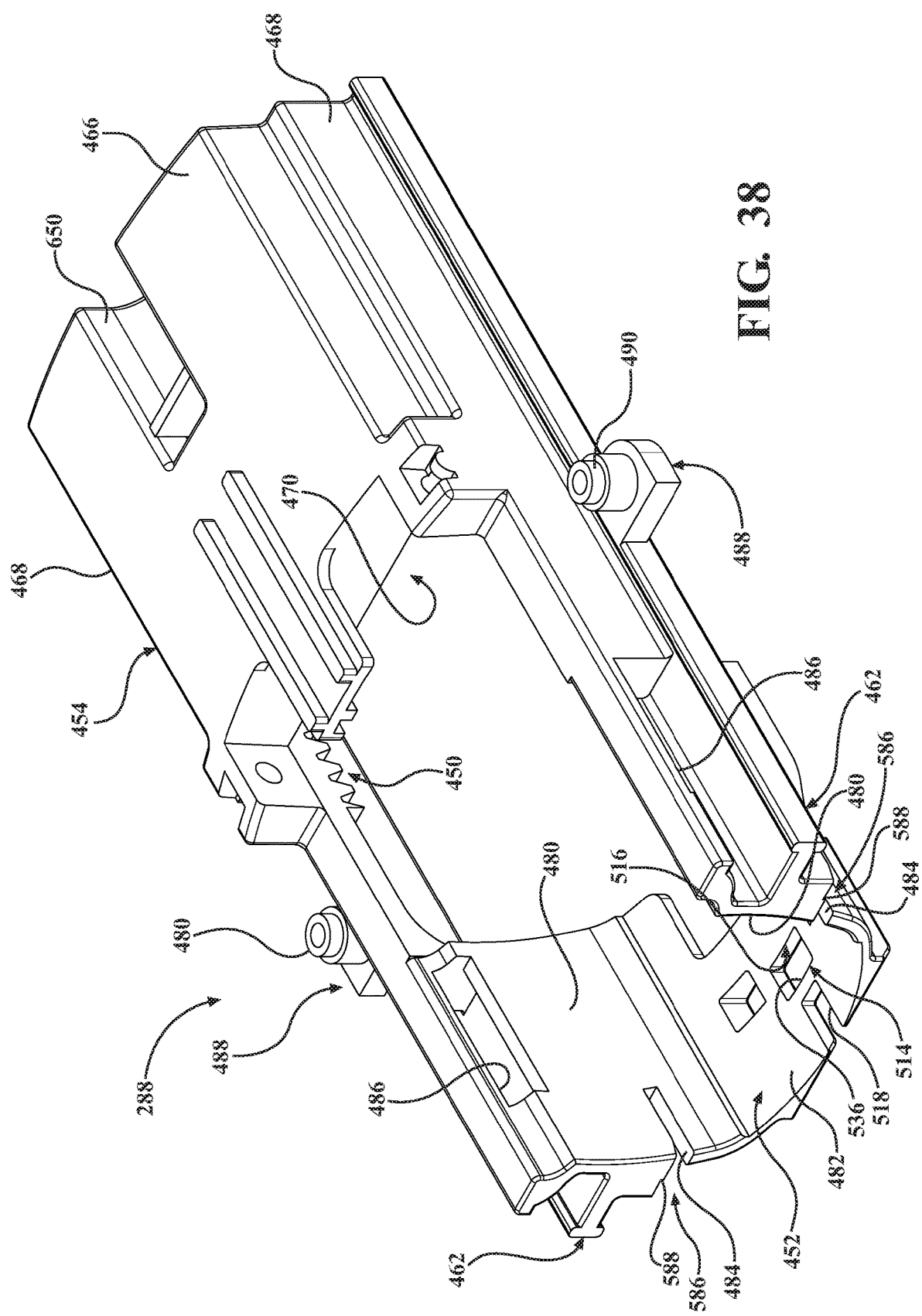
FIG. 38 is a top perspective view of the sled assembly.
Figure 39:
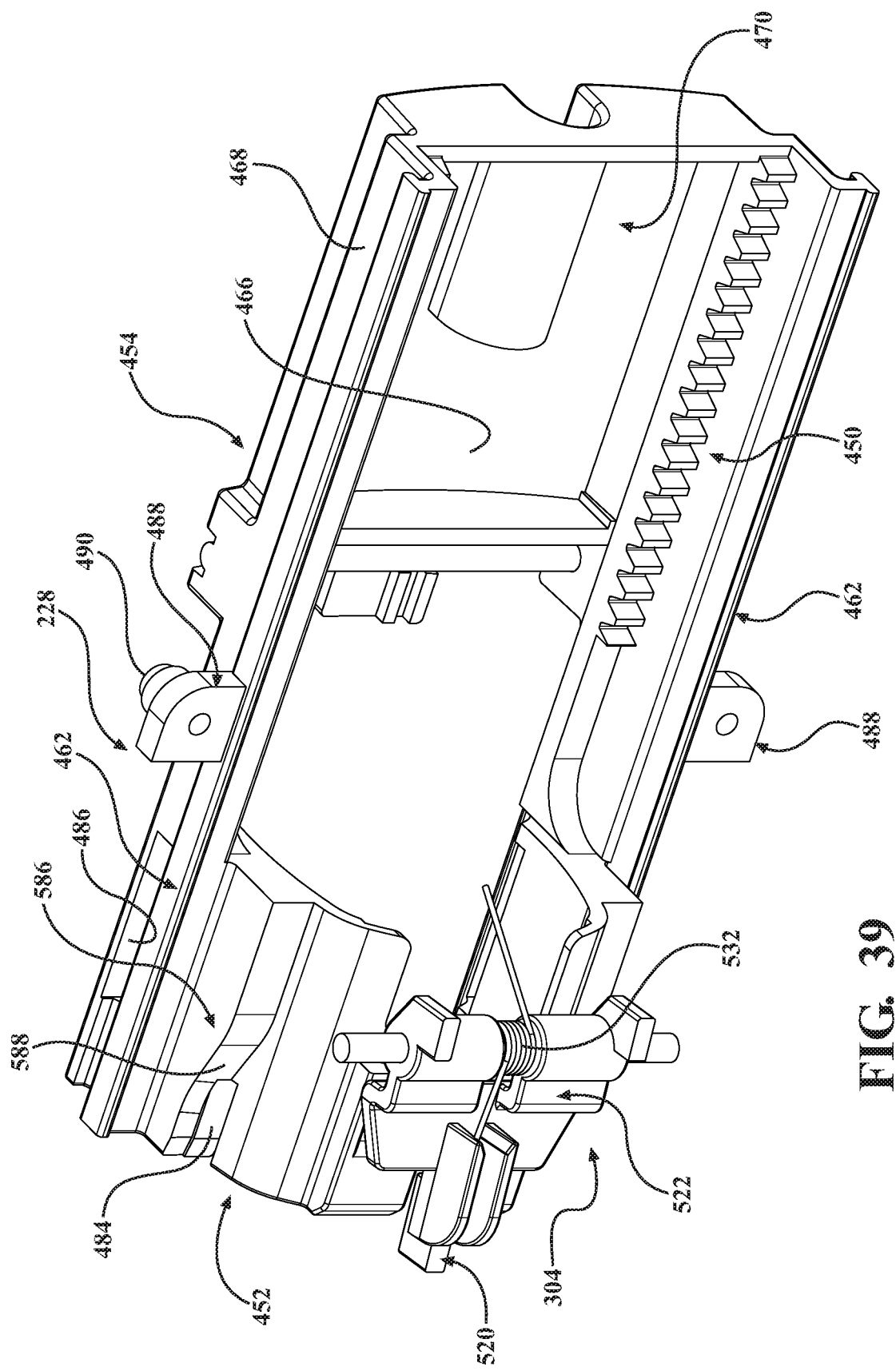
FIG. 39 is a bottom perspective view of the sled assembly. The sled lock assembly is shown engaging the sled assembly.

The roof 454 may be configured to selectively house at least a portion of the inlet mechanism 324 prior to the manifold 124 being inserted into the receiver 116 in the fully inserted operative position. Referring to FIGS. 27, 38 and 39, the roof 454 may cooperate with a second barrier 464 to selectively house at least a portion of the inlet mechanism 324. The roof 454 may include an upper wall 466, and opposing sides 468 extending downwardly from the upper wall 466 to define a cavity 470. The cavity 470 is sized and shaped to at least accommodate the inlet mechanism 324. At least one mount 472 is coupled to the roof 454 and/or the rails 462 with the second barrier 464 pivotably coupled to the mount(s) 472, for example, with a pin 474 extending laterally between two of the mounts 472. It should be appreciated that the second barrier may be positioned and/or coupled in suitable alternative manners. A biasing element 476, for example a torsion spring, may be coupled to the second barrier 464 and configured to urge the second barrier 464 to a closed configuration in which the second barrier 464 is oriented substantially vertically. In the closed configuration, the inlet mechanism 324 is bounded from above by the roof 454, the sides by the roof 454 and/or the lower and upper housings 268, 366, below by the lower housing 268, the rear by the lower housing 268, and the front by the second barrier 464. As a result, the inlet mechanism 324, including the suction fitting 326, which may be contaminated with residual waste material from a previous medical procedure, is inaccessible to the user to avoid any exposure to the same.

The second barrier 464 is configured to move from the closed configuration to an open configuration in which the second barrier 464 is pivoted about the pin 474 against the biasing element 476. For example, during insertion of the manifold 124 into the receiver 116, the sled assembly 288 is moved in the proximal direction, and the transfer gears 438 cause translation of the inlet mechanism 324 in the distal direction. The inlet mechanism 324 engages the second barrier 464, and pivots the second barrier 464 about the pin 474 (see FIG. 57). For example, the distal edge 422 of the first support element 414 contacts a proximal side of the second barrier 464 to impart the pivoting. With further translation of the sled assembly 288 in the proximal direction and corresponding translation of the inlet mechanism 324 in the distal direction, the second barrier 464 "rides up" the inlet mechanism 324 as the inlet mechanism 324 exits the cavity 470 defined by the roof 454. With the manifold 124 inserted into the receiver 116 in the fully inserted operative position, the second barrier 464 may be supported on a rib 478 extending upwardly from an upper aspect of the inlet mechanism 324, more particularly from the upper surface 420 of the first support element 414 (see FIG. 33). The second barrier 464 may be positioned proximal to the base wall 281 of the trunk 134 in the fully inserted operative position (see FIG. 57). Thus, the inlet mechanism 324 remains at least substantially inaccessible throughout the manifold 124 being inserted into (and removed from) the receiver 116. Removal of the manifold 124 from the receiver 116 moves the sled assembly 288 in the distal direction, and the transfer gears 438 causes translation of the inlet mechanism 324 in the proximal direction. As the inlet mechanism 324 enters the cavity 470 defined by the roof 454, the biasing element 476 urges the second barrier 464 to return to the closed configuration.

The sled assembly 288 may include the cradle 452 previously introduced. With continued reference to FIGS. 37 and 38, the cradle 452 may include opposing sides 480 and a lower wall 482 coupled to and extending between the opposing sides 480. In certain implementations, the opposing sides 480 may extend downwardly from the rails 462. The lower wall 482 may be arcuate in shape and contoured to the lower wall 202 of the manifold 124 such that the cradle 452 assumes a generally U-shaped configuration when viewed in elevation in the proximal-to-distal direction.

The cradle 452 of the sled assembly 288 includes at least one push feature 484 with a pair of the push features 484 to be described. The push features 484 may be configured to be engaged by the proximally-directed surfaces 286 of the one or more arms 284 of the manifold 124 as the manifold 124 is being inserted into the receiver 116. The engagement of the push features 484 and the proximally-directed surfaces 286 facilitate moving the sled assembly 288 in the proximal direction. The push features 484 may be slots extending proximally inward from a distal end of the sled assembly 288. The slots may be coplanar and/or oriented in the proximal-to-distal direction. The slots may include have a dimension at least equal to a thickness of proximal portion of the arms 284 including the proximally-directed surfaces 286.

The cradle 452 of the sled assembly 288 includes at least one window 486 with a pair of the windows 486 to be described. The windows 486 are sized and positioned to receive a respective one of the claws 292 as the manifold 124 is being inserted into the receiver 116. The engagement of the claws 292 and the distally-directed surfaces 290 of the catches 254 facilitate moving the sled assembly 288 in the distal direction during removal of the manifold 124 from the receiver 116. The windows 486 may be defined within a respective one of the opposing sides of the cradle 452. The windows 486 may be coplanar and/or oriented in the proximal-to-distal direction. The windows 486 may include a thickness at least equal to a thickness of the claws 292.

The claws 292 may be operably coupled to the sled assembly 288 at a respective one of a pair of hinges 488. The hinges 488 may be disposed on flanges extending laterally outward from a respective one of the rails 462. The hinges 488 may include a post feature 490 to which the claws 292 are pivotably coupled. With concurrent reference to FIG. 40, each of the claws 292 may include a shoulder 492 defining a bore 494 sized to receive the post feature 490. A first segment 496 may extend from the shoulder 492, and a second segment 498 may extend from the first segment 496 at a first elbow 500 to orient the second segment 498 relative to the first segment 496. Further, a third segment 502 may extend from the second segment 498 at a second elbow 503 to orient the third segment 502 relative to the first and second segments 496, 498. The third segment 502 may define an engagement surface 504 configured to engage a respective one of the distally-directed surface 290 of the catch 254 in a manner to be described.

The claws 292 each may include a guide 506. The guide 506 may extend downwardly from the first and/or second segments 496, 498 at a position approximate to the first elbow 500. The guide 506 is movably positioned within a track 508 defined within the lower housing 268. As best shown in FIGS. 30 and 32, the track 508 is disposed within the mating flange 458 of the lower housing 268. The track 508 may include a distal portion 510 and a proximal portion 512. The proximal portion 512 of the track may be oriented in the proximal-to-distal direction, and the distal portion 510 of the track 508 may be angled or oriented relative to the proximal portion 512. In certain implementations, the distal portion 510 may extend laterally outward from the proximal portion 512. The guide 506 is configured to slidably move within and between the distal and proximal portions 510, 512 of the track 508 of the lower housing 268. Yet, at the same time, the claws 292 may be pivotably coupled to the sled assembly 288 at the hinges 488, and the sled assembly 288 may be configured to translate relative to the lower housing 268. Thus, prior to insertion of the manifold 124 into the receiver 116, for example, the sled assembly 288 may be in a proximal-most position with the guides 506 within the distal portion 510 of the track 508. The distal portion 510 of the track 508 constrains the guides 506 such that the third segment 502 of the claws 292, including the engagement surfaces 504, are laterally outward of the windows 486 of the cradle 452 (see, e.g., FIG. 49). As the manifold 124 is being inserted into the receiver 116 and the sled assembly 288 is being moved in the proximal direction, the guides 506 slidably move from the distal portions 510 to the proximal portions 512 of the tracks 508. Owing to the distal portions 510 being angled or oriented relative to the proximal portions 512, the claws 292 pivot laterally inward about the hinges 488, and the third segment 502 of the claws 292, including the engagement surfaces 504, move through the windows 486 of the cradle 452 to engage the distally-directed surfaces 290 of the catches 254 (see, e.g., FIG. 59). With further translation of the sled assembly 288 in the proximal direction, the guides 506 slidably move within the proximal portions 512 of the tracks 508 oriented in the proximal-to-distal direction. The engagement surfaces 504 remain engaged with the distally-directed surfaces 290 of the catches 254. When it is desired to remove the manifold 124 from the receiver 116, the manifold 124 is moved in the distal direction. The engagement between the engagement surfaces 504 and the distally-directed surfaces 290 of the catches 254 facilitate the sled assembly 288 being translated distally together with the distal movement of the manifold 124. In particular, the proximal portions 512 of the tracks 508 oriented in the proximal-to-distal direction prevent the claws 292 from pivoting about the hinges 488, and thus the distal movement of the manifold 124 results in distal translation of the sled assembly 288 relative to the lower housing 268. Once the guides 506 encounter the distal portion 510 of the tracks 508, the claws 292 pivot laterally outward about the hinges 488, and the engagement surfaces 504 are removed from engagement with the distally-directed surfaces 290 of the catches 254. The aforementioned process will be described in greater detail with respect to each of the operative positions of insertion.

In one implementation, the claws 292 may be fixedly coupled to the sled assembly 288 and include a pair of flexible arms such that the second and third segments 498, 502 may flexibly move towards and away from the sled assembly 288 as the guides 506 move within the tracks 508. As a result, the engagement surfaces 504 move into and out of engagement with the distally-directed surfaces 290 of the catches 254 with flexing of the flexible arms.

Returning to FIG. 38, the sled assembly 288 may further include a lock interface 514 configured to be selectively coupled with the sled lock assembly 304 previously introduced. The lock interface 514 may include an aperture 516 defined within the lower wall 482 of the cradle 452. The lock interface 514 may further include a slot 518 defined within the lower wall 482 of the cradle 452. The aperture 516 and the slot 518 may be at least substantially aligned laterally, for example, along a plane of symmetry of the sled assembly 288 extending in the proximal-to-distal direction. The aperture 516 may be positioned proximal to the slot 518. With further reference to FIG. 29, it is appreciated that the slot 518 may be positioned adjacent to the spine slot 277 at least partially defining the opening 118 of the receiver 116 when the receiver 116 is in the first operative position. The slot 518 may be sized and shaped to removably receive a contact block 520 of a latch 522 of the sled lock assembly 304. The aperture 516 may be sized and shaped to removably receive a key 524 of the latch 522.

With further reference to FIGS. 28, 30 and 32, the lower housing 268 may include at least one mount 526 configured to couple the latch 522 to the lower housing 268. The mounts 526 may be supported on the base 370 and positioned adjacent to and laterally outward from the rails 428 extending in the proximal-to-distal direction. The mounts 526 may be spaced apart and positioned distal to the distal-most retention element 430. The mounts 526 include a hole configured to be aligned with bores 528 extending through the latch 522 of the sled lock assembly 304. A pin 530 may extend through the bores 528 of the latch 522 and the holes of the mounts 526 so as to pivotably couple the latch 522 to the lower housing 268 (see FIGS. 37 and 38). The mounts 526 are positioned such that, with the latch 522 pivotably coupled to the lower housing 268, the contact block 520 of the latch 522 selectively extends through the slot 518 and the key 524 of the latch 522 selectively extends through the aperture 516.

Figure 41:
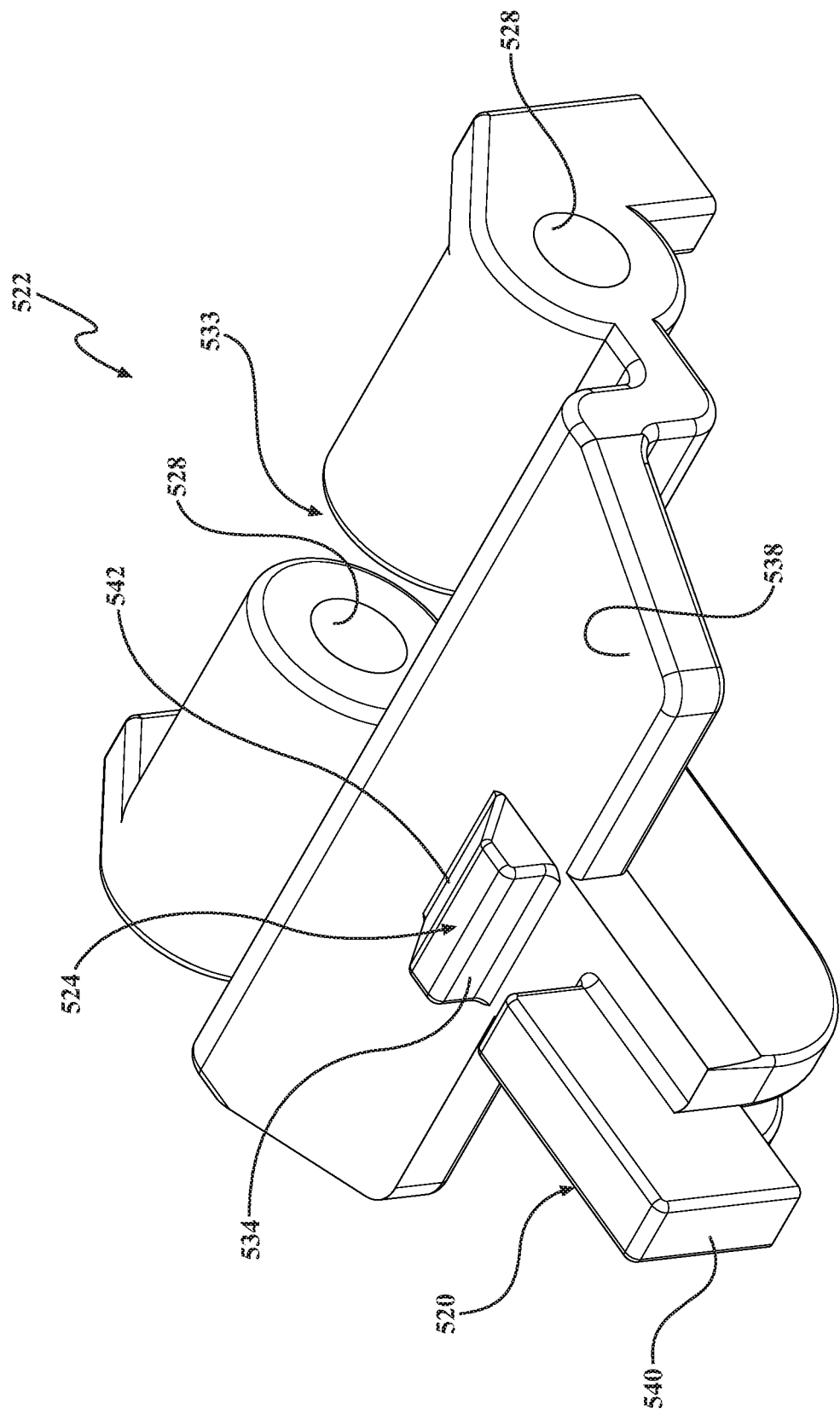
FIG. 41 is a perspective view of a latch of the sled lock assembly.
Figure 42:
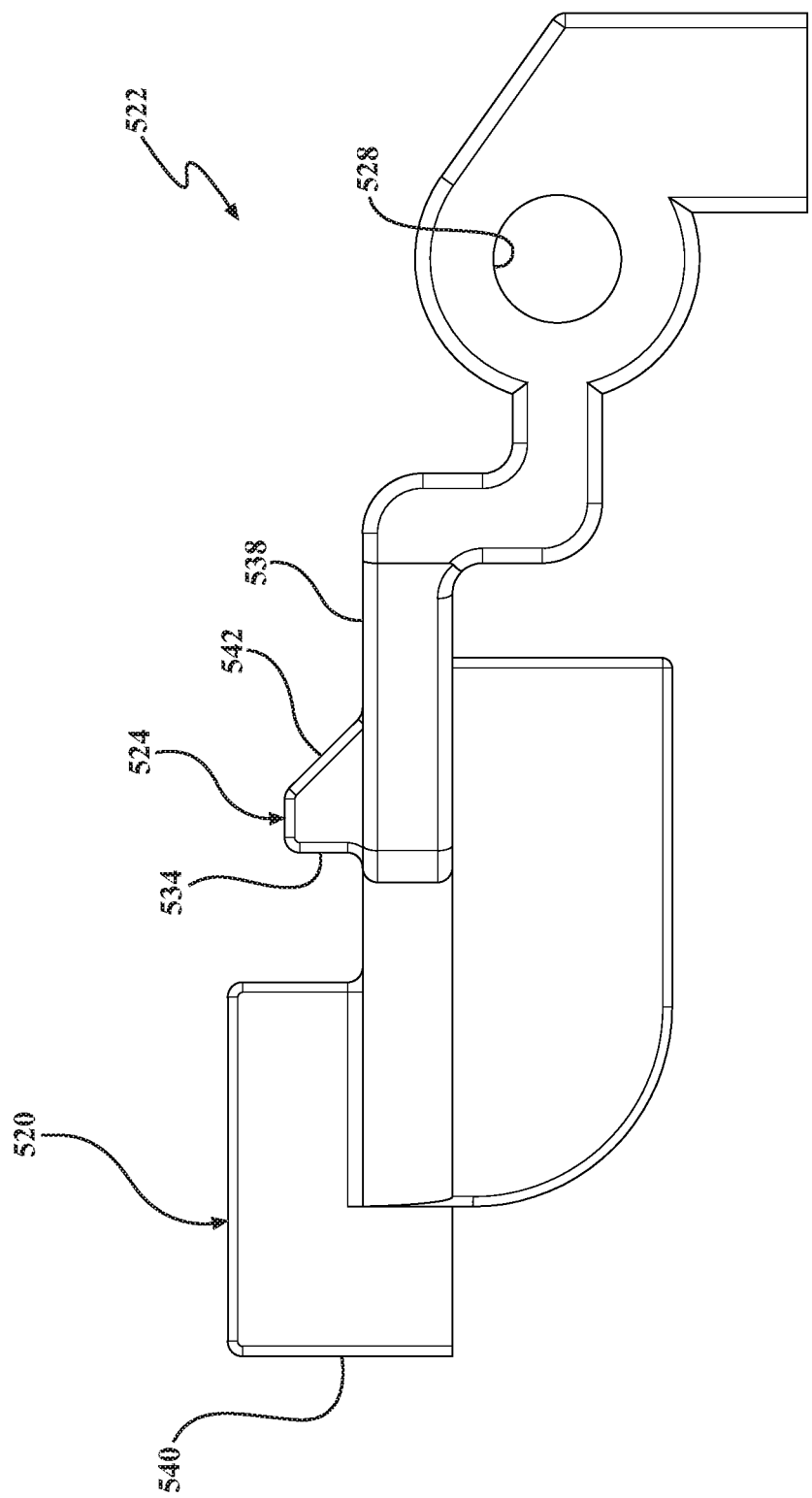
FIG. 42 is a side elevation view of the latch.

The sled lock assembly 304 may further include a biasing element 532, for example, a torsion spring, coupled to the latch 522 with the biasing element 532 configured to urge the latch 522 to a locked configuration in which a front surface 534 of the key 524 is in engagement with a front surface 536 at least partially defining the aperture 516. The biasing element 532 may be disposed in a gap 533 between the bores 528 of the latch 522 to be supported on the pin 530. In the locked configuration, an abutment surface 538 of the latch 522 may engage an underside of the cradle 452 proximal to the aperture 516. With continued reference to FIGS. 37, 38, 41 and 38, the front surface 534 is oriented to be at least substantially vertical when the latch 522 is in the locked configuration. Likewise, the front surface 536 of the aperture 516 may be oriented to be at least substantially vertical. As a result, when the key 524 of the latch 522 is extending through the aperture 516 in the locked configuration, the surfaces 536, 538 interfere to prevent translation of the sled assembly 288 relative to the lower housing 268 in the proximal direction. In other words, the receiver 116 is preventing from moving from the decoupled operative position unless the sled lock assembly 304 is moved from the locked configuration to an unlocked configuration in which the latch 522 is pivoted about the pin 530 to disengage the abutment surface 538 of the latch 522 from the front surface 536 of the aperture 516.

As previously described in detail, the spine 300 includes the proximally-directed surface 302, for example, the ramped surface. When the manifold 124 is oriented for insertion into the opening 118 of the receiver, the proximally-directed surface 302 of the spine 300 is aligned to engage a distally-directed surface 540 of the contact block 520. More particularly, the spine 300 is directed through the spine slot 277 at least partially defining the opening 118, and engages the distally-directed surface 540 of the contact block 520 (see FIG. 47). The engagement may pivot the latch 522 about the pin 530 against the bias of the biasing element 532. The pivoting of the latch 522 may disengage the abutment surface 538 of the latch 522 from the front surface 536 of the aperture 516, and the sled assembly 288 is permitted to be moved relative to the lower housing 268 in the proximal direction. It is appreciated that the distally-directed surface 540 of the contact block 520 is oriented at least substantially vertical in the locked configuration. As a result, the ramped surface of the spine 300, while optional, is particularly well suited to impart the desired pivoting to the latch 522 of the sled lock assembly 304. In other words, should the proximally-directed surface 302 of the spine 300 not be angled or oriented to deflect the at least substantially vertical distally-directed surface 540 of the contact block 520, the surfaces would engage flat-on-flat without moving the sled lock assembly 304 to the unlocked configuration, and the manifold 124 would be prevented from further insertion into the receiver 116. In certain implementations, the ramped surface may be oriented at an angle relative to horizontal, the distally-directed surface 540 of the contact block 520, and/or the downwardly-directed surface 320 within the range of approximately 20 to 70 degrees, and more particularly within the range of approximately 30 to 60 degrees, and even more particularly within the range of approximately 40 to 50 degrees. The angle between, for example, the proximally-directed surface 302 of the spine 300 and the distally-directed surface 540 of the contact block 520 may advantageously cooperate to prevent an unauthorized manifold from being inserted into the receiver 116 to the fully inserted operative position.

With the sled lock assembly 304 in the unlocked configuration, the sled assembly 288 may be translated relative to the lower housing 268 in the proximal direction. The biasing element 532 urges the latch 522 towards the locked configuration to slidably contact the downwardly-directed surface 320 as the manifold 124 is inserted into the receiver 116. As a result, it may be particularly desirable for the spine 300 to extend distally from the proximally-directed surface 302 to at least near the collar 168 in a continuous manner. In other words, the spine 300 may be devoid of slots or other discontinuities between its opposing ends, and/or the spine 300 may be of at least a substantially constant width, defined between the lower wall 262 of the trunk 134 and the downwardly-directed surface 320. The presence of a slot, for example, may result in the front surface 534 of the key 524 to engage such a slot and prevent further insertion of the manifold 124 into the receiver 116. As described above, however, the spine 300 may not extend continuously along the trunk 134 in all implementations.

When it is desired to remove the manifold 124 from the receiver 116, the manifold 124 is moved in the distal direction, and the sled assembly 288 is translated distally together with the distal movement of the manifold 124. The latch 522 slidably contacts the downwardly-directed surface 320 of the spine 300 under the influence from the biasing element 532. A ramped surface 542 of the key 524 that is opposite the front surface 534 encounters a distal edge of the cradle 452 of the sled assembly 288. The ramped surface 542 facilities the latch 522 pivoting about the pin 530 as the distal edge of the cradle 452 moves distally relative to the key 524. It is further noted that a width of the key 524 is less than a width of the slot 518. The latch 522 eventually encounters the aperture 516, and biasing element 532 moves the key 524 to within the aperture 516 such that the surfaces 534, 536 are in engagement. The aforementioned process will be described in greater detail with respect to each of the operative positions of insertion.

Figure 43:
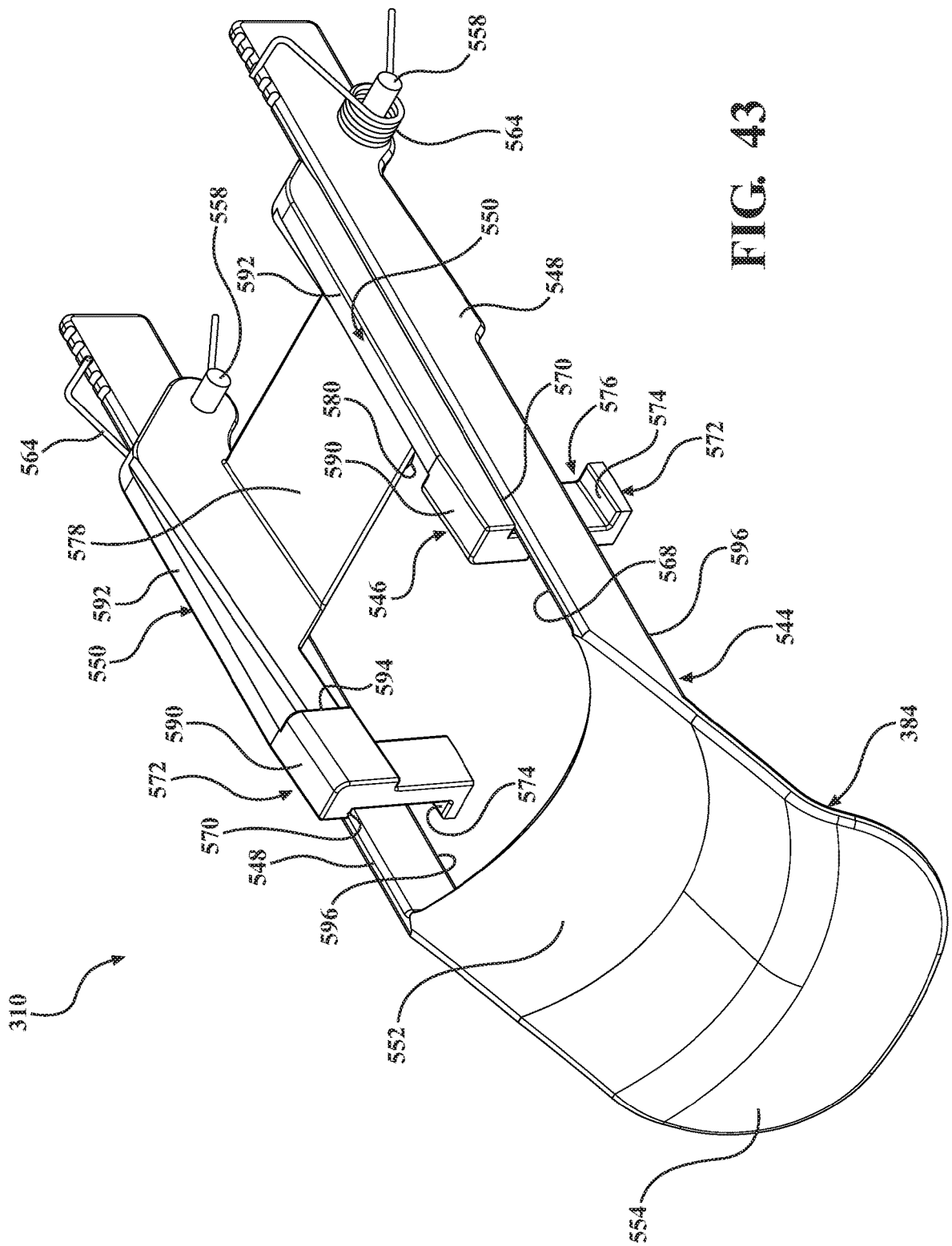
FIG. 43 is a perspective view of a locking assembly shown in a default configuration and/or an unlocked configuration.
Figure 44:
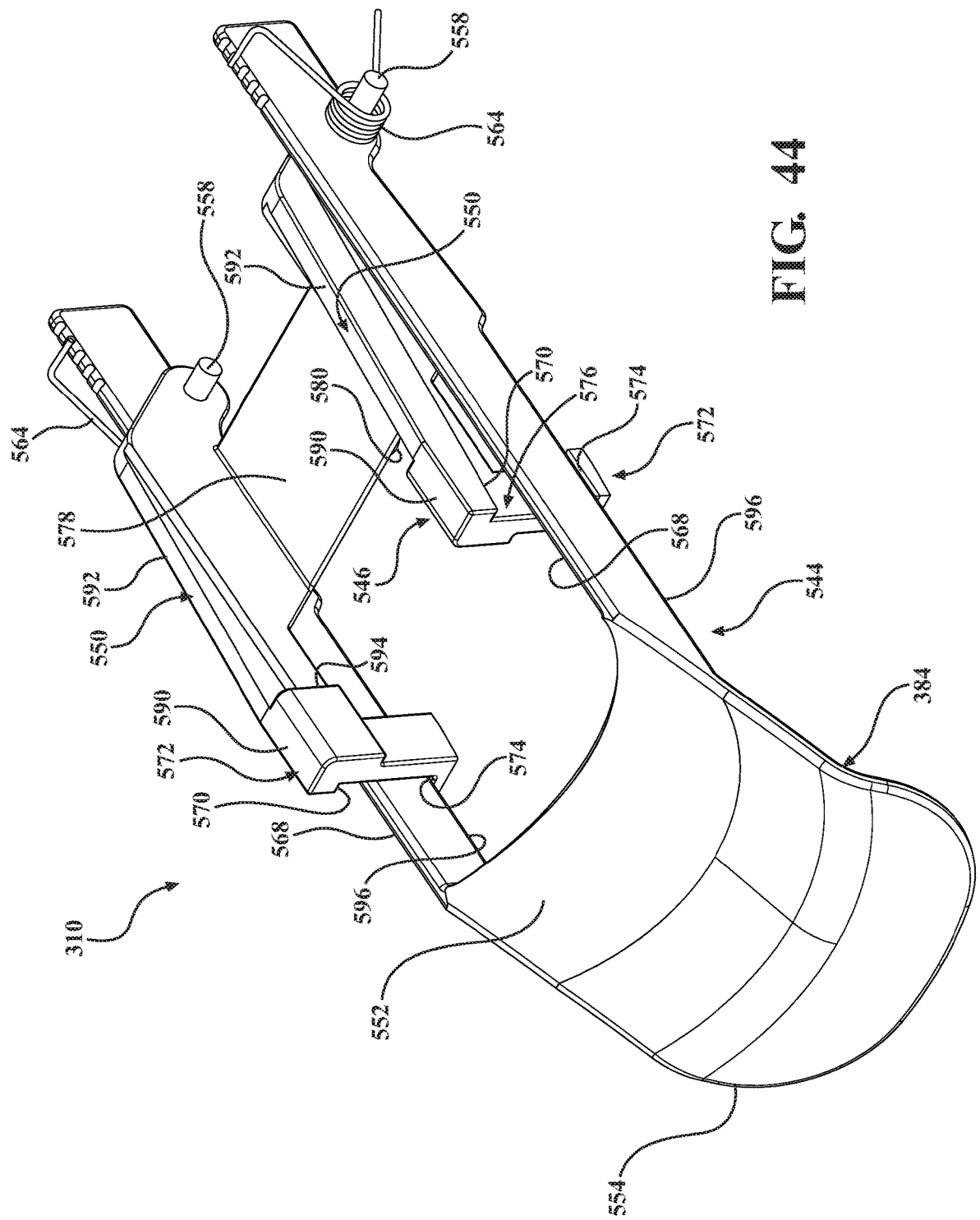
FIG. 44 is a perspective view of the locking assembly shown in a locked configuration.

Referring now to FIGS. 43 and 44, the locking assembly 310 of the receiver 116 previously introduced is configured to engage the distally-directed surfaces 308 of the manifold 124 after insertion of the manifold 124 to the fully inserted operative position. The locking assembly 310 being in a locked configuration selectively prevents distal movement of the manifold 124 (and thus the sled assembly 288) relative the receiver 116. The locking assembly 310 is configured to be actuated by the user to move the locking assembly 310 from the locked configuration to an unlocked configuration in which distal movement of the manifold 124 relative to the receiver 116 is permitted. FIG. 43 shows the relative positions of a release member 544 and a locking member 546 of the locking assembly 310 in a default configuration associated with the decoupled operative position (i.e., prior to insertion of the manifold 124 or after removal of the manifold 124 to and from the receiver 116, respectively). FIG. 43 may also generally reflect the relative positions of the release member 544 and the locking member 546 of the locking assembly 310 in an unlocked configuration. The unlocked configuration may be considered to differ from the default configuration by the manifold 124 being at least partially inserted into the receiver 116 and the locking assembly 310 not being in the locked configuration (i.e., prior to the manifold 124 being inserted to the fully inserted operative position and/or after actuating the locking assembly 310). FIG. 44 shows the locking assembly in the locked configuration. The default, unlocked, and locked configurations will be further described with reference to each of the operative positions of insertion.

The locking assembly 310 may include the release member 544, and the locking member 546 coupled to the release member 544. The release member 544 may include at least one lever 548, and the locking member 546 may include at least one lever 550. FIGS. 43 and 44 show each of the release and locking members 544, 546 including a pair of levers 548, 550 coupled to one another. Further description will be in the context of the pairs of levers 548, 550, however, it is understood a singular lever 548, 550 may be utilized. The levers 548 of the release member 544 may be coupled to one another with the tongue 384 previously introduced. The tongue 384 may include a proximal portion 552 sized and shaped to be disposed within the recess 382 of the brim 380 of the lower housing 268 (see FIG. 30), and a distal portion 554 flaring substantially downwardly in the distal direction relative to the proximal portion 552. The tongue 384, and in particular the proximal portion 552, may be concave so as to be at least substantially contoured with the brim 380 extending around the crown 376 of the receiver 116. The levers 548 may extend from the tongue 384 in the proximal-to-distal direction and be oriented parallel to and spaced apart from one another. The levers 548 of the release member 544 may extend to within the receiver volume 368 through slots 556 positioned adjacent the recess 382 of the brim 380 (see FIG. 31).

The levers 548 of the release member 544 may be coupled to the levers 550 of the locking member 546 with pins 558 such that the release and locking members 544, 546 are pivotable relative to one another. With reference to FIG. 30, the levers 548, 550 of each of the release and locking members 544, 546 are positioned within the cavity 378 of the lower housing 268 between mounts 560 extending from the base 370 and a respective one of the opposing sides 372. The levers 550 of the locking member 546 may be positioned adjacent and laterally outward to the mounts 560, and the levers 548 of the release member 544 may be positioned adjacent and laterally outward to the levers 550 of the release member 544. The pins 558 extend at least partially through holes in the mounts 560, the levers 548, 550, and at least partially through a hole disposed within a respective one of recesses 562 within the opposing sides 372 of the lower housing 268. A biasing element 564, for example a torsion spring, may operably couple each the levers 548 of the release member 544 to the lower housing 268. In certain implementations, the biasing elements 564 may also be positioned within a respective one of the recesses 562 within the opposing sides 372 of the lower housing 268. The biasing elements 564 are configured to urge the levers 548 of the release member 544 to pivot upwardly about the pins 558 such that an upper aspect 568 of the levers 548 engage an upper aspect of the slots 556 of the lower housing 268. The levers 548 engaging the slots 556 may prevent further upwardly pivoting, and the release member 544 may be considered in the default and unlocked configurations.

The upper aspect 568 of the levers 548 may also engage an upper engagement surface 570 of feet 572 of the locking member 546 in the default position. FIGS. 43 and 44 show two of the feet 572 disposed at or near a distal end of the levers 550 with the feet 572 at least substantially oriented perpendicular to the levers 550. The feet 572 include the upper engagement surface 570 spaced apart from a lower engagement surface 574 to define a gap 576 within which the levers 548 of the release member 544 are movably disposed. The biasing elements 564 may be configured to urge the levers 548 of the release member 544 to pivot upwardly about the pins 558 such that an upper aspect 568 of the levers 548 engage the upper engagement surfaces 570 of the feet 572 in the default and unlocked configurations.

Figure 34:
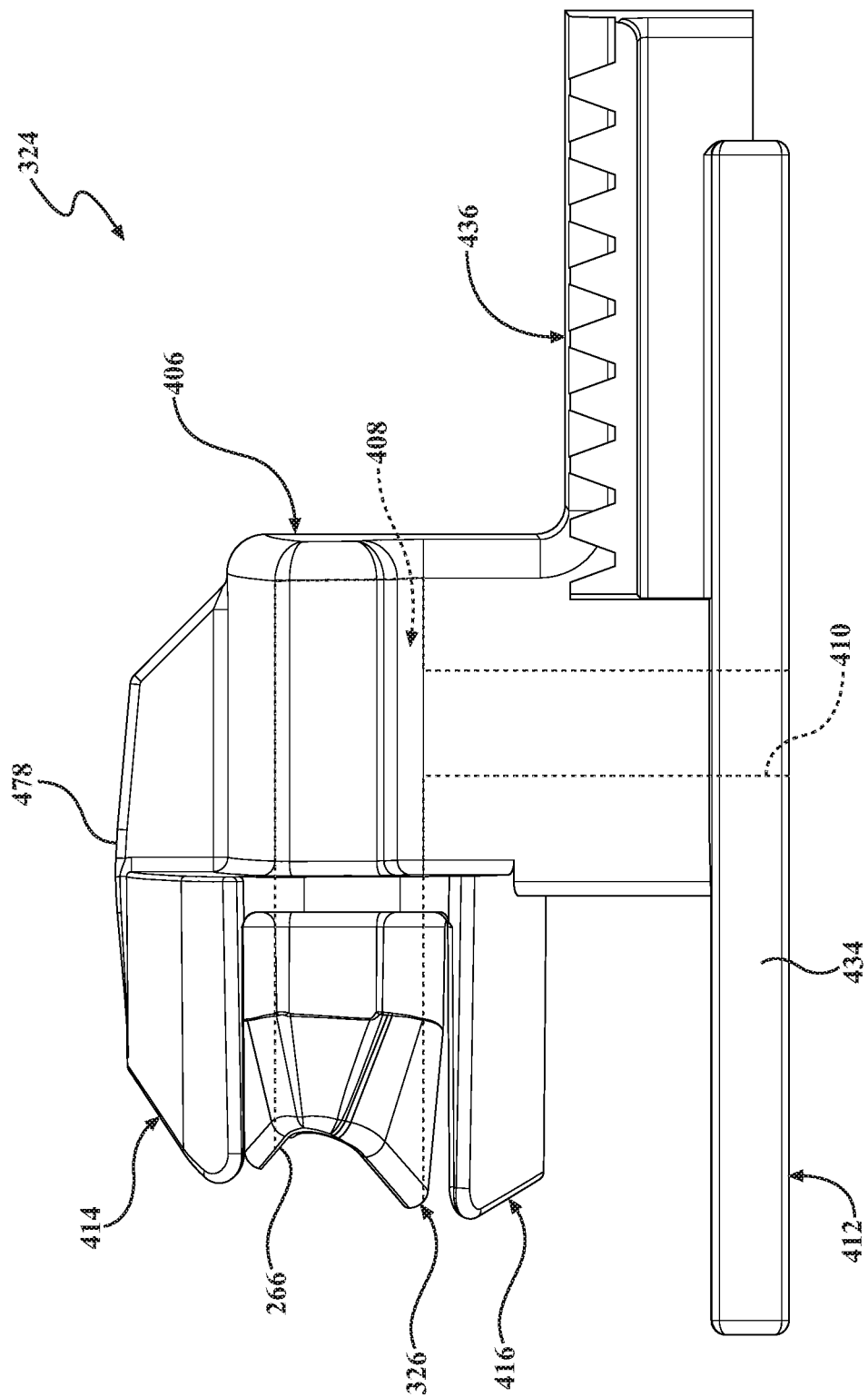
FIG. 34 is a side elevation view of the inlet mechanism.
Figure 35:
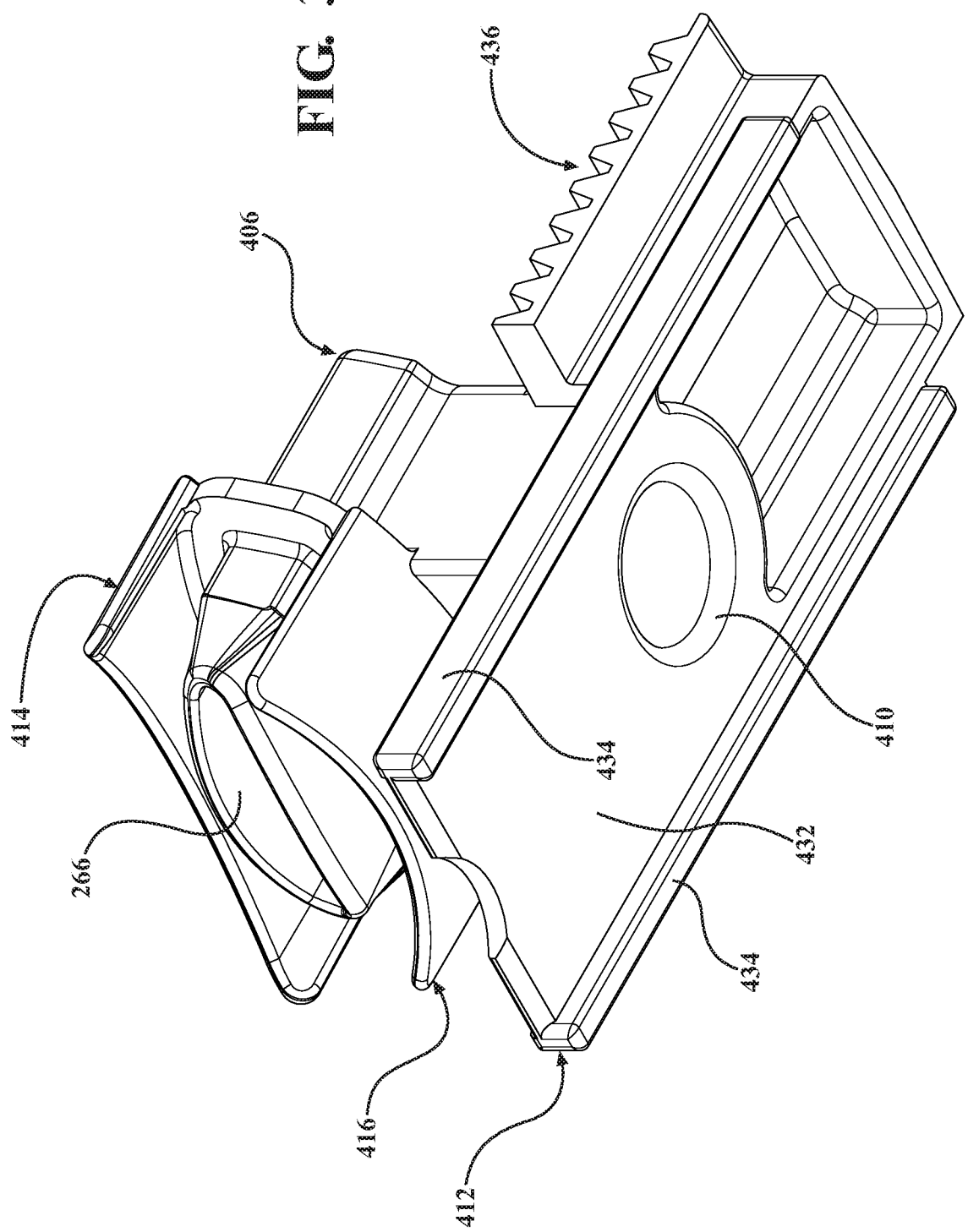
FIG. 35 is a bottom perspective view of the inlet mechanism.
Figure 36:
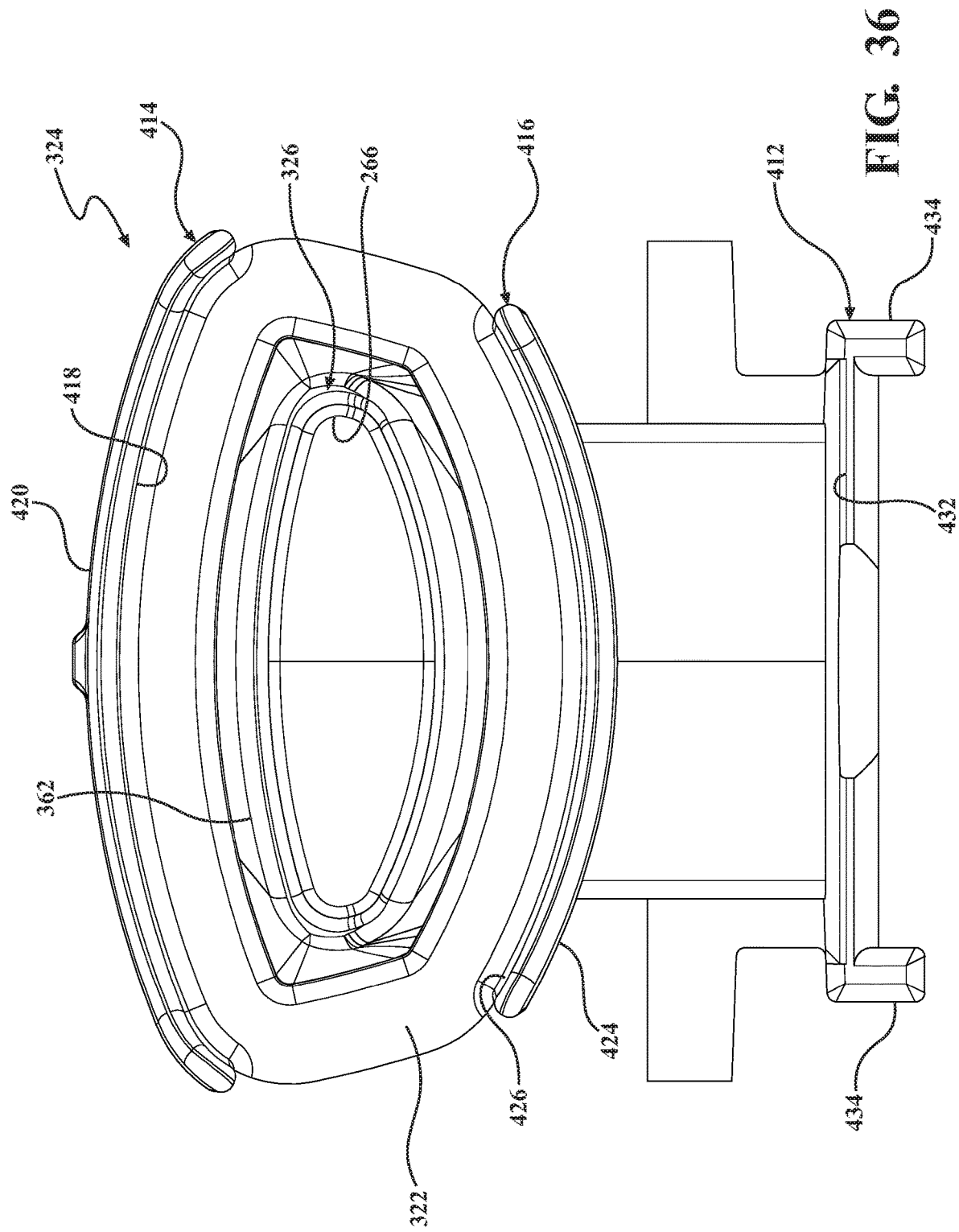
FIG. 36 is a front elevation view of the inlet mechanism.

The levers 550 of the locking member 546 may be coupled to one another with a crossbar 578. The crossbar 578 may be a plate-like structure extending laterally between inner aspects of the levers 550. A biasing element 580, for example a coil spring, may include an end disposed in engagement with an underside of the crossbar 578. An opposing end of the biasing element 580 may be supported in a boss 582 defined with the lower housing 268 (see FIGS. 30 and 32). The biasing element 580 may be configured to urge the levers 550 of the locking member 546 to pivot upwardly about the pins 558 such that upper aspects of the levers 550 engage tracks 586 of the cradle 452 of the sled assembly 288. With further reference to FIGS. 34 and 35, an underside of the cradle 452 include the tracks 586 positioned laterally outward from the opposing sides 480 of the cradle 452. The tracks 586 may be oriented in the proximal-to-distal direction. The tracks 586 each may include at least one surface 588 along which the upper aspects of the levers 550 slidably move as the sled assembly 288 moves in the proximal and/or distal directions. The surfaces 588 may be oriented generally downwardly so as to be in abutment with the upper aspects of the levers 550 oriented generally upwardly. Further, the upper aspect of the levers 550 may include a distal surface 590 and a proximal surface 592 oriented at an angle relative to the distal surface 590. FIGS. 43 and 44 show the proximal surface 592 sloping downwardly away from the distal surface 590 in the proximal direction.

With the sled assembly 288 positioned in the decoupled operative position, for example, the tracks 586 are positioned such that the surfaces 588 of the tracks 586 engage the distal surface 590 of the levers 550 and/or the proximal surface 592 of the levers 550 adjacent the distal surface 590. As the sled assembly 288 is moved in the proximal direction (as the manifold 124 is being inserted into the receiver 116), the tracks 586 slidably move along a length of the proximal surfaces 592 of the levers 550 which may, as mentioned, slope downwardly away from the distal surface 590. The downwardly sloping nature of the proximal surfaces 592 is effectively counteracted by the biasing element 580, which urges the crossbar 578, and thus the levers 550, upwardly to maintain contact between the surfaces 588 of the tracks 586 and the proximal surfaces 592 of the levers 550. The feet 572 are pivoted upwardly about the pins 558 relative to the release member 544, which is maintained in its default position by the engagement between the upper aspect 568 of the levers 548 and the slots 556 of the lower housing 268 as previously described.

Figure 65:
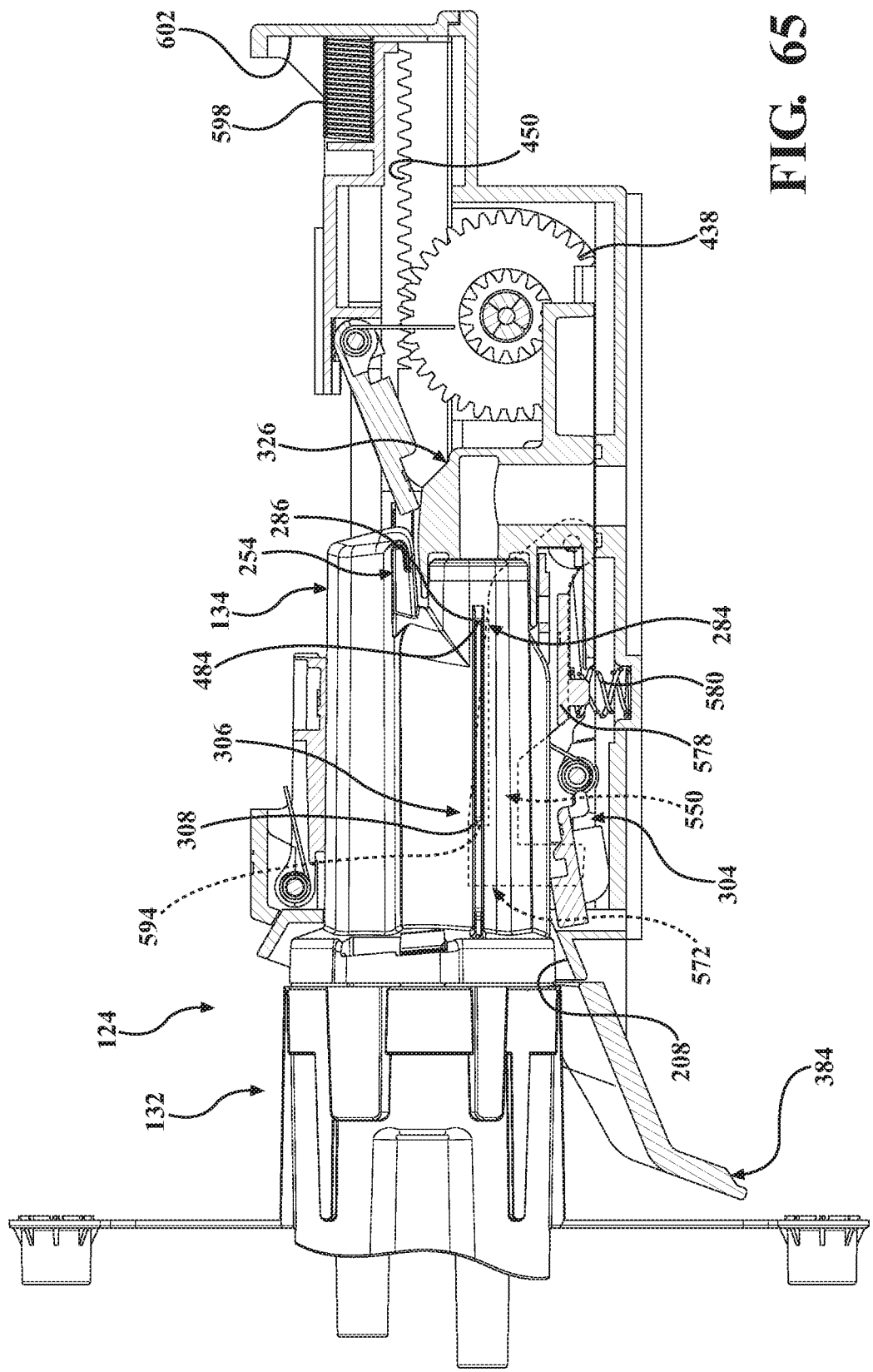
FIG. 65 is a sectional elevation view of the receiver of FIG. 60 taken along section lines 65-65 with the manifold shown in elevation and the locking assembly in the locked configuration.

Once the distally-directed surfaces 308 of the lock element 306 of the manifold 124 is positioned proximal to lock surfaces 594 of the feet 572 of the locking member 546, the biasing element 580 pivots the levers 550, and thus the feet 572, upwardly about the pins 558 such that the locking surfaces 594 are positioned distal to and in interference engagement with the distally-directed surfaces 308 of the manifold 124 (see FIG. 65). This may be considered the locked configuration, and the interference engagement of the locking surfaces 594 with the distally-directed surfaces 308 selectively prevents distal movement of the manifold 124 relative the receiver 116. FIG. 44 may be indicative of the locking assembly 310 in the locked configuration, and lower aspects 596 of the levers 548 may be adjacent to the lower engagement surfaces 574 of the feet 572. In other words, moving the locking assembly 310 from the unlocked configuration to the locked configuration may include the levers 548 moving within the gap 576 of the feet 572 from a position adjacent the upper engagement surfaces 570 to a position adjacent the lower engagement surfaces 574.

In one implementation, the locking member is configured to be pivoted inwardly such that the locking surfaces are positioned distal to and in interference engagement with the distally-directed surfaces 308 of the manifold 124. In such an implementation, the locking member are two locking member that are structurally separate and each pivotable about an axis in the proximal-to-distal direction. The locking members may be biased inwardly by respective biasing elements. The locking members may include a first pin situated within a recess of the lower housing 268, and a second pin positioned within a recess of the release member. As the sled assembly 288 is moved in the proximal direction (as the manifold 124 is being inserted into the receiver 116), the locking members are urged into contact with the laterally-directed surfaces 318 of the arms 284 (see FIG. 10). Once the distally-directed surfaces 308 of the lock element 306 of the manifold 124 is positioned proximal to lock surfaces of the locking members, the biasing element pivots the locking members laterally inwardly such that the locking surfaces are positioned distal to and in interference engagement with the distally-directed surfaces 308 of the manifold 124. This may be considered the locked configuration.

As mentioned, the locking assembly 310 is configured to be actuated by the user to move the locking assembly 310 from the locked configuration to the unlocked configuration. The input may be provided to the release member 544, and more particularly to the tongue 384 functioning as an actuator. The tongue 384 may be colored differently than adjacent components to provide an indication to the user that the tongue 384 functions as the actuator. The input to the release member 544 pivots the levers 548 downwardly about the pins 558 against the bias provided by the biasing elements 564. With the lower aspects 596 of the levers 548 adjacent to the lower engagement surfaces 574 of the feet 572 as previously mentioned, the downward pivoting of the levers 548 results in a corresponding downward pivoting of the levers 550 of the locking member 546 about the pins 558. The downward pivoting of the levers 550 is to an extent such that the locking surfaces 594 disengage the distally-directed surfaces 308 of the lock elements 306 of the manifold 124, and distal movement of the manifold 124 relative to the receiver 116 is thereby permitted. In one implementation, the input to the release member 544 urges the recess downwardly within which the second pin of the locking members are positioned. The locking members are pivot laterally outwardly against the bias from the biasing elements. The laterally-outward pivoting of the locking members is to an extent such that the locking surfaces disengage the distally-directed surfaces 308 of the lock elements 306 of the manifold 124, and distal movement of the manifold 124 relative to the receiver 116 is thereby permitted.

Referring now to FIGS. 3 and 37, a biasing element 598, for example a coil spring, may be operably coupled to the lower housing 268. The biasing element 598 may be disposed within a cavity 600 defined within the roof 454 of the sled assembly 288. An end of the biasing element 598 may be coupled to the sled assembly 288, and an opposing end of the biasing element 598 may be free when the manifold 124 is not in the fully inserted operative position. Thus, the biasing element 598 may be in a natural or unstressed state when the manifold 124 is not in the fully inserted operative position. As the manifold 124 is inserted into the receiver 116 and sled assembly 288 is translated in the proximal direction, the free end of the biasing element 598 nears the rear barrier 602 associated with the lower housing 268. With the manifold 124 in the fully inserted operative position, the free end of the biasing element 598 may engage the rear barrier 602, and the biasing element 598 may assume a deformed or stressed state in which potential energy is stored. As to be described further with reference to the operative positions, when the locking assembly 310 is in the locked configuration, the biasing element 598 may be in the deformed or stressed state. The input to the release mechanism 544 moves the locking assembly 310 from the locked configuration to the unlocked configuration, which may permit distal movement of the manifold 124 relative to the receiver 116. The biasing element 598 may release the stored potential energy to move the manifold 124 (and the sled assembly 288) in the distal direction. The distal movement of the manifold 124 may provide visual indication to the user that the manifold 124 is readied to be removed from the receiver 116. Additionally or alternatively, the position of the manifold 124 relative to the receiver 116 prior or subsequent to the locking assembly 310 assuming the locked and unlocked configurations, respectively, may provide indication to the user that the manifold 124 is not in the fully inserted operative position.

In certain implementations, one or more magnets may be utilized with complementary ferromagnetic material to cause a repulsion force to facilitate the aforementioned distal movement. In certain implementations, an electronic linear actuator may be operatively controlled by an electronic controller to move the manifold 124 in a desired manner. In certain implementations, a pneumatic linear actuator may be utilized. Other alternatives to the biasing element 598 are contemplated for providing movement of the manifold 124 (and the sled assembly 288) in the distal direction in response to the locking assembly assuming the unlocked configuration.

Referring now to FIGS. 3 and 45-65, each of the operative positions of insertion of the manifold 124 into the receiver 116 will be described in detail. FIG. 3 may be prior to insertion of the manifold 124 into the receiver 116 and/or after removal of the manifold 124 from the receiver 116, and representative of the decoupled operative position. The first and second barriers 392, 464 are in the closed configurations. The sled assembly 288 is in the distal-most position, and the sled lock assembly 304 is in the locked configuration preventing movement of the sled assembly 288 relative to the lower housing 268. The inlet mechanism 324 is in proximal-most position such that fluid communication between the suction outlet 410 and the receiver outlet 404 is prevented. The locking assembly 310 may be in the default configuration.

The manifold 124 is oriented for insertion into the opening 118 of the receiver 116. In particular, the manifold 124 is oriented such that the upper wall 260 of the trunk 134 is aligned with the upper segment 270 of the opening 118, the lower wall 262 of the trunk 134 is aligned with the lower segment 272 of the opening 118, and the opposing sides 264 are aligned with the opposing side segments 274 of the opening 118. Further, the trunk 134 of the manifold 124 may include orientation feature(s) 265 configured to require insertion of the manifold 124 into the opening 118 in a single orientation. With concurrent reference to FIGS. 8, 10 and 31, the orientation feature(s) 265 may include at least one transition surface 267 defining at least a portion of the upper wall 260 and/or the opposing sides 264. The transition surface(s) 267 may be considered change in contour from the upper wall 260 to the opposing sides 264. FIG. 10 shows the transition surfaces 267 resulting in the opposing sides 264 being relatively more vertically oriented than, for example, a substantially circular configuration. The orientation features 265 may include at least one undercut surface 269 defining at least a portion of the opposing sides 264. The undercut surfaces 269 may extend laterally inward from an adjacent upper surface of the opposing sides 264, and/or extend laterally outward from adjacent lower surface of the opposing sides 264. The undercut surfaces 269 may be contoured to the recesses 279 at least partially defining the opening 118 of the receiver 116. The transition surfaces 267 and/or the undercut surfaces 269 may cooperate with the upper wall 260, the lower wall 262, and the opposing sides 264 to define an entry profile of the manifold 124 that is insertable into the opening 118 in the single orientation. Further, the transition surfaces 267 and/or the undercut surfaces 269 may cooperate to provide visual distinctiveness to the shape of the manifold 124 for the user to readily discern the proper orientation for the manifold 124 to be inserted into the receiver 116. With the manifold 124 oriented as previously described, the arms 284 of the manifold 124 are aligned with the arm slots 278 of the opening 118, and the spine 300 of the manifold 124 is aligned with the spine slot 277 of the opening 118.

Figure 46:
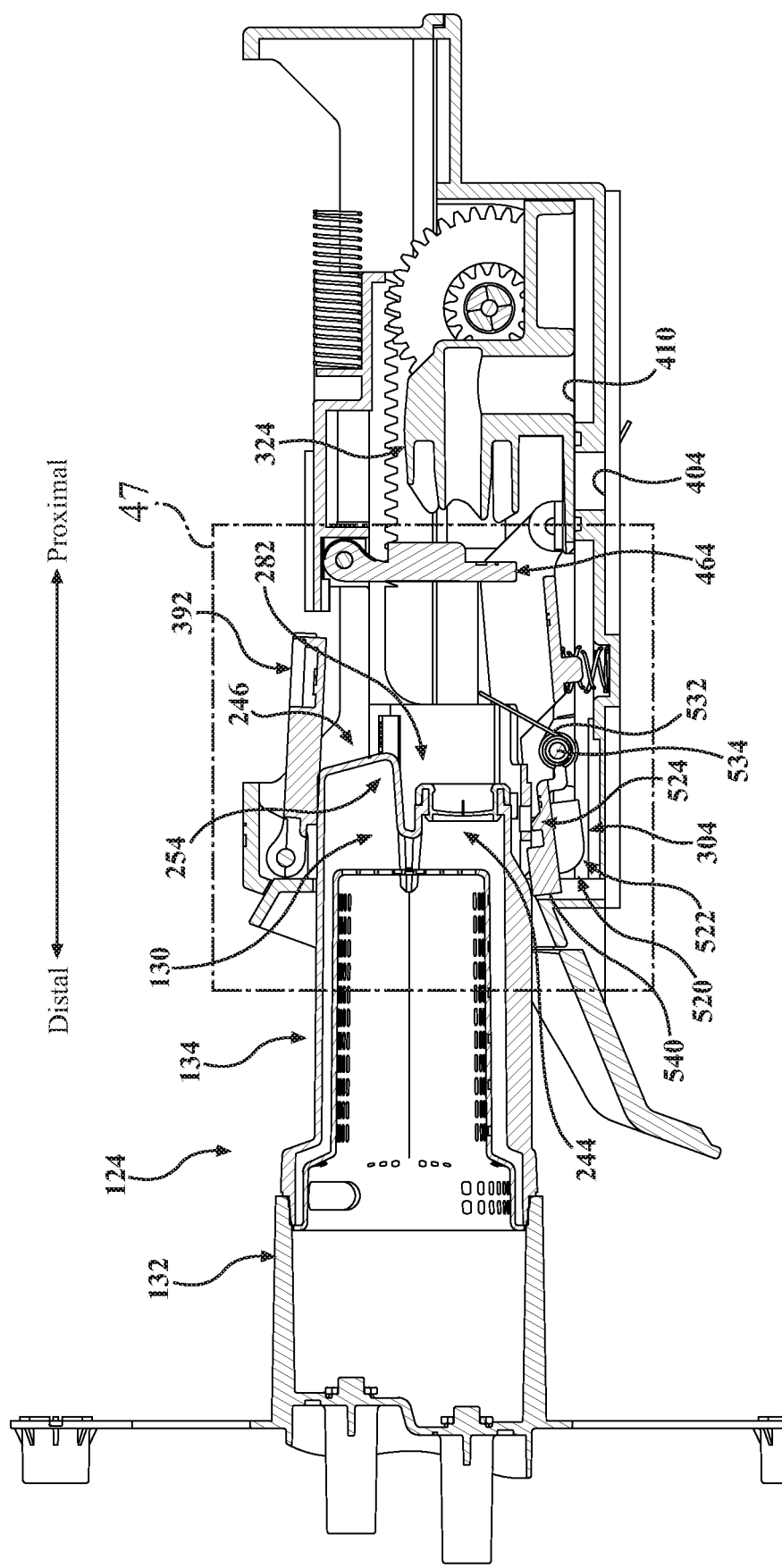
FIG. 46 is a sectional elevation view of FIG. 45 taken along section lines 46-46.
Figure 47:
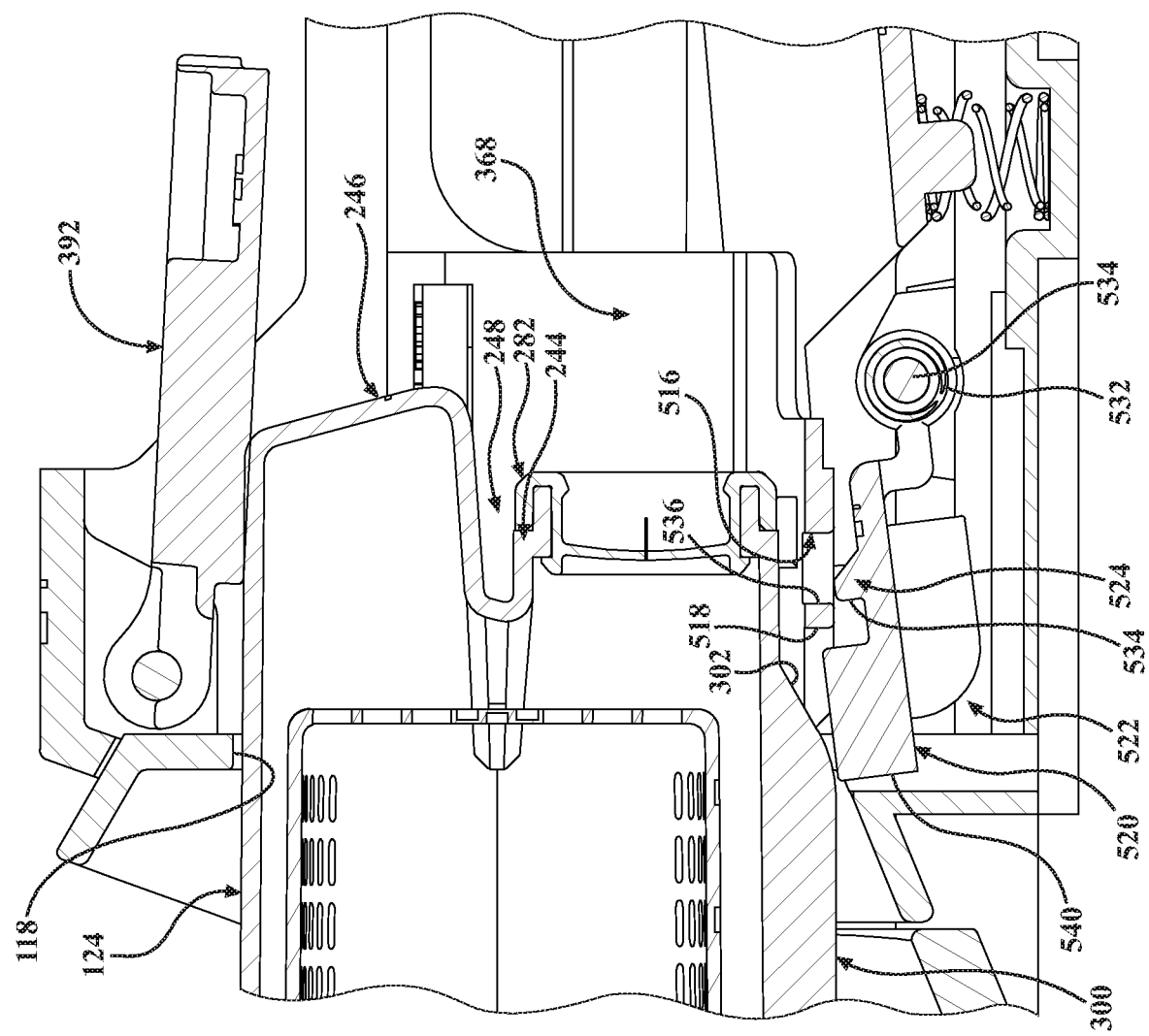
FIG. 47 is a detailed sectional elevation view of FIG. 46 within boundary 47.

FIGS. 45-49 show the manifold 124 at least partially inserted into the receiver 116 to a first operative position. The user may manipulate the manifold 124, for example, using the control surfaces 154 on the head 132, to move the base wall 281 of the second leg 246 through the opening 118 of the receiver 116 and engage and pivot the first barrier 392. The second leg 246 may enter the receiver volume 368, and/or the first leg 244 and the seal 282 may enter the receiver volume 368. The arms 284, including the proximally-directed surfaces 286, may pass through the arm slots 278 and enter the receiver volume 368, and the spine 300, including the proximally-directed surface 302, may at least partially pass through the spine slot 277 to engage the sled lock assembly 304. The proximally-directed surface 302 of the spine 300 may engage the contact block 520 of the sled lock assembly 304 prior to the arms 284 and/or the catches 254 engaging or being engaged by the receiver 116, respectively. As described, the proximally-directed surface 302 of the spine 300 may be positioned distal to the rim 276, distal to the distally-directed surfaces 290 of the catches 254, and distal to the proximally-directed surfaces 286 of the arms 284 (see FIG. 12). Despite the aforementioned distal relative position, it may be necessary for the proximally-directed surface 302 of the spine 300 to first move the sled lock assembly 304 from the locked configuration to the unlocked configuration so as to permit movement of the sled assembly 288 relative to the lower housing 268. As best shown in FIGS. 46 and 47, the proximally-directed surface 302 of the spine 300 engages the distally-directed surface 540 of the contact block 520. The engagement pivots the latch 522 about the pin 530 against the bias of the biasing element 532. The pivoting of the latch 522 disengages the abutment surface 538 of the latch 522 from the front surface 536 of the aperture 516. Thus, in certain implementations, the first operative position may be associated with or defined as the spine 300 engaging the lock assembly 304 and/or moving the sled lock assembly 304 from the locked configuration to the unlocked configuration. With the manifold 124 in the first operative position, the arms 284 may be at least partially positioned with the slots defining the push features 484, however, the proximally-directed surfaces 286 of the arms 284 may not be engaging the push features 484. Should, for example, purported arm(s) of an article engage the push features 484 prior the lock assembly 304 being moved to the unlocked configuration, insertion of the article may not be possible. Thus, the positioning and/or spacing of the proximally-directed surface 302 of the spine 300 in the proximal-to-distal direction relative to the rim 276 and/or the proximally-directed surfaces 286 of the arms 284 may be useful to prevent non-genuine articles from being used with the receiver 116. The locking assembly 310 may be considered to have moved from the default configuration to the unlocked configuration.

Figure 48:
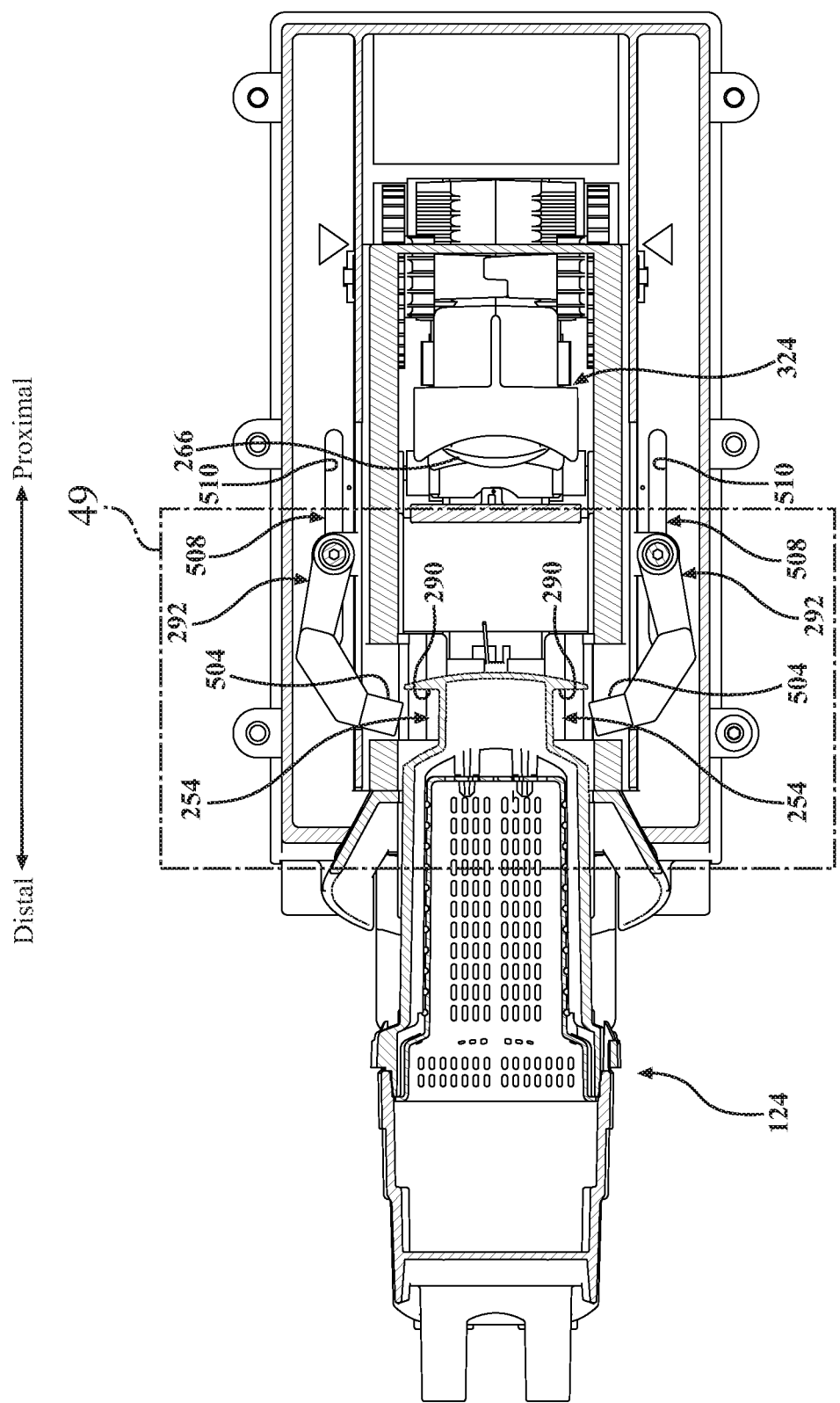
FIG. 48 is a sectional plan view of FIG. 46 taken along section lines 48-48.
Figure 49:
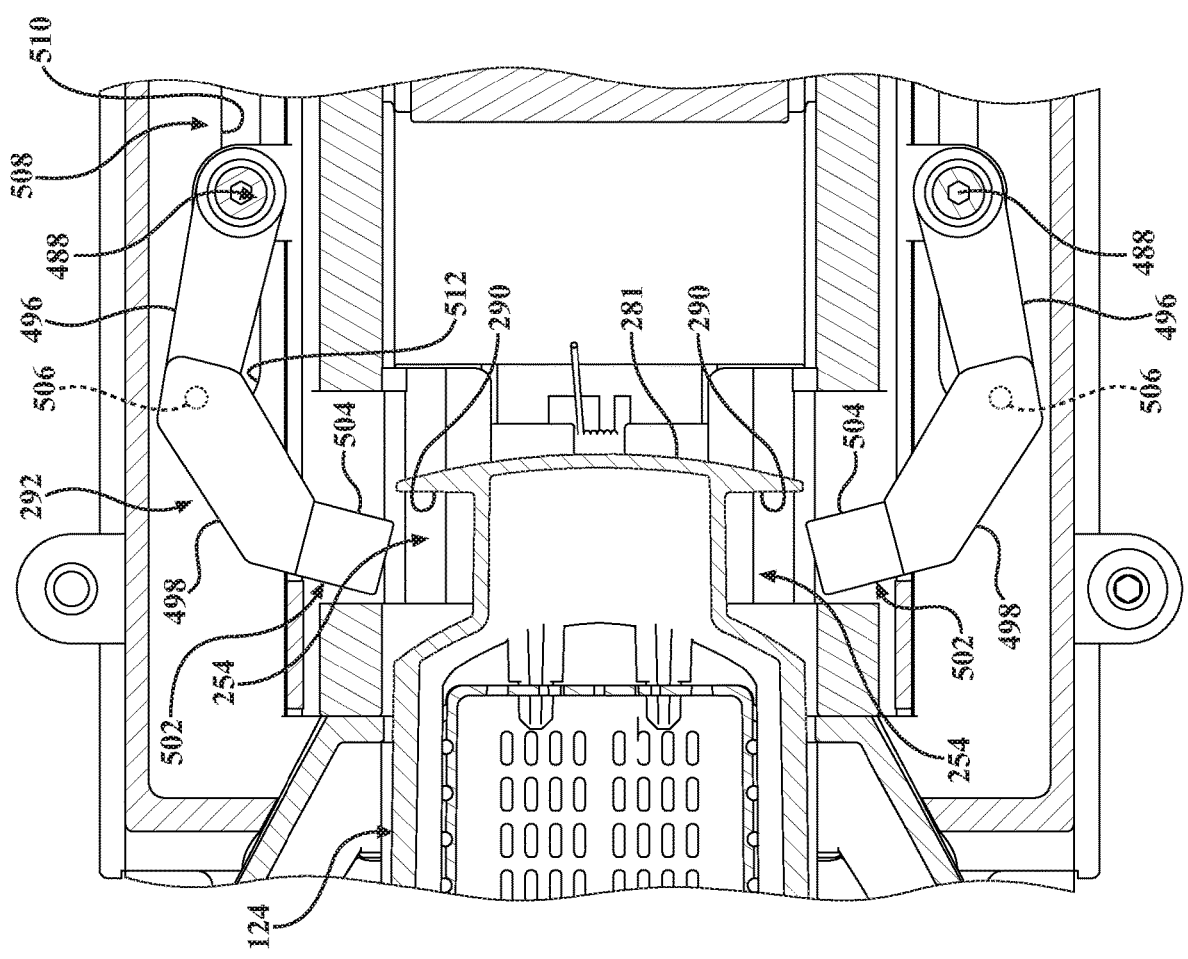
FIG. 49 is a detailed sectional elevation view of FIG. 48 within boundary 49-49.
Figure 50:
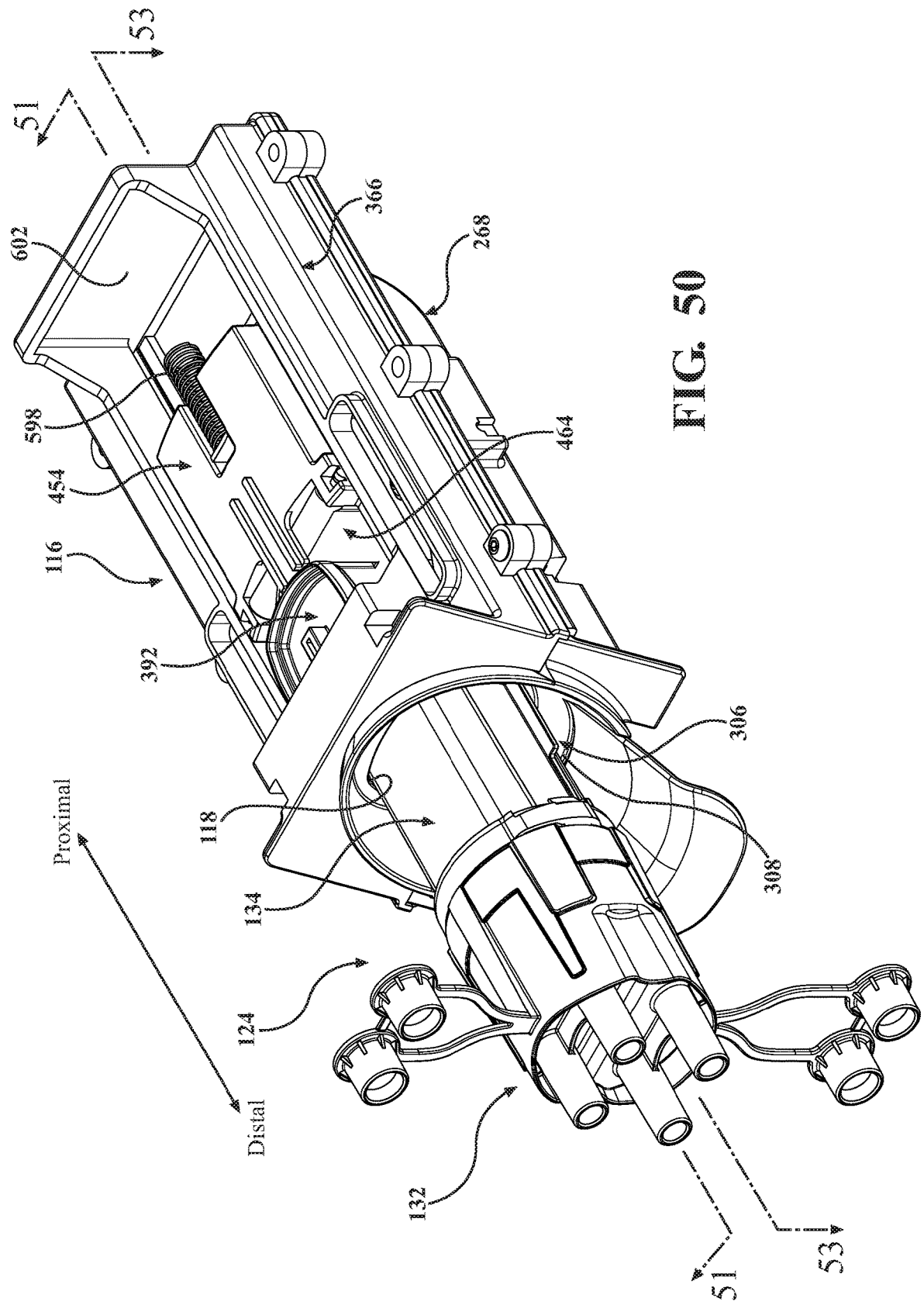
FIG. 50 is a perspective view of the manifold and the receiver in a second operative position.
Figure 51:
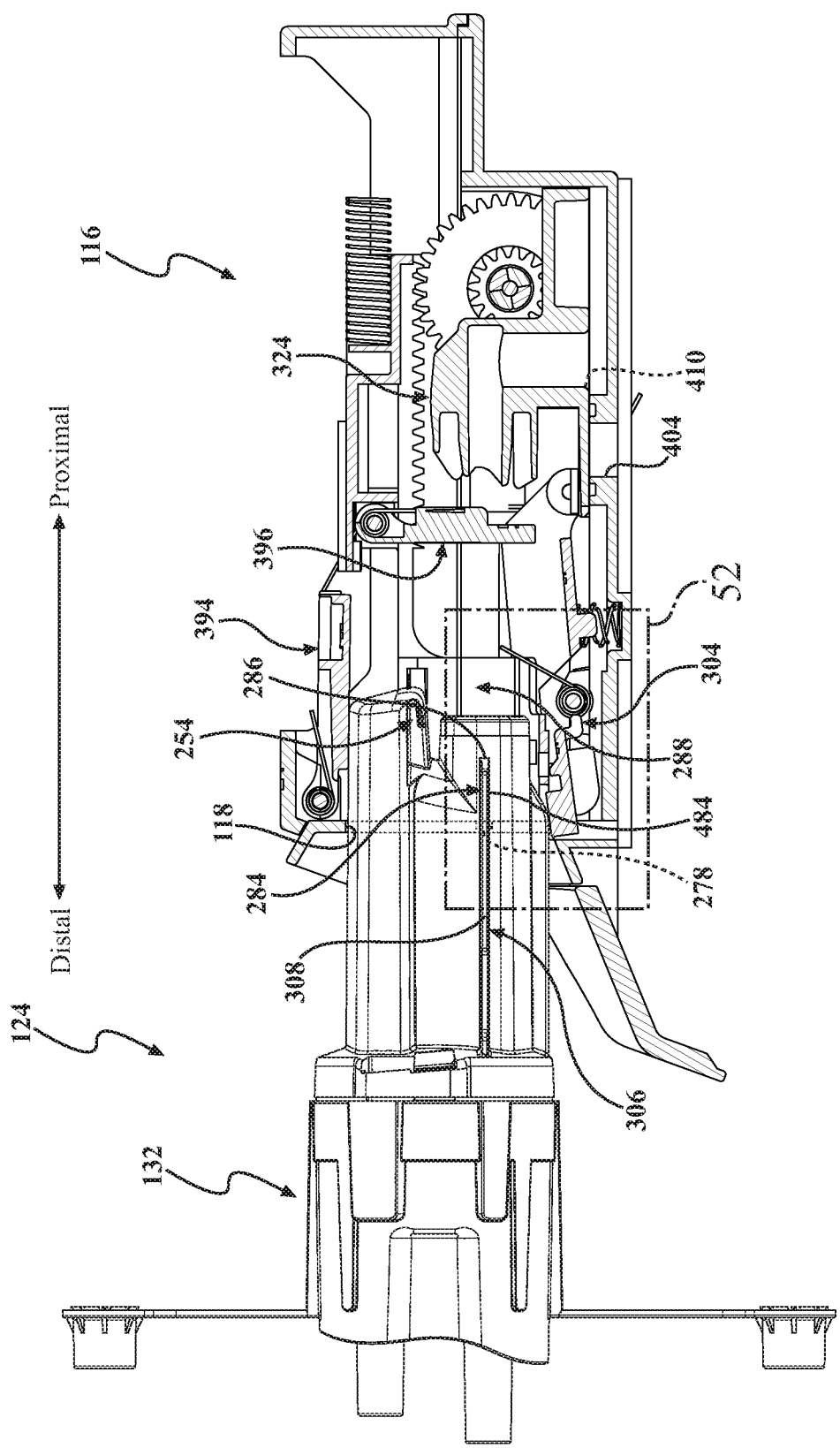
FIG. 51 is a sectional elevation view of the receiver of FIG. 50 taken along section lines 51-51 with the manifold shown in elevation.
Figure 52:
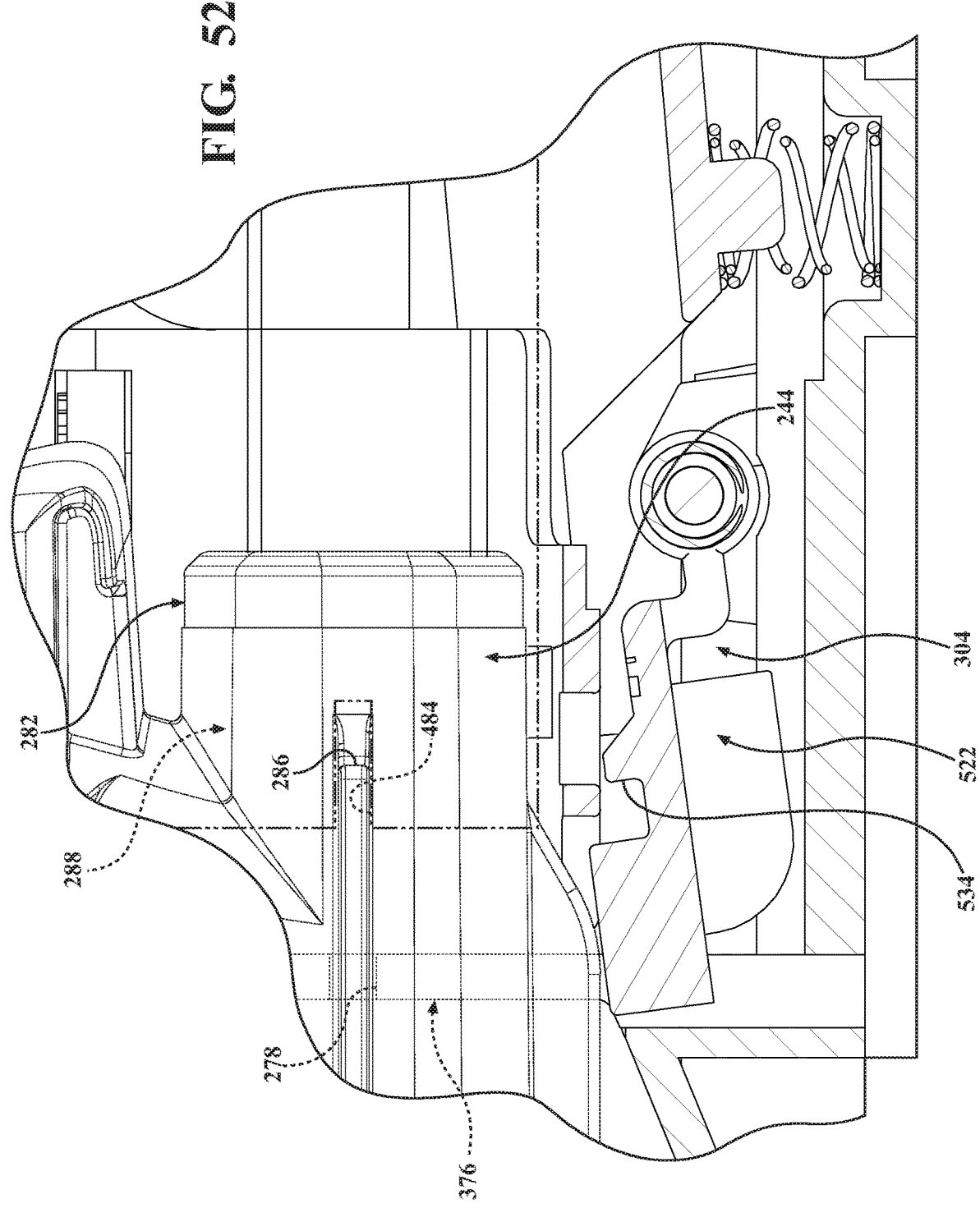
FIG. 52 is a detailed view of FIG. 51 within boundary 52.

Referring to the top plan views of FIGS. 48 and 49, with the manifold 124 in the first operative position, the claws 292 have yet to engage the catches 254. More particularly, the guides 506 may be positioned within the distal portion 512 of the tracks 508 of the lower housing 268 such that the third segment 502 of the claws 292, including the engagement surfaces 504, are laterally outward from the catches 254 of the manifold 124. The engagement surfaces 504 are not engaging the distally-directed surfaces 290 of the catches 254 in the first operative position. Further, in the first operative position, the sled assembly 288 may not have moved in the proximal direction, and thus the inlet mechanism 324 may not have moved in the distal direction in a corresponding manner. As a result, there may not be fluid communication between the suction outlet 410 and the receiver outlet 404, and any vacuum provided by the vacuum pump 110 does not extend to the suction inlet 266. The suction fitting 326 defining the suction inlet 266 is spaced apart from the seal 282 and/or the rim 276 in the proximal-to-distal direction.

FIGS. 50-54 show the manifold 124 at least partially inserted into the receiver 116 to a second operative position. The user may manipulate the manifold 124, for example, using the control surfaces 154 on the head 132, to move the manifold 124 from the first operative position to the second operative position. The second operative position may include the manifold 124 being positioned more proximal relative to the receiver 116 than the first operative position. The second operative position may be associated or defined as the arms 284 engaging the push features 484. The distance required to move the manifold 124 from the first operative position to the second operative position may be at least approximate a distance between the proximally-directed surface 302 of the spine 300 and the proximally-directed surfaces 286 of the arms 284 in the proximal-to-distal direction. With reference to FIG. 12, the distance may be at least substantially equal to the distance between plane S and plane A. In the second operative position, the sled assembly 288 may have yet to move in the proximal direction.

Figure 53:
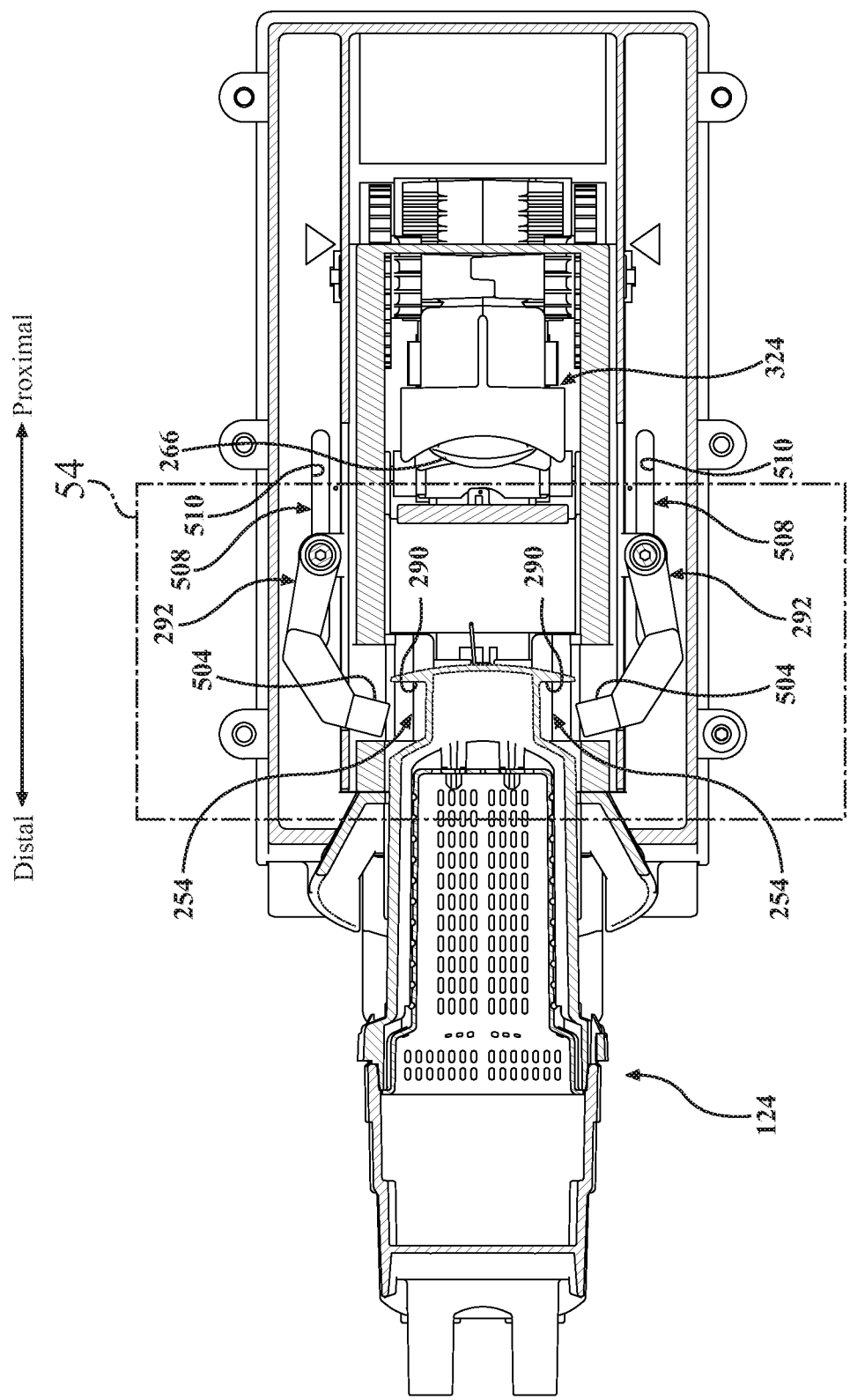
FIG. 53 is a sectional plan view of FIG. 50 taken along section lines 53-53.
Figure 54:
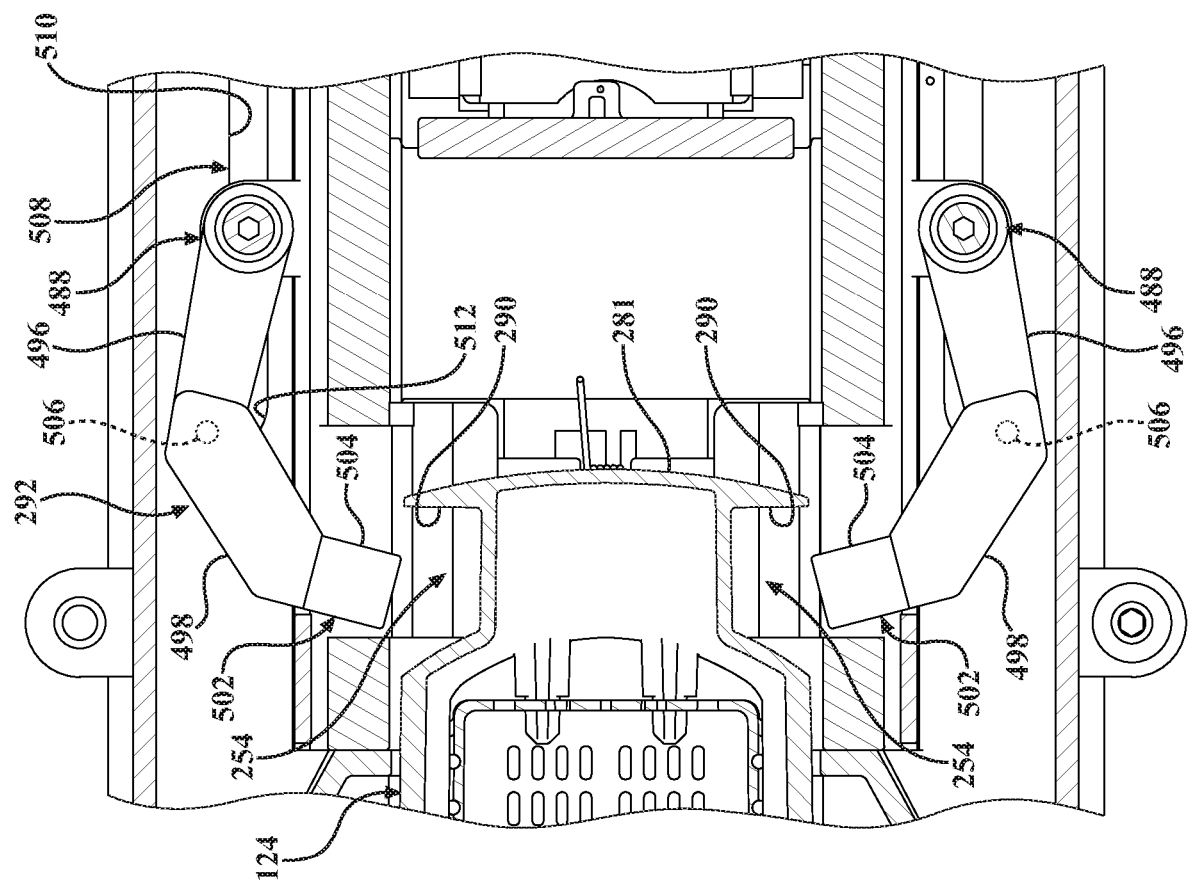
FIG. 54 is a detailed sectional elevation view of FIG. 53 within boundary 54.
Figure 55:
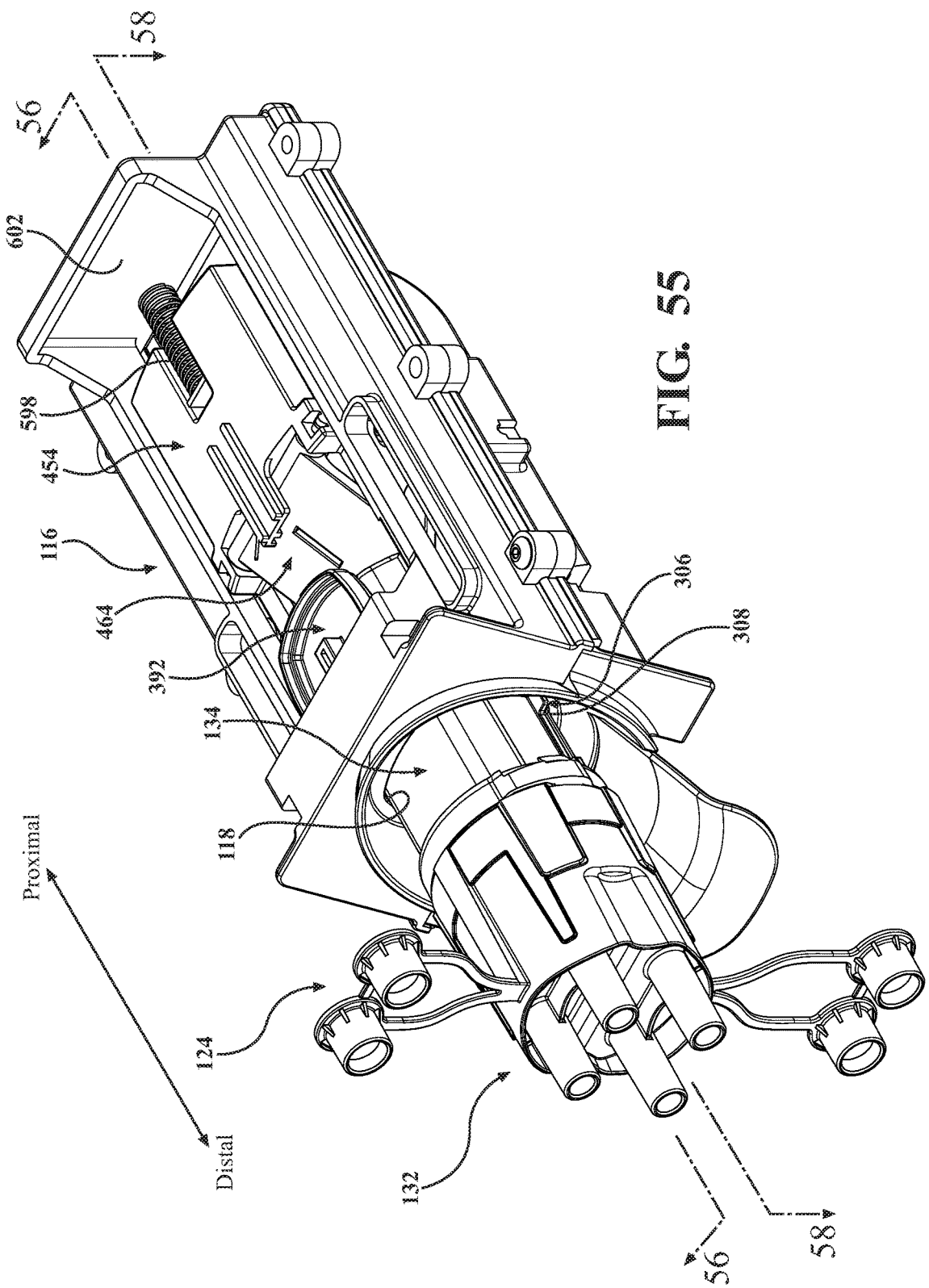
FIG. 55 is a perspective view of the manifold and the receiver in a third operative position.

With the manifold 124 and the receiver 116 in the second operative position, the sled lock assembly 304 remains in the unlocked configuration, as the latch 522 may slidably contact the downwardly-directed surface 320 of the spine 300. The locking assembly 310 may remain in the unlocked configuration, as the tracks 586 of the cradle may engage the levers 550 against the bias provided by the biasing element 580. Further, the top plan views of FIGS. 53 and 54 show the claws 292 have yet to engage the catches 254 in the second operative position, as the claws 292 remain laterally outward from the catches 254 of the manifold 124. Still further, in the second operative position, the inlet mechanism 324 may not have moved in the distal direction, and thus there may not be fluid communication between the suction outlet 410 and the receiver outlet 404. The suction fitting 326 remains spaced apart from the seal 282 and/or the rim 276 in the proximal-to-distal direction.

Figure 59:
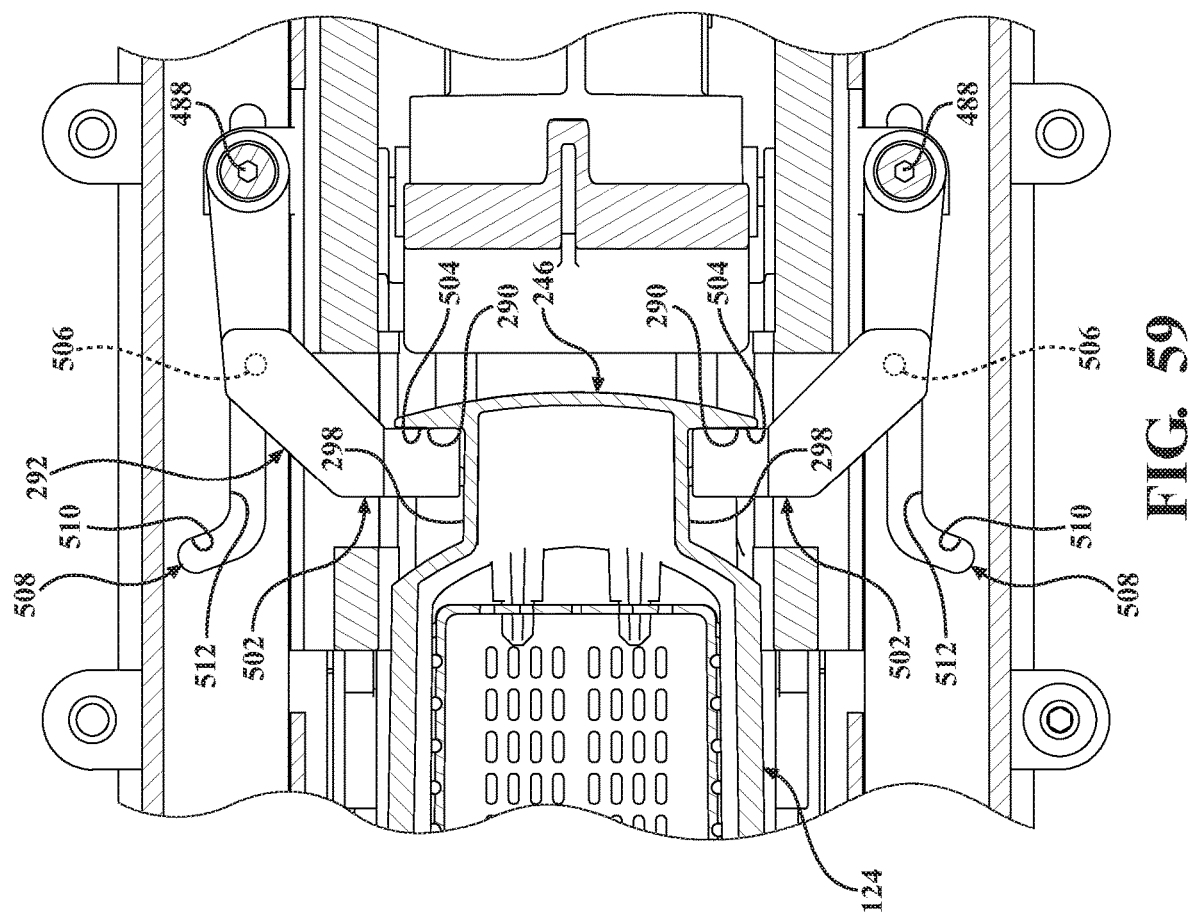
FIG. 59 is a detailed sectional elevation view of FIG. 58 within boundary 59.
Figure 60:
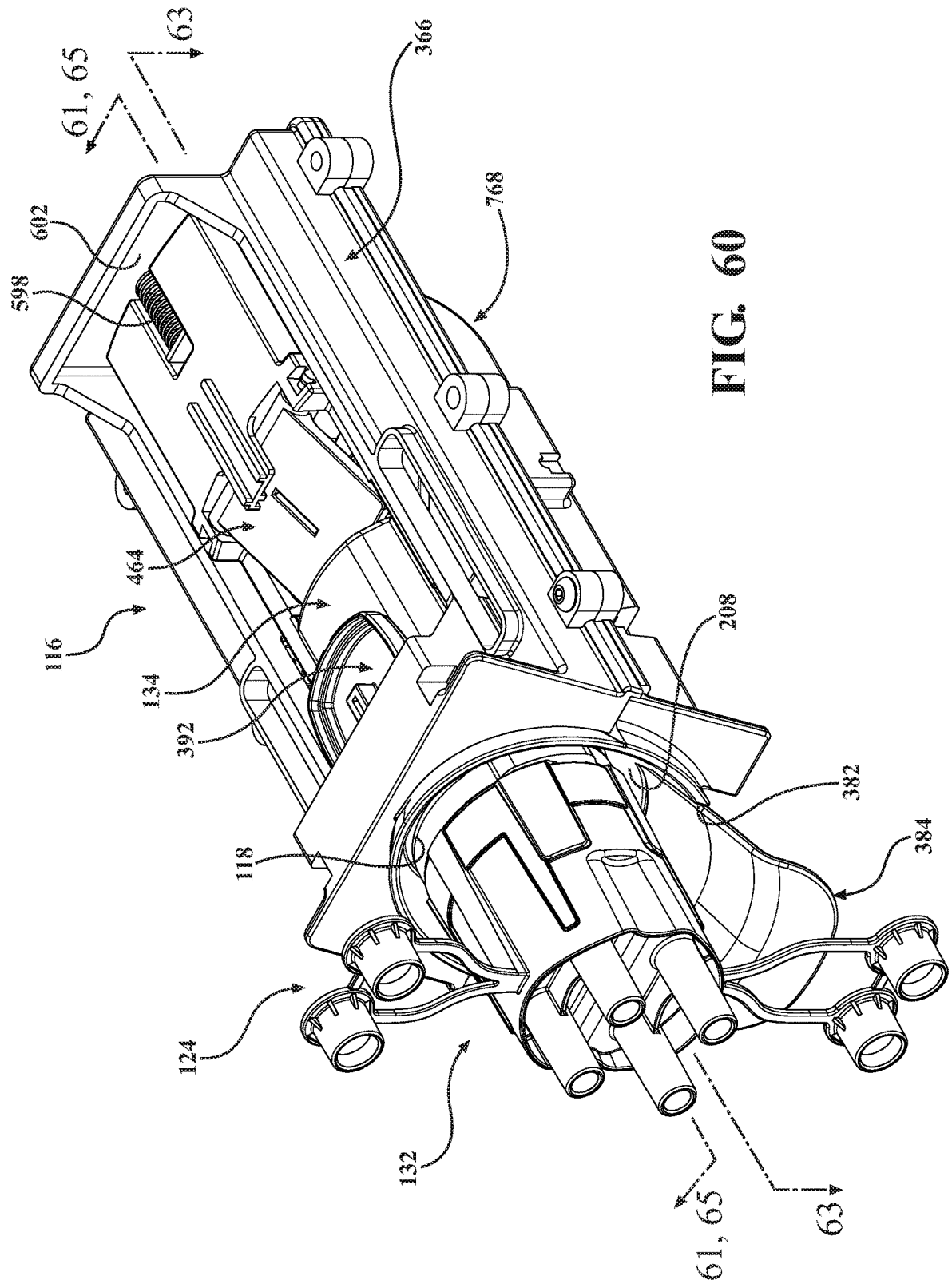
FIG. 60 is a perspective view of the manifold and the receiver in a fourth or fully inserted operative position.

FIGS. 55-59 show the manifold 124 at least partially inserted into the receiver 116 to a third operative position. The user may manipulate the manifold 124, for example, using the control surfaces 154 on the head 132, to move the manifold 124 from the second operative position to the third operative position. The third operative position may include the manifold 124 being positioned more proximal relative to the receiver 116 than the first and second operative positions. The third operative position may be associated or defined as the catches 254 of the manifold 124 being engaged by the claws 292 of the receiver 116, and more particularly the engagement surfaces 504 of the claws 292 being positioned adjacent to the distally-directed surfaces 290 of the catches 254. The distance required to move the manifold 124 from the second operative position to the third operative position may be at least approximate to a distance for the guides 506 of the claws 292 to move from the distal portions 510 of the tracks 508 to the proximal portions 512 of the tracks 508, thereby pivoting the claws 292 inwardly about the hinges 488. FIGS. 49 and 54 show the first and second operative positions, respectively, with the third segments 502 of the claws 292 positioned laterally outward from the catches 254 (and generally aligned with the third segments 502 of the claws 292 in the proximal-to-distal direction). The guides 506 of the claws 292 (shown in phantom) are positioned in the distal portions 510 of the tracks 508. As the manifold 124 is moved from the second operative position to the third operative position, the sled assembly 288 moves in the proximal direction. In particular, the proximally-directed surfaces 286 of the arms 284 are engaging the push features 484 of the sled assembly 288, and the user moving the manifold 124 in the proximal direction results in a corresponding movement of the sled assembly 288 in the proximal direction. As previously described, the claws 292 are coupled to the sled assembly 288 at the hinges 488. Thus, the movement of the sled assembly 288 in the proximal direction results in a corresponding movement of the claws 292 in the proximal direction. The distal portions 510 may extend laterally outward from the proximal portions 512, and thus the proximal portions 512 may be positioned laterally inward from the distal portions 510. As the claws 292 move in the proximal direction, the guides 506 pivot the claws 292 about the hinges 448 as the guides 506 follow the tracks 508 from the distal portions 510 to the proximal portions 512. FIG. 59 shows the guides 506 of the claws 292 (shown in phantom) positioned within the proximal portions 512 of the tracks 508. The inward pivoting may be to an extent that the engagement surfaces 504 of the claws 292 are positioned within the catches 254 and/or adjacent to the distally-directed surfaces 290 of the catches 254.

It is readily appreciated that moving the manifold 124 and the receiver 116 from the second operative position to the third operative position may require precise timing for the arms 284 to move the sled assembly 288 as the claws 292 pivoting inwardly to engage the catches 254. Should, for example, purported arms of an article engage the push features 484 with improperly positioned or absent catches, insertion of the article may not be possible. The receiver 116 may bind as the claws 292 may be prevented from pivoting inwardly to the extent necessary for the guides 506 to follow the tracks 508 of the receiver 116. Additionally or alternatively, should an article have improperly positioned or absent catches, returning the sled assembly 288 to the initial distal position as the manifold 124 is removed from the receiver 116 may not be possible. Subsequent operation of the medical waste collection system 100 may be compromised and/or subsequent insertion of another manifold into the receiver 116 may not be possible. Thus, the positioning and/or spacing of the catches 254 in the proximal-to-distal direction relative to the rim 276 and/or the proximally-directed surfaces 286 of the arms 284 may be useful to prevent non-genuine articles from being used with the receiver 116.

Figure 56:
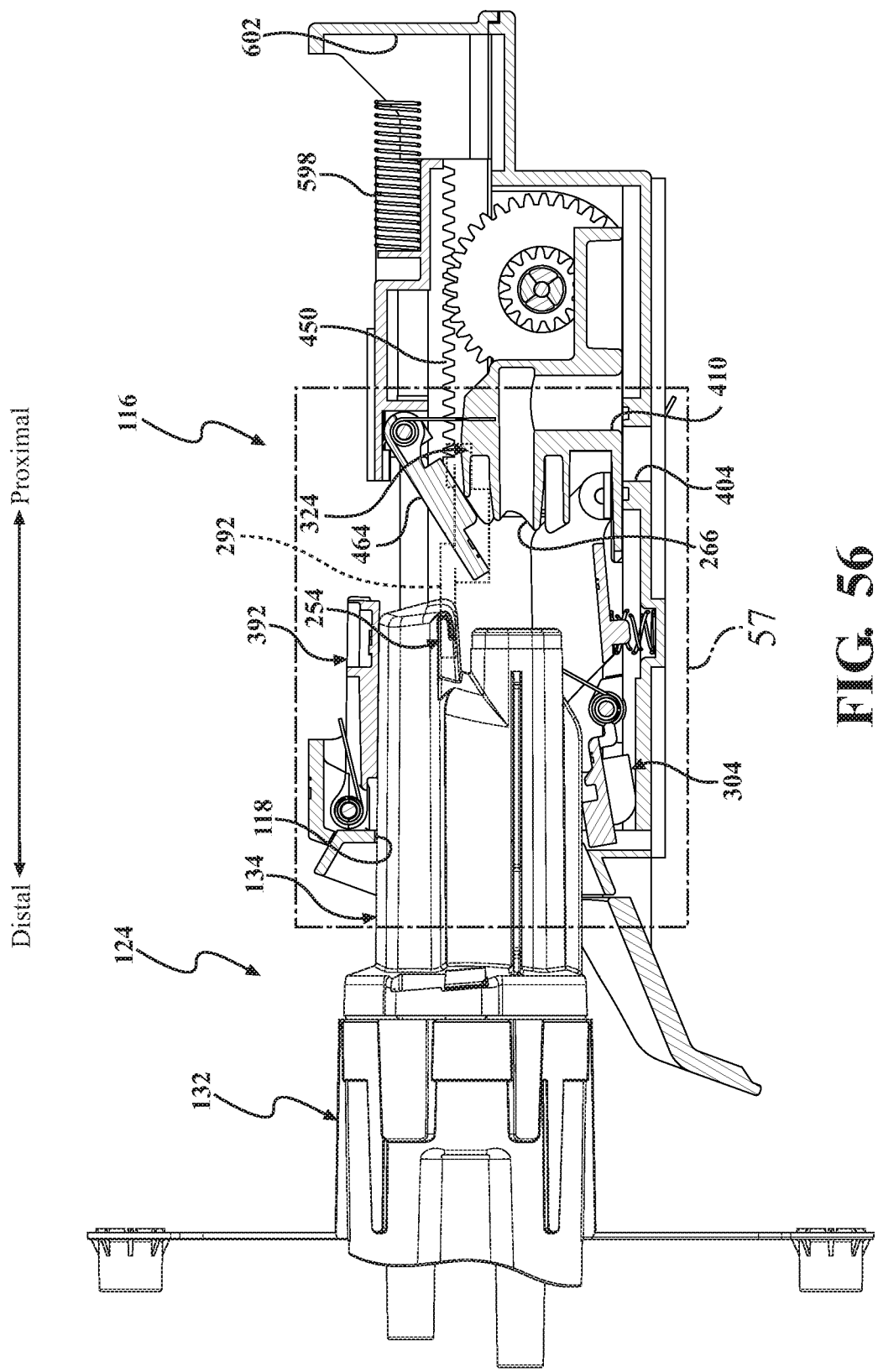
FIG. 56 is a sectional elevation view of the receiver of FIG. 55 taken along section lines 56-56 with the manifold shown in elevation.
Figure 57:
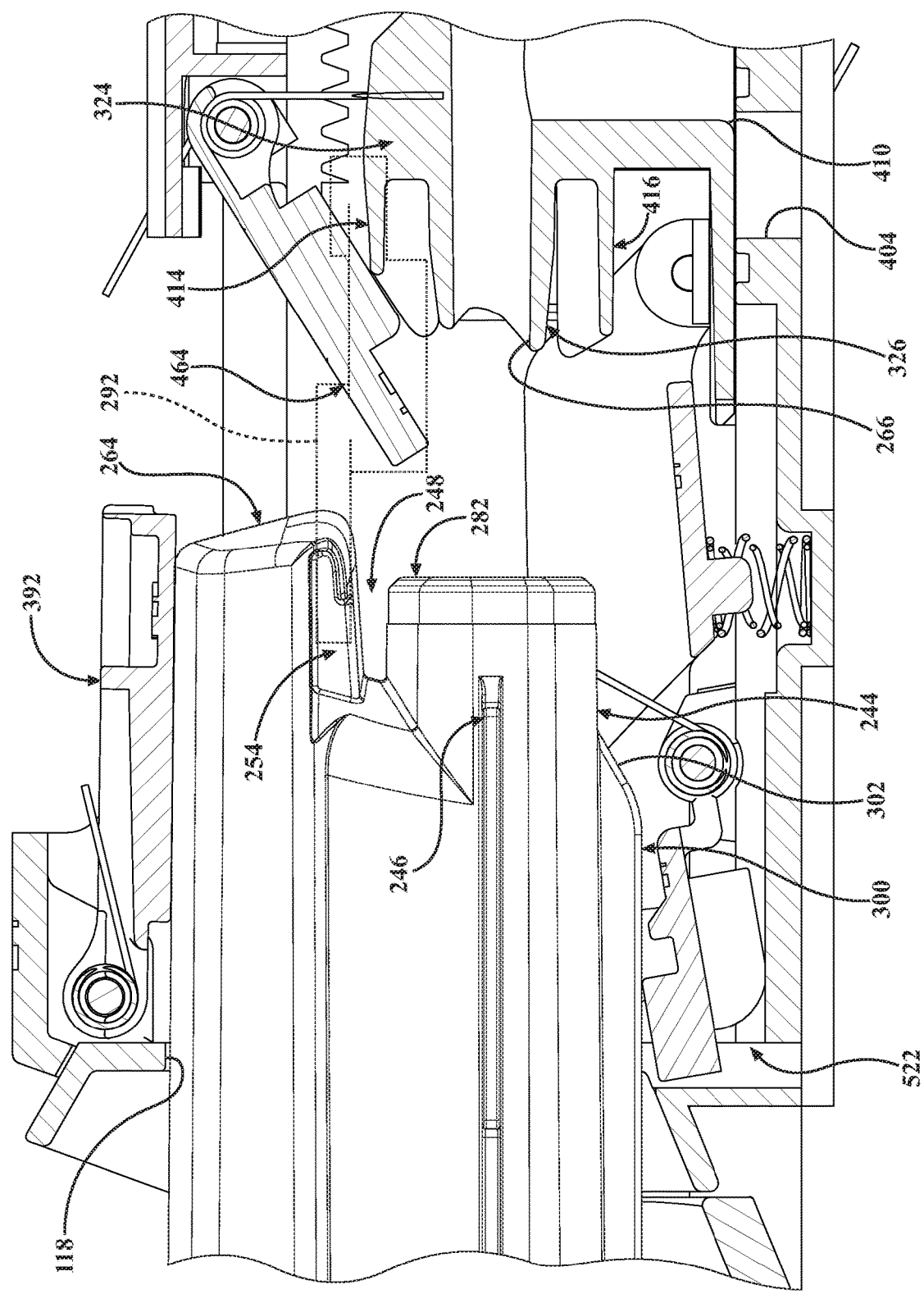
FIG. 57 is a detailed view of FIG. 56 within boundary 57.
Figure 58:
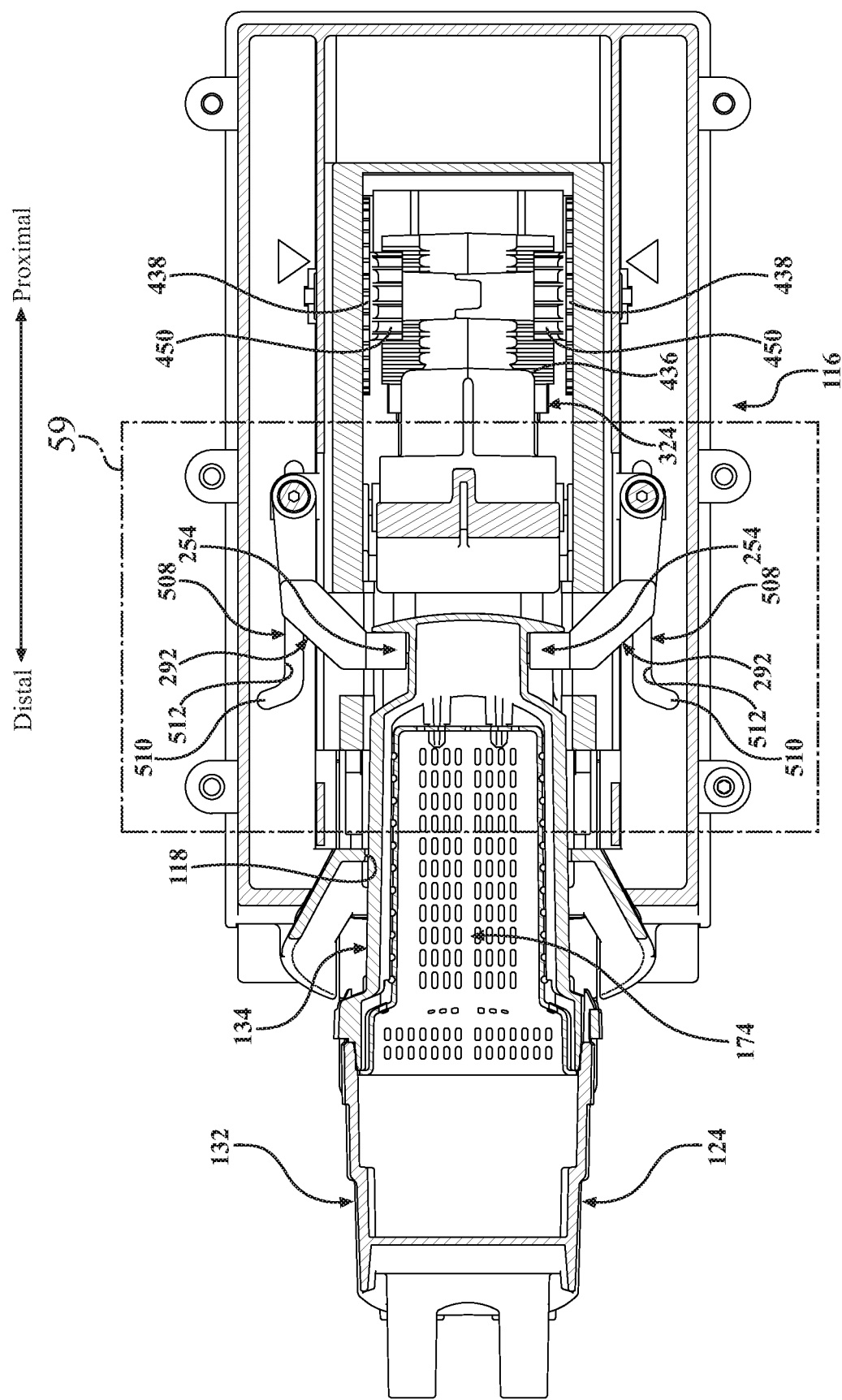
FIG. 58 is a sectional plan view of FIG. 55 taken along section lines 58-58.

With movement of the sled assembly 288 in the proximal direction as the manifold 124 is moved from the second operative position to the third operative position, the inlet mechanism 324 moves in the distal direction. The rack gears 450 of the sled assembly 288 translate with the movement of the sled assembly 288 to facilitate rotation of the output spur gears 448 and the input spur gears 446 of the transfer gears 438. The rotation of the input spur gears 446 impart translation to a respective one of the rack gears 436 of the inlet mechanism 324 in the distal direction. FIGS. 56 and 57 show the suction fitting 326 of the inlet mechanism 324 being closer to the outlet opening 242 of the manifold 124 relative to, for example, FIG. 46 showing the first operative position. The second barrier 464 may at least partially move from the closed configuration to the open configuration. The translation of the inlet mechanism 324 in the distal direction may engage the second barrier 464 to pivot the second barrier 464 about the pin 474 (see FIG. 57). The second barrier 464 may "ride up" the inlet mechanism 324 as the inlet mechanism 324 exits the cavity 470 defined by the roof 454. It is appreciated that suction fitting 326 remains spaced apart from the seal 282 and/or the rim 276 in the proximal-to-distal direction. Furthermore, with the movement of the inlet mechanism 324 in the distal direction, the suction outlet 410 of the inlet mechanism 324 moves towards alignment with the receiver outlet 404. FIG. 57 shows the suction outlet 410 nearing fluid communication with the receiver outlet 404. For the most part, the suction path at the interface between the suction outlet 410 and the receiver outlet 404 remains broken such that any vacuum provided by the vacuum pump 110 does not meaningfully extend to the suction inlet 266.

With the manifold 124 and the receiver 116 in the third operative position, the sled lock assembly 304 remains in the unlocked configuration, as the latch 522 may slidably contact the downwardly-directed surface 320 of the spine 300. The locking assembly 310 may remain in the unlocked configuration, as the tracks 586 of the cradle may engage the levers 550 against the bias provided by the biasing element 580. The free end of the biasing element 598 may remain spaced apart from the rear barrier 602 with the biasing element 598 in the natural or unstressed state.

FIGS. 60-64 show the manifold 124 inserted into the receiver 116 to a fourth operative position, also referred to herein as the fully inserted operative position. The user may manipulate the manifold 124, for example, using the control surfaces 154 on the head 132, to move the manifold 124 from the third operative position to the fourth operative position. The fourth operative position may include the manifold 124 being positioned more proximal relative to the receiver 116 than the first, second, and third operative positions. The fourth operative position may be associated with or defined as the suction fitting 326 coupling with the outlet opening 242 to establish fluid communication between the manifold volume 130 and the suction inlet 266. Additionally or alternatively, the fourth operative position may be associated with or defined as the suction fitting 326 extending through the outlet opening 242. Additionally or alternatively, the fourth operative position may be associated with or defined as the suction outlet 410 being in fluid communication with the receiver outlet 404. Additionally or alternatively, the fourth operative position may be associated with or defined as the locking assembly 310 moving from the unlocked configuration to the locked configuration to engage the lock elements 306 of the manifold 124 and retain the manifold 124 in the proximal-to-distal direction, for example, against the bias provided by the biasing element 598.

Figure 62:
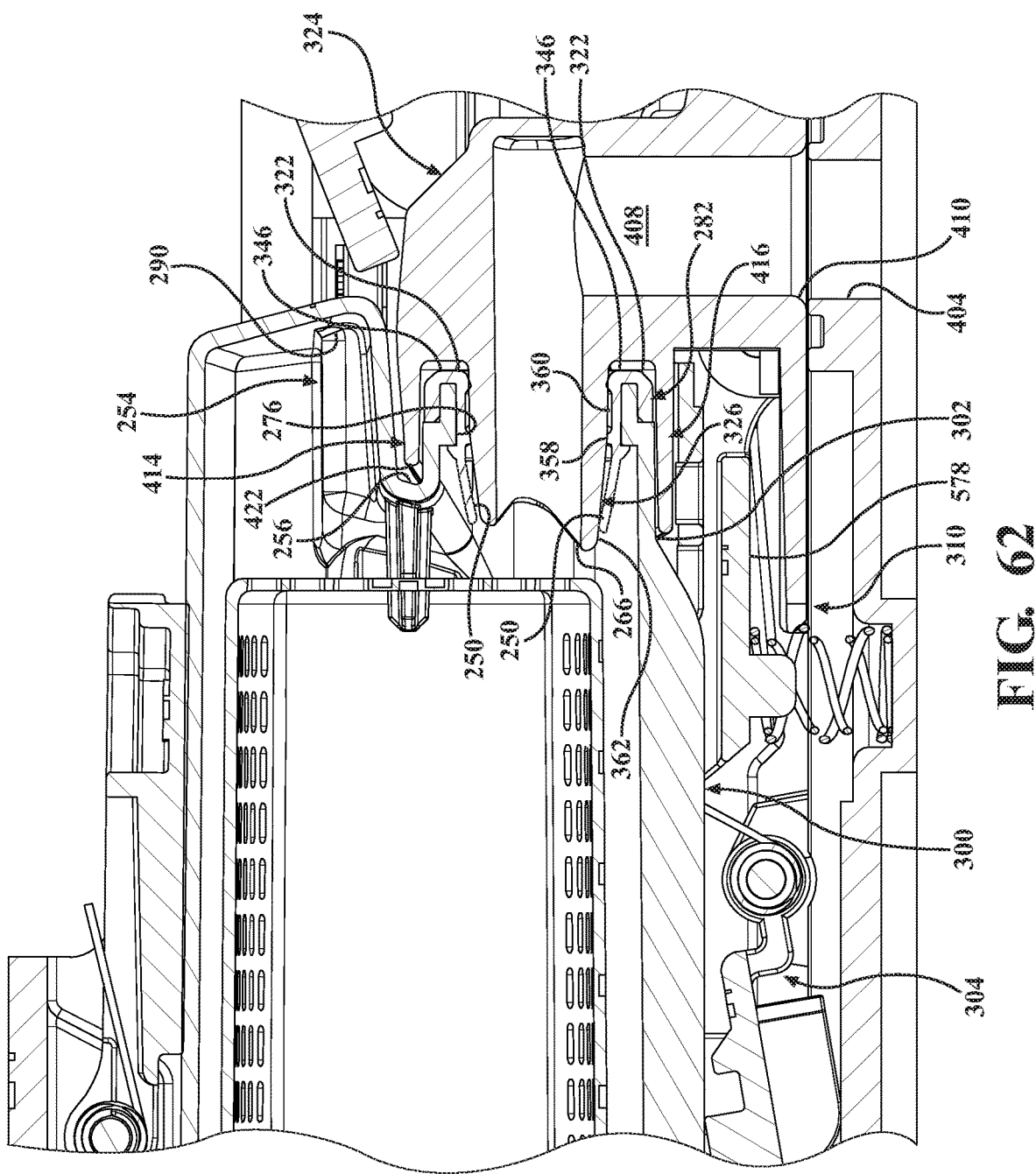
FIG. 62 is a detailed sectional elevation view of FIG. 61 within boundary 62.
Figure 63:
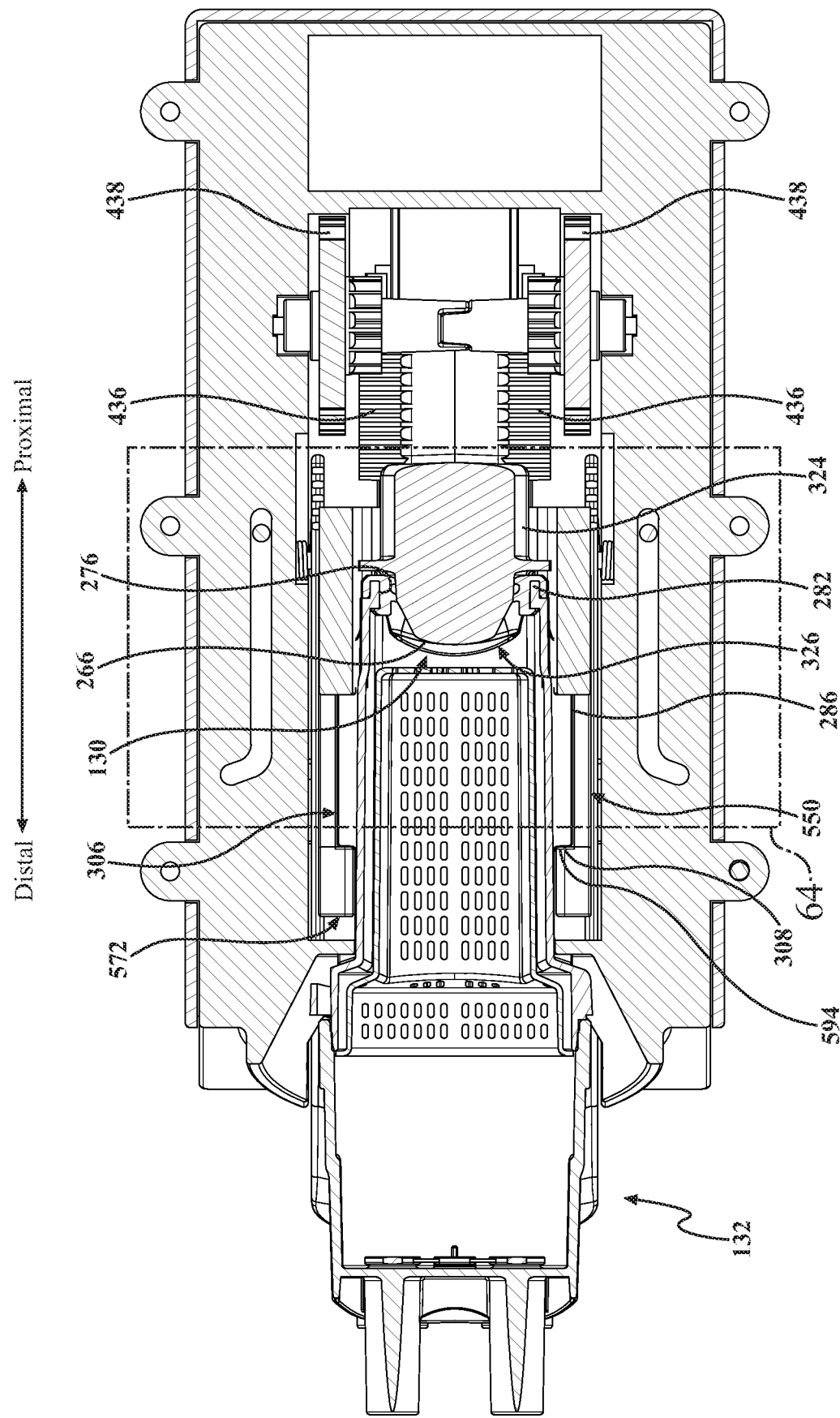
FIG. 63 is a sectional plan view of FIG. 60 taken along section lines 53-53.
Figure 64:
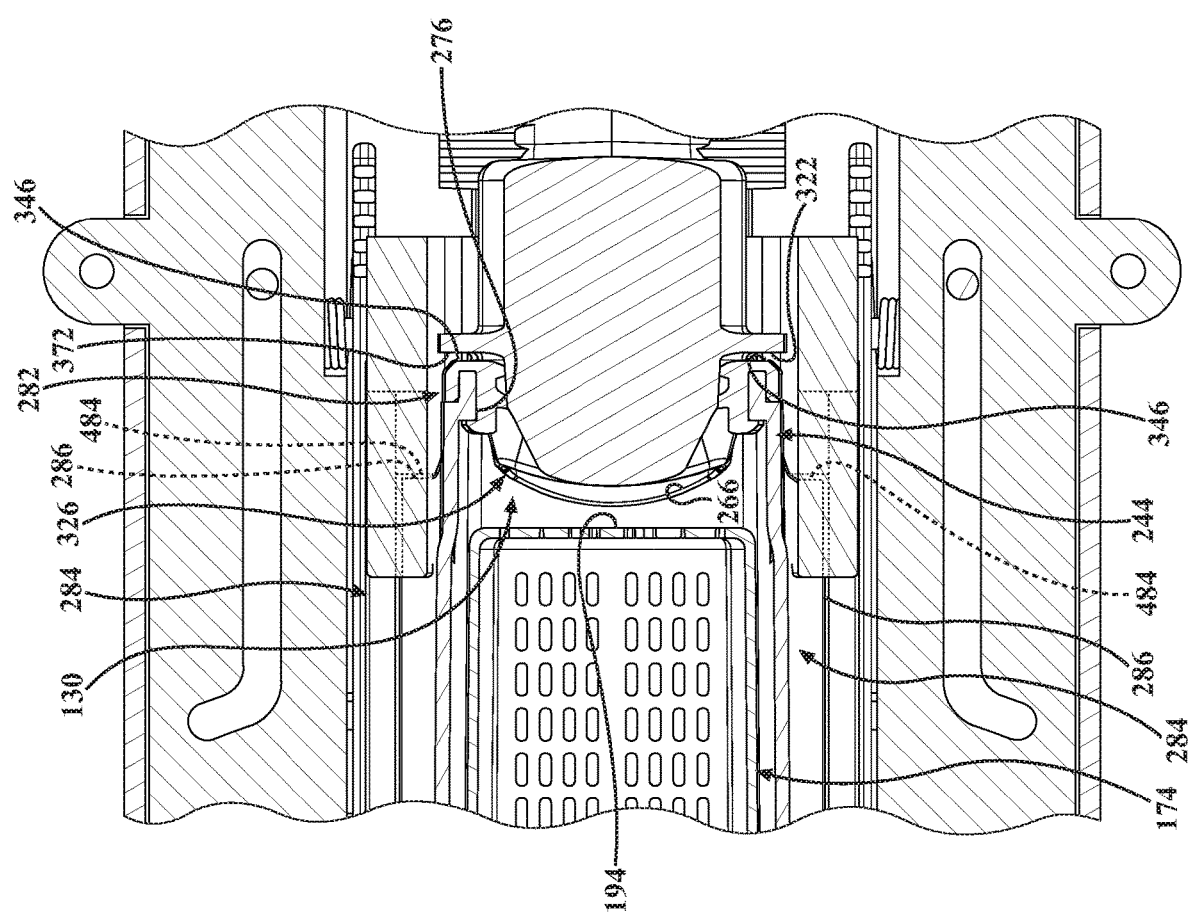
FIG. 64 is a detailed sectional elevation view of FIG. 63 within boundary 64.

As the manifold 124 is moved the proximal direction, the proximally-directed surfaces 248 continue to engage the push features 484 of the sled assembly 288, and the movement of the manifold 124 in the proximal direction results in the corresponding movement of the sled assembly 288 in the proximal direction. As previously described, the translation of the rack gears 450 of the sled assembly 288 facilitate rotation of the transfer gears 438, and rotation of the transfer gears 438 facilitate translation of the rack gears 436 of the inlet mechanism 324 in the distal direction. The inlet mechanism 324 and the manifold 124 move towards one another, and the suction fitting 326 of the inlet mechanism 324 may extend through the rim 276 defining the outlet opening 242 to establish fluid communication between the manifold volume 130 and the suction inlet 266. As best shown in FIGS. 62 and 64, the suction fitting 326 assumes a position within the manifold volume 130 at least partially defined by the first leg 244. In certain implementations, the suction fitting 326 penetrates the seal 282. In other implementations to be described, the suction fitting 326 abuts the seal 282 (see FIG. 102). The flaps 350 generally conform to the outer surface 362 of the suction fitting 326 to provide the aforementioned radial seal, and the radial sealing surface 358 may prevent the egress of any waste material collected in the annular pocket 360. Further, the sealing surface 346 of the seal 282 may be in abutment with the sealing surface 322 of the inlet mechanism 324 to provide the aforementioned face seal.

With the manifold 124 and the receiver 116 in the fourth operative position, the first support element 414 may be seated or nestled within the void 248 defined between the first and second legs 244, 246 of the manifold 124. FIG. 62 best shows the distal edge 422 of the first support element 414 positioned adjacent to the distal aspect 256 at least partially defining the void 248. Further, the second support element 416 may be adjacent the lower aspect of the first leg 244 and positioned in the proximal-to-distal direction between the proximally-directed surface 302 of the spine 300 and the rim 276. The second support element 416 may cooperate with the first support element 414 to facilitate ensuring that the manifold 124 is inserted to the proper insertion depth and/or supporting the manifold 124 within the receiver 116 in the fourth operative position.

Figure 61:
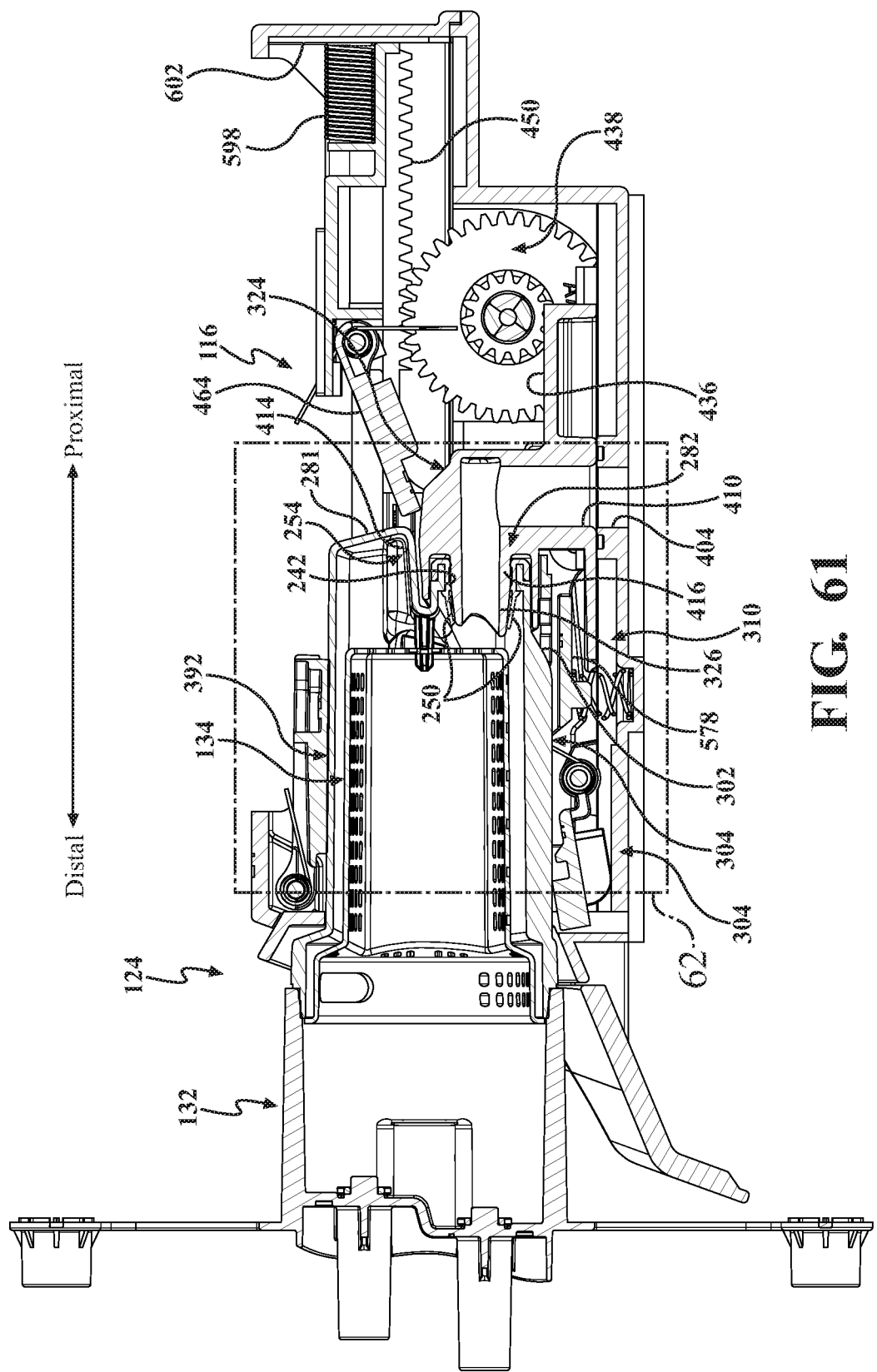
FIG. 61 is a sectional elevation view of FIG. 60 taken along section lines 61-61.

The movement of the inlet mechanism 324 in the distal direction, the suction outlet 410 of the inlet mechanism 324 is aligned with the receiver outlet 404, as best shown in FIGS. 61 and 62. The suction path at the interface between the suction outlet 410 and the receiver outlet 404 is established such that the vacuum provided by the vacuum pump 110 extends to the suction inlet 266 and into the manifold volume 130 (and thus to the suction tube(s) 120 that may be coupled to the manifold 124).

With the manifold 124 and the receiver 116 in the fourth operative position, the locking assembly 310 may move the unlocked configuration to the locked configuration. With further reference to FIG. 65, the locking assembly 310 of the receiver 116 engages the distally-directed surfaces 308 of the lock element 306 to selectively prevent distal movement of the manifold 124 relative the receiver 116. The biasing element 580 may urge the levers 550 of the locking member 546 (shown in phantom) to pivot upwardly about the pins 558 to maintain engagement with the tracks 586 of the cradle 452 of the sled assembly 288. As a result, the feet 572 disposed at or near a distal end of the levers 550 are biased into engagement with a lower surface of the arms 284 as the manifold 124 is moving from the third operative position to the fourth operative position. Owing to the surfaces 588 generally sloping downwardly, once the locking element 306 is positioned proximal to the feet 572, the biasing element 580 may urge the levers 550 of the locking member 546 to pivot upwardly to position the locking surfaces 594 adjacent to the distally-directed surfaces 308 of the manifold 124. The interference engagement of the locking surfaces 594 with the distally-directed surfaces 308 selectively prevents distal movement of the manifold 124 relative the receiver 116. The free end of the biasing element 598 may engage the rear barrier 602, and the biasing element 598 may assume the deformed or stressed state with a tendency to urge the manifold 124 distally relative to the receiver 116, and the lock assembly 310 being in the locked configuration prevents such relative distal movement.

With the manifold 124 and the receiver 116 in the fourth operative position, the engagement surfaces 504 of the claws 292 remain positioned within the catches 254 and/or adjacent to the distally-directed surfaces 290 of the catches 254. Further, the sled lock assembly 304 remains in the unlocked configuration, as the latch 522 may slidably contact the downwardly-directed surface 320 of the spine 300.

It is readily appreciated that moving the manifold 124 and the receiver 116 from the third operative position to the fourth operative position may require precise timing for the suction fitting 326 to extend through the outlet opening 242 (e.g., the sealing surface 346 of the seal 282 being in abutment with the sealing surface 322 and/or the first support element 414 being at least partially positioned within the void 248) with the locking assembly 310 engaging the lock element 306 of the manifold 124 in the locked configuration. Should, for example, an article lack properly positioned lock features and features defining a void, full insertion of the article may not be possible. Without full insertion, for example, the sled assembly 288 may assume a position in the proximal-to-distal direction insufficient to permit operation of the medical waste collection system 100 (e.g., a controller 122 may prevent operation of the vacuum pump 110). Thus, the positioning, dimensions, and/or spacing of the first leg 244, the second leg 246, the void 248, the rim 276, and/or the lock elements 306 may be useful to prevent non-genuine articles from being used with the receiver 116.

Figure 66:
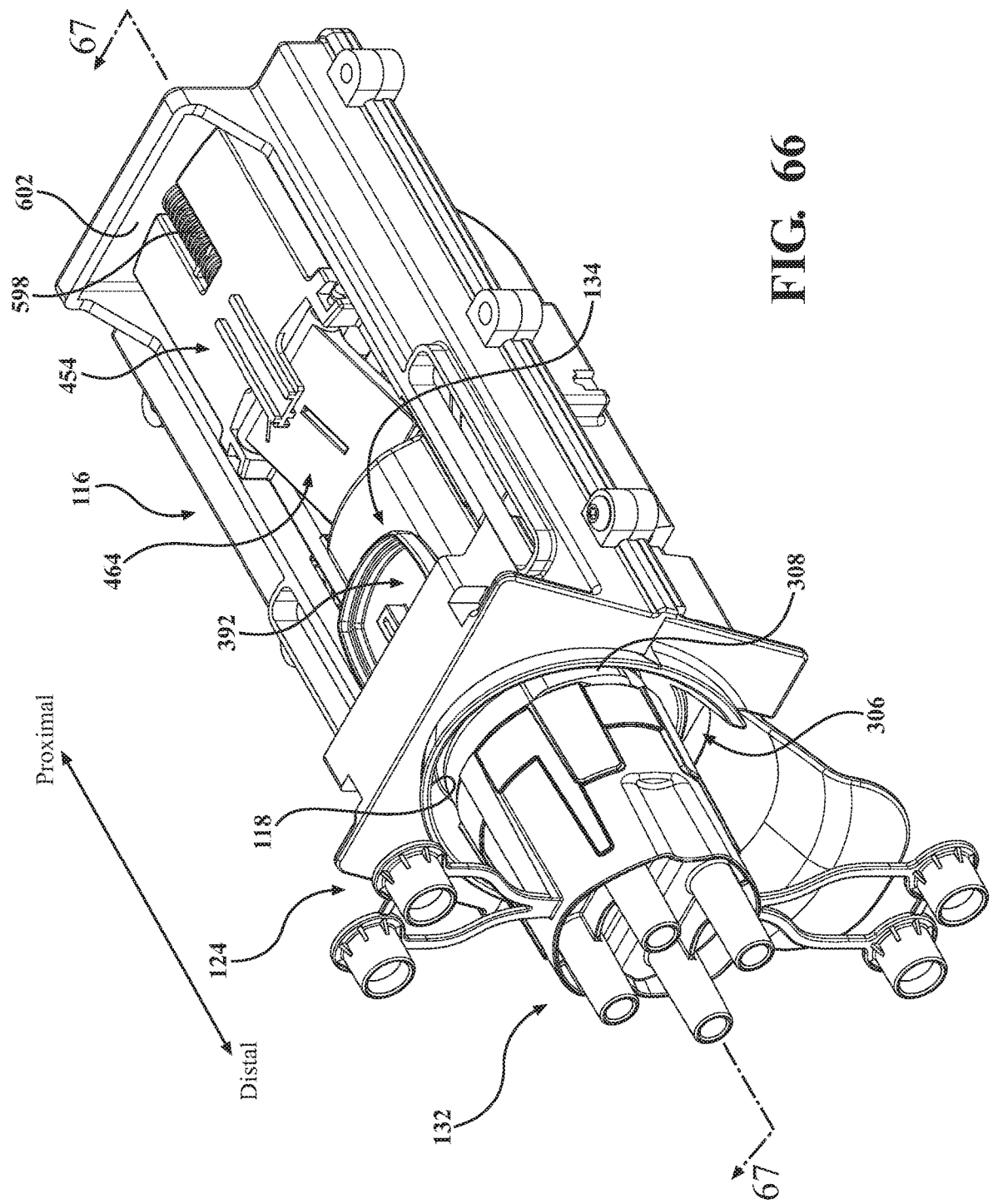
FIG. 66 is a perspective view of the manifold and the receiver with the locking assembly in the unlocked configuration.
Figure 67:
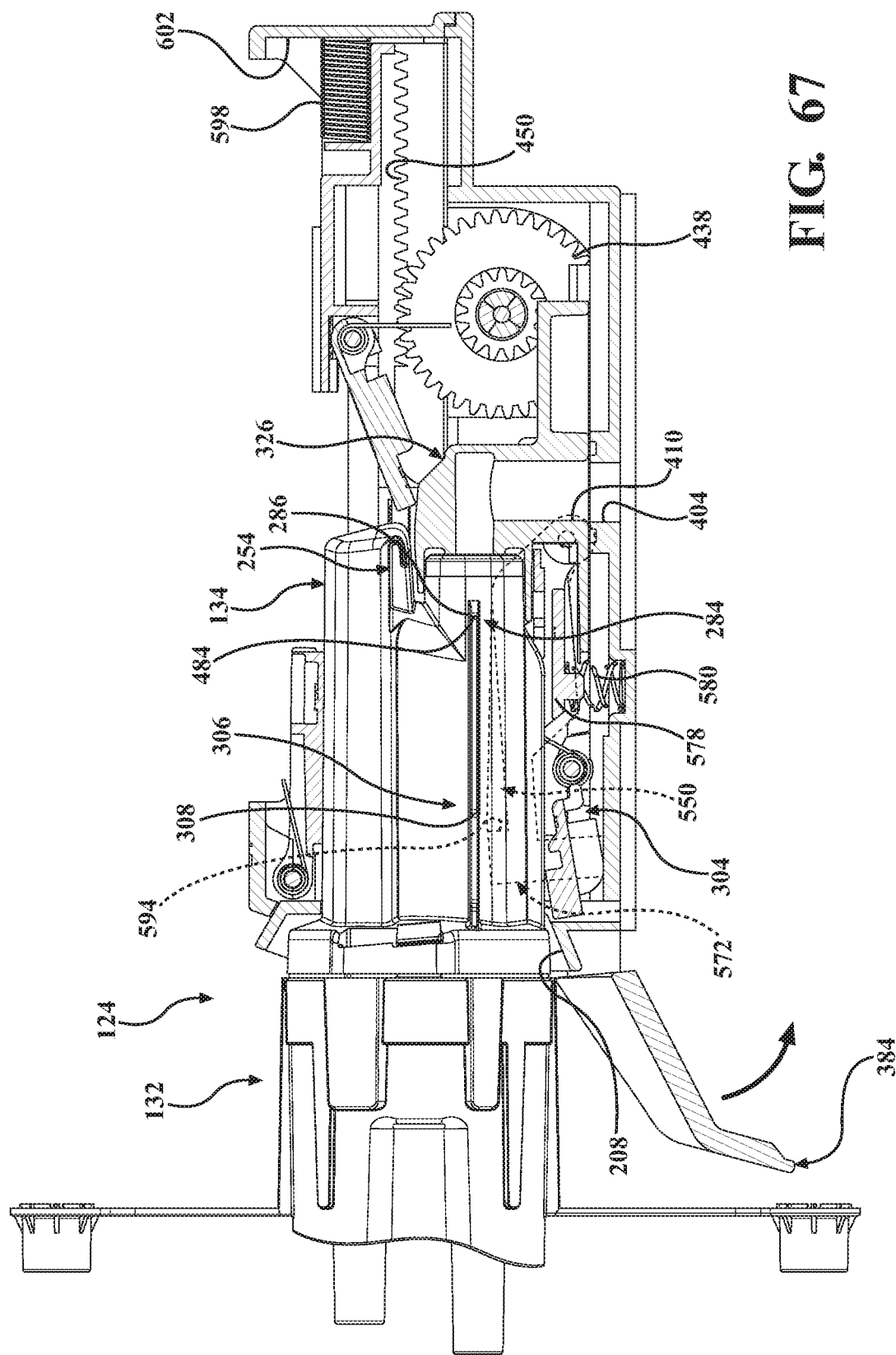
FIG. 67 is a sectional elevation view of the receiver of FIG. 66 taken along section lines 67-67 with the manifold shown in elevation.

The locking assembly 310 may be actuated by the user to be moved from the locked configuration to the unlocked configuration in which distal movement of the manifold 124 relative to the receiver 116 is permitted. Referring now to FIGS. 66 and 67, the input may be provided to the tongue 384 such as depressing the tongue 384. FIG. 66 shows a gap 604 between the tongue 384 and the recess 382 of the brim 208 with the gap indicative that the tongue 384 is depressed in an actuated state. As previously described, the input to the tongue 384 pivots the release member 544 downwardly against the bias provided by the biasing elements 564, which results in a corresponding downward pivoting of the locking member 546 against the bias provided by the biasing element 580. The downward pivoting of the levers 550 may disengage the locking surfaces 594 from the distally-directed surfaces 308 of the lock element 306 of the manifold 124, and distal movement of the manifold 124 relative to the receiver 116 is thereby permitted. With the locking assembly 310 no longer constraining distal movement of the manifold 124 relative to the receiver 116, the biasing element 598 may release the potential energy stored in the deformed or stressed state, and the manifold 124 (and the sled assembly 288) may move in the distal direction. The movement of the sled assembly 288 in the distal direction results in movement of the inlet mechanism 324 in the proximal direction, and thus suction path at the interface between the suction outlet 410 and the receiver outlet 404 may be almost immediately broken upon actuating the locking assembly 310 to the unlocked configuration.

The manifold 124 may be removed from the receiver 116 in a manner at least similar to a reverse of the aforementioned first through fourth operative positions. The user may manipulate the manifold 124, for example, using the control surface 154 on the head 132, to move the manifold 124 in the distal direction. As the manifold 124 is moved in the distal direction, the distally-directed surfaces 290 of the catches 254 engage the engagement surfaces 504 of the claws 292 such that the sled assembly 288 is moved in the distal direction in a corresponding manner. The guides 506 of the claws 292 prevent the claws 292 from pivoting about the hinges 488 while the guides 506 are slidably moving within the proximal portion 510 of the tracks 508. The suction fitting 326 exits the seal 282 and the rim 276 that defines that outlet opening 242. The interference engagement between the seal 282 and the rim 276 may prevent the seal 282 from being decoupled during removal of the suction fitting 326 from the outlet opening 242. The close tolerancing of the first and second support elements 414, 416 of the inlet mechanism 324 may further assist with preventing the decoupling of the seal 282 from the rim 276. The lip 340 of the seal 282 engaging the interior step 338 of the first leg 244 may even further assist with preventing the decoupling of the seal 282 from the rim 276. The guides 506 of the claws 292 assume position within the distal portions 512 of the tracks 508, and the claws 292 pivot laterally outward about the hinges 488 (see FIG. 54). Further removal of the manifold 124 disengages the arms 284, from the pushing features 484 of the sled assembly 288, and still further removal of the manifold 124 positions the proximally-directed surface 302 of the spine 300 distal to the contact block 520 of the sled lock assembly 304. The biasing element 532 of the sled lock assembly 304 urges the latch 522 to pivot upwardly about the pin 530 such that the front surface 534 of the key 524 is in engagement with a front surface 536 at least partially defining the aperture 516, and the sled lock assembly 304 returns to the locked configuration. A subsequent manifold 124 may be inserted into the receiver 116 as desired. Throughout the period the manifold 124 is being removed and/or replaced, the suction path at the interface between the suction outlet 410 and the receiver outlet 404 remains broken such that any vacuum provided by the vacuum pump 110 does not meaningfully extend to the suction inlet 266.

Referring now to FIGS. 68-73, an implementation of the inverted trunk 134' of the manifold 124 is shown in which the first leg 244' is positioned above the second leg 246' with certain structures located in a corresponding manner. In many respects, the inverted trunk 134' may be similar to that previously described with like numerals (plus a prime symbol (')) corresponding to like components, and any disclosure common to the corresponding components may be considered omitted in the interest of brevity should not be construed as limiting. It should be understood that complementary components on the receiver 116 may be modified in an appropriate manner to permit the inverted trunk 134' to be inserted into and removed from the receiver 116 in the manners previously described. Further, it should be understood that, while discussed in the context of the inverted trunk 134', which may be integrated with or coupled to any suitable head, for example the head 132 previously described, the disclosure may be applicable to the housing 128 and/or the manifold 124 more generally.

Figure 68:
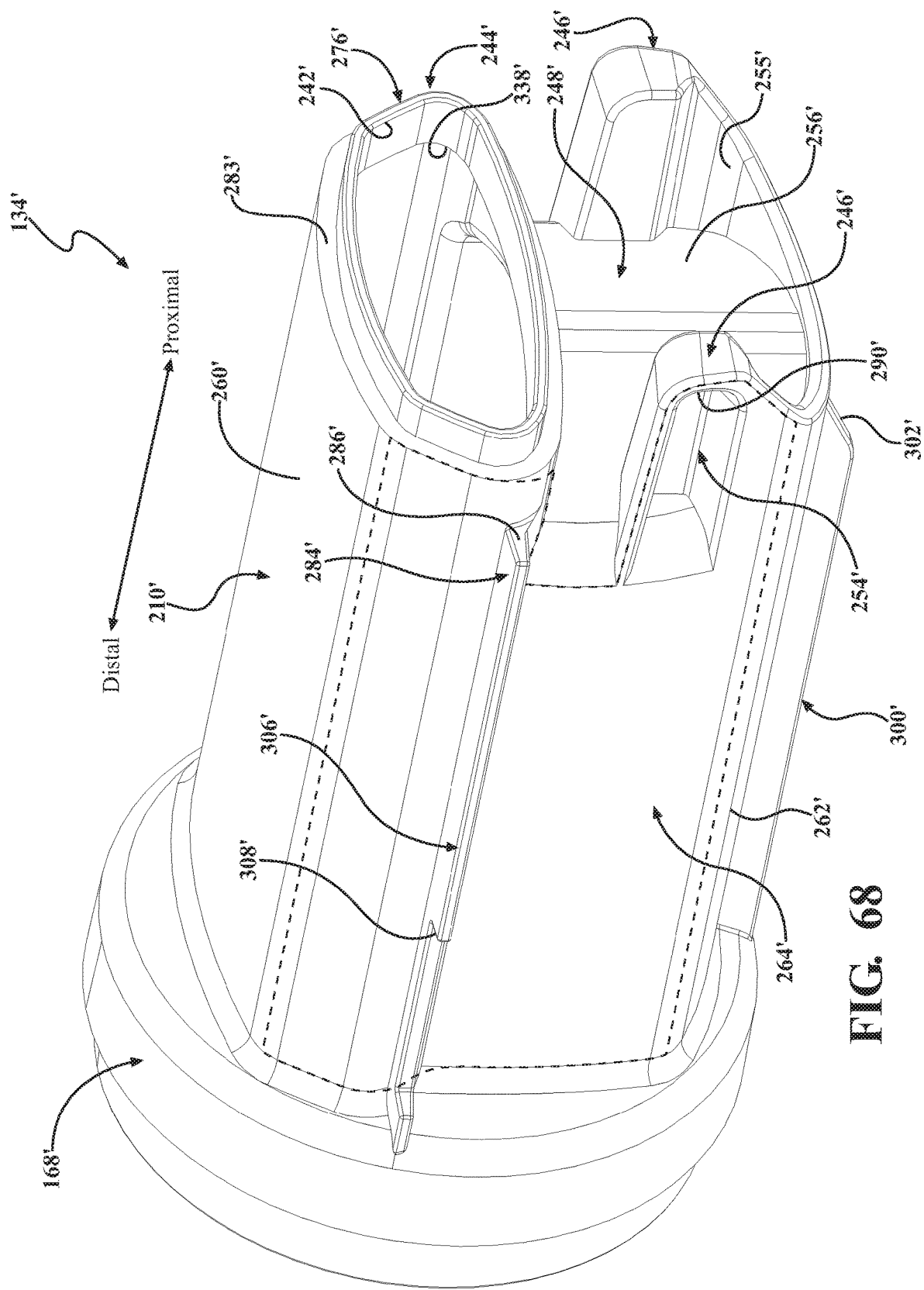
FIG. 68 is a rear perspective view of an inverted trunk of the manifold.
Figure 69:
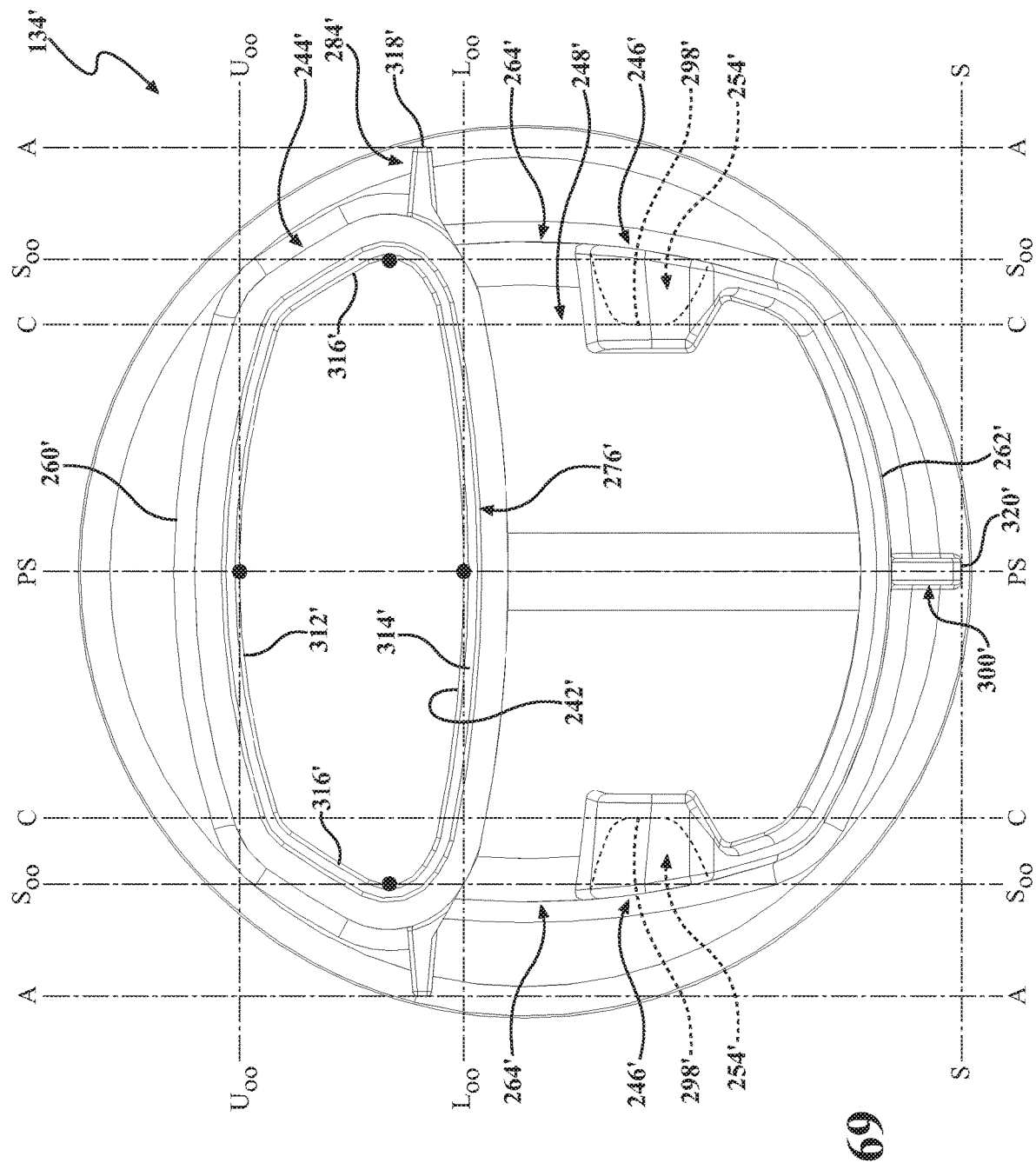
FIG. 69 is a rear elevation view of the inverted trunk of FIG. 68.

The inverted trunk 134' may define the outlet opening 242'. The inverted trunk 134' may include the body portion 210', the first leg 244', and/or the second leg 246. The first leg 244' and/or the second leg 246' may extend from the body portion 210', and more particularly one or both of the first and second legs 244', 246' may extend proximally from the body portion 210'. The first and second legs 244', 246' may be spaced apart from one another to at least partially define the void 248', as best shown in the perspective view of FIG. 64 and the side elevation views of FIGS. 70 and 71. The catch(es) 254' may be generally standalone structures such that the catches 254' and the upper aspect 252' of the first leg 244' define the void 248. Further, as contemplated previously, the inverted trunk 134' may include more than two legs, and despite the presence of a strut 255' coupling the catches 254', it may be considered that the inverted trunk 134' includes the first leg 244' and a pair of the second legs 246'. The void 248' may be further defined by a distal aspect 256' of the body portion 210', and the first and/or second legs 244', 246' may extend from the distal aspect 256'. FIGS. 68 and 69 show the distal aspect 256' extending from the first leg 244' to the strut 255' near the lower wall 262' of the inverted trunk 134'. For convention, the vertical plane perpendicular to the proximal-to-distal direction and extending through a proximal-most point of the distal aspect 256' may be considered the boundary (B) separating the body portion 210' and the first and/or second legs 244', 246', as identified in FIG. 70. A portion of the inverted trunk 134' distal to the boundary (B) may be considered the body portion 210', and upper and lower portions of the inverted trunk 134' proximal to the boundary (B) may be considered the first and second legs 244', 246', respectively.

As mentioned, the first leg 244' may be positioned above the second leg(s) 246' when the manifold 124 is oriented for insertion into the opening of the receiver. The inverted trunk 134' may include the upper wall 260', the lower wall 262', and the opposing sides 264'. The opposing sides 264' and the lower wall 262' may cooperate to form at least a portion of the second leg(s) 246', and the opposing sides 264' and the upper wall 260' may cooperate to form at least a portion of the first leg 244'.

Figure 71:
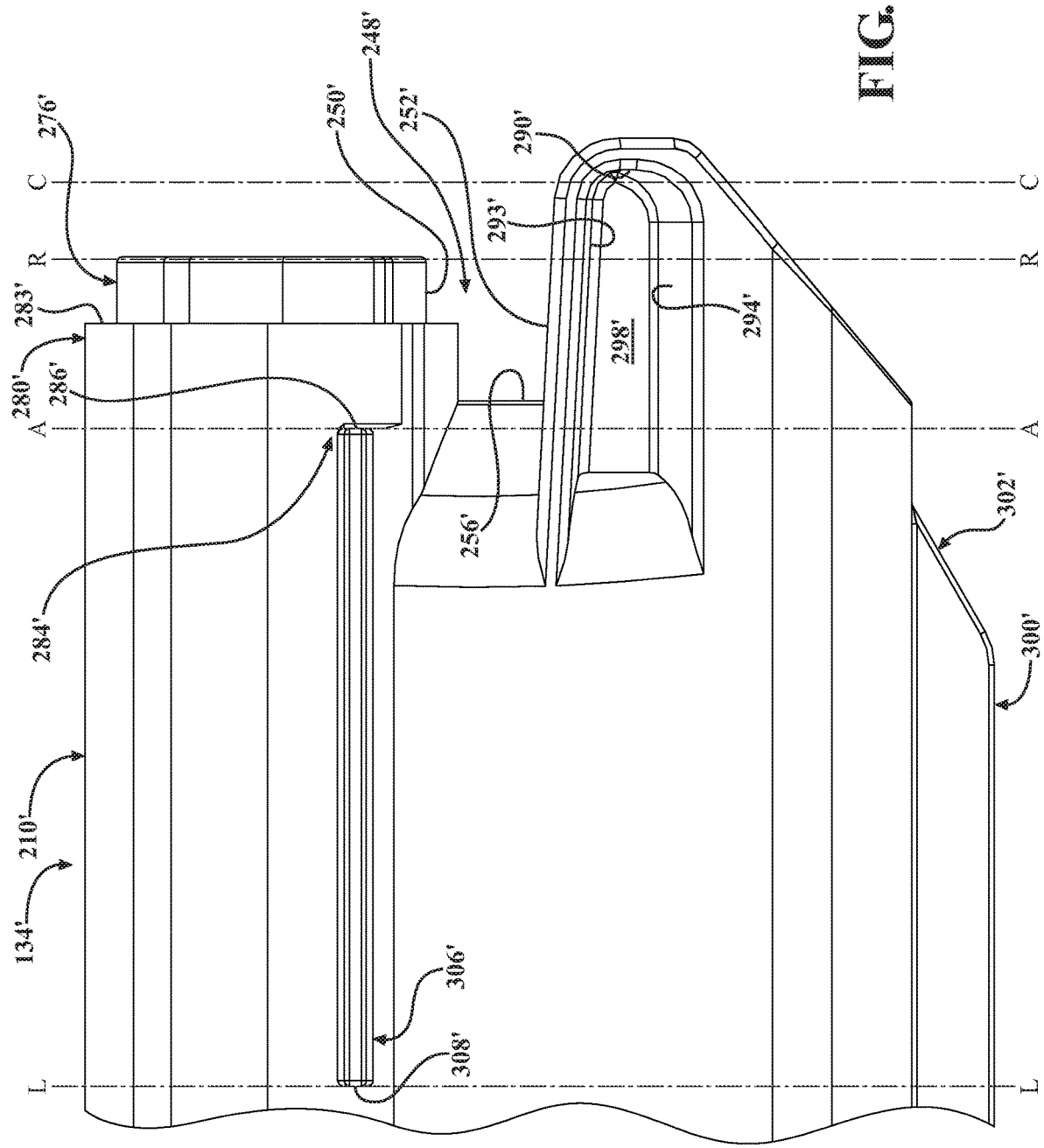
FIG. 71 is a detailed side elevation view of a portion of the inverted trunk of FIG. 68.
Figure 72:
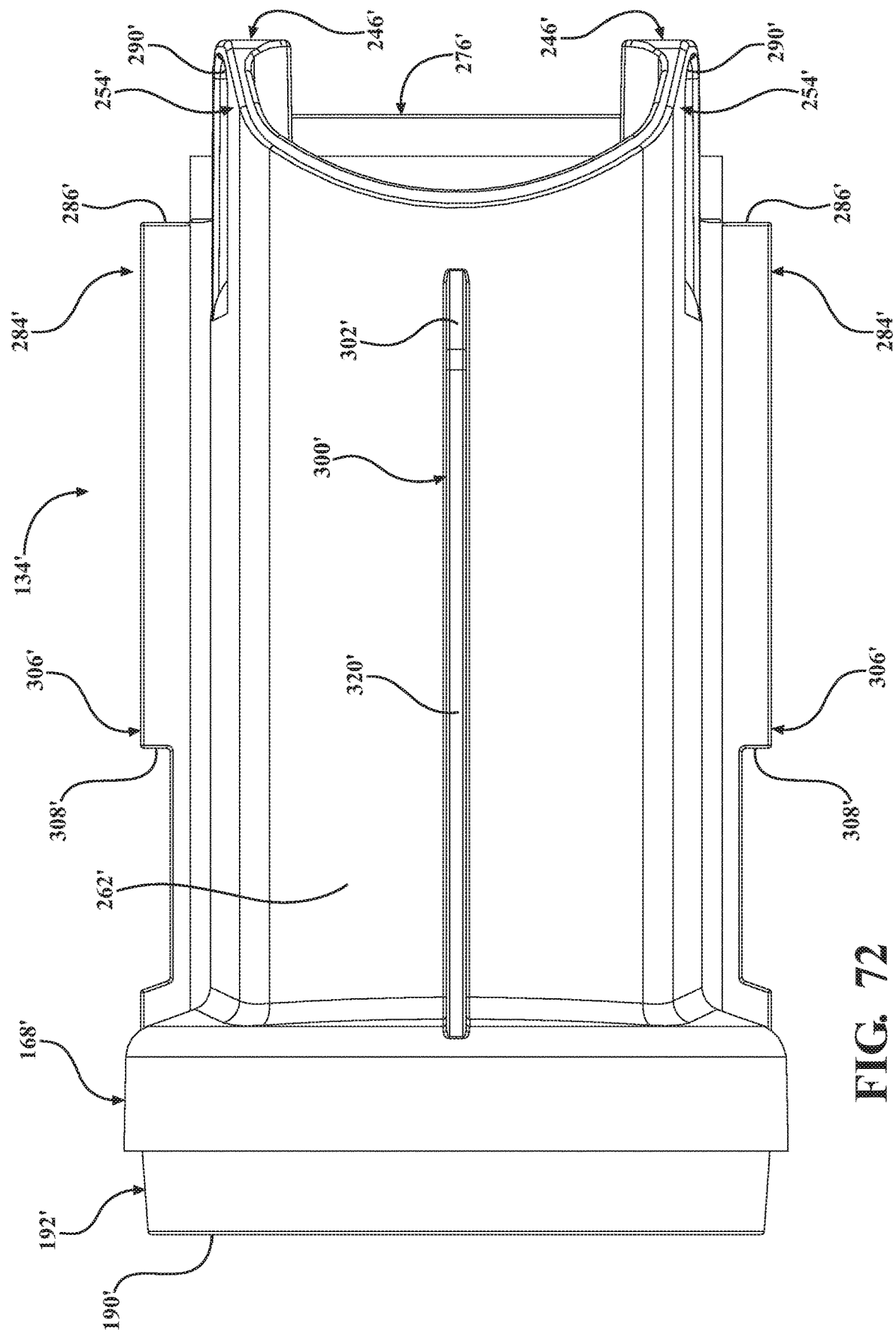
FIG. 72 is a bottom plan view of the inverted trunk of FIG. 68.
Figure 73:
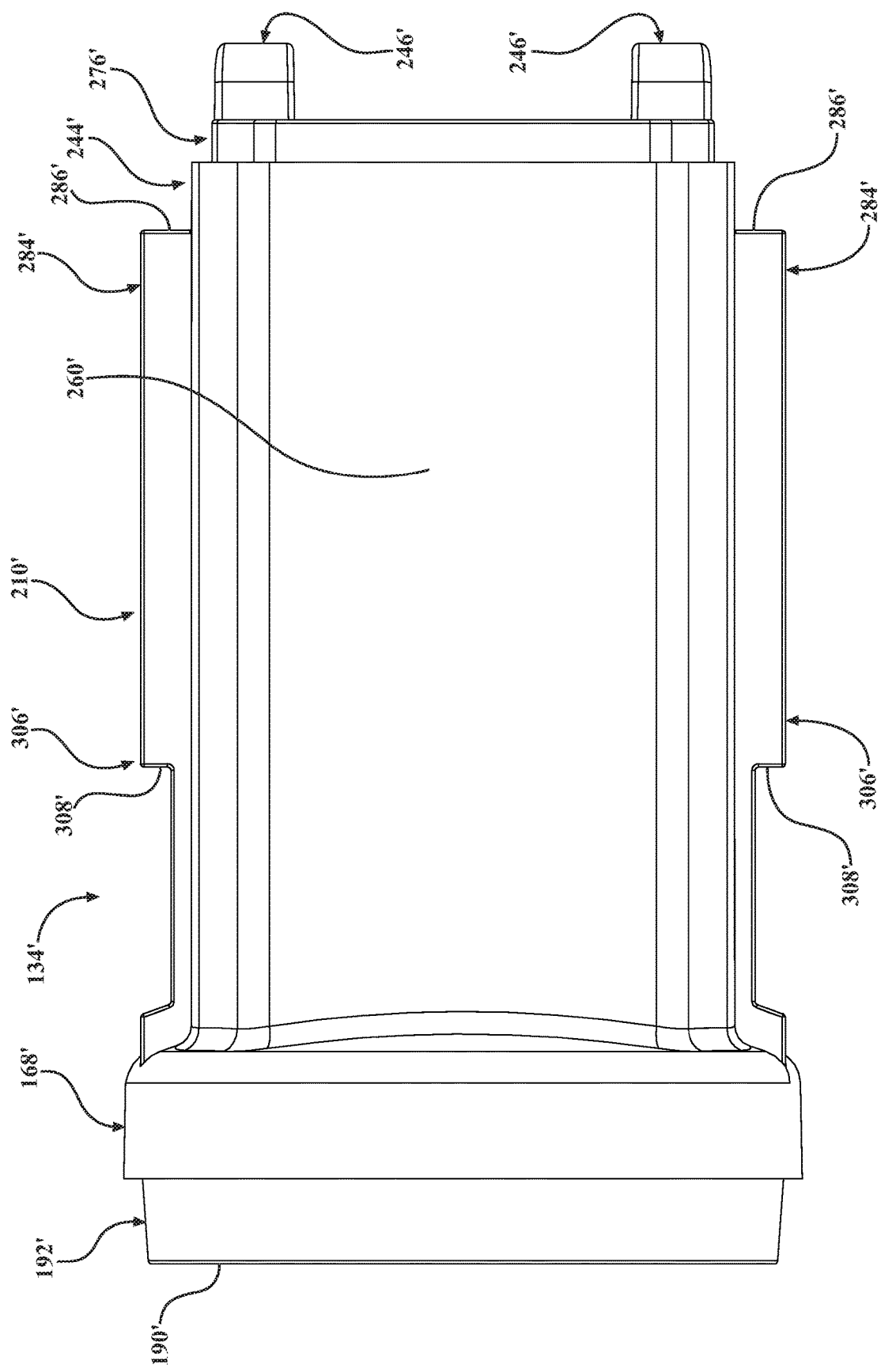
FIG. 73 is a top plan view of the inverted trunk of FIG. 68.

The inverted trunk 134' may include the rim 276' defining the outlet opening 242'. The rim 276' may be disposed on the first leg 244', and more particularly at or near a proximal end of the first leg 244'. The step 283' may extend radially inward from the tubulate wall 280' at least partially defining the first leg 244' with the rim 276' extending proximally from the step 283'. FIG. 71 includes the vertical plane perpendicular to the proximal-to-distal direction and extending through the rim 276', identified as (R), indicative of a proximal-to-distal location of the rim 276'. The rim 276' may include a width greater or larger than a height such that the outlet opening 242' is non-circular. The tubulate wall 280' may also include a width greater or larger than a height, and the dimensions of the rim 276' may be approximately equal to the dimensions of the tubulate wall 280' such that the outlet opening 242' is shaped complementarily to and/or to approximate a cross section of the first leg 244'. The rim 276' may be configured to be coupled with the seal 282'.

The manifold 124 includes the arm(s) 284' extending outwardly from the inverted trunk 134'. The arms 284' may extend outwardly from at least one of the body portion 210 and the first leg 244'. In other words, the arms 284' may extend away from the manifold volume 130. With particular reference to FIG. 71, at least a portion of the arms 284' (one shown) extend outwardly from the body portion 210'. Further, the arms 284' may extend outwardly from the opposing sides 264' of the inverted trunk 134', and more particularly extend laterally outward from the opposing sides 264'. The arms 284' may be of any suitable length. The arms 284' include the proximally-directed surfaces 286'. The proximally-directed surfaces 286' may be positioned distal to the boundary (B) of FIG. 70, and hence the arms 284' may be considered to extend laterally outward from only the body portion 210'. FIG. 71 includes the vertical plane perpendicular to the proximal-to-distal direction and extending through the proximally-directed surfaces 286', identified as (A), indicative of a proximal-to-distal location of the proximally-directed surfaces 286' of the arms 284'. The proximally-directed surfaces 286' of the arms 284' may be positioned distal to the rim 276', and thus the rim 276' may be positioned proximal to the proximally-directed surfaces 286' (i.e., plane A is distal to plane R, and plane R is proximal to plane A).

Figure 70:
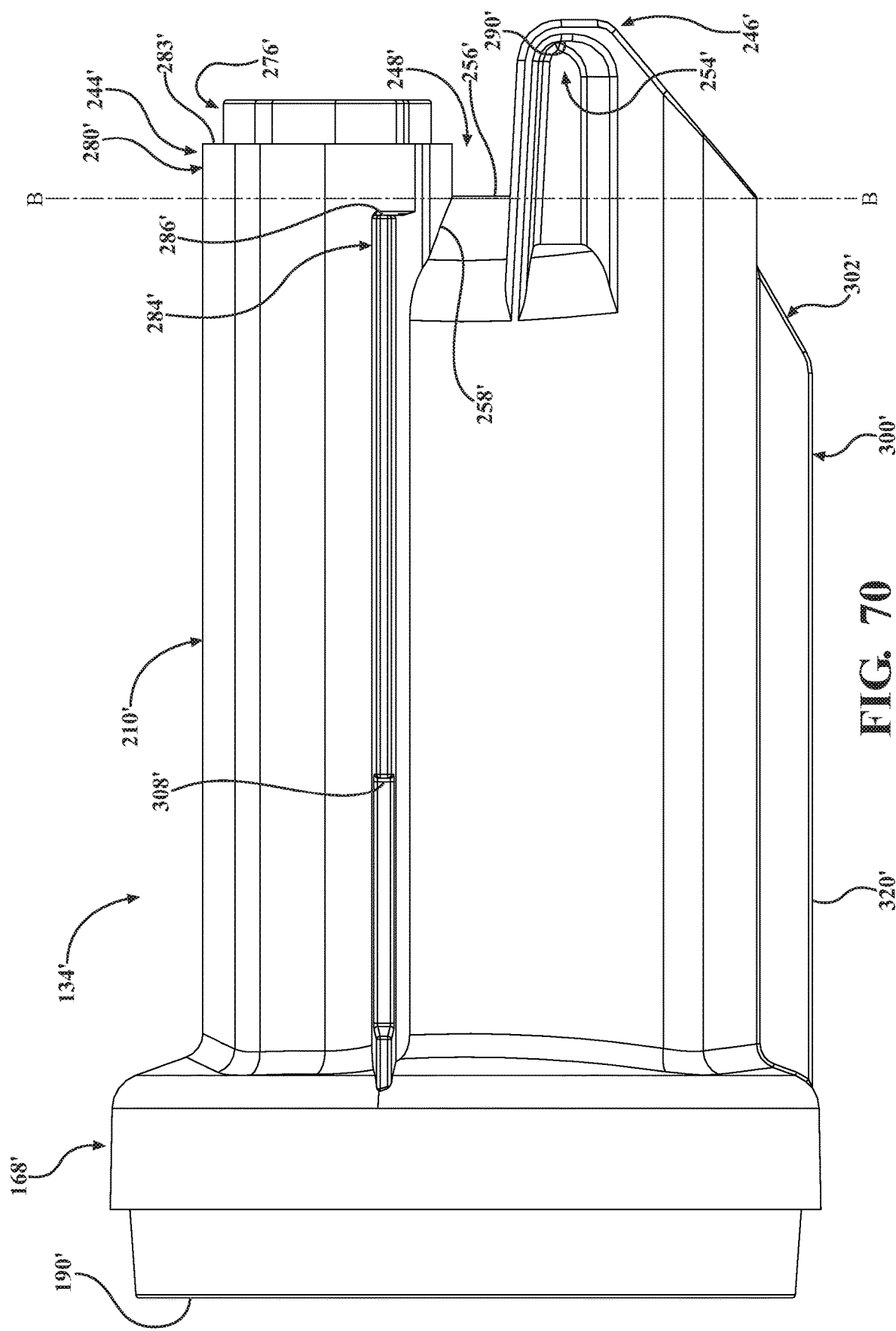
FIG. 70 is a side elevation view of the inverted trunk of FIG. 68.

The manifold 124 includes the catch(es) 254', for example, as the aforementioned standalone structure and/or considered disposed on the second leg(s) 246'. The rim 276' and the catches 254' may be spaced apart from one another by the void 248'. More particularly, the rim 276' on the first leg 244' may be spaced apart from the catches 254' on the second leg(s) 246' by the void 248'. FIGS. 70 and 71 show the rim 276' on the first or upper side of the void 248', and the catches 254' on the second or lower side of the void 248'. Further, the rim 276' is positioned above the catches 254' when the manifold 124 is oriented for insertion into the opening 118 of the receiver 116. Owing to the geometry of the second leg(s) 246', the catches 254' appear as a hook-like structure including the distally-directed surfaces 290' along a bend between the opposing upper and lower aspects 293', 294'. The catches 254' include the laterally-directed surfaces 298' such that the catches 254' are shaped as recesses within the inverted trunk 134'. The distally-directed surfaces 290' of the catches 254' may be positioned proximal to the boundary (B) of FIG. 66. FIG. 71 includes the vertical plane perpendicular to the proximal-to-distal direction and extending through the distally-directed surfaces 290', identified as (C), indicative of a proximal-to-distal location of catches 254'. The distally-directed surfaces 290' of the catches 254' may be positioned proximal to the rim 276', and thus the rim 276' may be positioned distal to the distally-directed surfaces 290' (i.e., plane C is proximal to plane R, and plane R is distal to plane C). Further, the distally-directed surfaces 290' of the catches 254' may be positioned proximal to the proximally-directed surfaces 286' of the arms 284', and thus the proximally-directed surfaces 286' of the arms 284' may be positioned distal to the distally-directed surfaces 290' (i.e., plane C is proximal to plane A, and plane A is distal to plane C).

The manifold 124 may include the spine 300' extending outwardly from the inverted trunk 134'. With particular reference to FIG. 70, the spine 300' may extend outwardly from the inverted trunk 134' distal to the boundary (B) such that the spine 300' extends outwardly from the body portion 210'. Further, the spine 300' may extend outwardly from the bottom wall 262' of the inverted trunk 134', and more particularly extend downwardly from the bottom wall 262'. The spine 300' includes the proximally-directed surface 302', for example, the ramped surface tapering towards the lower wall 262' of the inverted trunk 134' in the proximal direction to define a proximal end of the spine 300'. FIG. 71 includes the vertical plane perpendicular to the proximal-to-distal direction and extending through a proximal end of the proximally-directed surface 302', identified as (S), indicative of a proximal-to-distal location of the proximally-directed surface 302' of the spine 300.' The proximally-directed surface 302' of the spine 300' may be positioned distal to the rim 276', and thus the rim 276' may be positioned proximal to the proximally-directed surface 302' (i.e., plane S is distal to plane R, and plane R is proximal to plane S). Further, the proximally-directed surface 302' of the spine 300' may be positioned distal to the distally-directed surface(s) 290' of the catch(es) 254', and thus the distally-directed surface(s) 290' of the catch(es) 254' may be positioned proximal to the proximally-directed surface 302' (i.e., plane S is distal to plane C, and plane C is proximal to plane S). Still further, the proximally-directed surface 302' of the spine 300' may be positioned distal to the proximally-directed surface(s) 286' of the arm(s) 284', and thus the proximally-directed surface(s) 286' of the arm(s) 284' may be positioned proximal to the proximally-directed surface 302 (i.e., plane S is distal to plane A, and plane A is proximal to plane S).

The manifold 124 may include the lock element(s) 306' extending outwardly from the inverted trunk 134'. The lock elements 306' each may include a distally-directed surface 308' at a distal end of the elongate structure opposite the proximally-directed surface 286' of the arms 284. The lock element(s) 306' may extend outwardly from at least one of the body portion 210' and the first leg 244'. The lock elements 306' may be positioned distal to the boundary (B) of FIG. 66, and hence the lock elements 306' are extending laterally outward from only the body portion 210. The lock elements 306' may extend outwardly from the opposing sides 264' of the inverted trunk 134', and more particularly extend laterally outward from the opposing sides 264'. FIG. 71 includes the vertical plane perpendicular to the proximal-to-distal direction and extending through the distally-directed surfaces 308', identified as (L), indicative of a proximal-to-distal location of the lock elements 306'. The distally-directed surfaces 308' of the lock elements 306' may be positioned distal to the rim 276', and thus the rim 276' may be positioned proximal to the distally-directed surfaces 308' (i.e., plane L is distal to plane R, and plane R is proximal to plane L). Further, the distally-directed surfaces 308' of the lock elements 306' may be positioned distal to the distally-directed surfaces 290' of the catches 254', and thus the distally-directed surfaces 290' of the catches 254' may be positioned proximal to the distally-directed surfaces 308' (i.e., plane L is distal to plane C, and plane C is proximal to plane L). Still further, the distally-directed surfaces 308' of the lock elements 306' may be positioned distal to the proximally-directed surfaces 286' of the arms 284', and thus the proximally-directed surfaces 286' of the arms 284' may be positioned proximal to the distally-directed surfaces 308' (i.e., plane L is distal to plane A, and plane A is proximal to plane L). Still yet further, the distally-directed surfaces 308 of the lock elements 306' may be positioned distal to the proximally-directed surface 302 of the spine 300', and thus the proximally-directed surface 302' of the spine 300' may be positioned proximal to the distally-directed surfaces 308' (i.e., plane L is distal to plane S, and plane S is proximal to plane L). As previously explained in detail, the relative positioning in the proximal-to-distal direction of each of the rim 276', the proximally-directed surfaces 286' of the arms 284', the distally-directed surfaces 290' of the catches 254', the proximally-directed surface 302' of the spine 300', and/or the distally-directed surfaces 308' of the lock elements 306' are advantageously tuned to facilitate precise operative timing of complementary components of the receiver 116 as the manifold 124 is inserted within the receiver 116.

Referring to FIG. 69, the outlet opening 242' may be oblong and defined by the rim 276' including the upper segment 312', the lower segment 314', and the opposing side segments 316'. The vertical and horizontal planes in the proximal-to-distal direction and extending through each of the opposing lateral-most points, the uppermost point, and the lowermost point of the outlet opening 242', respectively, are labelled ($S_{oo}$), ($U_{oo}$), and ($L_{oo}$), respectively. The vertical plane in the proximal-to-distal direction and bifurcating the outlet opening 242' may be the vertical plane of symmetry (PS). The outlet opening 242' may be positioned entirely within an upper half of the inverted trunk 134' when the manifold 124 is oriented for insertion within the opening 118 of the receiver 116. The positioning of the outlet opening 242' within the upper half may particularly advantageous to avoid inadvertent egress of the waste material from the manifold volume 130. In other words, the waste material that is not drawn through the seal 282 under the influence of the vacuum may descend under the influence of gravity within the manifold volume 130. The waste material may collect within a portion of the manifold volume 130 defined by the lower wall 262' and bounded proximally by the second leg(s) 246' and/or the distal aspect 256'. Further, during removal of the manifold 124 including the inverted trunk 134' from the receiver 116 in manners previously described, the likelihood of egress of the waste material through the seal 282 (as the suction fitting 262 is being removed through the seal 282) is appreciably reduced, as minimal waste material may be present on a distal side of the seal 282 (having descended within the manifold volume 130).

The arms 284' may include the laterally-directed surfaces 318' that cooperate to define a width that is greater or larger than the width of the rim 276' and the outlet opening 242'. FIG. 69 shows vertical planes in the proximal-to-distal direction extending through the laterally-directed surfaces 318', identified as (A), indicative of lateral positions of the arms 284'. The laterally-directed surfaces 318' of the arms 284' may be positioned farther from the plane of symmetry (PS) than the respective lateral-most points of the outlet opening 242' (i.e., the planes (A) are at a greater distance from the vertical plane of symmetry (PS) than the planes $S_{oo}$). Likewise, the lock elements 306' the laterally-directed surfaces that cooperate to define a width that is greater or larger than the width of the rim 276' and the outlet opening 242'. The catches 254' (identified in phantom in FIG. 69) may be positioned in a lower half of the inverted trunk 134' when the manifold 124 is oriented for insertion within the opening 118 of the receiver 116. The catches 254' may be positioned below the lowermost point of the outlet opening 242'. Further, the laterally-directed surfaces 298' of the catches 254' may cooperate to define a width that is less than the width of the rim 276' and the outlet opening 242'. FIG. 69 shows vertical planes in the proximal-to-distal direction extending through each of the laterally-directed surfaces 298, identified as (C), indicative of lateral positions of the catches 254'. The laterally-directed surfaces 298' of the catches 254' are positioned nearer to the plane of symmetry (PS) than the respective lateral-most points of the outlet opening 242' (i.e., the planes C are at a lesser distance from the plane of symmetry (PS) than the planes $S_{oo}$).

The spine 300' may be positioned in the lower half of the inverted trunk 134' when the manifold 124 is oriented for insertion within the opening 118 of the receiver 116. The spine 300' may be positioned below the lowermost point of the outlet opening 242'. Further, the spine 300' may be coplanar with the plane of symmetry (PS). FIG. 69 shows the horizontal plane in the proximal-to-distal direction and extending through the downwardly-directed surface 320' of the spine 300', identified as (S), indicative of a downward position of the spine 300'. The downwardly-directed surface 320' of the spine 300' is positioned below the lowermost point of the outlet opening 242' (i.e., the plane S is below the plane $L_{oo}$).

In at least some respects, the positioning and/or spacing of the catches 254, 254' in the proximal-to-distal direction relative to the rim 276, 276' and/or the proximally-directed surfaces 286, 248' of the arms 284, 246' and/or the distally-directed surfaces 308, 308' of the lock elements 306, 306' may be useful to prevent non-genuine articles from being used with the receiver 116. Additional security features may be provided which prevent non-genuine articles from being used with the receiver 116. As previously mentioned, the controller 122 (see FIG. 2) may prevent operation of the vacuum pump 110 should the manifold 124 not be inserted into the receiver 116 to the fourth or fully inserted operative position. The arrangement may be facilitated with at least one sensor, for example, Hall sensors, suitably positioned on the sled assembly 288, the lower housing 268, the upper housing 366, or any other suitable component of the receiver 116. Thus, should an article not include the requisite structure(s) that permit the manifold 124 to assume the fourth or fully inserted operative position, the sensor(s) may not transmit the appropriate signal to the controller 122. The controller 122 not permit operation of the medical waste collection system 100. Similarly, the controller 122 may prevent operation of the vacuum pump 110 should the receiver 116 not be cycled through the decoupled operative position after each instance the manifold 124 is inserted and/or removed from the receiver 116. The arrangement may also be facilitated with the sensor(s) configured to detect, for example, a magnet 676 coupled to the sled assembly 288, as shown in FIG. 27. The magnet 676 may be coupled to any suitable structure of the sled assembly 288 or receiver 166. FIG. 27 shows the magnet 676 being positioned laterally off-center, which may be particularly desirable so as to avoid interference with a data reader to be described that detects a radiofrequency identification (RFID) tag 606. Thus, should an article not include the requisite structure(s) (e.g., the catches 254) that permit the manifold 124 to facilitate the sled assembly 288 move to the fully inserted operative position and/or return to the decoupled operative position, the sensor(s) may not transmit the appropriate signal to the controller 122, and the controller 122 not permit operation of the medical waste collection system 100.

In certain implementations, the sensor is configured to transmit the appropriate signal to the controller 122 based on a presence or absence of the manifold 124 in the receiver 116. The controller 122 is configured to generate and transmit an offload signal to the docking controller 105, the off-load signal operative to cause the docking controller 105 to operate the off-load pump 103 of the docking station 101 to draw waste from the waste container(s) 106, 108 to the docking station 101. In other words, the off-load pump 103 of the docking station 101 is controlled based on whether the manifold 124 is present or absent in the receiver 116 of the medical waste collection system 100. For example, if the manifold 124 is inserted into the receiver 116 to the fully inserted operative position, the controller 122 transmits the offload signal to the docking controller 105 to prevent operation of the off-load pump 103. The controller 122 may transmit the offload signal to the docking controller 105 to permit operation of the off-load pump 103 if no manifold 124 is detected in the receiver 116. As a result, it may be required to remove the manifold 124 from the receiver 116 prior to being permitted to operate the docking station 101 to empty and/or clean the waste container(s) 106, 108 of the medical waste collection system 100. The reverse configuration is also contemplated in which the manifold 124 is required to be present in the receiver 116 prior to being permitted to operate the docking station 101.

In certain implementations, the radiofrequency identification (RFID) tag 606 may be coupled to the manifold 124 and positioned to be detected by a sensor (e.g., a data reader) of the medical waste collection system 100. Referring to FIG. 3, the RFID tag 606 may be disposed on the upper wall 260 of the trunk 134. More particularly, the RFID tag 606 may be at least partially positioned on the upper wall 260 defining the body portion 210, and/or the RFID tag 606 may be at least partially positioned on the upper wall 260 defining the second leg 246. As previously mentioned, the upper wall 260 may be generally horizontally-oriented when the manifold 124 is oriented for insertion into the receiver 116. Further, FIGS. 8, 10 and 11 show the upper wall 260 as being slightly arcuate but substantially flat. It is appreciated that reliability of detection of RFID tags may be generally improved when the RFID tag is disposed on a substantially flat surface. Thus, in addition to the substantially flat contour of the upper wall 260 at least partially defining the orientation feature(s) 265, the contour may provide sufficient surface area for coupling of the RFID tag 606 with improved detection by the data reader of the medical waste collection system 100.

The RFID tag 606 may be configured to be detected by the data reader when the manifold 124 is in the first, second, third, and/or fourth operative positions. In particular, the RFID tag 606 may be configured to be detected by the data reader when the manifold 124 is in the fourth or fully inserted operative position in the receiver 116. For example, for a specifically-tuned strength of the interrogating radio waves from the data reader, the data reader may be positioned on the receiver 116 such that the RFID tag 606 is only detectable when the manifold 124 is in the fourth or fully inserted operative position in the receiver 116. Should an article be incapable of being inserted to the fourth or fully inserted operative position for reasons previously described, no data communication is established between the RFID tag 606 and the reader, and the controller 122 may prevent operation of the medical waste collection system 100. In certain implementations, the RFID tag 606 may include memory storing data for determining whether the manifold 124 is usable with the medical waste collection system 100. The RFID tag 606 transmits the data from the memory to the data reader, and the controller 122 of the medical waste collection system 100 authenticates the manifold 124. If the authentication is successful, the medical waste collection system 100 may be operated as intended. Certain aspects of utilizing RFID may be disclosed in commonly owned International Publication Number WO 2007/1038425, published Sep. 13, 2007, the entire contents of which are hereby incorporated by reference. Alternative methods of automatic identification and data capture (AIDC) are contemplated, for example, bar codes, magnetic stripes, optical character recognition (OCR), smart cards, and the like.

Referring now to FIGS. 74-77, the manifold 124 may include the housing 128 having a first housing portion 608 and a second housing portion 610 removably coupled to the first housing portion 608. Owing to the presence of a cartridge seal 612 to be described, the second housing portion 610 may be considered a replacement cartridge of the manifold 124. The cartridge seal 612 and the replacement cartridge may realize several advantages, for example, requiring only the first housing portion 608 be replaced after a surgical procedure to maintain an aseptic barrier. Additionally or alternatively, the removable coupling between the first and second housing portions 608, 610 in the manner to be described may provide for easier cleaning and/or sanitizing of the internal components of the first housing portion and/or the second housing portion 608, 610.

Figure 74:
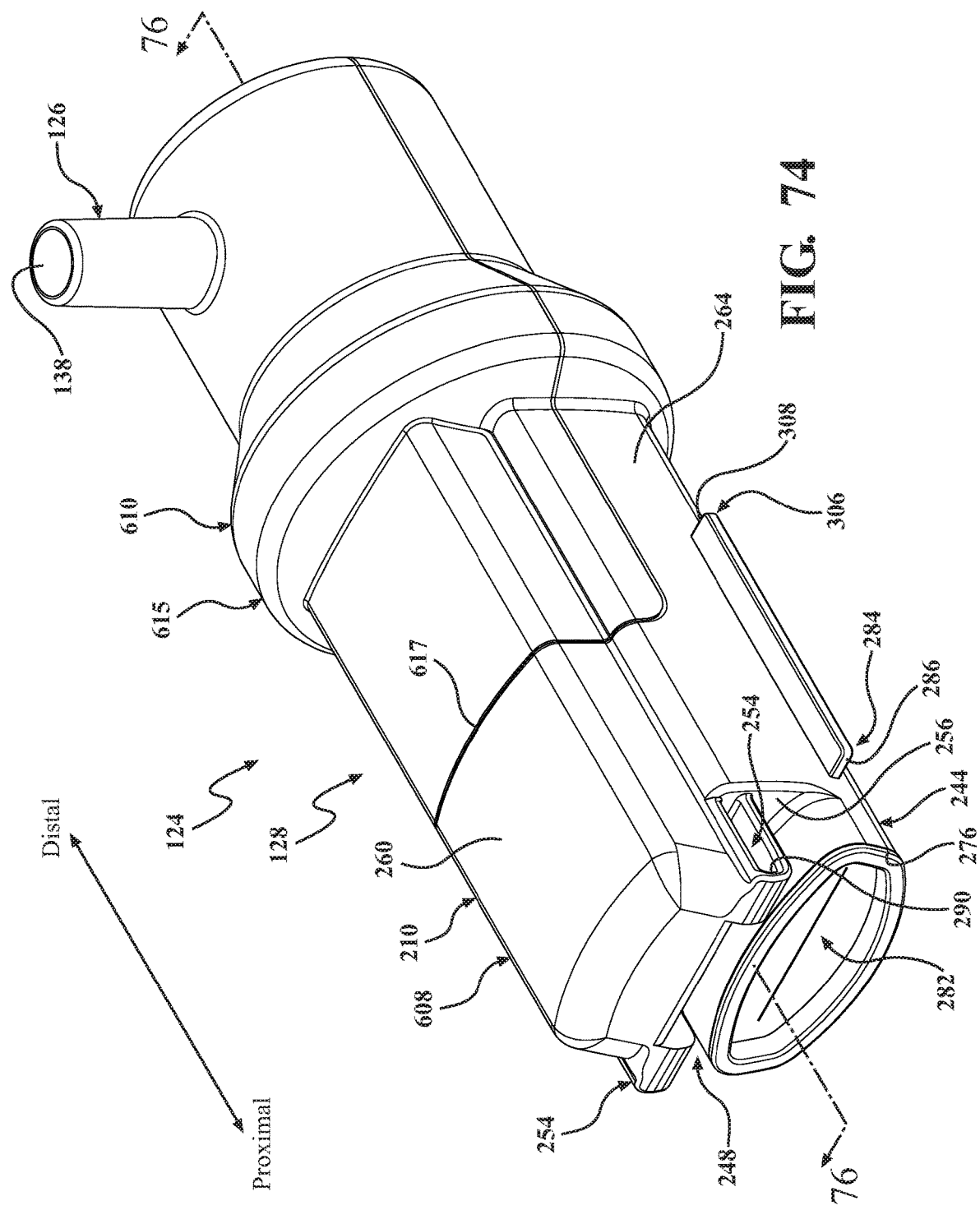
FIG. 74 is a rear perspective view of a manifold.
Figure 75:
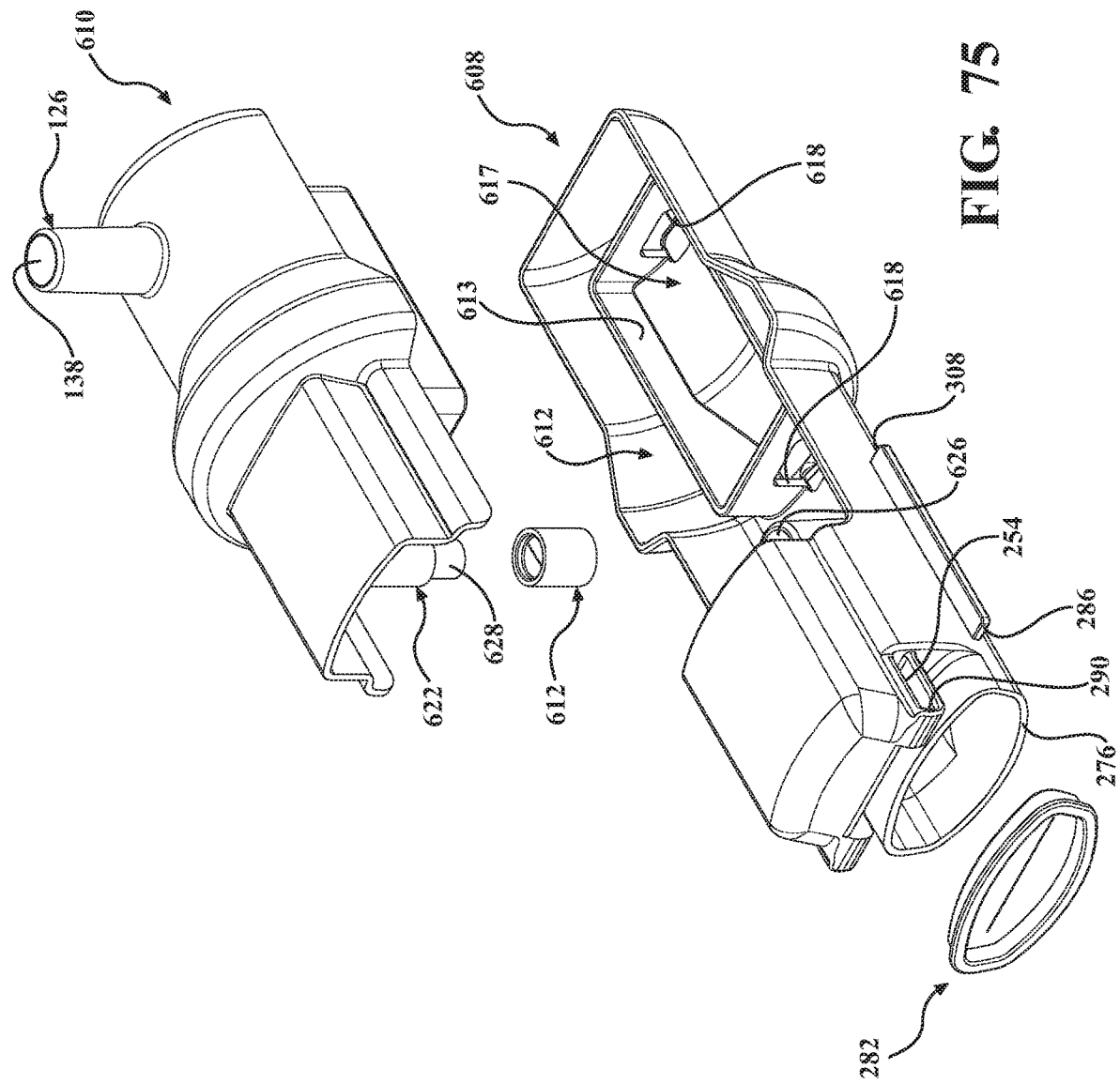
FIG. 75 is an exploded view of the manifold of FIG. 74.

FIGS. 74 and 75 show the first housing portion or base portion 608 as generally L-shaped in profile and defining a cavity 613. The second housing portion or cartridge 610 is sized and shaped to be at least partially disposed within the cavity 613 such that the adjacent surfaces of the base portion 608 and the cartridge 610 are contoured to one another. More partially, FIG. 74 shows the upper wall 260 and the opposing sidewalls 260 (one shown) of the housing 128 being partially formed by complementary surfaces on each of the base portion 608 and the cartridge 610. The resulting arrangement may be the base portion 608 and the cartridge 610 cooperatively providing for a shape at least similar to the trunk 134 of the manifold 124 previously described. As a result, at least a portion of the base portion 608 and the cartridge 610 are sized to be inserted into the opening 118 of the receiver 116 in the proximal direction and removed in the distal direction. Further, an annulus 615 may be at least partially formed by complementary surfaces on each of the base portion 608 and the cartridge 610 with the annulus 615 and a distal region of the housing 128 being sized and shaped at least somewhat similar to the head 132 of the manifold 124 previously described.

The base portion 608 may include the rim 276 defining the outlet opening 242, as best shown in FIG. 75. Further, owing to the implementation of the base portion 608 illustrated in FIGS. 74-76, the base portion 608 may include the body portion 210, the first leg 244, the second leg 246, and the void 248 at least partially defined by the second leg 246 and the first leg 244. Further, the arm(s) 246, the spine 300, the lock feature(s) 306, and/or the catch(es) 254 may be disposed on the base portion 608. More particularly, the arm 284 may extend outwardly from the base portion 608 or laterally outward from a portion of the side 264 of the base portion 608. The arm 284 includes the proximally-directed surface 286. Similarly, the lock element 306 may extend outwardly from the base portion 608 or laterally outward from a portion of the sides 264 of the base portion 608. The lock element 306 may include the distally-directed surface 308 positioned distal the proximally-directed surface 286 of the arm 284. The spine 300 may extend outwardly from the base portion 608, and more particularly downwardly from the bottom wall 262 of the base portion 608. The spine 300 includes the proximally-directed surface 302 positioned proximal to the distally-directed surface 308 of the lock element 306 and distal to the proximally-directed surface 286 of the arm 284. The optional catch 254 may be disposed on the second leg 246 formed by the base portion 608. The catch 254 includes the distally-directed surface 290 positioned proximal to the rim 276, proximal to the proximally-directed surface 286 of the arm 284, proximal to the proximally-directed surface 302 of the spine 300, and proximal to the distally-directed surface 308 of the lock element 306.

The catch 254 and the rim 276 may be spaced apart by the void 248, and the rim 276 may be positioned below the catch 254 when the manifold 124 is oriented for insertion into the opening 118 of the receiver 116. It is contemplated that alternative configurations are contemplated where, for example, one or more of the arm(s) 246, the lock feature(s) 306, and/or the catch(es) 254 may be disposed on the cartridge 610. FIG. 74 shows an interface boundary 617 extending about the housing 128 in a manner providing the generally L-shaped profile of the base portion 608 to accommodate the arm(s) 246, the lock feature(s) 306, and the catch(es) 254. In another example, the interface boundary 617 may be at least a substantially horizontal plane to divide the housing 128 in a manner in which the catch(es) 246 are disposed on the cartridge 610, and the arm(s) 246 and the lock feature(s) 306 are disposed on the base portion 608 (see, e.g., FIG. 86).

Figure 76:
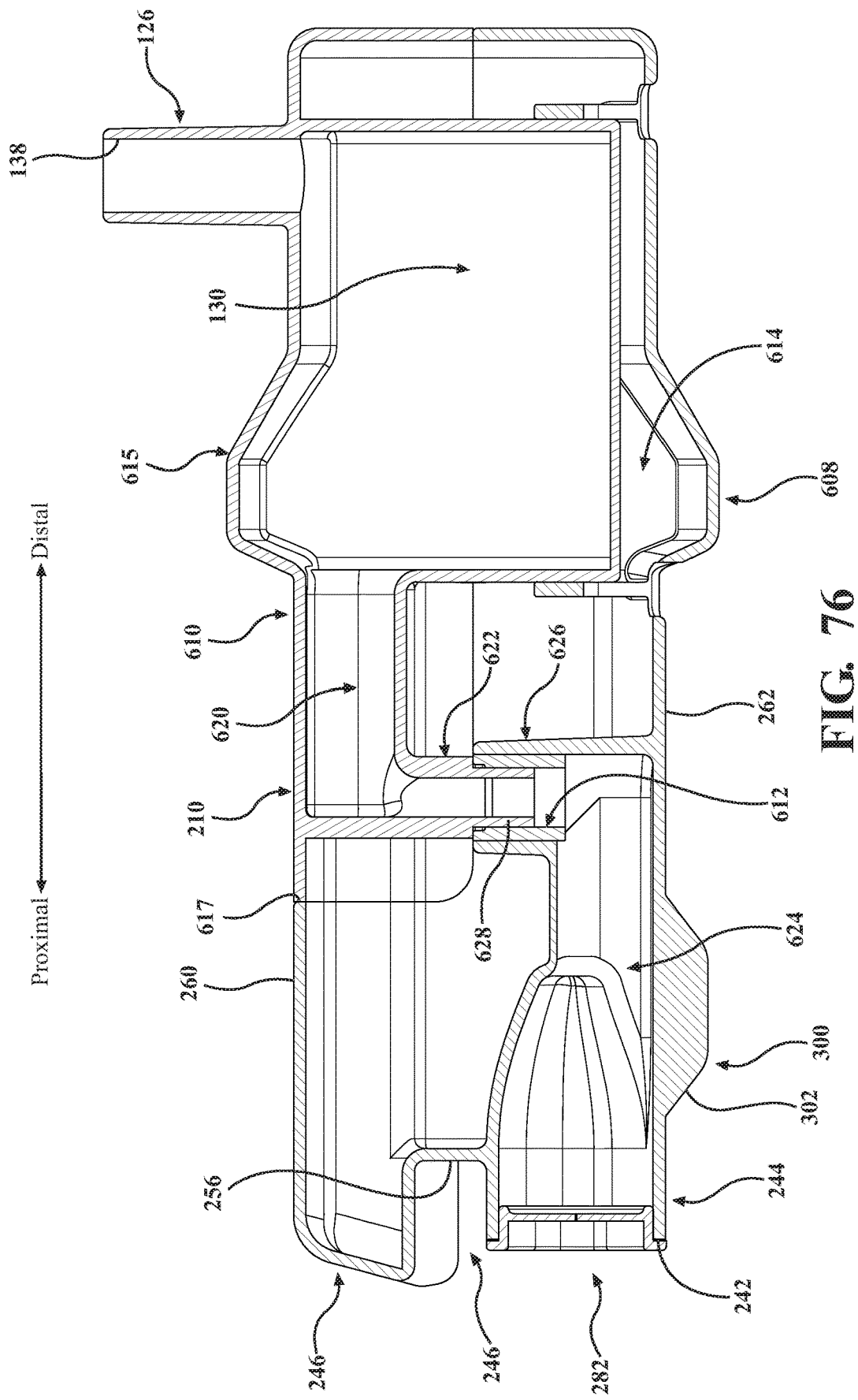
FIG. 76 a sectional elevation view of the manifold of FIG. 74 taken along section lines 76-76.

Referring now to FIGS. 75 and 76, the base portion 608 may include an upstanding wall 614 within the cavity 613 to define a socket 617 sized to receive a main body 616 of the cartridge 610. The socket 617 is shown as rectangular in shape, but other suitable geometries are contemplated. The base portion 608 may also include at least one retention feature 618 configured to releasably engage a complementary retention feature (not shown) on the cartridge 610. FIG. 75 shows the retention features 618 as two openings through opposing aspects of the upstanding wall 614 with the openings configured to releasably receive protrusions of the cartridge 610 in a detent arrangement.

Figure 77:
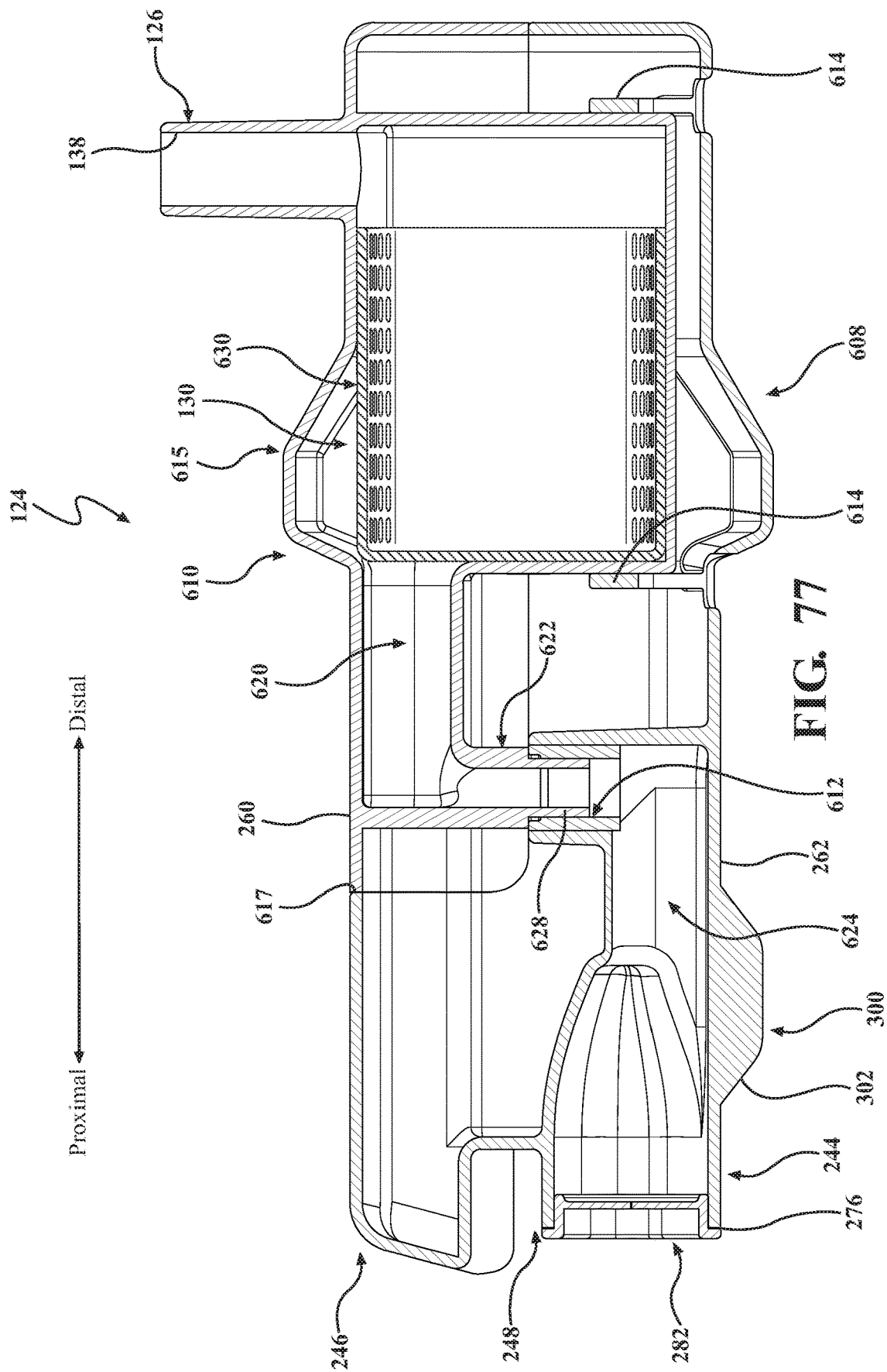
FIG. 77 is a sectional elevation view of the manifold of FIG. 75 taken along section lines 76-76 with a tissue trap disposed within a manifold volume.
Figure 78:
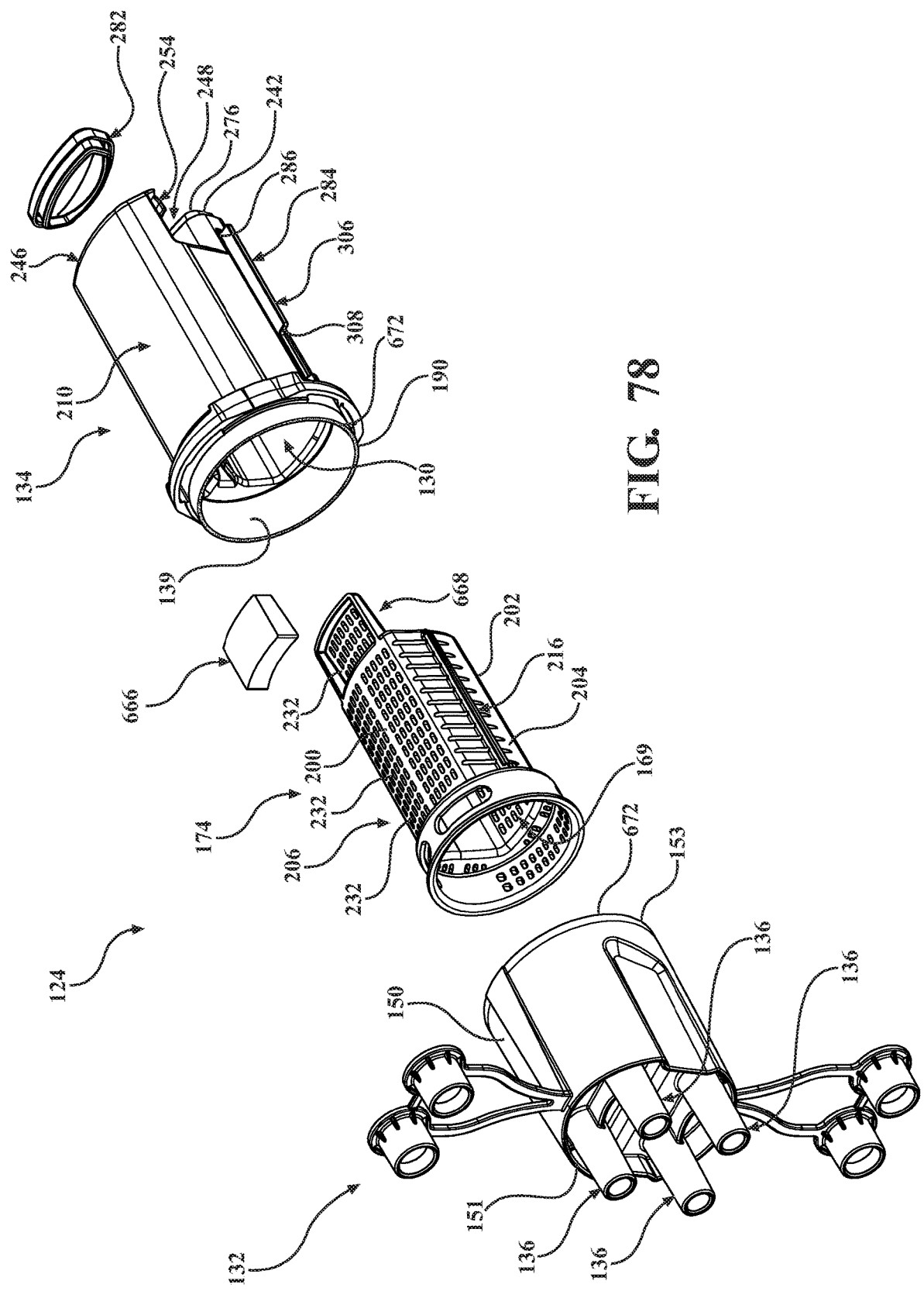
FIG. 78 is an exploded view of a manifold including a filter element including a tray, and a use indicator.
Figure 79:
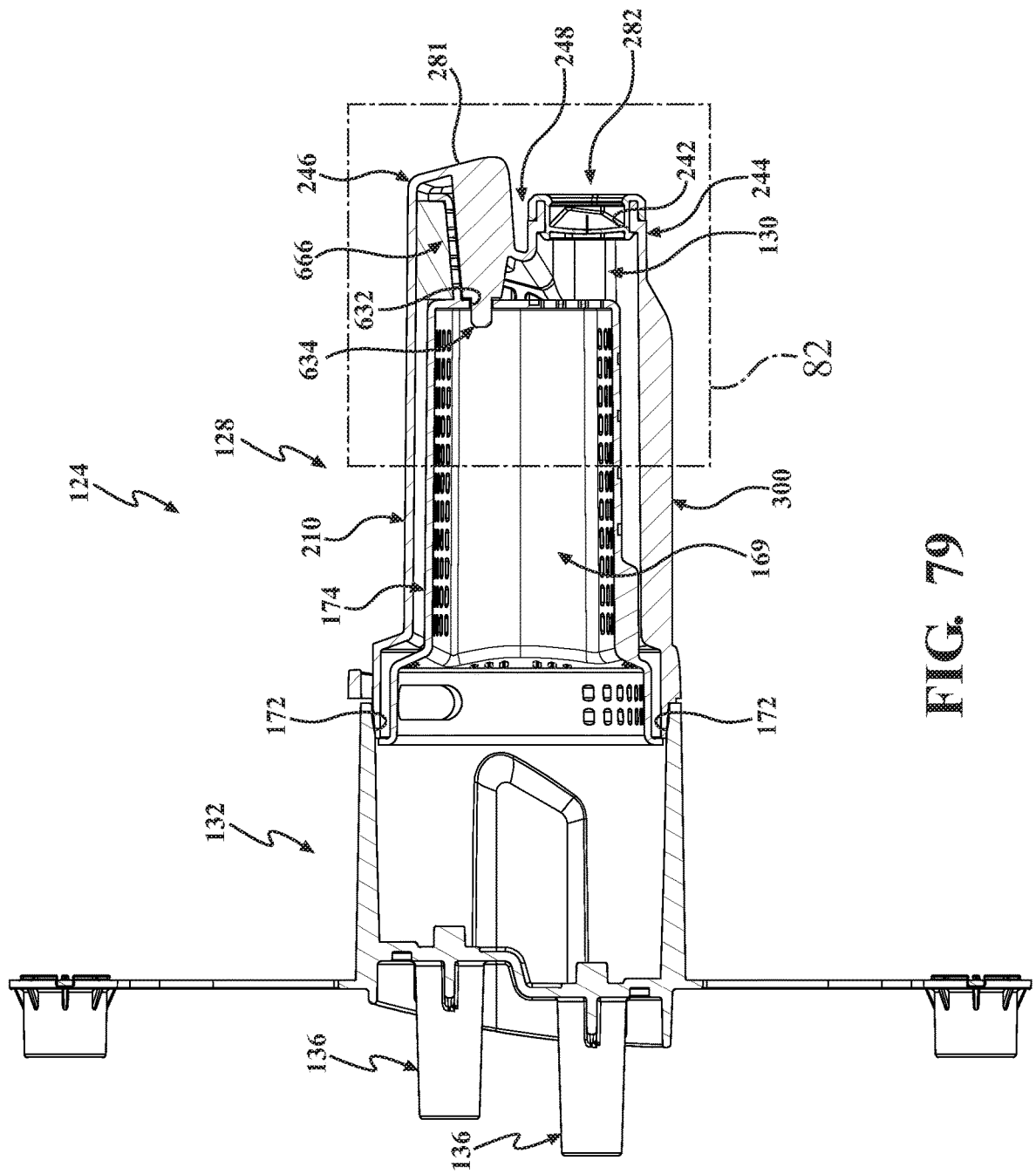
FIG. 79 is a sectional elevation view of the manifold of FIG. 78.

The cartridge 610 may include the inlet fitting 126 defining the inlet bore 138, and the main body 616 may define the manifold volume 130 in communication with the inlet bore 138. As previously described, the inlet fitting 126 is configured to be removably coupled with the suction tube 120 to provide a suction path from the suction tube 120 to the manifold volume 130. The cartridge 610 may also define a first channel 620 in communication with the manifold volume 130. As best shown in FIGS. 76 and 77, the first channel 620 may be a tubular structure extending from the main body 616. The cartridge 610 may include a first stem 622 defining a portion of the first channel 620.

The base portion 608 may define a second channel 624 in communication with the outlet opening 242. The second channel 624 may extend through at least a portion of the first leg 244. FIGS. 76 and 77 show the second channel 624 being a tubulate structure extending distally to a second stem 626 defining a portion of the second channel 624. The second stem 626 is oriented perpendicular to the first leg 244 such that the second stem 626 extends upwardly from the bottom wall 262 of the manifold 124. The cartridge seal 612 may be coupled to the first stem 622 or the second stem 626. With the cartridge seal 612 coupled to the second stem 626 (and the seal 282 coupled to the rim 276), the second channel 624 may define a closed fluid volume when the cartridge 610 is not coupled to the base portion 608. In other words, the cartridge seal 612 is configured to seal an interface between the first and second channels 620, 624 when the cartridge 610 and the base portion 608 are removably coupled to one another.

The cartridge 610 may be removably coupled to the base portion 608 to establish fluid communication between the first channel 620 and the second channel 624. In particular, the main body 616 is situated in the socket 614 and the second stem 626 includes a neck 628 that extends through the cartridge seal 612. The first stem 622 may be at least partially situated within the second stem 626 to establish fluid communication between the first channel 620 and the second channel 624, as best shown in FIGS. 76 and 77.

The manifold 124 may be inserted into the receiver 116 in the manner previously described, and the suction tube 120 may be coupled to the inlet fitting 126. During operation of the medical waste collection system 100, the suction path may extend from the suction tube 120 through the inlet bore 138, the manifold volume 130, the first channel 620, the second channel 624, and the outlet opening 242. Referring now to FIG. 76, a tissue trap 630 may be disposed in the manifold volume 130. The tissue trap 630 may be at least similar to the filter element 174 previously described, and the tissue trap 630 may be configured to capture a tissue entrained with the suction path. Subsequent to operation of the medical waste collection system 100, the manifold 124 may be removed in the manner previously described, and the cartridge 610 decoupled from the base portion 608. The cartridge 610 may include a lid (not shown) or other means to provide for removal of the tissue trap 630 from the cartridge 610, after which the tissue sample may be retrieved for further processing and examination (e.g., pathology). Thus, the manifold 124 may provide for ease with collection and retrieval of a tissue sample. Further, a new cartridge may provide for a subsequent procedure without needing to replace the base portion 608.

Whether it be due to expense, convenience, and/or other reasons, users may attempt to reprocess a previously used manifold in which it is necessary to remove contamination. It is readily appreciated that the filter element 174 may include intricate geometries (e.g., the holes 230 and the pores 232) that become contaminated with the waste material during operation of the medical waste collection system 100. Thus, efforts to reprocess a previously used manifold may require removing the filter element 174, and thereafter cleaning and replacing the filter element 174 or inserting another, unused filter element. As a result, limiting removal of the filter element 174 is at least one advantageous manner in which the manifold 124 of the present disclosure discourages reprocessing of the same.

Figure 80:
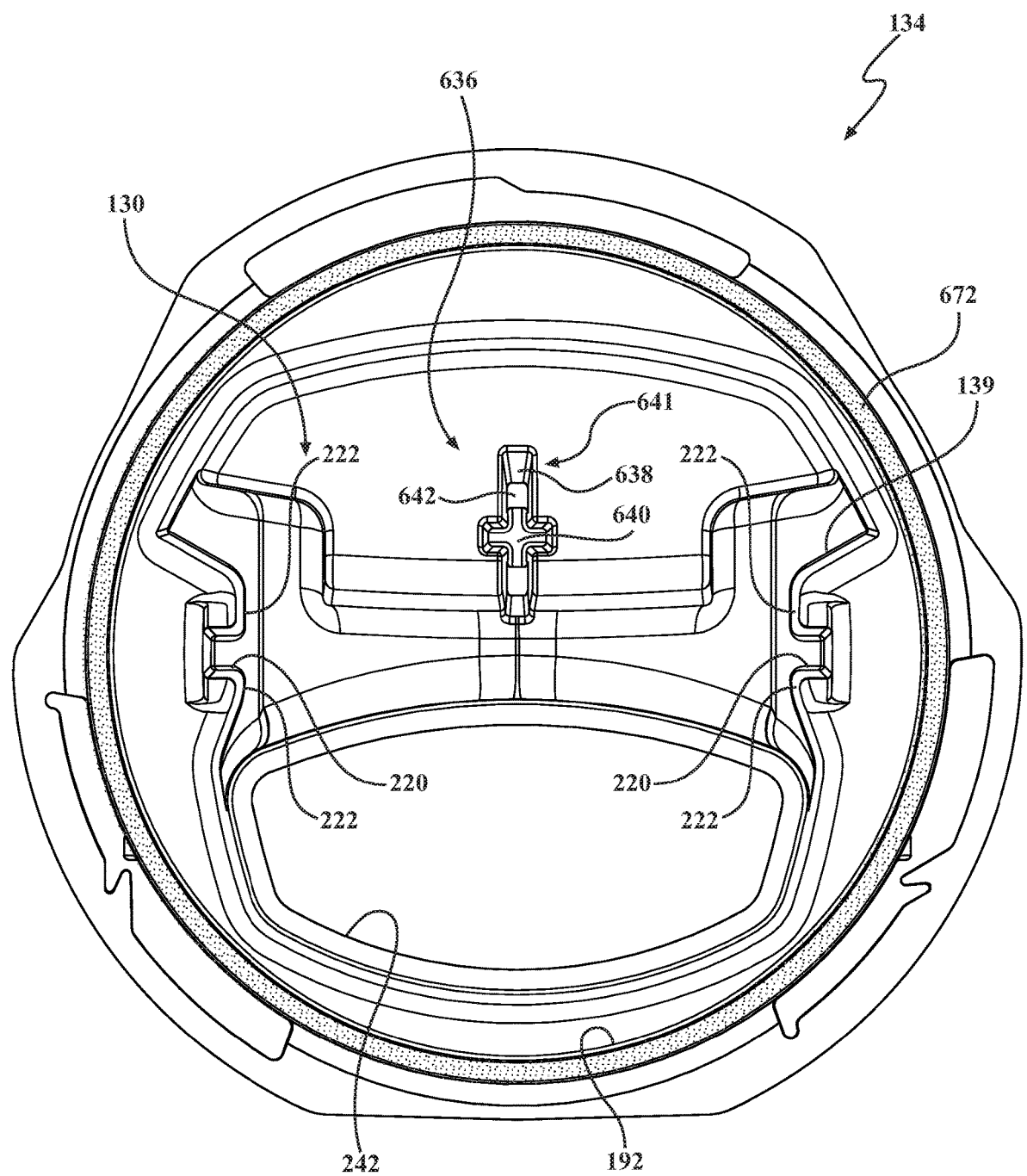
FIG. 80 is a front elevation view of a trunk of the manifold of FIG. 78.
Figure 81:
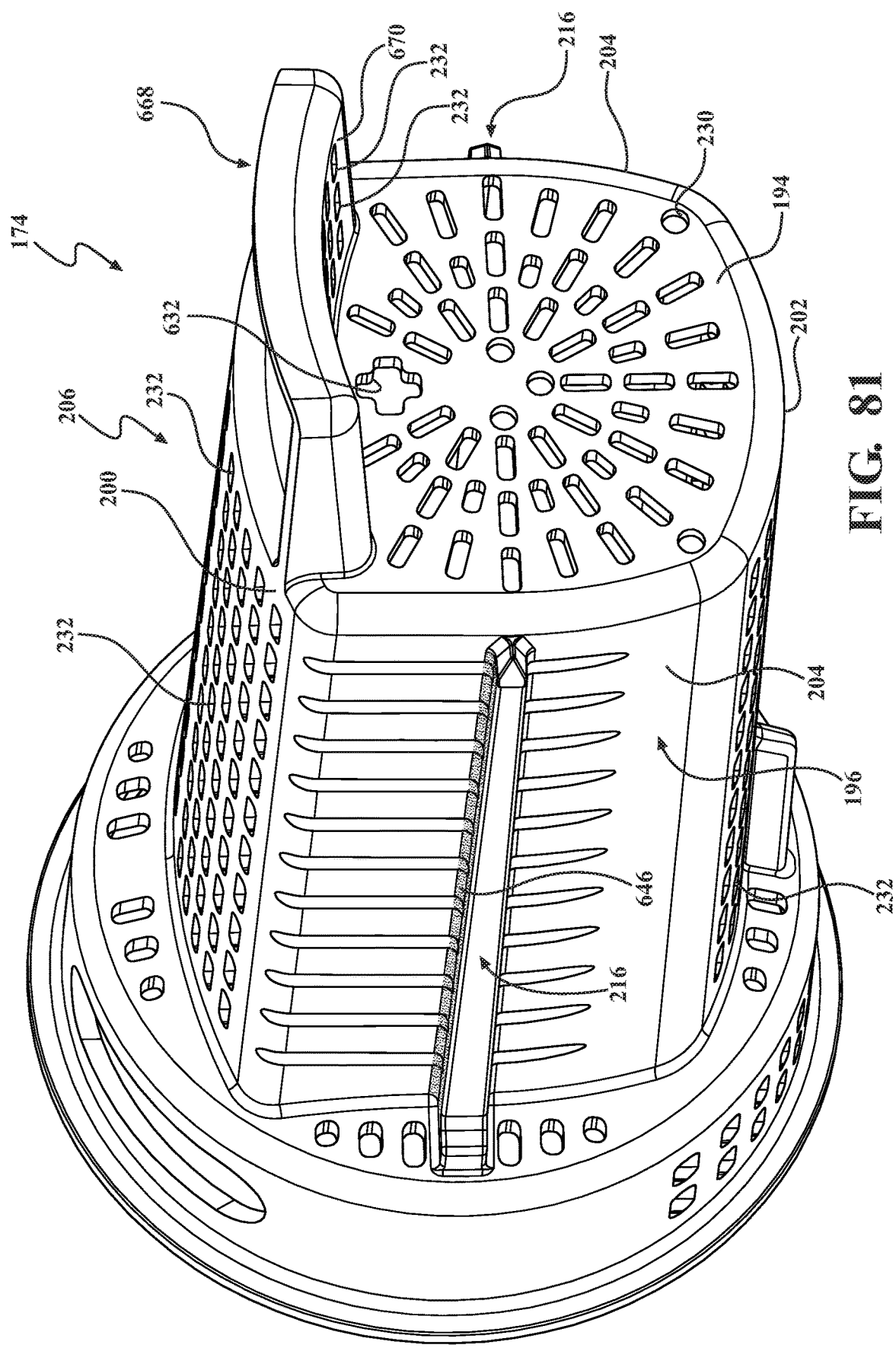
FIG. 81 is a rear perspective view of the filter element of the manifold of FIG. 78.

Referring now to FIGS. 78-82A, the filter element 174 may include a keyway 632 separate from the apertures, and more particularly from the holes 230 and the pores 232. The keyway 632 may be defined within the base wall 194 of the basket 206, as best shown in FIG. 81. The keyway 632 is shown as a singular aperture that is cruciform in shape and laterally centered between the opposing sides 204 of the basket 206, and further positioned offset towards the upper wall 200 of the basket 206. It is understood that more than one keyway may be provided, and the keyway(s) may be positioned in any suitable manner. The cruciform shape is but one example, and other geometries are contemplated; e.g., a circle, ellipse, triangle, square, rectangle, stellate, etc. It is further understood that the keyway 632 may be shaped the same or differently than the apertures.

Figure 82:
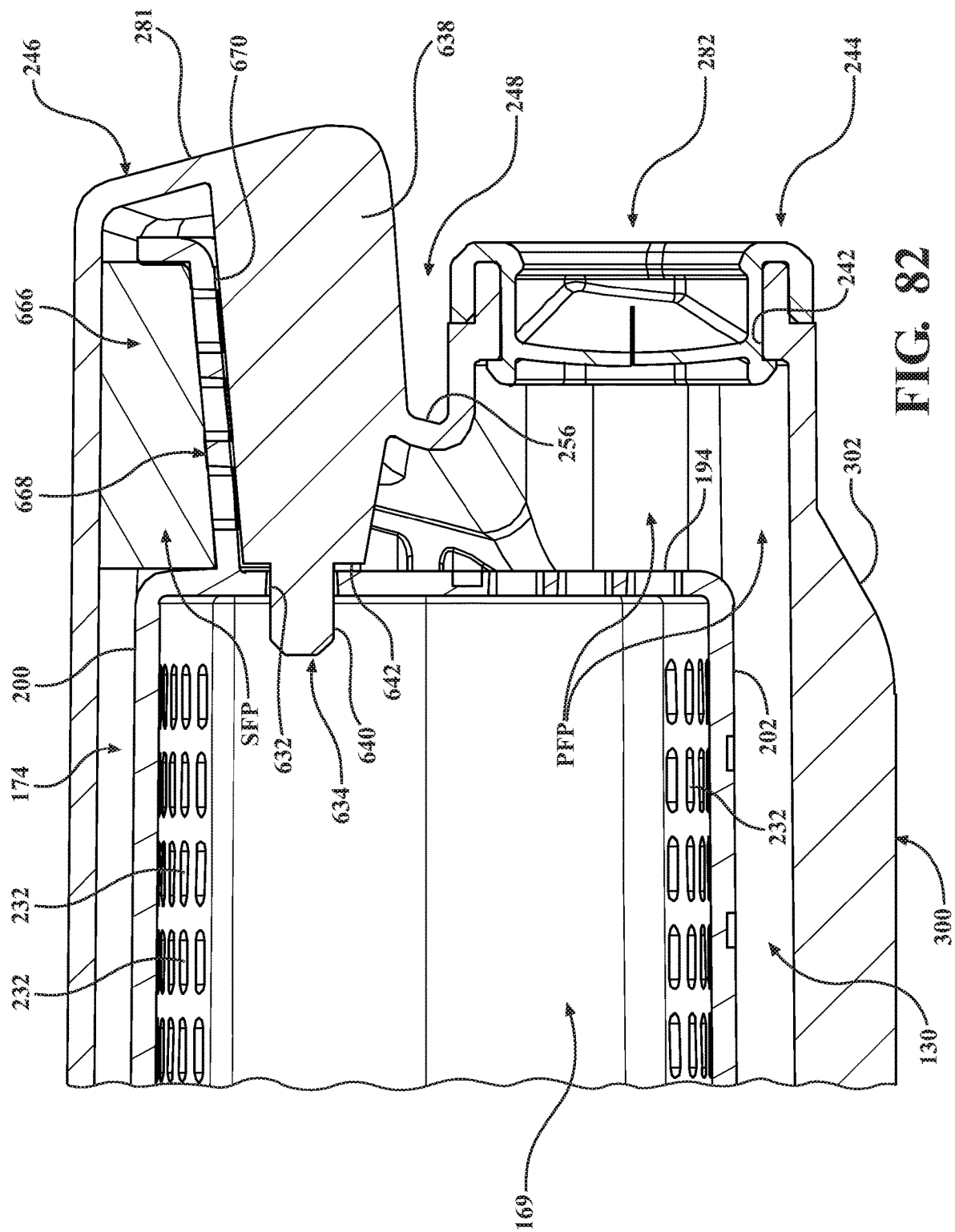
FIG. 82 is a sectional elevation view of a portion of the trunk of the manifold of FIG. 79 within detail 79, with a projection extending through a keyway of the filter element.
Figure 82A:
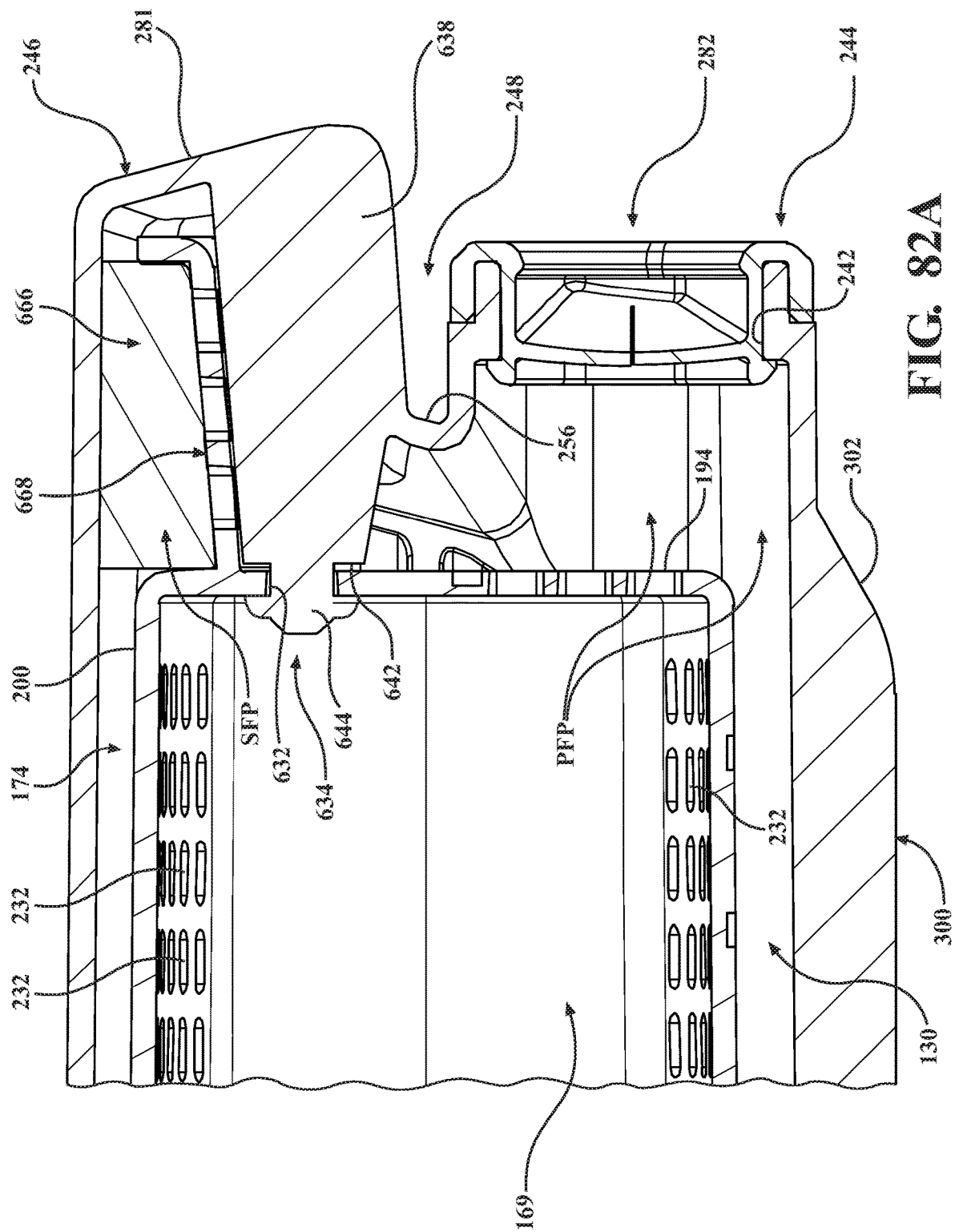
FIG. 82A is a sectional elevation view of the portion of the trunk of FIG. 82, with the projection joining the filter element to the housing via thermoplastic staking.

The manifold 124 may include a projection 634 extending from an inner surface 139 of the housing 128. Referring to FIGS. 80, 82 and 82A, the projection 634 extends from a base wall 281 of the trunk 134. In particular, an interior of the second leg 246 may define a cavity 636 in communication (or comprising a part of) the manifold volume 130. In other words, the second leg 246 may be at least partially hollow. The projection 634 may be disposed within the cavity 636 of the second leg 246 and extend distally from the base wall 281 to a position within the manifold volume 130 distal to the distal aspect 256 of the trunk 134. In certain implementations, the projection 634 is integrally formed with the housing 128. With particular reference to FIGS. 82 and 82A, the projection 634 may include a strut portion 638 and a tip portion 640. The tip portion 640 may be smaller in cross section than a cross section of the strut portion 638. In other words, a transition from the strut portion 638 to the tip portion 640 may include a step 642. The step 642, among other advantages, facilitates that the filter element 174 is fully seated within the manifold volume 130. In other words, the step 642 may act as a stop to abut the base wall 194 of the basket 206 when the tip portion 640 extends through the keyway 632 in the manner to be described.

The projection 634, and in particular the tip portion 640, is configured to extend through the keyway 632. The engagement of the tip portion 640 and the keyway 632 reduce "play" (e.g., inadvertent proximal, distal, lateral, and/or rotational movement from component tolerances or the like). Further, the projection 634 and the keyway 632, in view of their relative shapes, dimensions, and/or positions, may cooperate to prevent an unauthorized filter element from being coupled with the trunk 134, for example, during attempted reprocessing of the manifold 124. For example, the specific shape(s) of the keyway 632 may ensure that only genuine filter elements 174 are compatible, otherwise the projection 634 interferes with the unauthorized filter element and prevents it from being fully seated within the trunk 134 of the housing 128, and thereby further preventing the head 132 from being properly coupled to the trunk 134.

The projection 634 is joined to the filter element 174 such that removal of the filter element 174 from the housing 128 requires mutilation of the manifold 124. In certain implementations, the projection 634 is secured to the filter element 174 via interference fit, for example, thermoplastic staking. In other words, during assembly of the manifold 124, the filter element 174 is inserted into the trunk 134 such that the tip portion 640 extends through the keyway 632, after which the tip portion 640, through the joining process, is softened and deformed to radially expand so as to form an interference fit between the projection 634 and the filter element 174, as shown in FIG. 82A. In other words, a head 644 may be formed through the joining process with the head 644 having a radial dimension greater than that of the keyway 632. The thermoplastic staking may or may not result in the projection 634 and the filter element 174 being fused to one another. Relative to other aspects of the present disclosure wherein fusing is described, the joining through thermoplastic staking may simply result in a mechanical locking of the components. Other suitable, related joining processes include, thermal tooling, thermal punch (or hot punch), hot air cold upset, ultrasonic staking, old forming, infrared staking, impulse staking, etc.

The joining of the filter element 174 and the housing 128, through thermoplastic staking or otherwise, requires mutilation of the manifold 124 in order to remove the filter element 174 for reprocessing. As used herein, mutilation may be considered to include disfiguring, or making imperfect by removing or irreparably damaging parts. Example of mutilation includes plastic deformation through breaking, rupturing, snapping, and the like. For example, applying a mechanical force on the filter element 174 of sufficient magnitude to remove the filter element 174 may result in the head 644 breaking from the strut portion 638 of the projection 634. For another example, applying a mechanical force on the filter element 174 of sufficient magnitude to remove the filter element 174 may result in the base wall 194 of the filter element 174 rupturing in a manner that renders the filter element 174 unusable. For still another example, applying a mechanical force on the filter element 174 of sufficient magnitude to remove the filter element 174 may result in the housing 128 rupturing in a manner that renders the housing 128 unusable. The characteristics of the projection 634 may be designed such that the second leg 246 ruptures. It should be appreciated that any structure of the housing 128 may be ruptured during removal of the filter element 174, for example the upper wall 200, the lower wall 202, the opposing sides 204, and the first leg 244.

Figure 83:
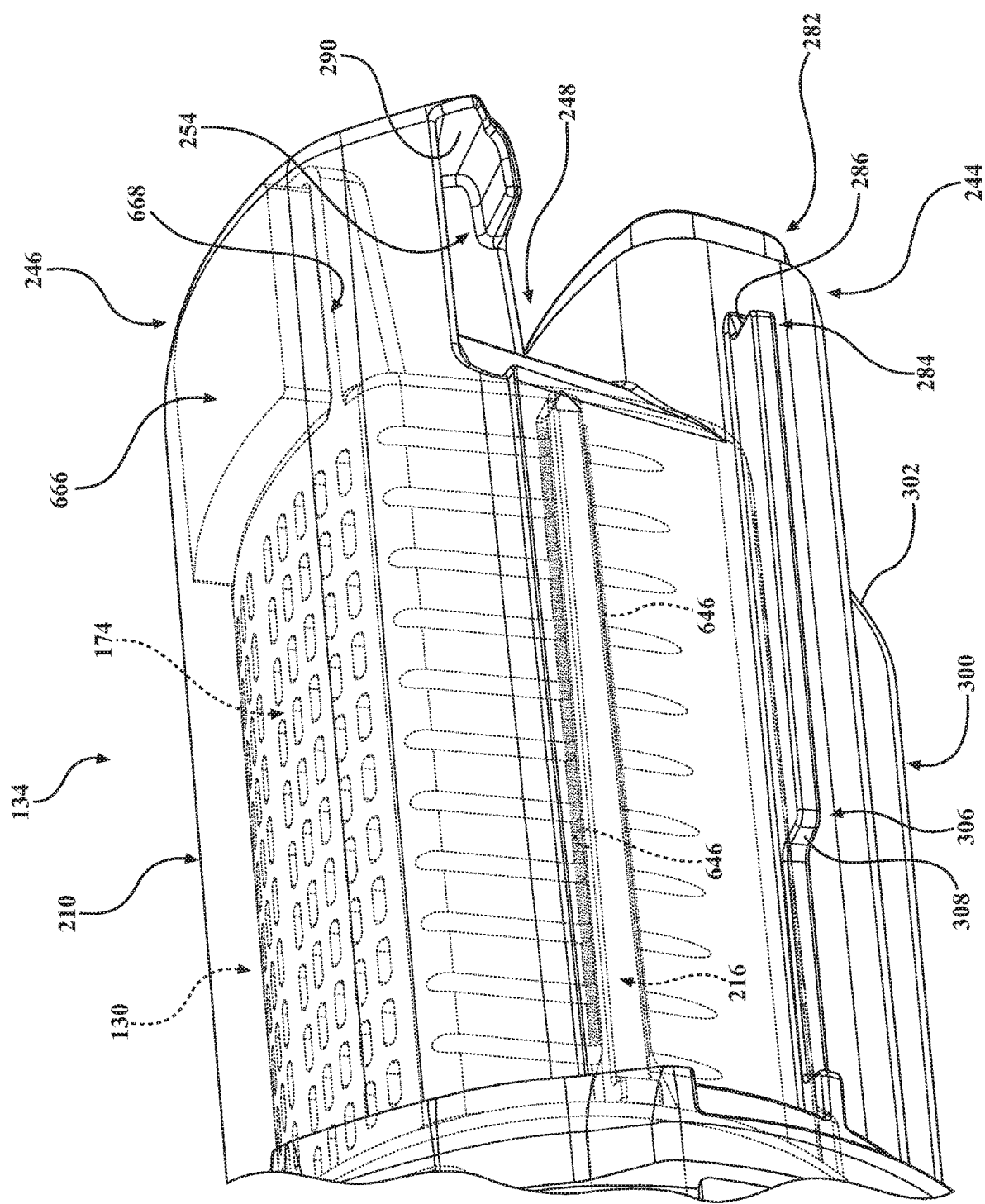
FIG. 83 is a perspective view of a portion of the manifold including the filter element fused to the housing via laser welding.

Referring now to FIG. 83, the filter element 174 may be bonded to the inner surface 139 of the housing 128 such that removing the filter element 174 from the housing 128 requires further mutilation of the manifold 124. In one implementation, the filter element 174 is fused to the housing 128, thereby creating a permanent bond. For example, the filter element 174 is fused to the inner surface 139 of the housing 128 via laser welding at one or more laser interface 646. With concurrent reference to FIGS. 6 and 7, the filter element 174 may the guide(s) 216 extending laterally outward from one of the opposing sides 204 of the basket 206 and oriented in the proximal-to-distal direction. The guides 216 may be sized and oriented to be slidably inserted within complementary slots 220 defined between parallel railings 222 extending laterally inward from the inner surface of the body portion 210 of the trunk 134. FIG. 81 shows two guides 216 extending laterally outward from the opposing sides 204, and FIG. 80 shows two complementary slots 220 extending laterally inward from opposing inner surfaces of the body portion 210.

With the filter element 174 inserted into the manifold volume 130, as best shown in FIG. 83, the guides 216 may be fused to the slots 220, for example, via laser welding. As a result, the laser weld interfaces 646 may extend in the proximal-to-distal direction on upper and lower surfaces of the guides 216 and adjacent surfaces of the railings 222 defining the slots 220. As mentioned, the fusing of the filter element 174 and the housing 128, through laser welding or otherwise, requires mutilation of the manifold 124 in order to remove the filter element 174 for reprocessing. For example, applying a mechanical force on the filter element 174 of sufficient magnitude to remove the filter element 174 may result in the guides 216 of the filter element 174 rupturing in a manner that renders the filter element 174 unusable. For another example, applying a mechanical force on the filter element 174 of sufficient magnitude to remove the filter element 174 may result in the body portion 210 of the housing 128 rupturing in a manner that renders the housing 128 unusable. It is understood that the fusing of the filter element 174 and the housing 128 via laser welding may be in addition to or in lieu of the joining of the filter element 174 and the housing 128 via thermoplastic staking or otherwise. Particularly when used in combination, the manifold 124 of the present disclosure may advantageously prevent removal of the filter element 174 from the housing 128, and thus meaningful reprocessing of the same.

Certain reprocessing methods may seek to clean and/or sanitize the manifold 124 without removal of the filter element 174. The manifold 124 of the present disclosure further prevents reprocessing of the same by providing a use indicator 666 disposed within the manifold volume 130. The use indicator 666 is configured to absorb medical waste, such as solid or liquid medical waste during operation the medical waste collection system 100. Thus, efforts to effectively reprocess the manifold 124 without removal of the filter element 174 will be increasingly unlikely, as it is typically unfeasible to sanitize or clean the use indicator (with the absorbed medical waste) to the extent necessary. The inclusion of the use indicator reduces the likelihood of improper re-use. As used herein, the term medical waste refers to any material that contacts the use indicator 666 and renders it improper for further clinical use with that patient or upon another patient. Contaminants include, for example, bodily fluids, such as blood, excretory material such as urine or fecal fluids or solids, exfoliated cells, lymphatic material, exudates, mucosal secretions, and the like, which may contain proteins, metabolic products, bacterial flora, viruses, or endogenous compounds generated by normal or pathological processes in the body.

The use indicator 666 may define a tortuous path such that solid medical waste is retained in the use indicator after the manifold has been used. The use indicator 666 is configured to absorb contaminants during clinical use of the manifold. The absorbed contaminants may be visible against the use indicator 666. For example, the use indicator 666 may be formed from a lightly-colored material, such as white material, that stains when exposed to blood or other contaminants. The lightly-colored material may be impregnated with particular, for example, colored particles, so as to form a gel when wetted with liquid waste material.

The use indicator 666 may be formed from a porous material, such as the foam insert. The foam insert may have a porosity ranging from 30-70% of the total volume. The average pore may have a size ranging from 0.001 to 0.030 inches. The use indicator 666 may be formed of a variety of different materials. For example, the use indicator 666 may comprise polyethylene, polyurethane, or combinations thereof. The use indicator 666 may be formed of a material selected from the group consisting of a foam, an open-cell foam, a closed-cell foam, and a fibrous material. The use indicator 666 may be hydrophilic, such that it readily absorbs medical waste that it contacts. The use indicator 666 may be selected such that it is insoluble when exposed to aqueous cleaning solutions. Alternatively, the use indicator 666 may be a screen or a porous cube-like structure.

The use indicator 666, such as a foam insert, may be placed in a position within the manifold volume 130 to make removal of the use indicator 666 difficult, especially if the filter element 174 is not first removed. For example, with reference to FIGS. 82, 82A and 83, the use indicator 666 may be disposed within the second leg 246. The filter element 174 may include a tray 668 sized to support the use indicator 666. With concurrent reference to FIGS. 81 and 83, the filter element 174 includes the aforementioned basket 206 that defines a filter volume 169. More particularly, the base wall 194 and the least one side 196 extending distally from the base wall 194 may define the filter volume 169. The tray 668 may extend proximally from the basket 206, and in particular from the base wall 194, as best shown in FIGS. 77 and 81. In other words, the tray 668 extends from the base wall 194 in a direction opposite in which the side 196 extends from the base wall 194. The tray 668 and the basket 206 may be integrally or separately formed.

Furthermore, the tray 668 may be positioned near the upper wall 206 of the filter element 174 such that, with the tray 668 extending proximally from the base wall 194, the tray 668 is disposed within the second leg 246 of the housing 128. With particular reference to FIGS. 82 and 82A, the tray 668 may be disposed within the second leg 246 above the projection 166. As a result, the tray 668 may be external to the filter volume 169, and thus the use indicator 666 may be positioned within the manifold volume 130 but external to the filter volume 169. Owing to the geometry of the housing 128 and the apertures of the filter element 174, a primary flow path (PFP) and a secondary flow path (SFP) may be established. The primary flow path includes the waste material being directed generally downwardly through the filter volume 169 and the apertures of the filter element 174 towards the outlet opening 242 and the seal 282. The secondary flow path includes the waste material being directed generally upwardly through the filter volume 169, the apertures of the filter element 174, and a gap defined between the upper wall 200 of the filter element 174 towards the use indicator 666. The tray 668 may also include apertures (e.g., pores 232) configured to permit liquid to pass through a lower wall 670 on which the use indicator 666 is supported to facilitate saturating the use indicator 666 with the liquid or contaminating the use indicator with solid medical waste. Owing to the nature and positioning of the use indicator 666, efforts to clean and/or sanitize the manifold 124 without removal of the filter element 174 are hindered. The providing of the use indicator 666 may be particularly beneficial in combination with the joining and/or fusing of the filter element 174 and the housing 128 in the manners previously described.

In addition to discouraging removal of the filter element 174 from the housing 128, preventing initial access to the manifold volume 130 and the filter element 174 may further hinder reprocessing efforts. In certain implementations, the head 132 and the trunk 134 are fused to one another. For example, the head 132 and the trunk 134 may be fused through spin welding at a spin welding interface 672 (see FIGS. 4 and 6). Other suitable joining processes are contemplated, such as solvent bonding, adhesives, mechanical fastening, and the like. The spin welding interface 672 may be cooperatively defined by a proximally-directed surface of the head 132 and a distally-directed surface of the trunk 134.

Assembling of the manifold 124 may include positioning the use indicator 666 on the tray 668 of the filter element 174 or otherwise placing the use indicator in the manifold volume. The components may be directed into the trunk 134 of the housing 128 such that the guides 216 slidably engage the slots 220. The railings 222 defining the slots 220 may be formed from laser-transparent material, and the guides 216 of the filter element 174 may be formed from laser-absorbing material. The laser weld interfaces 646 are formed by laser welding the guides 216 and the railings 222. The step of directing the components into the trunk 134 may further position the tip portion 640 of the projection 634 through the keyway 632 of the filter element 174. Before, concurrent, or after the fusing of the filter element 174 of the housing 128, the filter element 174 may be joined to the housing 128 by thermoplastic staking of the projection 634. After the valve is coupled to the head 132, the head 132 may be fused to the trunk 134 via spin welding to form the spin welding interface 672. The seal 282 may be coupled to the rim 276 to cover the outlet opening 242 at any suitable time.

In alternative implementations, the head 132 and the trunk 134 are removably coupled to one another, for example, as described in the aforementioned U.S. patent application Ser. No. 16/383,218, which again is hereby incorporated by reference in its entirety. The removable coupling between the head 132 and the trunk 134 may provide access to the manifold volume 130 within which the filter element 174 is disposed. Among other advantages, accessing the filter element 174 may allow the user to retrieve waste material collected within the filter element 174, most notably a polyp or tissue sample, for further examination and processing during certain surgical procedures. The manifold volume 130 of the trunk 134 may be accessed through a distal opening 190 at least partially defined by a neck 192 of the trunk 134, as shown in FIG. 4. Commonly owned International Publication No. WO 2013/090579, published Jun. 20, 2013, the entire contents of which is hereby incorporated by reference, discloses a manifold including a tissue trap for collecting the polyp or the tissue sample. In certain implementations, the manifold 124, including the head 132, may include further features to facilitate collection of tissue sample(s).

According to certain methods of reprocessing the manifold 124, the head 132 may be decoupled from the trunk 134 in which at least one of the head 132 and the trunk 134 is mutilated at or adjacent to the spin weld interface 672. The filter element 174 may be removed from the manifold volume 130 in which at least one of the housing 128, the filter element 174, and the projection 634 is mutilated. The filter element 174 may be fused to the housing 128 via the laser welding such that the filter element 174 is mutilated at or adjacent to the laser weld interface 646. The projection 634 may be joined to the filter element 174 via the thermoplastic staking such that that the projection 634 is severed or mutilated. The use indicator 666 may be removed, for example, from the tray 668 of the filter element 174. The use indicator 666 may be sized such that it is larger than the pores of the filter element 174. In addition, the composition of the use indicator 666 may be selected such that it is insoluble in typical cleaning compositions. Various chemistries are contemplated.

At least one of the used housing 128 and the used filter element 174 may be cleaned and/or sterilized. In one example, the cleaned filter element is reinserted into the manifold volume 130. In another example, another filter element, i.e., a new filter element, may be provided and inserted into the manifold volume 130. The filter element may be inserted into the manifold volume 130 without replacing the removed use indicator 666 with another use indicator. Further, the filter element may be inserted into the manifold volume 130 without fusing and/or joining the filter element to the housing 128 in manners previously described. The head 132 may be reattached to the trunk 134 through a suitable joining means, and/or another head may be provided and attached to the trunk 134.

Figure 84:
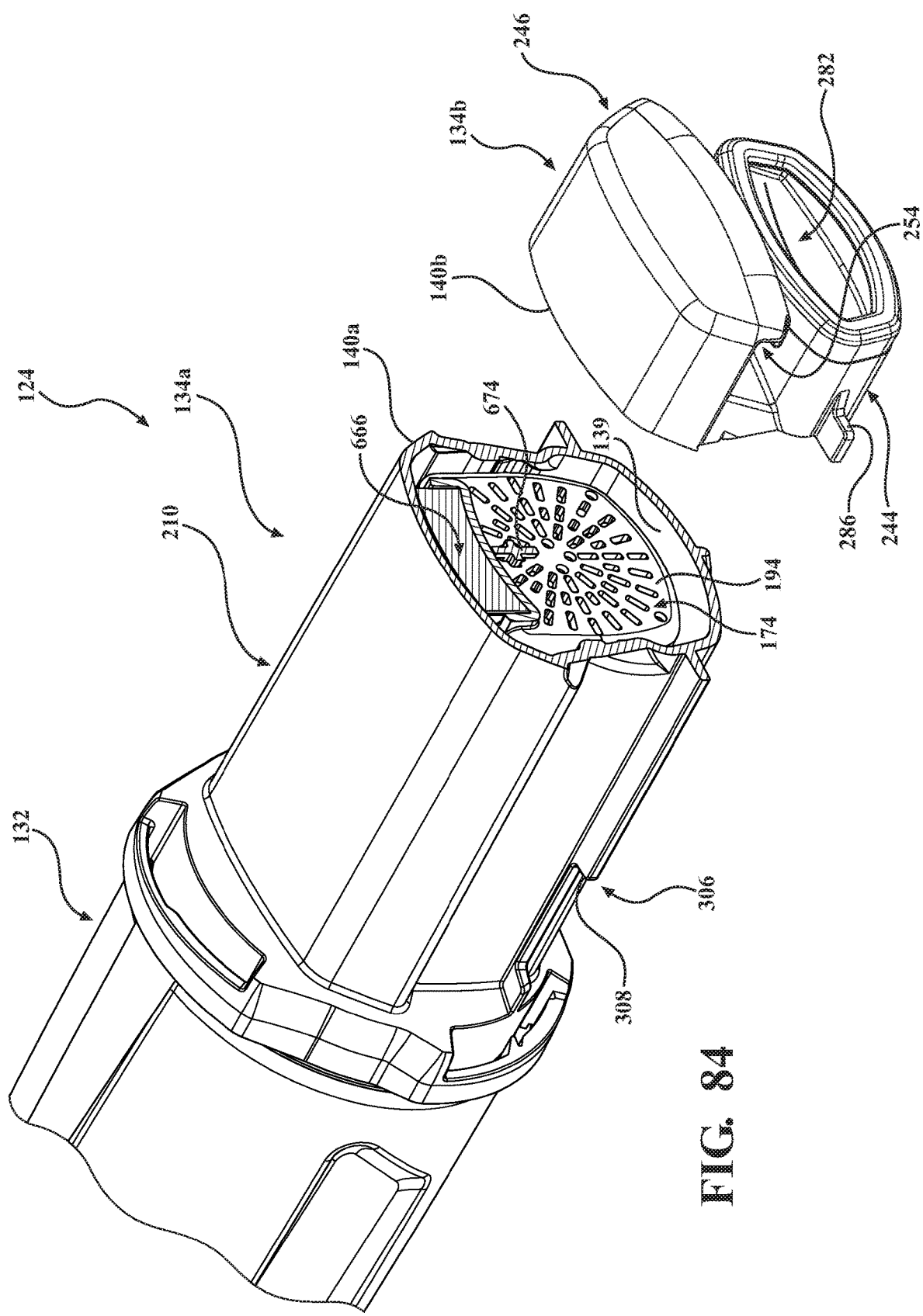
FIG. 84 is a rear perspective view of the manifold of FIG. 78 including a severing of a portion of the trunk for accessing the manifold volume.

Referring now to FIG. 84, reprocessing attempts may include severing at least a portion of the manifold 124 from remaining portions of the manifold 124. In particular, the trunk 134 may be severed into a first trunk portion 134a and a second trunk portion 134b (also referred to as a severed portion). The severing into the first and second trunk portions 134a, 134b may result in end surfaces 140a, 140b on respective one of the first and second trunk portions 134a, 134b. A location of the severing may be along the manifold 124 in the proximal-to-distal direction such that the filter element 174 and/or the use indicator 666 is accessible. An entire cross section of the manifold 124 may be severed, and in certain implementations the second leg 246 is severed. The severing may be performed in a plane substantially transverse to a longitudinal axis of the manifold. FIG. 84 shows the second leg 246 being severed an axial position between the outlet opening 242 and the base wall 194 of the filter element 174. The severing of the housing 128 may include severing the projection 634, generally referenced with numeral 674 in FIG. 84. The use indicator 666 and/or the tray 668 may be severed, and the portion(s) of the use indicator 666 may be removed.

With the trunk 134 severed into the first and second trunk portions 134a, 134b, the manifold volume 130 is accessible. In one reprocessing method after the severing, at least one of the housing 128 and the filter element 174 may be cleaned. The portion(s) of the severed projection 634 may or may not be removed before cleaning the housing 128 and/or the filter element 174. The severed portion of the trunk 134b, at least the second leg 246, may be reattached to the housing 128 to re-enclose the manifold volume 130. The severed portion may be reattached through any suitable joining process, for example, adhesives, fasteners, and the like. It is appreciated that severing the housing 128 in the aforementioned manner eliminates the need to mutilate the manifold 124 at the spin weld interface 672 and/or mutilate the manifold 124 at the laser weld interface 646. Severing the housing 128 may also enable one to more effectively clean the housing 128. As an alternative to severing a portion of the manifold, a reprocessing method could include milling a hole into the second leg and removing the use indicator through the milled hole.

The step of cleaning the used housing and/or filter element may include one or more of the following steps: submersion of one or more components of the manifold in a detergent mixture, ultrasonic cleaning, rinsing, etc. As mentioned above, the method of reprocessing may include sterilizing the manifold. The sterilizing step may include pasteurization, which requires heating, traditional chemical methods, such as chamber methods, which require flooding a chamber with a sterilant, usually a mix of ethylene oxide (commonly referred to EtO) and other gases, and micro-dose methods, which require introducing a sterilant, such as EtO.

As previously mentioned, in certain implementations the manifold 124 may not define the manifold volume 130. In other words, the waste material may not pass from the suction tube 120 to the manifold volume 130 defined by the housing 128, to the outlet opening 242. Rather, in certain implementations to be described, a device 125 may include the components for engaging the complementary components of the receiver 116 as previously described, but otherwise a portion of the suction tube 120 is configured to extend through the housing 128 of the device 125. With the portion of the suction tube 120 extending through the housing 128, a void space 702 of the housing 128 may not be in fluid communication with the suction tube 120 as the waste material passes through the suction tube 120 to the suction fitting 326 of the inlet mechanism 324. In such an arrangement, the housing 128 of the device 125 may be considered an adapter for engaging and actuating the receiver 116. FIGS. 85-102 illustrate several implementations of the manifolds configured to achieve the arrangement. Like numerals correspond to like components of the device 125 previously described, and any disclosure common to the corresponding components may be considered omitted in the interest of brevity should not be construed as limiting.

Figure 85:
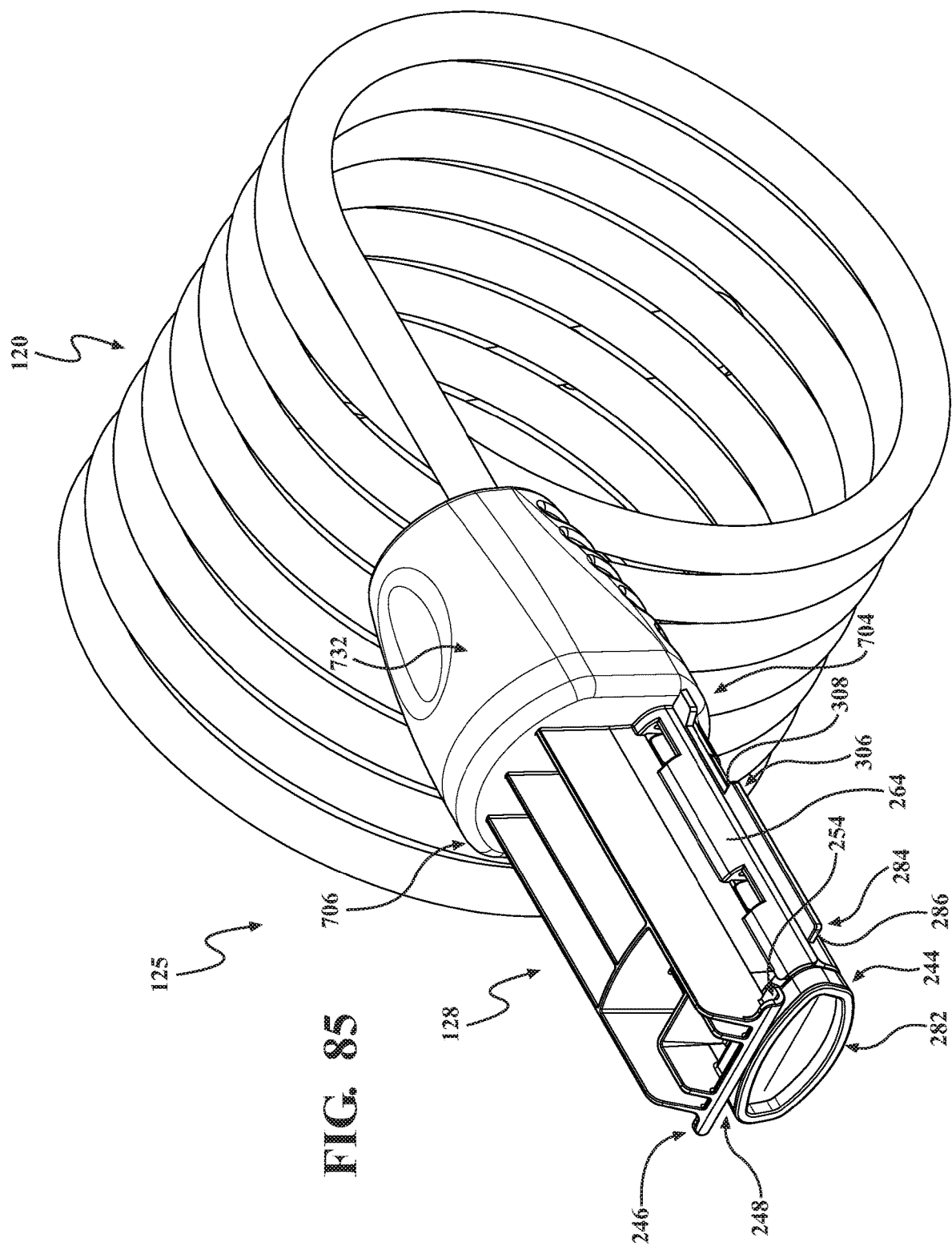
FIG. 85 is a rear perspective view of a device coupled to the suction tube.
Figure 86:
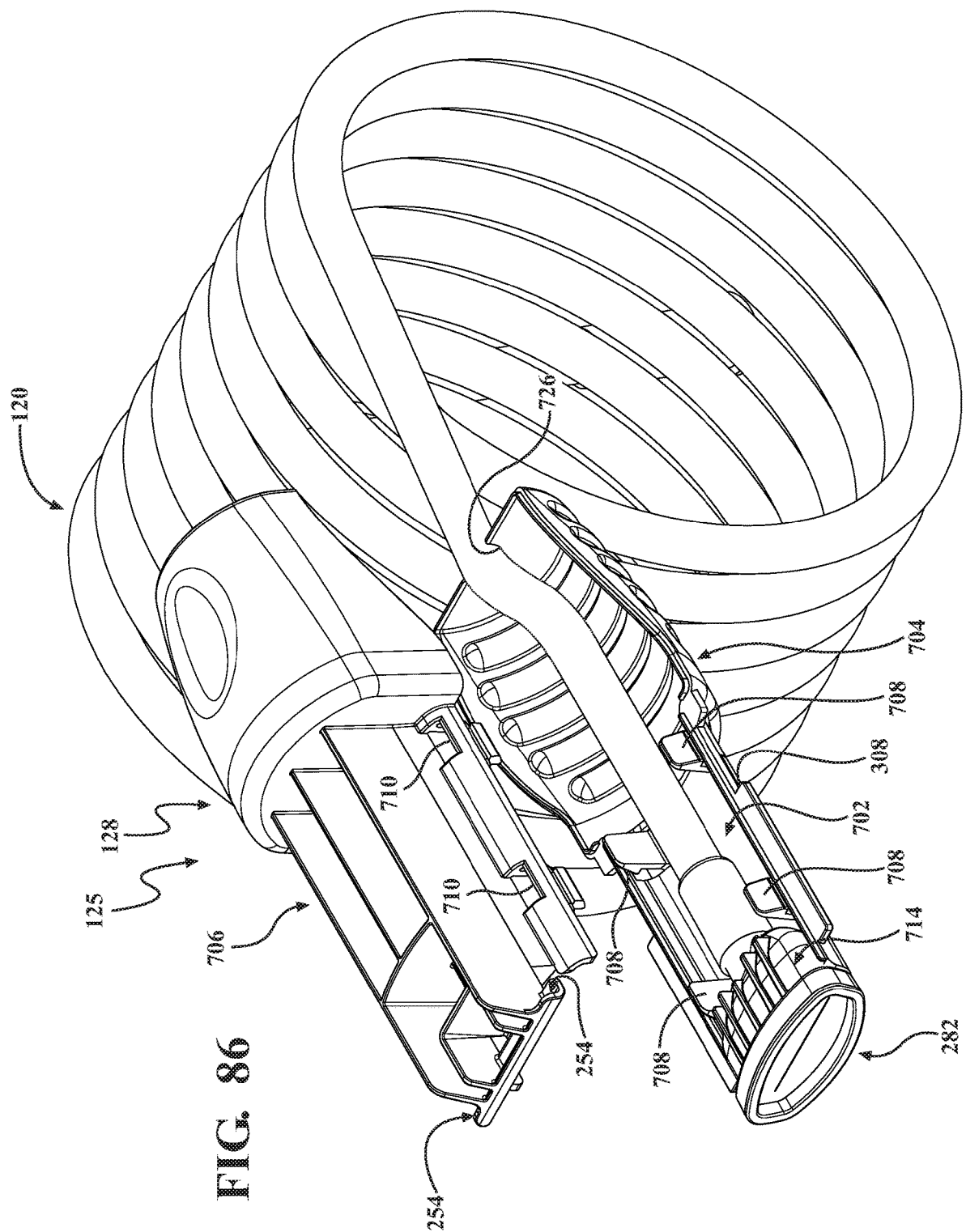
FIG. 86 is a partial exploded view of the device of FIG. 85 with the suction tube coupled to the device.
Figure 87:
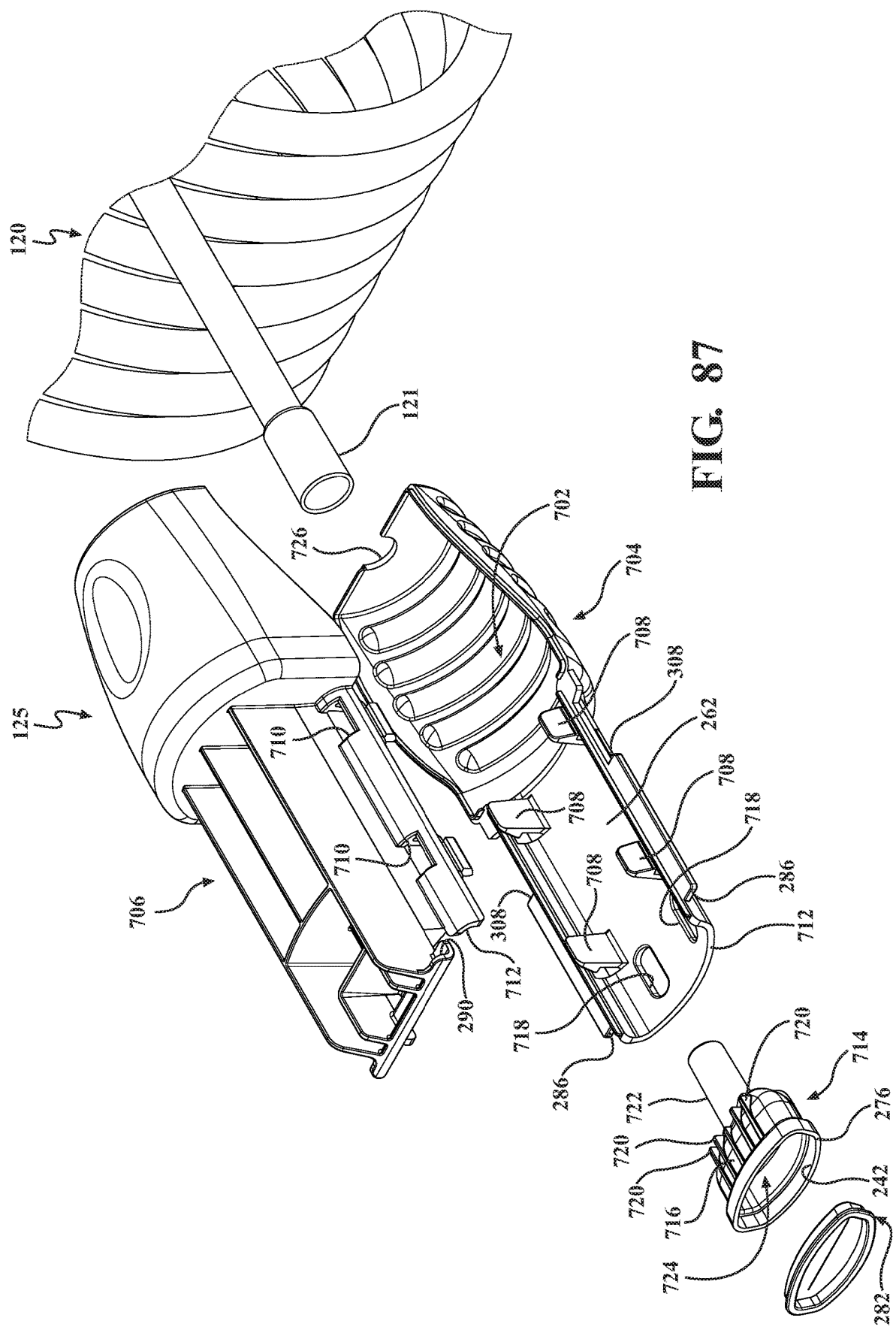
FIG. 87 is an exploded view of the device of FIG. 85 with the suction tube decoupled from the device.

Referring to FIGS. 85-87, the housing 128 of the device 125 includes a first housing portion 704 and a second housing portion 706 coupled to the first housing portion 704. The first and second housing portions 704, 706 may be considered lower and upper housing portions, respectively, but other suitable configurations are contemplated. The first and second housing portions 704, 706 may define respective cavities such that, when the first and second housing portions 704, 706 are coupled to one another, the void space 702 is formed. The first and second housing portions 704, 706 may be coupled to one another with at least one tab 708 configured to engage at least one slot 710; however, other suitable fastening means are contemplated. As best shown in FIG. 86, a portion of the suction tube 120 extends through the void space 702 and is coupled to a tube adapter 714 to be described.

The first housing portion 704 and/or the second housing portion 706 may include a lip 712 defining an adapter opening. As best shown in FIGS. 86 and 87, each of the first housing portion 704 and the second housing portion 706 include a portion of the lip 712 that, when the first and second housing portions 704, 706 are coupled to one another, collectively define the adapter opening. Further, owing to the implementation of the first and second housing portions 704, 706, the first and second housing portions 704, 706 may include the body portion 210, and the first leg 244, and the second housing portion 706 may include the second leg 246. The void 248 is at least partially defined the second leg 246 and the first leg 244. Further, the arm(s) 246, the spine 300, the lock feature(s) 306, and/or the catch(es) 254 may be disposed on one of the first housing portion 704 and the second housing portion 706. More particularly, in the illustrated implementation, the arm 284 may extend outwardly from the first housing portion 704 or laterally outward from a portion of the side 264 of the first housing portion 704. The arm 284 includes the proximally-directed surface 286. Similarly, the lock element 306 may extend outwardly from the first housing portion 704 or laterally outward from a portion of the sides 264 of the first housing portion 704. The lock element 306 may include the distally-directed surface 308 positioned distal the proximally-directed surface 286 of the arm 284. The spine 300 may extend outwardly from the first housing portion 704, and more particularly downwardly from the bottom wall 262 of the first housing portion 704 (not shown in FIGS. 85-87). The spine 300 includes the proximally-directed surface 302 positioned proximal to the distally-directed surface 308 of the lock element 306 and distal to the proximally-directed surface 286 of the arm 284. The catch 254 may be disposed on the second leg 246 formed by the second housing portion 706. The catch 254 includes the distally-directed surface 290 positioned proximal to the lip 712, proximal to the proximally-directed surface 286 of the arm 284, proximal to the proximally-directed surface 302 of the spine 300, and proximal to the distally-directed surface 308 of the lock element 306. The catch 254 and the rim 276 may be spaced apart by the void 248, and the lip 712 may be positioned below the catch 254 when the device 125 is oriented for insertion into the opening 118 of the receiver 116. It is contemplated that alternative configurations are contemplated where, for example, one or more of the arm(s) 246 and/or the lock feature(s) 306 may be disposed on the second housing portion 706, and/or the catch(es) 254 may be disposed on the first housing portion 704.

The tube adapter 714 is best shown in FIG. 87 and includes a body portion 716. The body portion 716 may be configured to be removably or fixedly coupled to the housing 128. FIG. 87 shows two apertures 718 extending through the bottom wall 262, and the body portion 716 may include two complementary protrusions (not shown) configured to be disposed within the apertures 718 to at least partially retain the tube adapter 714 relative to the housing 128. Further, the body portion 716 may include at least one rib 720 configured to engage the housing 128 in a friction fit arrangement. Additional joining means are contemplated, for example, adhesive, fasteners, and the like.

The tube adapter 714 includes an inlet port 722 coupled to the body portion 716. The inlet port 722 extends distally from the body portion 716 and defines a bore. The inlet port 722 is disposed within the void space 702 of the housing 128 and configured to be coupled to a coupler 121 of the suction tube 120 to establish fluid communication between the suction tube 120 and the bore. As a result, with the suction tube 120 coupled to the inlet port 722, a portion of the suction tube 120 extends through the void space 702 of the housing 128, as best shown in FIG. 86. Further, the body portion 716 defines a fluid volume 724 and includes the rim 276 defining the outlet opening 242 of the device 125. The outlet opening 242 is in communication with the fluid volume 724 and the bore of the inlet port 722. The fluid volume 724 may be considered separate from the void space 702 (i.e., not in fluid communication) when the suction tube 120 is coupled to the inlet port 722.

The housing 128 may further define a distal aperture 726 in communication with the void space 702. FIG. 87 shows the distal aperture 726 partially defined by a semicircular recess within the first housing portion 704, and a second semicircular recess (not shown) in the second housing portion 706. The distal aperture 726 is configured to permit the suction tube 120 to extend distally from within the void space 702 to external to the device 125. The distal aperture 726 may also be sized to facilitate retention of the suction tube 120 with the housing 128.

Referring now to FIG. 88, the device 125 in many respects is similar to that of FIGS. 85-87 with the tube adapter 714 effectively being integrated with the housing 128, and more particularly the first housing portion 704. Whereas the device 125 of FIGS. 85-87 show the tube adapter 714 as a discrete component that is either fixedly or removably coupled to the first housing portion 704 (i.e., with the protrusions and ribs 720), the manifold of FIG. 88 shows the body portion 716 and the inlet port 722 integrally formed with the same. Suitable manufacturing techniques for doing so may include injection molding and additive manufacturing, among others.

Because the void space 702 does not form part of the suction path during operation of the medical waste collection system 100, the form factor of the housing 128 may be of any suitable shape necessary to accommodate the components that engage complementary components of the receiver 116, as previously described. For example, FIGS. 89-93 show the housing 128 as a unitary structure having a lattice-like frame 728. In other words, the housing 128 may include webs 730 arranged to form the frame in which the void space 702 is in communication with the ambient external the housing 128. Suitable manufacturing techniques for doing so may include injection molding and additive manufacturing, among others.

Figure 89:
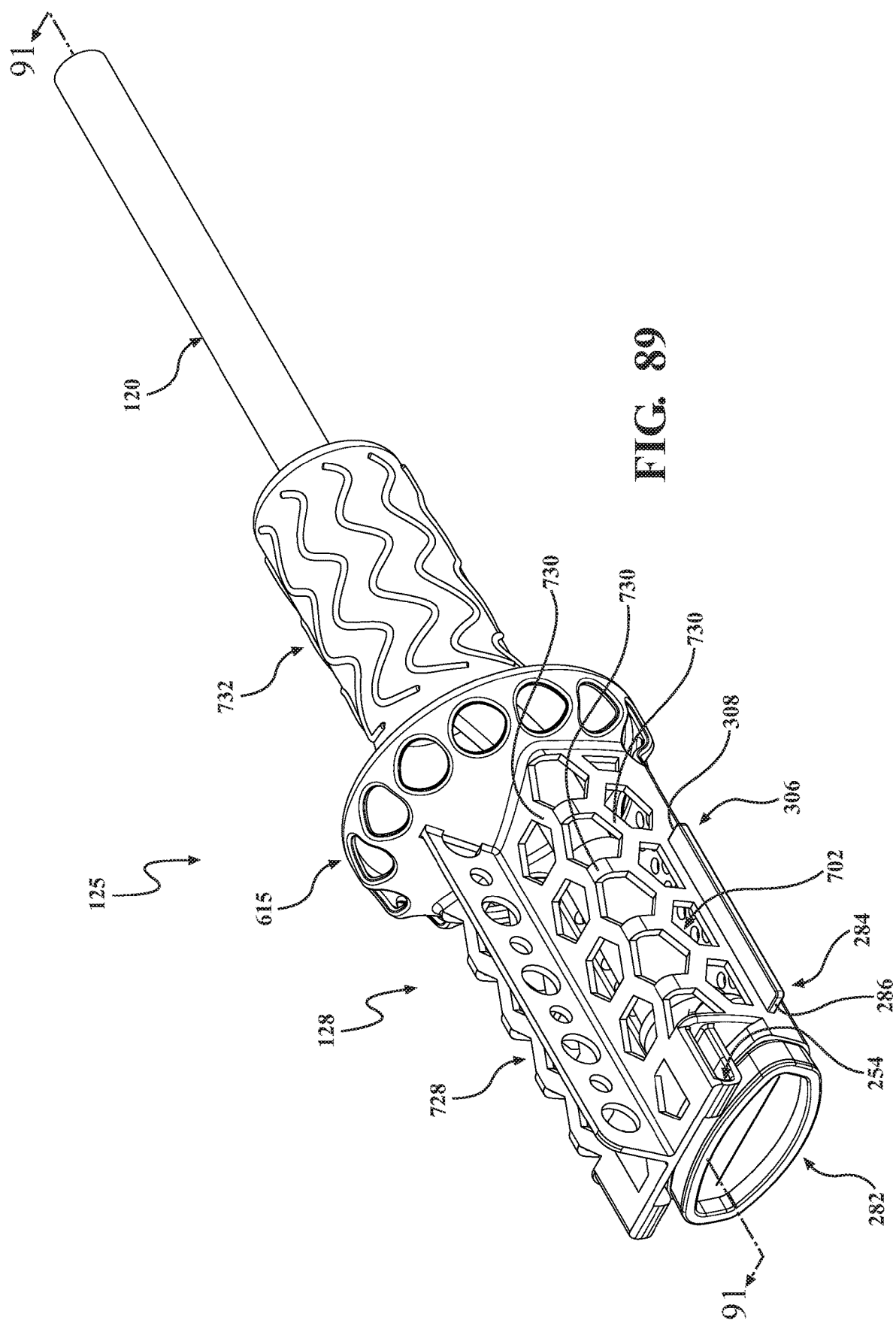
FIG. 89 is a rear perspective view of a device coupled to the suction tube.

With the frame 728 formed as shown, a portion of the suction tube 120 is configured to extend through the void space 702. It is also appreciated that the frame 728 is sized and shaped to accommodate the arm(s) 246, the spine 300, the lock feature(s) 306, and/or the catch(es) 254 as previously described. The housing 128 may include a grip 732, for example, extending distally from the annulus 615 as shown in FIG. 89. The grip 732 may be sized and shape to be easily manipulated by the user to facilitate inserting and removing the device 125 from the receiver 116.

Figure 90:
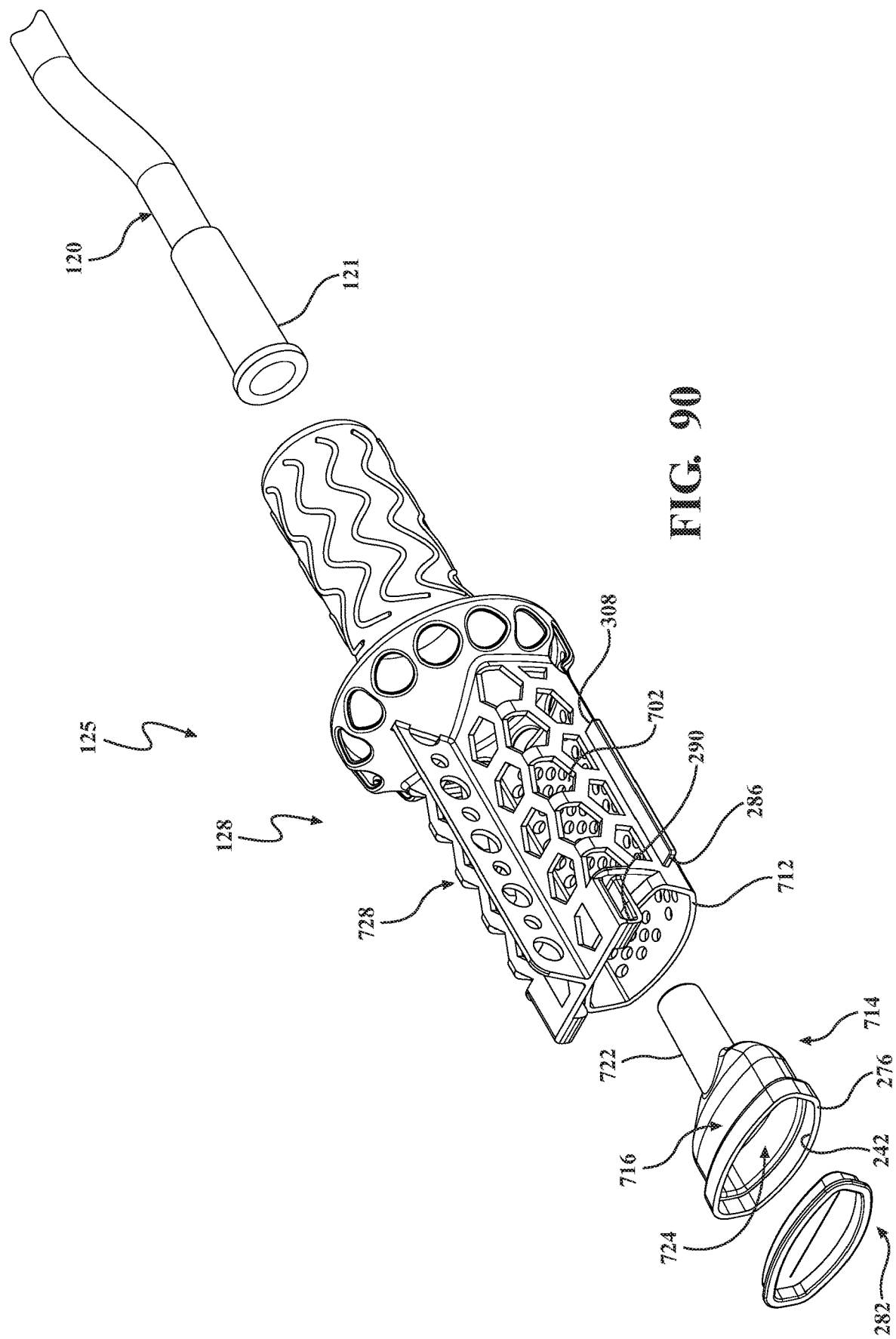
FIG. 90 is an exploded view of the device of FIG. 89 with the suction tube decoupled from the manifold.
Figure 91:
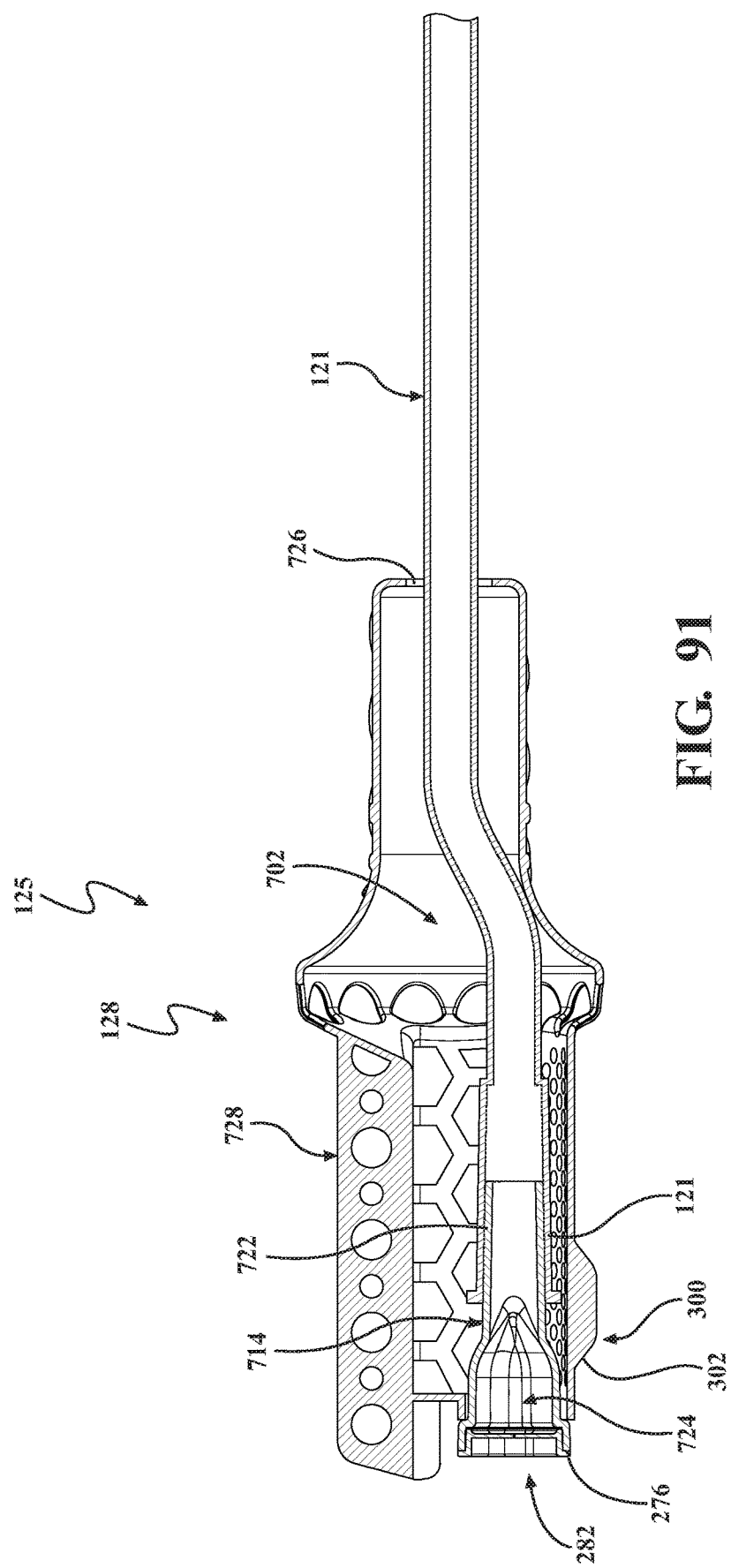
FIG. 91 is a sectional elevation view of the device of FIG. 89 taken along section lines 91-91.
Figure 92:
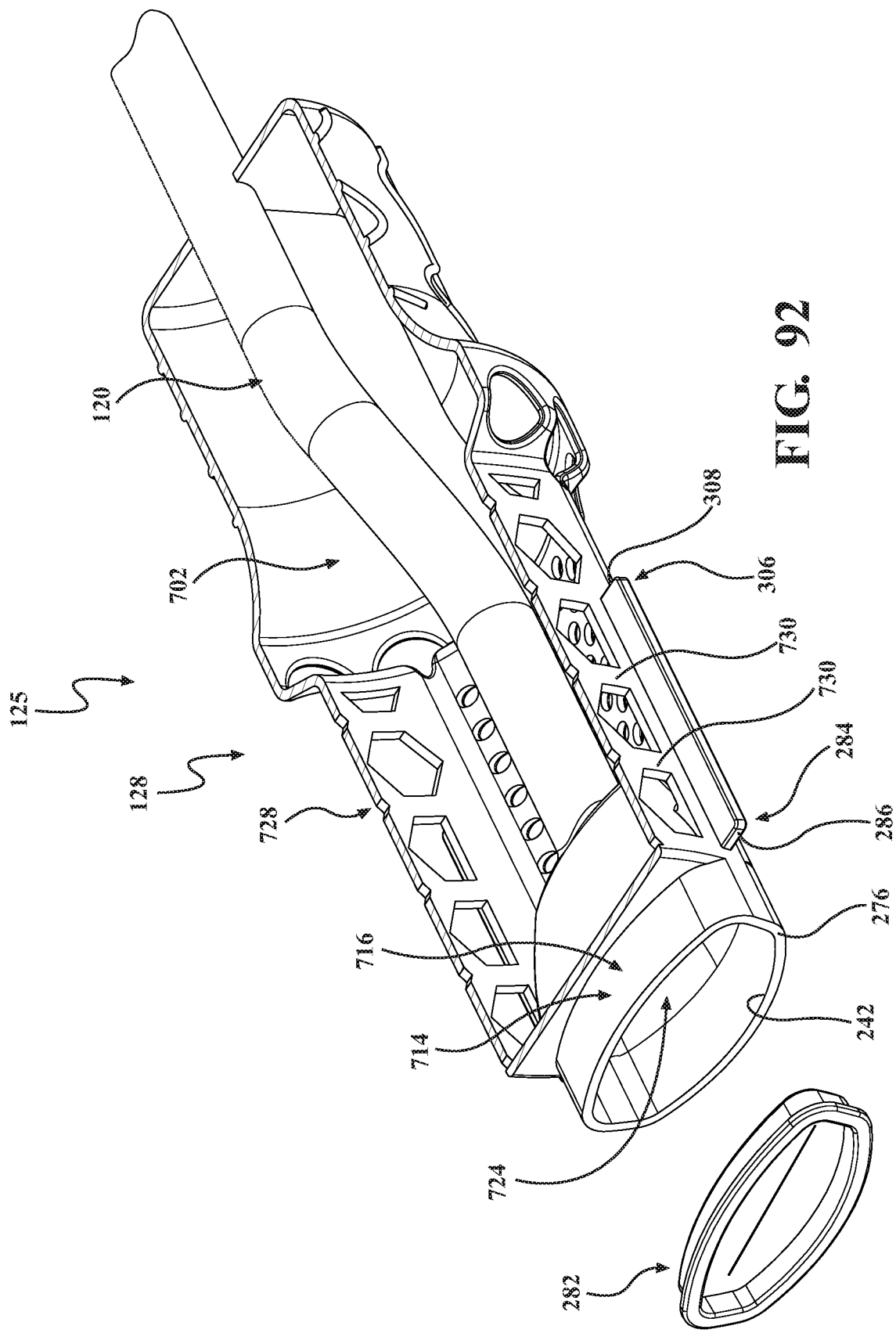
FIG. 92 is a sectional perspective view of a device coupled to the suction tube with a seal exploded from the device.
Figure 93:
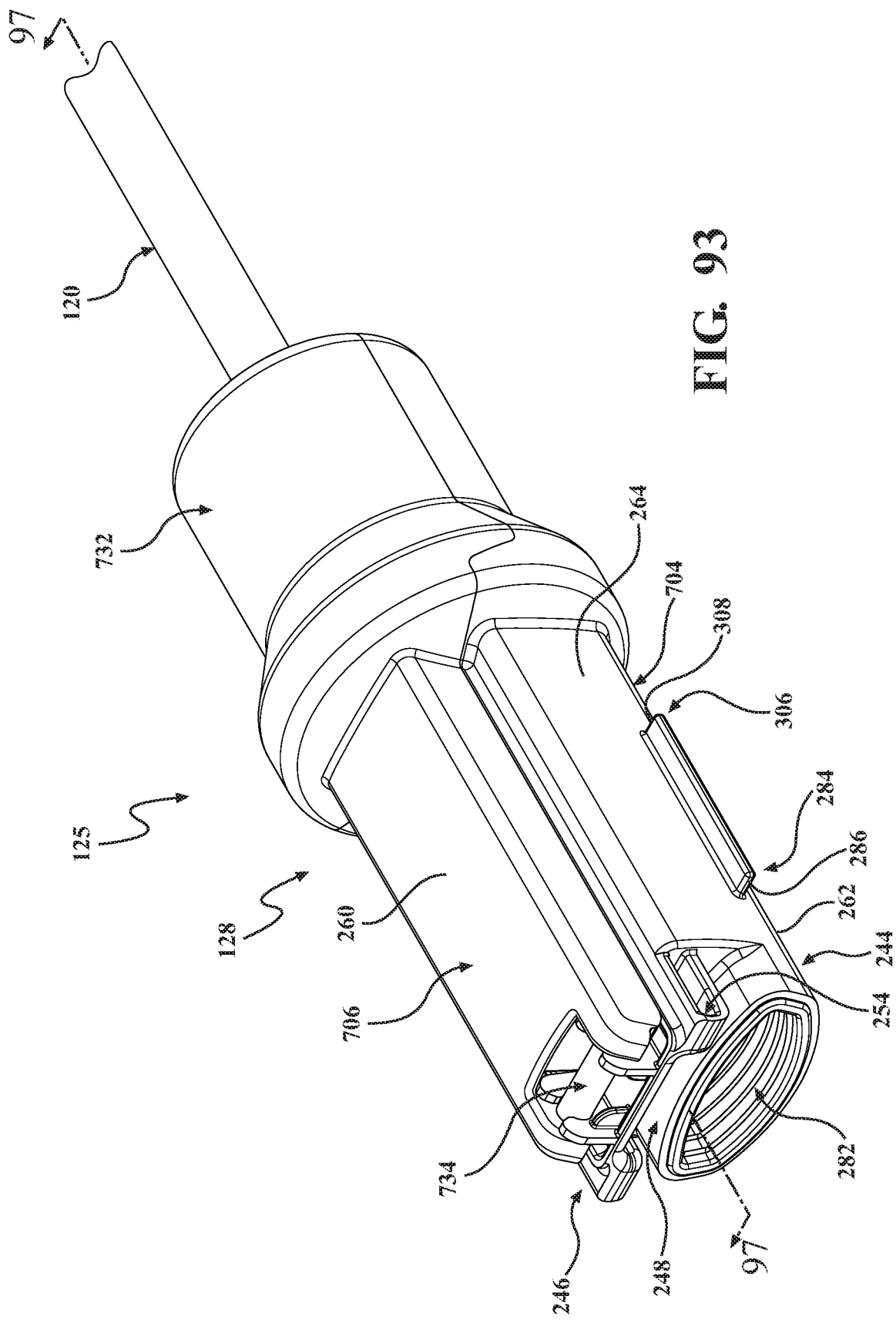
FIG. 93 is a rear perspective view of a device coupled to the suction tube.

Referring to FIGS. 90 and 91, the tube adapter 714 may be fixedly or removably coupled to the lip 712 of the housing, and the seal 282 may be coupled to the rim 276 of the tube adapter 714 defining the outlet opening 242. FIG. 92 shows the tube adapter 714 integrally formed with the frame 728 of the housing 128. The tube adapter 714 defines the fluid volume 724 that is separate from the void space 702 when the suction tube 120 is coupled to the inlet port 722 of the tube adapter 714. The device 125 may be inserted into the receiver 116 before the suction tube 120 is inserted through the distal aperture 726 into the void space 702 to be coupled to the inlet port 722, or the suction tube 120 may be inserted through the distal aperture 726 into the void space 702 to be coupled to the inlet port 722 prior to the insertion of the device 125 and suction tube 120 into the receiver 116.

In certain implementations, the first housing portion 704 and the second housing portion 706 may be movably coupled to one another so as to provide access to the void space 702. Referring now to FIGS. 93-97, the first and second housing portions 704, 706 are pivotably coupled to one another at a hinge 734. For example, the second housing portion 706 is configured to pivot about the hinge 734 to move the device 125 from a closed configuration shown in FIG. 93 in which the void space 702 is inaccessible, to an open configuration shown in FIG. 94 in which the void space 702 is accessible for reasons to be described.

The first and second housing portions 704, 706 may include the body portion 210, the first housing portion 704 may include the first leg 244 and the second leg 246. The void 248 is at least partially defined the second leg 246 and the first leg 244. In such an arrangement, the second housing portion 706 may be considered a cover including the upper wall 260 at a portion of the opposing sides 264. The arm(s) 246, the spine 300, the lock feature(s) 306, and/or the catch(es) 254 may be disposed on one of the first housing portion 704 and the second housing portion 706. More particularly, in the illustrated implementation, the arm 284 may extend outwardly from the first housing portion 704 or laterally outward from a portion of the side 264 of the first housing portion 704. The arm 284 includes the proximally-directed surface 286. Similarly, the lock element 306 may extend outwardly from the first housing portion 704 or laterally outward from a portion of the sides 264 of the first housing portion 704. The lock element 306 may include the distally-directed surface 308 positioned distal the proximally-directed surface 286 of the arm 284. The spine 300 may extend outwardly from the first housing portion 704, and more particularly downwardly from the bottom wall 262 of the first housing portion 704 (see FIGS. 95 and 86). The spine 300 includes the proximally-directed surface 302 positioned proximal to the distally-directed surface 308 of the lock element 306 and distal to the proximally-directed surface 286 of the arm 284. The catch 254, which may be optional, may be disposed on the second leg 246 formed by the first housing portion 704. The catch 254 includes the distally-directed surface 290 positioned proximal to the rim 276, proximal to the proximally-directed surface 286 of the arm 284, proximal to the proximally-directed surface 302 of the spine 300, and proximal to the distally-directed surface 308 of the lock element 306. The catch 254 and the rim 276 may be spaced apart by the void 248, and the rim 276 may be positioned below the catch 254 when the device 125 is oriented for insertion into the opening 118 of the receiver 116.

Figure 94:
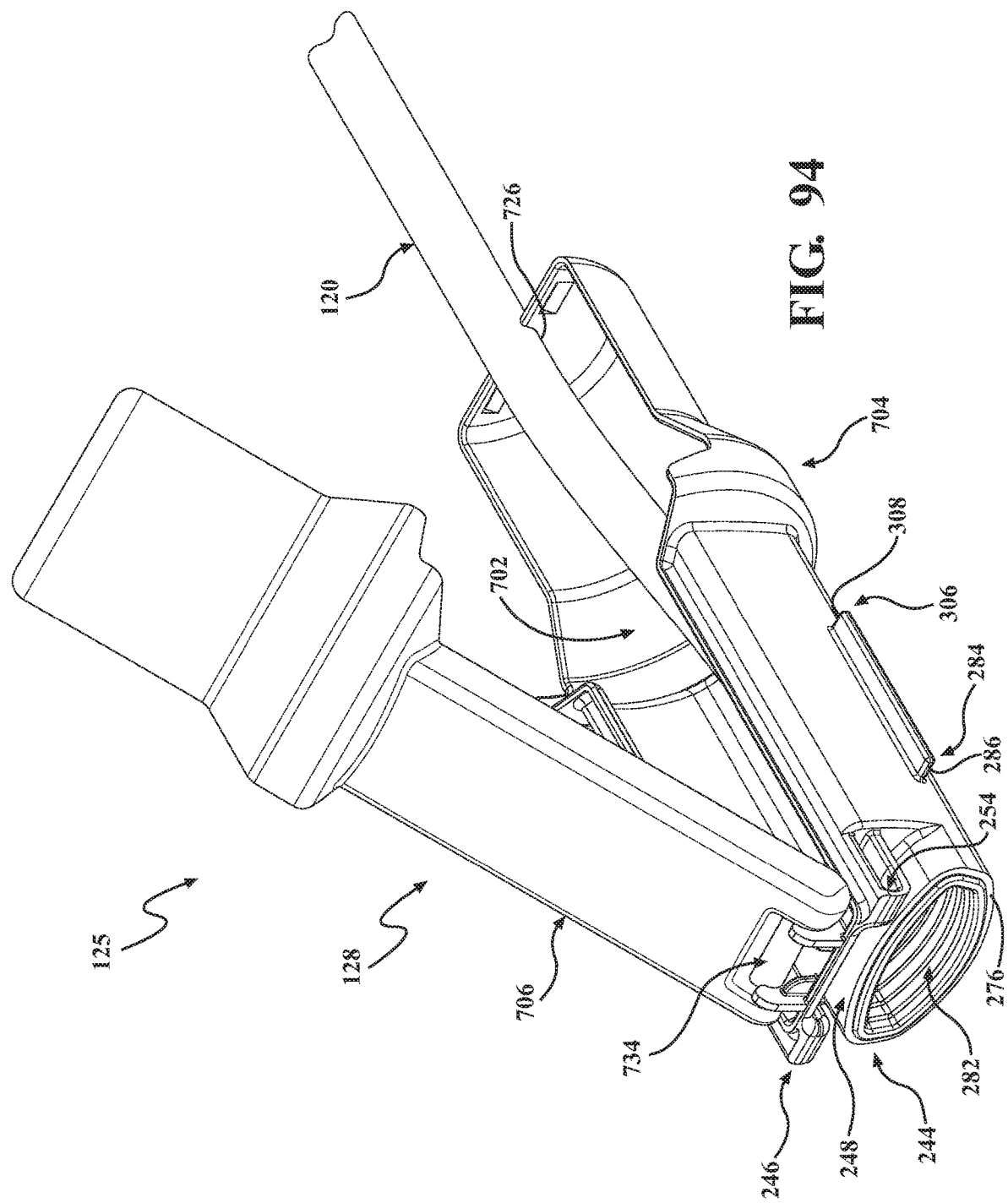
FIG. 94 is a rear perspective view of the device of FIG. 93 in an open configuration.
Figure 95:
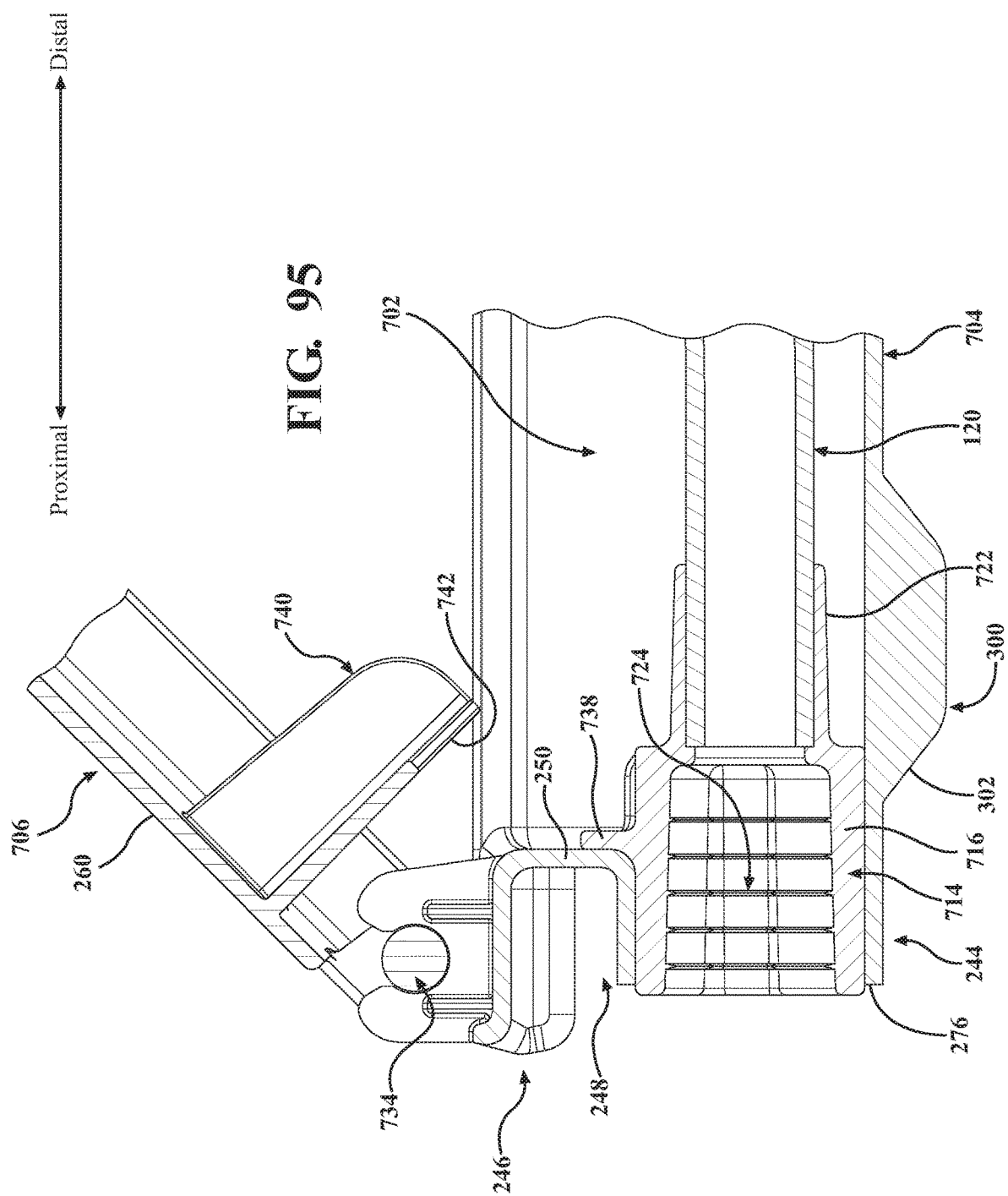
FIG. 95 is a partial sectional elevation view of the device of FIG. 93 in the open configuration with a tube adapter and the suction tube disposed within a void space of the housing of the device.
Figure 96:
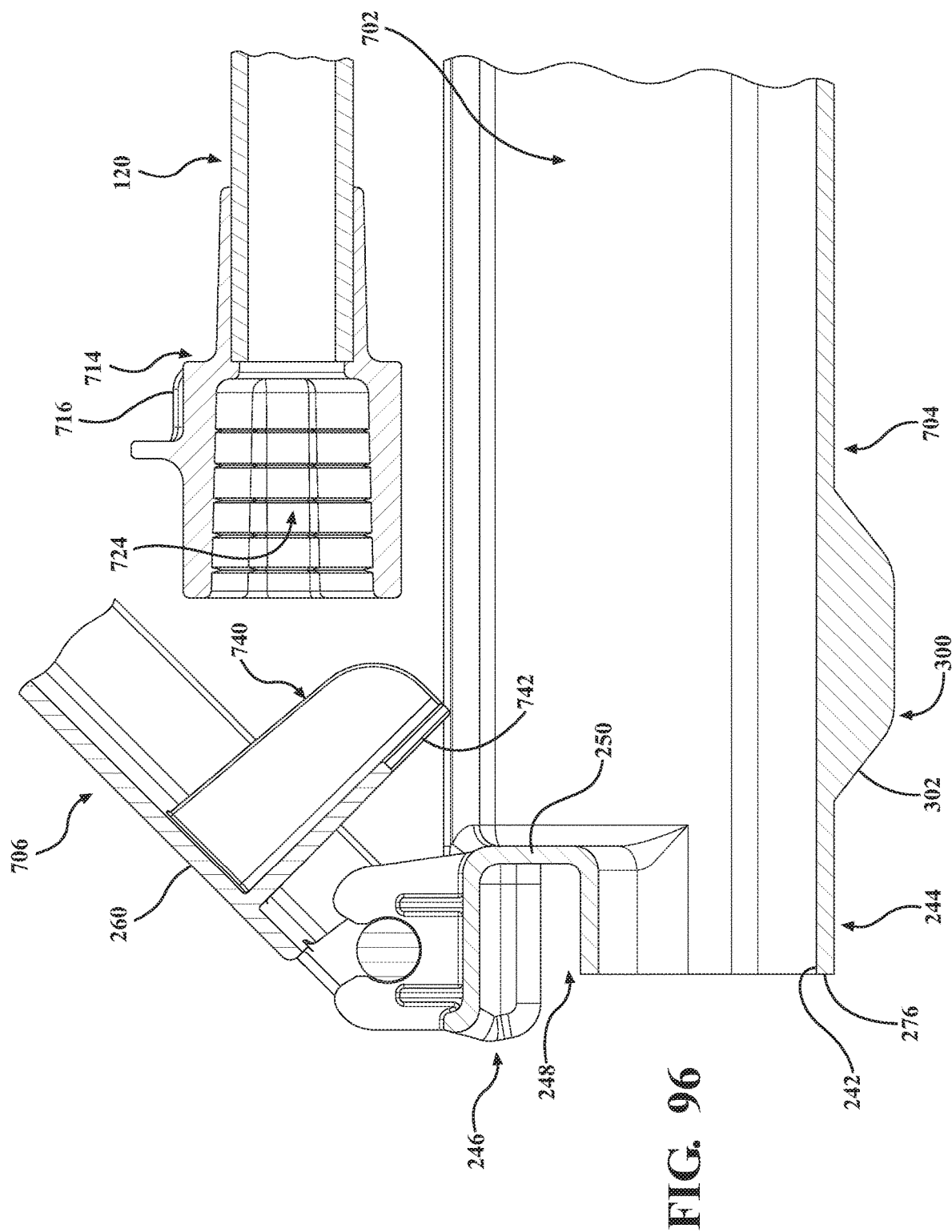
FIG. 96 is a partial sectional elevation view of the device of FIG. 93 in the open configuration with the tube adapter and the suction tube removed from the void space.

FIG. 94 shows the suction tube 120 extending through the distal aperture 726 such that at least a portion of the suction tube 120 is disposed within the void space 702. Further, FIGS. 95 and 96 show the tube adapter 714 being removably coupled to the housing 128. With the tube adapter 714 coupled to the housing 128, the inlet port 722 is disposed within the void space 702 and configured to be fixedly or removably coupled with the suction tube 120. The seal 282 previously described may be coupled to the tube adapter 714, or alternatively a seal 736 to be described (see FIGS. 98-102) may be coupled to the tube adapter 714.

With reference to FIGS. 95 and 96, moving the device 125 between the closed and open configurations may advantageously facilitate replacement of the suction tube 120 and the tube adapter 714 between uses of the device 125. Further, with the suction tube 120 extending through the void space 702 to the outlet opening 242 such that the void space 702 is not in fluid communication with the suction path, the housing 128 may not become meaningfully contaminated during use. In other words, the housing 128 may be considered an adapter to engage complementary components of the receiver 116, and the suction tube 120 is arranged in a near-direct or direct connection with the suction inlet 266 of the receiver 116. FIG. 95 shows the suction tube 120 and the tube adapter 714 either prior to installation or removal from the housing 128. For example, the suction tube 120 and the tube adapter 714 may be directed through the void space 702 such that the body portion 716 is disposed within the first leg 244 of the housing 128. The non-circular shape of the outlet opening 242 defined by the rim 276 and a complementary non-circular shape of the body portion 716 of the tube adapter 714 may require insertion in a singular orientation. The tube adapter 714 is inserted into the first leg 244 until a flange 738 abuts an inner surface of the distal aspect 250 of the housing 128. The interference engagement of the flange 738 and the distal aspect 250 prevent further proximal movement of the tube adapter 714 (and the suction tube 120) relative to the housing 128.

Figure 97:
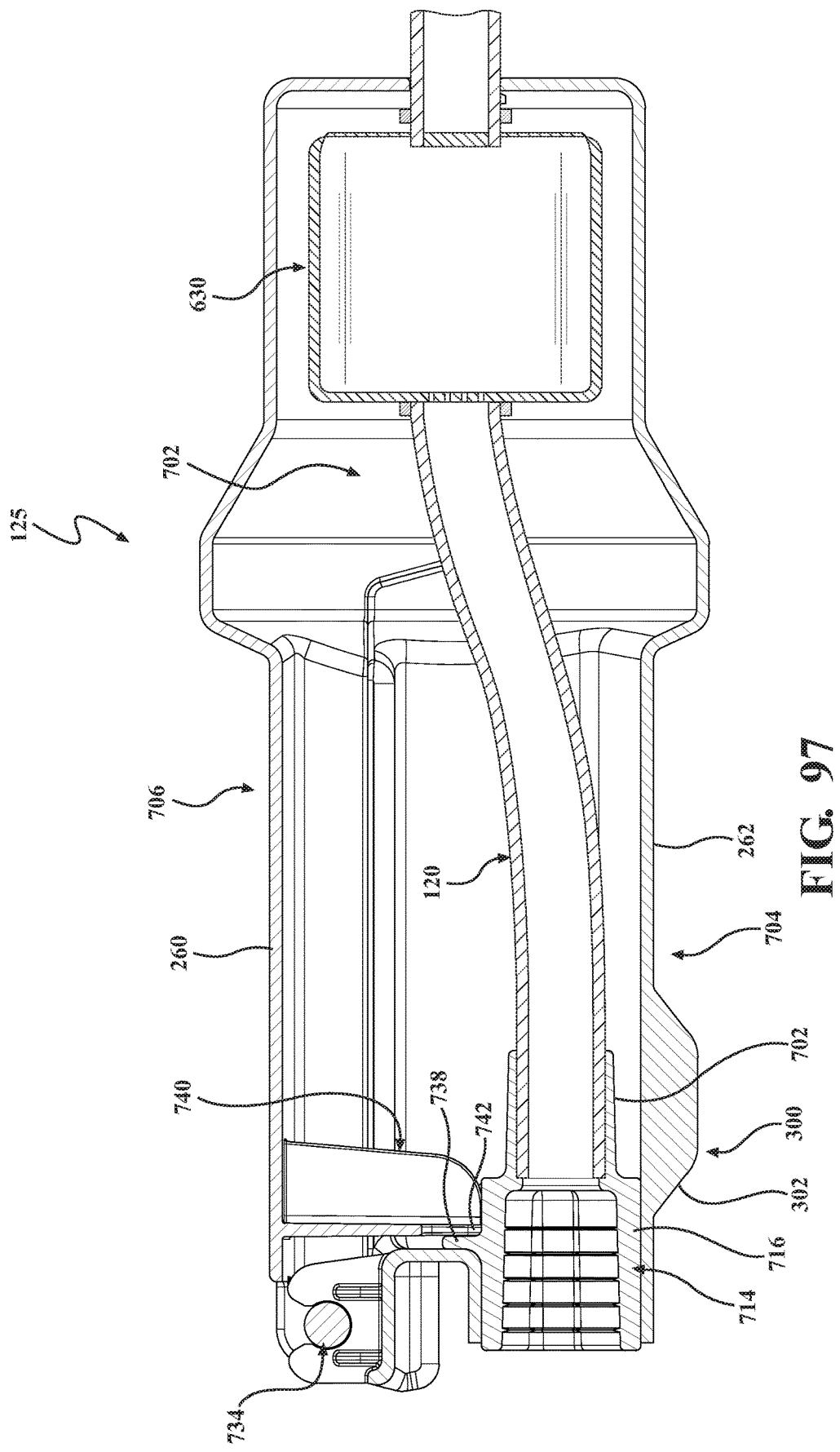
FIG. 97 is a sectional elevation view of the manifold of FIG. 93 taken along section lines 97-97 with a tissue trap disposed within the void space.
Figure 98:
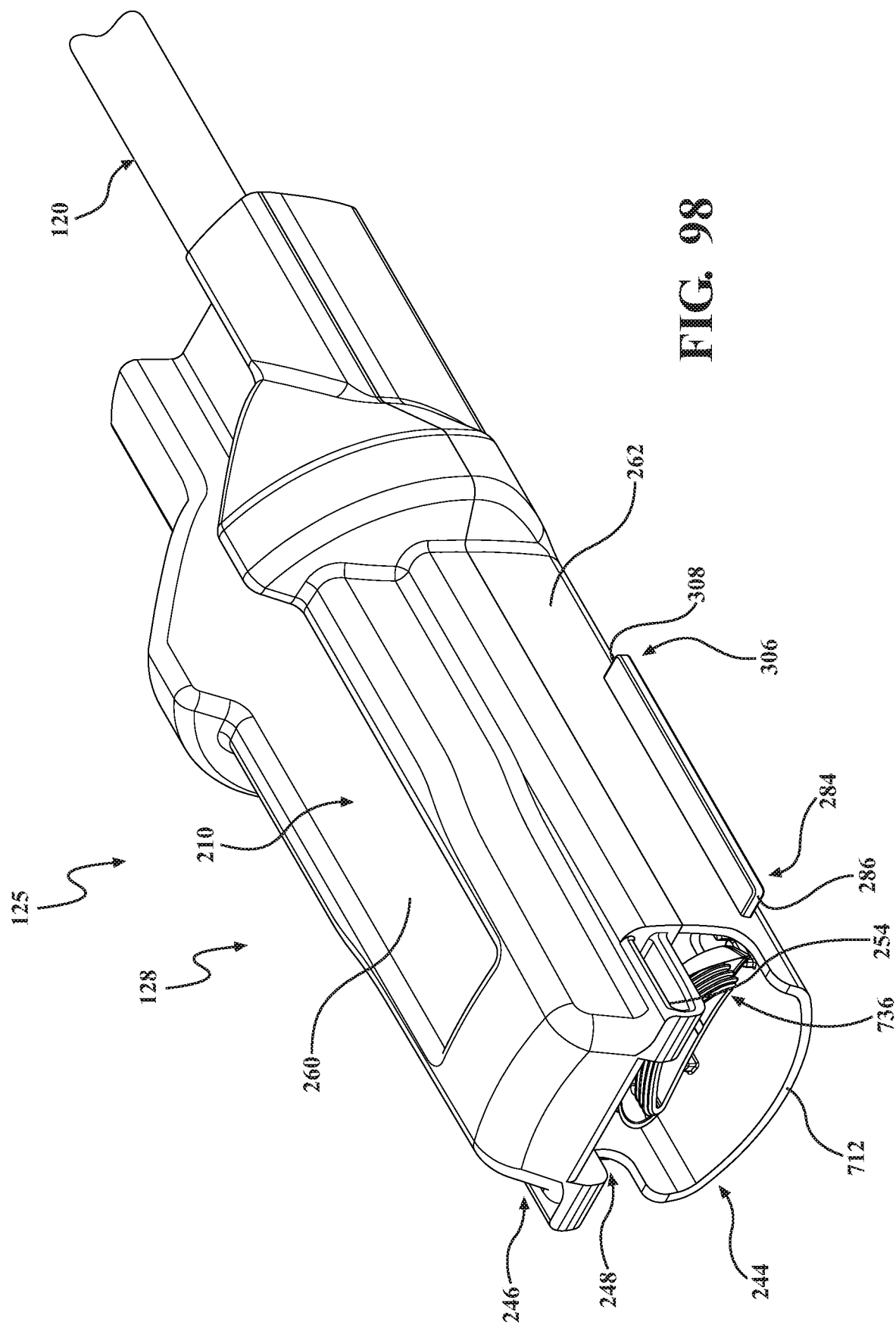
FIG. 98 is a rear perspective view of a device coupled to the suction tube.

With concurrent reference to FIG. 97, the second housing portion 706 is pivoted relative to the first housing portion 704 about the hinge 734 to the closed configuration. The housing 128 includes at least one retaining feature 740 configured to retain the tube adapter 714 when the manifold is in the closed configuration. In particular, the retaining feature 740 may include a protrusion 742 extending downwardly from an underside of the upper wall 260 of the housing 128. The protrusion 742 pivots with the pivoting of the second housing portion 706. With the device 125 in the open configuration, there is sufficient clearance between the protrusion 742 and the flange 738 to permit insertion and/or removal of the tube adapter 714. With the device 125 in the closed configuration, as shown in FIG. 97, the protrusion 742 engages the flange 738 opposite the distal aspect 250 such that the tube adapter 714 is prevented from being removed. The device 125, including the tube adapter 714 and suction tube 120 coupled thereto, may be inserted into the receiver 116 for operation of the medical waste collection system 100.

Moreover, moving the device 125 from the closed configuration to the open configuration may provide the tissue trap 630 being removably disposed within the housing 128. FIG. 97 shows the tissue trap 630 being coupled in-line to the suction tube 120 and disposed within the void space 702. During operation of the medical waste collection system 100, a tissue sample may be collected in the tissue trap 630. After operation of the medical waste collection system 100, the device 125, including the tube adapter 714 and suction tube 120 coupled thereto, may be removed from the receiver 116. The second housing portion 706 is pivoted relative to the first housing portion 704 about the hinge 734 to move the device 125 from the closed configuration to the open configuration. The tube adapter 714 and suction tube 120 may be removed from the housing 128. In certain implementations, the tissue trap 630 may be removed from the void space 702 and the tissue sample retrieved from the tissue trap 630.

After removal of the tube adapter 714, the housing 128 may be cleaned, for example, autoclaved. The housing 128 may be formed from materials capable of withstanding temperatures typical of autoclaving. For example, the housing 128 may be formed from polypropylene, polypropylene copolymer (PPCO), polycarbonate, Teflon perfluoroalkoxy alkanes (PFA), fluorinated ethylene propylene (FEP), or ethylene tetrafluoroethylene (ETFE), or the like. Metals and composites are also contemplated. The pivotable arrangement of the first and second housing portions 704, 706 as well as the removing of the tube adapter 714 provides for relatively simplified geometries that can be adequately cleaned through known techniques. It is contemplated that the housing 128 formed from autoclavable materials with geometries that can be adequately cleaned through known techniques may be applicable to any of the implementations of the device 125 described herein.

In certain implementations in which the tube adapter 714 includes the seal, the tube adapter 714 and the seal may be removed from the housing 128. Another tube adapter (and seal and/or suction tube) may be coupled to the housing 128, and the device 125, including the tube adapter 714 and suction tube 120 coupled thereto, may be inserted into the receiver 116 for repeat operation of the medical waste collection system 100.

Referring now to FIGS. 98-101, an implementation of the device 125 is shown in which the seal 736 is utilized for coupling to the suction inlet 266 of the inlet mechanism 324. The housing 128 of the device 125 includes the first housing portion 704 and the second housing portion 706 collectively defining the void space 702, but the housing 128 may be a single piece of unitary construction (see FIG. 89-92).

The first housing portion 704 and/or the second housing portion 706, may include the body portion 210, and the first leg 244, and the second housing portion 706 may include the second leg 246. The void 248 is at least partially defined the second leg 246 and the first leg 244. Further, the arm(s) 246, the spine 300, the lock feature(s) 306, and/or the catch(es) 254 may be disposed on one of the first housing portion 704 and the second housing portion 706. More particularly, in the illustrated implementation, the arm 284 may extend outwardly from the first housing portion 704 or laterally outward from a portion of the side 264 of the first housing portion 704. The arm 284 includes the proximally-directed surface 286. Similarly, the lock element 306 may extend outwardly from the first housing portion 704 or laterally outward from a portion of the sides 264 of the first housing portion 704. The lock element 306 may include the distally-directed surface 308 positioned distal the proximally-directed surface 286 of the arm 284. The spine 300 may extend outwardly from the first housing portion 704, and more particularly downwardly from the bottom wall 262 of the first housing portion 704 (not shown in FIGS. 98-101). The spine 300 includes the proximally-directed surface 302 positioned proximal to the distally-directed surface 308 of the lock element 306 and distal to the proximally-directed surface 286 of the arm 284. The catch 254 may be disposed on the second leg 246 formed by the second housing portion 706. The catch 254 includes the distally-directed surface 290 positioned proximal to the lip 712, proximal to the proximally-directed surface 286 of the arm 284, proximal to the proximally-directed surface 302 of the spine 300, and proximal to the distally-directed surface 308 of the lock element 306. The catch 254 and the rim 276 may be spaced apart by the void 248, and the lip 712 may be positioned below the catch 254 when the device 125 is oriented for insertion into the opening 118 of the receiver 116.

Figure 99:
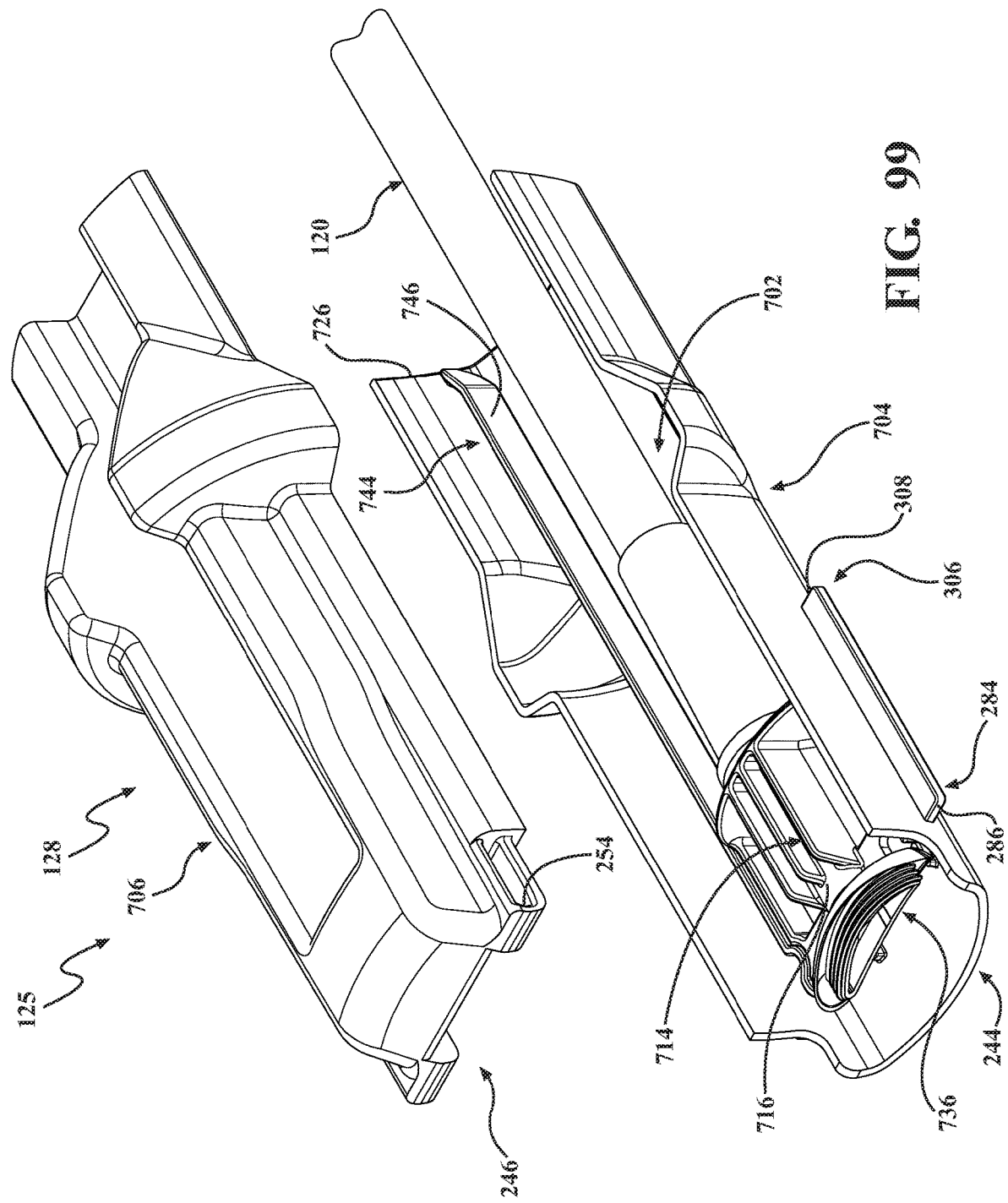
FIG. 99 is a partial exploded view of the device of FIG. 98 with the tube adapter and the suction tube coupled to the device.
Figure 100:
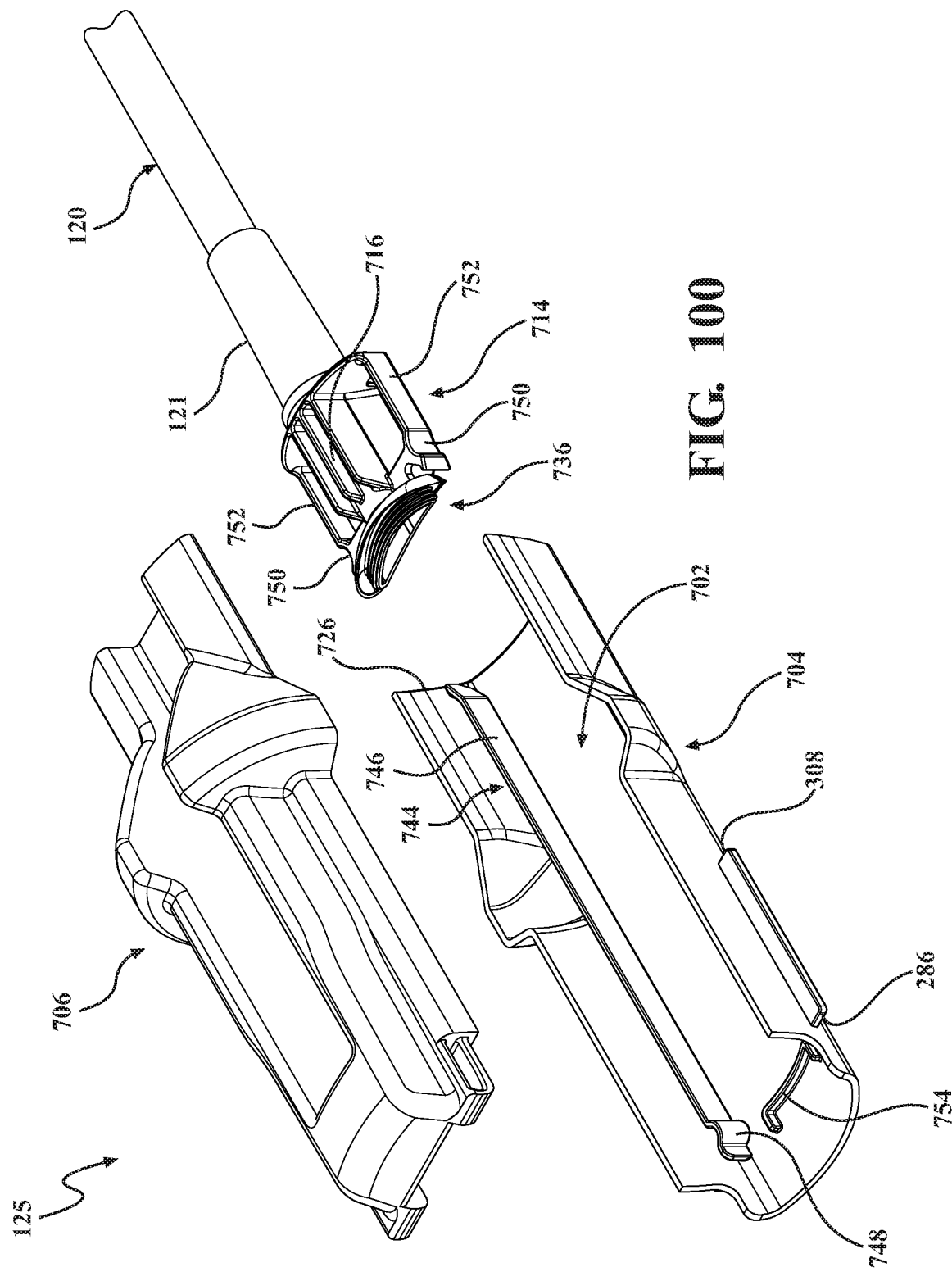
FIG. 100 is an exploded view of the device of FIG. 98 with the suction tube decoupled from the device.
Figure 102:
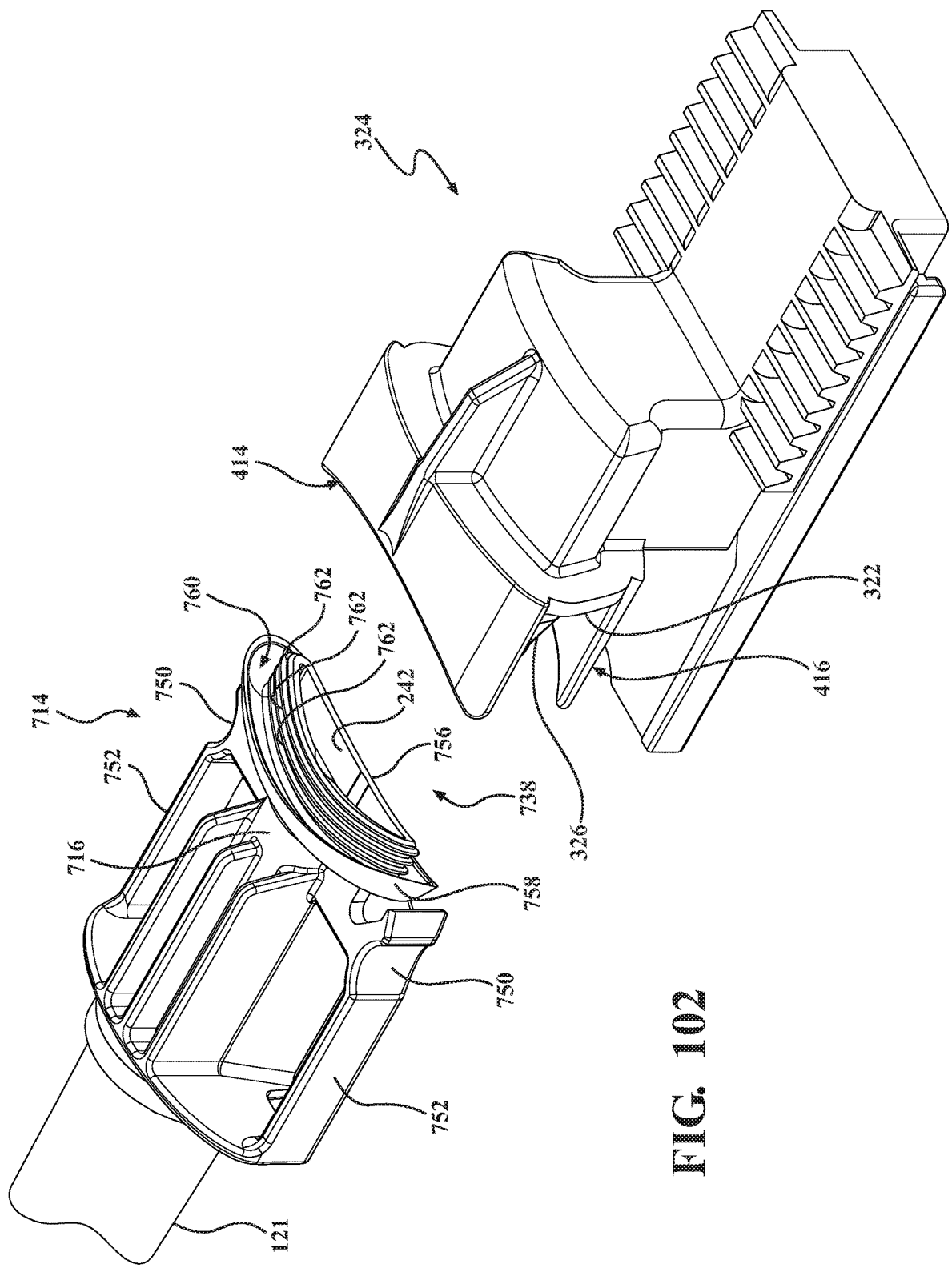
FIG. 102 is a perspective view of inlet mechanism of the receiver spaced apart from the tube adapter including a seal configured to provide a face seal with a suction inlet of the inlet mechanism.

The tube adapter 714 is best shown in FIGS. 99, 100 and 102 and includes the body portion 716 may be configured to be removably or fixedly coupled to the housing 128. FIG. 99 shows the device 125 including at least one guide feature 744 configured to facilitate removable coupling of the tube adapter 714 with the housing 128. The guide feature 744 may be opposing rails 746 (one shown) disposed within the void space and extending in the proximal-to-direction. The rails 746 have a distal end near the distal aperture 726 and a proximal end within or near the first leg 244. The guide feature 744 may further include a retaining feature 748, for example, a protrusion or detent, configured to be removably engaged with a complementary retaining feature 750 of the tube adapter 714 to be described. The tube adapter 714 further includes the inlet port 722 configured to be disposed within the void space 702 of the housing 128 and coupled to the suction tube 120 to establish fluid communication between the suction tube 120 and the bore. As a result, with the suction tube 120 coupled to the inlet port 722, a portion of the suction tube 120 extends through the void space 702 of the housing 128, as best shown in FIG. 95. Further, the body portion 716 defines the fluid volume 724 separate from the void space 702 (i.e., not in fluid communication) when the suction tube 120 is coupled to the inlet port 722.

Figure 101:
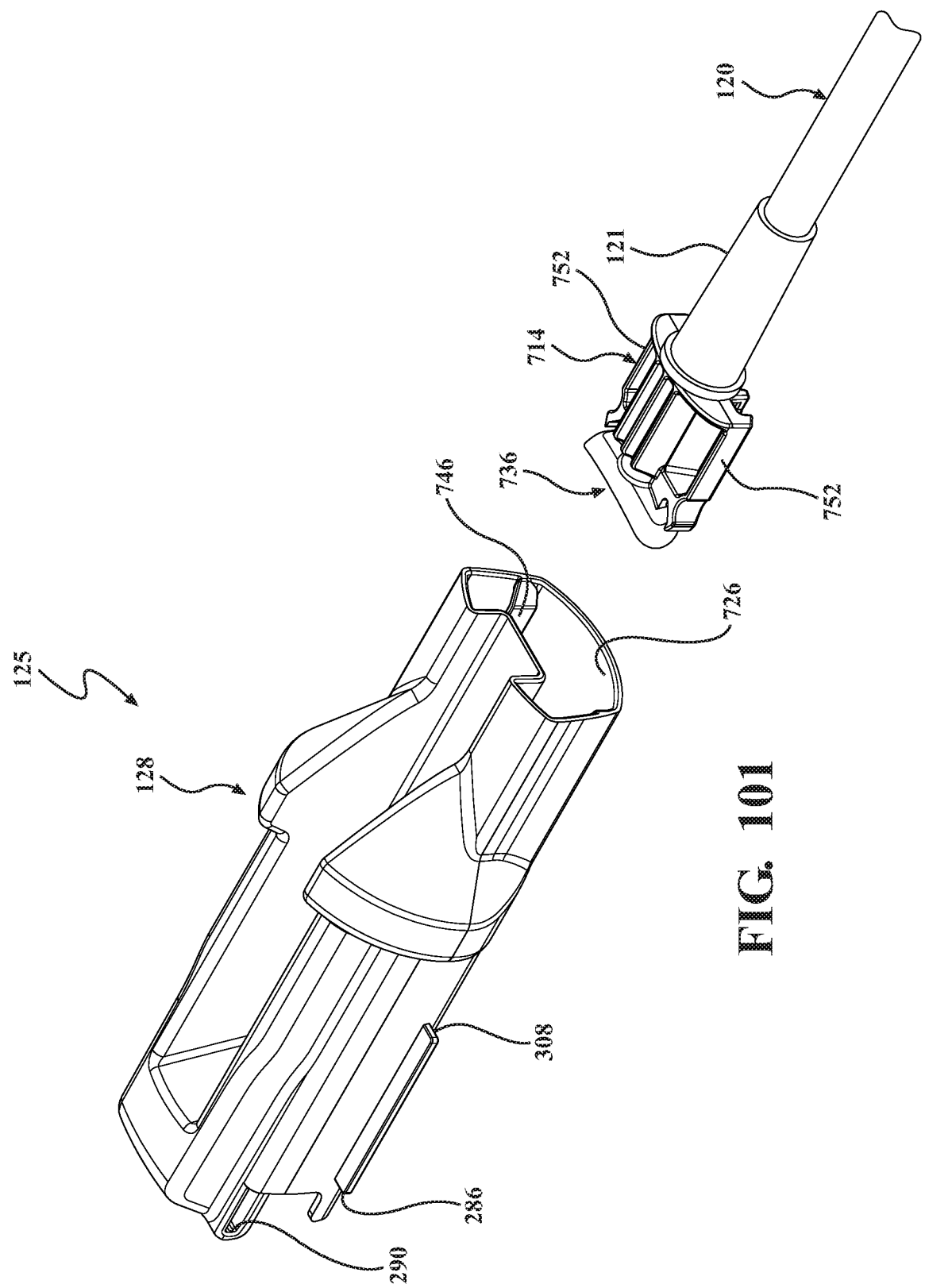
FIG. 101 is a front perspective view of the device of FIG. 98 with the suction tube decoupled from the device.

The housing 128 may further define the distal aperture 726 in communication with the void space 702, which may be collectively defined by respective recesses on the first and second housing portions 704, 706. The distal aperture 726 is configured to permit the suction tube 120 to extend distally from within the void space 702 to external to the device 125. As best shown in FIG. 101, the distal aperture 726 may be sized and shaped to the tube adapter 714 such that the tube adapter 714, with the suction tube 120 coupled thereto, may be directed through the distal aperture 726 and into the void space 702 of the housing 128. The tube adapter 714 may be directed through the distal aperture 726 before or after the housing 128 is inserted into the receiver 116 in manners previously described.

According to a method of coupling the suction tube 120 and the device 125 to the medical waste collection system 100, the housing 128 is inserted into the opening 118 of the receiver 116. The tube adapter 714 and the suction tube 120 may not yet be coupled to the housing 128 such that, with the housing 128 is inserted into the opening 118 of the receiver 116, fluid communication is established between the void space 702 and the suction inlet 266. In other words, as the housing 128 is inserted into the receiver 116, the engagement of the arm(s) 284 moves the sled assembly 288 in the proximal direction, and the inlet mechanism 324 including the suction inlet 266 moves in the distal direction in the manner previously described. The suction inlet 266 is positioned within the void 248 between the first and second legs 244, 246 and generally opens into the void space 702 of the housing 128.

The tube adapter 714 may be directed through the distal aperture 726. The inlet fitting 121 of the suction tube 120 may be coupled to the tube adapter 714 before or after the tube adapter 714 is directed through the distal aperture 726. An insertion tool (not shown) may be used to move the tube adapter 714 through the void space 702 of the housing 128. Flanges 752 extending from the body portion 716 of the tube adapter 714 slidably move along and/or relative to the guide feature 744, in particular the rails 746, as the tube adapter 714 is moved proximally through the void space 702. The tube adapter 714 contacts a stop 754, best shown in FIG. 100, sequentially or simultaneously with the retaining feature 750 of the tube adapter 714 engaging the retaining feature 748 of the housing 128. For example, the detents engage the recesses in an interference engagement. The axial positioning of the retaining feature 750 within the housing 128 is such that, as the complementary retaining features 748, 750 engage, the tube adapter 714 sealingly engages the suction inlet 266. Fluid communication is established between the suction tube 120 and the receiver 116 of the medical waste collection system 100, and fluid communication is disestablished between the receiver 116 and the void space 702 of the housing 128. The medical waste collection system 100 may be operated in manners previously described.

In certain implementations, the aforementioned arrangement does not necessarily require the housing 128 be removed between uses of the medical waste collection system 100. For example, the tube adapter 714 and the suction tube 120 may be removed, and another tube adapter and suction tube may be directed through the distal aperture 726 with the housing 128 remaining inserted within the receiver 116. Additionally or alternatively, the detachable nature of the tube adapter 714 and the housing 128 may provide for easier reprocessing of the device 125. More particularly, the internal geometries of the housing 128 of FIGS. 98-101 and relatively simple and accessible in a cleaning operation. In one method, the housing 128 and the tube adapter 714 may be removed from the opening 118 of the receiver 116 such that suction is broken between the seal and the suction fitting 326 of the receiver 116. The tube adapter 714 may be decoupled from the housing 128, and the housing 128 may be cleaned. For example, the housing 128 may be autoclaved through known techniques. Another tube adapter (i.e., a second tube adapter and a second seal) may be coupled to the cleaned housing 128, and the housing 128 may be inserted into the opening 118 such that suction is established between the second seal of the second tube adapter and the suction fitting 326 of the receiver 116.

In implementations in which the tube adapter 714 is directed through the housing 128 after the housing 128 is operably coupled with the receiver 116, the seal 736 to coupled to the body portion 716 tube adapter 714 may be particularly well suited to engage the suction fitting 326 of the inlet mechanism 324. It is to be understood that the seal 736 may be formed integral with the body portion 716, or the seal 736 and the body portion 716 may be discrete components. Referring now to FIG. 102, a rear perspective view of the tube adapter 714 is shown spaced apart from the inlet mechanism 324 to show details of the seal 736. The seal 736 may include an inner flange 756 and an outer flange 758 spaced apart from one another to define a gap 760. In certain implementations of the housing 128 in which the seal 736 is utilized, such as that shown in FIGS. 98-100, the housing 128 may not define the outlet opening 242, but rather the inner flange 756 of the seal 736 defines the outlet opening 242 of the device 125. The gap 760 may be shaped complementary to the suction fitting 326 of the inlet mechanism 324. In particular, each of the inner and outer flanges 756, 758 may be non-circular in axial section complementary to the axial section of the suction fitting 326 that is non-circular. The outer flange 758 may be sized slightly larger than the suction fitting 326, and the inner flange 756 may be sized slightly less than the suction fitting 326 such that, when the seal 736 engages the suction fitting 326, a distal rim of the suction fitting 326 is positioned within the gap 760 in sealing engagement to provide the face seal. The seal 736 may be flexible so as to resiliently deform and/or be compressed against the suction fitting 326. The sealing surface provided by the seal 736 may be non-planar. Further, the seal 736 may be include ribs 762 configured to engage an inner surface of the suction fitting 326 to provide an internal seal. The ribs 762 may extend radially outwardly from the inner flange 756.

In operation, the seal 736 axially approaches the suction fitting 326 and engages the suction fitting 326 in the aforementioned manner to provide the face seal and the internal seal. This may be in contrast to the previously described seal 282 in which the suction fitting 326 extends through the seal 282 and the sealing surface 346 provides the face seal with the sealing surface 322 of the inlet mechanism 324 (see FIG. 62). As a result, the seal 736 need not be dimensioned to contact the sealing surface 322 of the inlet mechanism 324, and thus the first leg 244 of the housing 128 may be dimensioned differently than previously described or absent all together. With no first leg 244, for example, there may be an absence of the void 248. It is also to be understood that the seal 736 may be utilized with any implementation of the housing 128 of the device 125 described throughout the present disclosure.

Certain implementations may be described with reference to the following exemplary clauses:

Clause 1—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising a rim defining the outlet opening; a filter element disposed within the manifold volume; an arm extending outwardly from the housing and comprising a proximally-directed surface; a lock element extending outwardly from the housing, the lock element comprising a distally-directed surface positioned distal to the proximally-directed surface of the arm; a spine extending outwardly from the housing, the spine comprising a proximally-directed surface positioned proximal to the distally-directed surface of the lock element and distal to the proximally-directed surface of the arm; and a catch comprising a distally-directed surface positioned proximal to the proximally-directed surface of the arm, wherein the rim and the catch are spaced apart by a void, and wherein the rim is positioned below the catch when the manifold is oriented for insertion into the opening of the receiver.

Clause 2—The manifold of clause 1, wherein the proximally-directed surface of the arm is positioned distal to the rim, and the distally-directed surface of the catch is positioned proximal to the rim.

Clause 3—The manifold of clauses 1 or 2, wherein the housing further comprises a body portion having a distal aspect, a first leg extending proximally from the distal aspect, and a second leg extending proximally from the distal aspect, wherein the second leg is spaced apart from the first leg by the void.

Clause 4—The manifold of clause 3, wherein each of the first and second legs comprises a respective cross-sectional area smaller than a cross-sectional area of the body portion.

Clause 5—The manifold of any one of clauses 1-4, wherein the housing comprises an upper wall, a lower wall, and opposing sides each extending between the upper and lower walls when the manifold is oriented for insertion into the opening of the receiver, wherein the spine extends downwardly from the lower wall.

Clause 6—The manifold of clause 5, wherein the arm and the lock element each extend laterally from one of the opposing sides.

Clause 7—The manifold of any one of clauses 1-6, wherein the proximally-directed surface of the spine comprises a ramped surface tapering towards the housing in a proximal direction.

Clause 8—The manifold of any one of clauses 5-7, wherein the arm comprises a pair of arms each extending laterally from a respective one of the opposing sides, wherein laterally-directed surfaces of the pair of arms cooperate to define a width that is larger than a width of the rim.

Clause 9—The manifold of any one of clauses 3-8, wherein the second leg includes a cavity defining a portion of the manifold volume such that the cavity is in fluid communication with the outlet opening.

Clause 10—The manifold of any one of clauses 3-9, wherein the arm extends outwardly from one of the body portion and the first leg, wherein the lock element extends outwardly from one of the body portion and the first leg, wherein the spine extends outwardly from one of the body portion and the first leg, and wherein the catch is disposed on the second leg.

Clause 11—The manifold of any one of clauses 1-10, wherein the rim has a width larger than a height to define the outlet opening as being non-circular.

Clause 12—The manifold of clause 11, further comprising a seal coupled to the rim, the seal further comprising a seal body shaped to cover the non-circular outlet opening.

Clause 13—The manifold of clause 11, wherein the non-circular outlet opening comprises opposing lateral-most points relative to a vertical plane of symmetry, an uppermost point, and a lowermost point, wherein the arm comprises a laterally-directed surface positioned farther from the vertical plane of symmetry than one of the opposing lateral-most points of the outlet opening.

Clause 14—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising a body portion extending to a distal aspect, a first leg extending proximally from the distal aspect, and a second leg spaced apart from the first leg to define a void; a filter element disposed within the manifold volume; an arm extending outwardly from one of the body portion and the first leg, the arm comprising a proximally-directed surface; a lock element extending outwardly from one of the body portion and the first leg, the lock element comprising a distally-directed surface positioned distal to the proximally-directed surface of the arm; a catch disposed on the second leg and comprising a distally-directed surface positioned proximal to the proximally-directed surface of the arm; and a spine extending outwardly from one of the body portion, the first leg, and the second leg, the spine having a proximal end positioned distal to the distally-directed surface of the catch and distal to the proximally-directed surface of the arm.

Clause 15—The manifold of clause 14, wherein the second leg extends proximally from the distal aspect.

Clause 16—The manifold of clauses 14 or 15, wherein the first leg comprises a rim defining the outlet opening, wherein the proximally-directed surface of the arm is positioned distal to the rim, and wherein the distally-directed surface of the catch is positioned proximal to the rim.

Clause 17—The manifold of any one of clauses 14-16, wherein the first leg is positioned below the second leg when the manifold is oriented for insertion into the opening of the receiver.

Clause 18—The manifold of any one of clauses 14-17, wherein the spine further comprises a ramped surface with at least a portion of the ramped surface defining the proximal end of the spine.

Clause 19—The manifold of any one of clauses 14-18, wherein each of the first and second legs comprises a respective cross-sectional area smaller than a cross-sectional area of the body portion.

Clause 20—The manifold of any one of clauses 14-19, wherein the rim has a width larger than a height to define the outlet opening as being non-circular.

Clause 21—The manifold of clause 20, wherein the arm comprises a pair of arms each extending laterally from a respective one of opposing sides one of the body portion and the first leg, wherein laterally-directed surfaces of the pair of arms cooperate to define a width that is larger than the width of the rim.

Clause 22—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising an upper wall, a lower wall, and opposing sides each extending between the upper and lower walls when the manifold is oriented for insertion into the opening of the receiver, the housing further comprising a rim defining the outlet opening; a filter element disposed within the manifold volume; an arm extending laterally outward from one of the opposing sides and comprising a proximally-directed surface; a catch comprising a distally-directed surface positioned proximal to the proximally-directed surface of the arm, wherein the catch is located on a first side of a void separate from the manifold volume and separate from the outlet opening, with the rim located on a second side of the void opposite the first side; and a spine extending downwardly from the lower wall, the spine comprising a ramped surface positioned distal to the distally-directed surface of the catch.

Clause 23—The manifold of clause 22, wherein the rim is positioned: distal to the distally-directed surface of the catch, proximal to the proximally-directed surface of the arm, and proximal to the ramped surface of the spine.

Clause 24—The manifold of clauses 22 or 23, further comprising a lock element extending laterally outward from one of the opposing sides, the lock element comprising a distally-directed surface positioned: distal to the proximally-directed surface of the arm, distal to the distally-directed surface of the catch, and distal to the rim.

Clause 25—The manifold of any one of clauses 22-24, wherein the arm comprises a pair of arms each extending laterally from a respective one of the opposing sides, wherein laterally-directed surfaces of the pair of arms cooperate to define a width that is greater than the width of the rim.

Clause 26—The manifold of any one of clauses 22-25, wherein the housing further comprises a first leg, and a second leg spaced apart from the first leg to define the void, wherein the first leg comprises at least a portion of the lower wall and at least a portion of the opposing sides, and the second leg comprises at least a portion of the upper wall and at least a portion of the opposing sides.

Clause 27—The manifold of any one of clauses 22-26, wherein the rim has a width larger than a height to define an outlet opening that is non-circular, the manifold further comprising a seal coupled to the rim.

Clause 28—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising a rim defining the outlet opening; a filter element disposed within the manifold volume; an arm extending outwardly from the housing and comprising a proximally-directed surface positioned distal to the rim; a lock element extending outwardly from the housing, the lock element comprising a distally-directed surface positioned distal to the proximally-directed surface of the arm and distal to the rim; and a catch comprising a distally-directed surface positioned proximal to the proximally-directed surface of the arm and proximal to the rim, wherein the rim and the catch are spaced apart by a void external to the housing.

Clause 29—The manifold of clause 28, further comprising a spine extending outwardly from the housing and comprising a ramped surface positioned: distal to the rim, distal to the proximally-directed surface of the arm, and proximal to the proximally-directed surface of the lock element.

Clause 30—The manifold of clauses 28 or 29, wherein the housing further comprises a body portion having a distal aspect, a first leg extending proximally from the distal aspect, and a second leg extending proximally from the distal aspect, the second leg extending proximally from the distal aspect and spaced apart from the first leg by the void.

Clause 31—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a rim defining the outlet opening; an arm extending outwardly from the housing; and a catch including a distally-directed surface positioned proximal to the arm and the rim, wherein the rim and the catch are spaced apart by a void, and wherein the rim is positioned above or below the catch when the manifold is oriented for insertion into the opening of the receiver.

Clause 32—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a rim defining the outlet opening; arms extending outwardly from the housing; lock elements extending outwardly from the housing; a spine extending outwardly from the housing; and catches proximal to the arm, proximal to the rim, proximal to the lock elements, and proximal to the spine.

Clause 33—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a rim having a width greater or larger than a height to define an outlet opening that is non-circular; and a catch including a distally-directed surface positioned proximal to the rim, wherein the rim and the catch are spaced apart by a void, and wherein the rim is positioned below the catch when the manifold is oriented for insertion into the opening of the receiver.

Clause 34—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume an outlet opening in fluid communication with the manifold volume, the housing including an upper wall, a lower wall, and opposing sides each extending between the upper and lower walls when the manifold is oriented for insertion into the opening of the receiver; arms extending outwardly from a respective one of the opposing sides of the housing and each including a proximally-directed surface; and a spine extending outwardly from the housing, the spine including a proximally-directed surface positioned distal to the proximally-directed surfaces of the arms, wherein the arms and the spine being elongate and oriented in the proximal-to-distal direction, and wherein the spine is positioned angularly equidistant between the arms.

Clause 35—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a body portion, a first leg extending proximally from the body portion, and a second leg spaced apart from the first leg to define a void; an arm extending outwardly from one of the body portion and the first leg to a first distance relative to a vertical plane of symmetrical oriented in the proximal-to-distal direction, wherein the arm includes a proximally-directed surface; a catch disposed on the second leg and including a distally-directed surface positioned proximal to the proximally-directed surface of the arm, wherein the catch is at a second distance relative to the vertical plane of symmetry with the second distance being less than the first distance.

Clause 36—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a body portion, a first leg extending proximally from the body portion, and a second leg spaced apart from the first leg to define a void, wherein an entry profile of the manifold is at least partially defined by cross sections of the first and second legs defined in a vertical plane perpendicular to the proximal-to-distal direction with the entry profile having a shape complementary the opening of the receiver; an arm extending laterally outward from the housing to a position beyond the entry profile; a catch disposed on the second leg and including a recess within the entry profile.

Clause 37—A manifold for a medical waste collection system, wherein the medical waste collection system includes a receiver defining an opening into which the manifold is configured to be inserted, the manifold including: a housing defining a manifold volume and an outlet opening in fluid communication with the manifold volume, the housing including a body portion, a first leg extending proximally from the body portion, and a second leg spaced apart from the first leg to define a void; an arm extending outwardly from the housing and configured to engage a push feature of the receiver as the manifold is being inserted within the opening; and orientation features including a transition surface being a change in contour between an upper wall and one of opposing sides of the housing, and an undercut surface defining at least a portion of the opposing sides, wherein the orientation feature and the arm are complementarily arranged to require insertion of the manifold within the opening of the receiver in a single orientation.

Clause 38—A manifold for a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a body portion, a first leg extending proximally from the body portion and including an upper aspect, and a second leg including a lower aspect spaced apart from the upper aspect of the first leg to define a void, wherein the void is further defined by a distal aspect of the body portion extending between the upper and lower aspects such that the void is slot-shaped; an arm extending outwardly from the housing and including a proximally-directed surface; and a catch disposed on the second leg and including a distally-directed surface positioned proximal to the proximally-directed surface of the arm and proximal to the outlet opening.

Clause 39—A manifold for a medical waste collection system, wherein the medical waste collection system includes a receiver defining an opening into which the manifold is configured to be inserted in a proximal direction and removed in a distal direction opposite the proximal direction, the receiver including an inlet mechanism having a first support element, the manifold including: a housing defining a manifold volume and an outlet opening in fluid communication with the manifold volume, the housing including a body portion including a distal aspect, a first leg extending proximally from the distal aspect, and a second leg extending from the distal aspect and spaced apart from the first leg to define a void, wherein the void includes a depth in the proximal-to-distal direction sized to receive the first support element of the inlet mechanism to ensure the manifold is inserted into the receiver to a proper insertion depth.

Clause 40—A manifold for coupling a suction tube to a medical waste collection system, wherein the medical waste collection system includes a receiver defining an opening into which the manifold is configured to be inserted in a proximal direction and removed in a distal direction opposite the proximal direction, the receiver including a sled assembly, a sled lock assembly, and a locking assembly, the manifold comprising: a housing defining a manifold volume and an outlet opening in fluid communication with the manifold volume, the housing comprising a rim defining the outlet opening; an inlet fitting for coupling to the suction tube; an arm extending outwardly from the housing and comprising a proximally-directed surface configured to engage the sled assembly during insertion of the manifold to facilitate moving the sled assembly in the proximal direction; a lock element extending outwardly from the housing, the lock element comprising a distally-directed surface configured to engage the locking assembly after insertion of the manifold into the receiver; a spine extending outwardly from the housing, the spine comprising a proximally-directed surface configured engage the sled lock assembly to permit movement of the sled assembly in the proximal direction; and a catch comprising a distally-directed surface configured to engage the receiver and facilitate movement of the sled assembly in the distal direction during removal of the manifold from the receiver.

Clause 41—A manifold for coupling a suction tube to a medical waste collection system, wherein the medical waste collection system includes a receiver defining an opening into which the manifold is configured to be inserted in a proximal direction and removed in a distal direction opposite the proximal direction, the receiver including a sled assembly, a sled lock assembly, and a locking assembly, the manifold comprising: a housing defining a manifold volume and an outlet opening in fluid communication with the manifold volume, the housing comprising a rim defining the outlet opening, the housing comprising a body portion extending to a distal aspect, a first leg extending proximally from the distal aspect, and a second leg spaced apart from the first leg to define a void; an inlet fitting for coupling to the suction tube; an arm extending outwardly from one of the body portion and the first leg, the arm configured to engage the sled assembly during insertion of the manifold to facilitate moving the sled assembly in the proximal direction; a lock element extending outwardly from one of the body portion and the first leg, the lock element configured to engage the locking assembly of the receiver after insertion of the manifold into the receiver; a catch disposed on the second leg and configured to engage the receiver and facilitate movement of the sled assembly in the distal direction during removal of the manifold from the receiver; and a spine extending outwardly from one of the body portion, the first leg, and the second leg, the spine configured to engage the sled lock assembly to permit movement of the sled assembly in the proximal direction.

Clause 42—A manifold for coupling a suction tube to a medical waste collection system, wherein the medical waste collection system includes a receiver defining an opening into which the manifold is configured to be inserted in a proximal direction and removed in a distal direction opposite the proximal direction, the receiver including a sled assembly, a sled lock assembly, and a locking assembly, the manifold comprising: a housing defining a manifold volume and an outlet opening in fluid communication with the manifold volume, the housing comprising an upper wall, a lower wall, and opposing sides each extending between the upper and lower walls when the manifold is oriented for insertion into the opening of the receiver, the housing further comprising a rim defining the outlet opening; an inlet fitting for coupling to the suction tube; an arm extending laterally outward from one of the opposing sides and configured to engage the sled assembly during insertion of the manifold to facilitate moving the sled assembly in the proximal direction; a catch located on a first side of a void separate from the manifold volume and separate from the outlet opening, with the rim located on a second side of the void opposite the first side, wherein the catch is configured to engage the receiver and facilitate movement of the sled assembly in the distal direction during removal of the manifold from the receiver; and a spine extending downwardly from the lower wall and configured to engage the sled lock assembly to permit movement of the sled assembly in the proximal direction.

Clause 43—A manifold for coupling a suction tube to a medical waste collection system, wherein the medical waste collection system includes a receiver defining an opening into which the manifold is configured to be inserted in a proximal direction and removed in a distal direction opposite the proximal direction, the receiver including a sled assembly, a sled lock assembly, and a locking assembly, the manifold comprising: a housing defining a manifold volume and an outlet opening in fluid communication with the manifold volume, the housing comprising a rim defining the outlet opening; an inlet fitting for coupling to the suction tube; an arm extending outwardly from the housing and comprising a proximally-directed surface configured to engage the sled assembly during insertion of the manifold to facilitate moving the sled assembly in the proximal direction; a lock element extending outwardly from the housing, the lock element comprising a distally-directed surface configured to engage the locking assembly of the receiver after insertion of the manifold into the receiver; and a catch comprising a distally-directed surface configured to engage the receiver and facilitate movement of the sled assembly in the distal direction during removal of the manifold from the receiver, wherein the rim and the catch are spaced apart by a void external to the housing.

Clause 44—A manifold for a medical waste collection system, wherein the medical waste collection system includes a receiver defining an opening into which the manifold is configured to be inserted, the manifold including: a housing defining a manifold volume an outlet opening in fluid communication with the manifold volume, the housing including an upper wall, a lower wall, and opposing sides each extending between the upper and lower walls when the manifold is oriented for insertion into the opening of the receiver; an arm extending laterally from one of the opposing sides and including a proximally-directed surface; a spine extending downwardly from the lower wall; and a radiofrequency identification (RFID) tag disposed on the upper wall with the RFID tag including memory storing data for determining whether the manifold is usable with the medical waste collection system with the RFID tag adapted to be in electronic communication with the data reader when the manifold is coupled with the manifold receiver.

Clause 45—A manifold for a medical waste collection system, wherein the medical waste collection system includes a receiver defining an opening into which the manifold is configured to be inserted the manifold including: a housing defining a manifold volume and an outlet opening in fluid communication with the manifold volume, the housing including a rim having a width larger than a height to define the outlet opening as being non-circular; a seal including a seal body, an inner seal rim coupled to the seal body, and an outer seal rim spaced apart from the inner seal rim to define a groove sized to receive the rim such that the seal is coupled to the housing with interference engagement with the seal body covering the non-circular outlet opening.

Clause 46—A manifold for a medical waste collection system, wherein the medical waste collection system includes a receiver defining an opening into which the manifold is configured to be inserted, the manifold including: a housing defining a manifold volume and an outlet opening in fluid communication with the manifold volume, the housing including a body portion, a first leg extending proximally from the body portion, and a second leg spaced apart from the first leg to define a void, wherein an inner surface of the first leg defines an interior step; a seal including a seal body, an outer seal rim coupled to the seal body to define a cavity, an inner seal rim to define a groove sized to be coupled to the rim with interference engagement, a lip extending radially outwardly from the inner seal rim and including a retention surface configured to be in interference engagement with the interior step of the first leg to facilitate maintaining the interference engagement between the seal and the rim.

Clause 47—A manifold for a medical waste collection system, wherein the medical waste collection system includes a receiver defining an opening into which the manifold is configured to be inserted, the manifold including: a housing defining a manifold volume and an outlet opening in fluid communication with the manifold volume, the housing including a head including an inlet fitting, and a trunk defining the outlet opening, wherein each of the head and the trunk include complementary coupling features configured to removably couple the head and the trunk to one another such that an upper aspect of the head is aligned with an upper wall of the trunk, and a lower aspect of the head is aligned a lower wall of the trunk.

Clause 48—The manifold of clause 47, wherein the complementary coupling features include a pair of keys and a pair of keyways each disposed on a respective one of the head and the trunk with each of the pairs of keys and keyways diametrically opposed to one another.

Clause 49—A manifold for coupling a suction tube to a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a rim defining the outlet opening; an inlet fitting for coupling to the suction tube, wherein the manifold assembly defines a fluid path to be placed in fluid communication with the medical waste collection system with the inlet fitting disposed in the fluid path; an arm extending outwardly from the housing and including a proximally-directed surface; a lock element extending outwardly from the housing, the lock element including a distally-directed surface positioned distal to the proximally-directed surface of the arm; a spine extending outwardly from the housing, the spine including a proximally-directed surface positioned proximal to the distally-directed surface of the lock element and distal to the proximally-directed surface of the arm; and a catch including a distally-directed surface positioned proximal to the proximally-directed surface of the arm, wherein the rim and the catch are spaced apart by a void, and wherein the rim is positioned below the catch when the manifold assembly is oriented for insertion into the opening of the receiver.

Clause 50—A manifold for coupling a suction tube to a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a body portion extending to a distal aspect, a first leg extending proximally from the distal aspect, and a second leg spaced apart from the first leg to define a void; an inlet fitting for coupling to the suction tube, wherein the manifold assembly defines a fluid path to be placed in fluid communication with the medical waste collection system with the inlet fitting disposed in the fluid path; an arm extending outwardly from one of the body portion and the first leg, the arm including a proximally-directed surface; a lock element extending outwardly from one of the body portion and the first leg, the lock element including a distally-directed surface positioned distal to the proximally-directed surface of the arm; a catch disposed on the second leg and including a distally-directed surface positioned proximal to the arm; and a spine extending outwardly from one of the body portion, the first leg, and the second leg, the spine including a proximal end positioned distal to the catch and proximal to the proximally-directed surface of the arm.

Clause 51—A manifold for coupling a suction tube to a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including an upper wall, a lower wall, and opposing sides each extending between the upper and lower walls when the manifold assembly is oriented for insertion into the opening of the receiver, the housing further including a rim defining the outlet opening; an inlet fitting for coupling to the suction tube, wherein the manifold assembly defines a fluid path to be placed in fluid communication with the medical waste collection system with the inlet fitting disposed in the fluid path; an arm extending laterally outward from one of the opposing sides and including a proximally-directed surface; a catch including a distally-directed surface positioned proximal to the proximally-directed surface of the arm, wherein the catch is located on a first side of a void separate from the manifold volume and separate from the outlet opening, with the rim located on a second side of the void opposite the first side; and a spine extending downwardly from the lower wall, the spine including a ramped surface positioned distal to the distally-directed surface of the catch.

Clause 52—A manifold for coupling a suction tube to a medical waste collection system, wherein the medical waste collection system includes a receiver defining an opening into which the manifold is configured to be inserted in a proximal direction and removed in a distal direction opposite the proximal direction, the manifold including: a housing defining a manifold volume and an outlet opening in fluid communication with the manifold volume, the housing including a rim defining the outlet opening; an inlet fitting for coupling to the suction tube, wherein the manifold assembly defines a fluid path to be placed in fluid communication with the medical waste collection system with the inlet fitting disposed in the fluid path; an arm extending outwardly from the housing and including a proximally-directed surface positioned distal to the rim; a lock element extending outwardly from the housing, the lock element including a distally-directed surface positioned distal to the proximally-directed surface of the arm and distal to the rim; and a catch including a distally-directed surface positioned proximal to the proximally-directed surface of the arm and proximal to the rim, wherein the rim and the catch are spaced apart by a void external to the housing.

Clause 53—A medical waste collection system for collecting medical waste material through a manifold during a medical procedure, the medical waste collection system including: a waste container; a receiver coupled to the waste container and comprising a housing defining an opening into which the manifold is configured to be inserted in a proximal direction and removed in a distal direction opposite the proximal direction, wherein the housing further defines an receiver outlet and includes an inlet mechanism coupled to the housing so as to be movable in the proximal and distal directions, wherein the inlet mechanism includes a suction inlet, and a suction outlet in fluid communication with the suction inlet, wherein the suction outlet is not in fluid communication with the receiver outlet when the manifold is not in a fully inserted operative position; the receiver including a sled assembly movably coupled to the housing and coupled to the inlet mechanism, wherein the sled assembly is configured to be engaged by the manifold during insertion of the manifold into the receiver to be moved in the proximal direction to facilitate the inlet mechanism moving correspondingly in the distal direction to establish fluid communication between the suction outlet and the receiver outlet as the manifold assumes the fully inserted operative position, and further establish fluid communication between the waste container and the manifold.

Clause 54—The medical waste collection system of clause 53, wherein the sled assembly is configured to be moved in the distal direction during removal of the manifold from the receiver to facilitate the inlet mechanism moving correspondingly in the proximal direction to break fluid communication between the suction outlet and the receiver outlet.

Clause 55—The medical waste collection system of clause 53, further including a transfer gear operatively coupling the sled assembly and the inlet mechanism to facilitate the respective movements of the sled assembly and the inlet mechanism in the proximal and distal directions.

Clause 56—The medical waste collection system of clause 53, wherein the receiver further includes a first barrier pivotably coupled to the housing, and a first biasing element coupled to the first barrier configured to bias the first barrier towards a closed position to selectively cover at least a portion of the opening of the receiver when the manifold is in a decoupled operative position.

Clause 57—The medical waste collection system of clause 56, wherein the receiver further includes a second barrier pivotably coupled to the sled assembly and positioned proximal to the first barrier, and a second biasing element coupled to the second barrier configured to bias the second barrier towards a closed position, wherein movement of the inlet mechanism moving in the distal direction engages the second barrier to move the second barrier from the closed position to an open position in which the suction inlet of the inlet mechanism is exposed to the manifold being inserted towards the fully inserted operative position.

Clause 58—The medical waste collection system of clause 53, wherein the receiver further includes a claw movably coupled to the housing and pivotably coupled to the sled assembly, wherein the claw is configured to engage the manifold in the fully inserted operative position and facilitate the movement of the sled assembly in the distal direction in response to the manifold being removed in the distal direction.

Clause 59—A medical waste collection system for collecting medical waste material through a manifold during a medical procedure, the medical waste collection system including: a waste container; a receiver coupled to the waste container and comprising a housing defining an opening into which the manifold is configured to be inserted in a proximal direction and removed in a distal direction opposite the proximal direction; the receiver including a sled assembly movably coupled to the housing and configured to be engaged by the manifold during insertion of the manifold into the receiver, and a locking assembly including a locking member having an engagement surface, and a release member coupled to the locking member, and a biasing element biasing the locking assembly to a locked configuration in which the engagement surface engages the manifold in a fully inserted operative position to prevent distal movement of the manifold and the sled assembly, and an actuator coupled to the release member and configured to receive an input from a user to move the locking assembly from the locked configuration to an unlocked configuration in which the engagement surface disengages from the manifold to permit the movement of the manifold and the sled assembly in the distal direction.

Clause 60—The medical waste collection system of clause 59, wherein the receiver further includes a second biasing element coupled to the sled assembly and configured to be in a deformed state and storing potential energy when the locking assembly is in the locked configuration such that, as the locking assembly is moved from the locked configuration to the unlocked configuration, the second biasing element releases the stored potential energy to facilitate movement of the sled assembly in the distal direction.

Clause 61—The medical waste collection system of clause 59, wherein the actuator is a tongue positioned distal to the opening.

Clause 62—A medical waste collection system for collecting medical waste material through a manifold during a medical procedure, the medical waste collection system including: a waste container; a receiver coupled to the waste container and comprising a housing defining an opening into which the manifold is configured to be inserted in a proximal direction and removed in a distal direction opposite the proximal direction; the receiver including a sled assembly movably coupled to the housing and configured to be engaged by the manifold and moved in the proximal direction during insertion of the manifold into the receiver, and a sled lock assembly including a latch, and a biasing element coupled to the latch and configured to bias the latch to a locked configuration in which the latch engages the sled assembly to prevent movement of the sled assembly in the proximal direction, wherein insertion of the manifold into the receiver to a first operative position moves the sled lock assembly from the locked configuration to an unlocked configuration in which the latch disengages from the sled assembly to permit movement of the sled assembly in the proximal direction.

Clause 63—The medical waste collection system of clause 62, wherein the sled assembly includes an aperture, and the latch includes a key configured to engage with the aperture of the sled assembly when the sled lock assembly is in the locked configuration.

Clause 64—The medical waste collection system of clause 63, wherein the latch of the sled lock assembly includes a contact block positioned distal to the key and having a distally-directed surface configured to be engaged by the manifold in the first operative position, wherein the distally-directed surface is at least substantially vertical as to require a complementary engagement surface of the manifold to be angled relative to the distally-directed surface.

Clause 65—A medical waste collection system for collecting medical waste material through a manifold during a medical procedure, the medical waste collection system including: a waste container; a receiver coupled to the waste container and comprising a housing defining an opening into which the manifold is configured to be inserted in a proximal direction and removed in a distal direction opposite the proximal direction; the receiver including a sled assembly movably coupled to the housing and configured to be engaged by the manifold during insertion of the manifold into the receiver to be moved in the proximal direction; the receiver including a claw movably coupled to the housing and pivotably coupled to the sled assembly, wherein the claw is configured to engage the manifold in the fully inserted operative position and facilitate the movement of the sled assembly in the distal direction in response to the manifold being moved in the distal direction during removal of the manifold from the receiver.

Clause 66—The medical waste collection system of clause 65, wherein the housing defines a track including a proximal portion and a distal portion angled relative to the proximal portion, wherein the claw includes a guide movably positioned within the track, wherein movement of the sled assembly in the proximal direction facilitates the guide moving from the distal portion of the track to the proximal portion of the track to inwardly pivot the claw about a pivot to engage the manifold.

Clause 67—A medical waste collection system for collecting medical waste material through a manifold during a medical procedure, the medical waste collection system including: a waste container; a vacuum source configured to provide a vacuum on the waste container; a controller in communication with the vacuum source and configured to control the vacuum source; a receiver coupled to the waste container and comprising a housing defining an opening into which the manifold is configured to be inserted in a proximal direction and removed in a distal direction opposite the proximal direction; the receiver including a sled assembly movably coupled to the housing and configured to be engaged by the manifold during insertion of the manifold into the receiver to be moved in the proximal direction; a sensor in communication with the controller and configured to output a signal indicative of a position of the sled assembly in the proximal-to-distal direction, wherein the controller is configured to control the vacuum source based on the signal from the sensor.

Clause 68—The medical waste collection system of clause 67, wherein configured to output a signal indicative of whether the manifold is inserted into the receiver to a fully inserted operative position, wherein the controller is configured to prevent operation of the vacuum source based on the signal from the sensor when the manifold is not inserted into the receiver to the fully inserted operative position.

Clause 69—A manifold for a medical waste collection system, wherein the medical waste collection system includes a receiver defining an opening into which the manifold is configured to be inserted and removed, the manifold including: a housing defining a manifold volume and including at least one inlet fitting for receiving a suction tube, the inlet fitting defining a fluid path into the manifold volume; an outlet opening defining the fluid path out of the manifold volume; and arms configured to actuate a sled assembly of the receiver as the manifold is pushed into the receiver, the arms extending laterally from the housing in a direction away from the manifold volume and being located on opposite sides of a vertical plane of symmetry extending through the manifold in a proximal-to-distal direction.

Clause 70—A manifold for a medical waste collection system, wherein the medical waste collection system includes a receiver defining an opening into which the manifold is configured to be inserted and removed, the receiver including an inlet mechanism having a first support element, the manifold including: a housing defining a manifold volume and including at least one inlet fitting for receiving a suction tube, the inlet fitting defining a fluid path into the manifold volume; an outlet opening defining the fluid path out of the manifold volume; and a void having a depth extending in a proximal-to-distal direction and configured to accommodate the first support element of the inlet mechanism.

Clause 71—A manifold for a medical waste collection system, wherein the medical waste collection system includes a receiver defining an opening into which the manifold is configured to be inserted and removed, the manifold including: a housing defining a manifold volume and including at least one inlet fitting for receiving a suction tube, the inlet fitting defining a fluid path into the manifold volume; an outlet opening defining the fluid path out of the manifold volume; and catches configured to be engaged by claws of the medical waste collection unit for engaging the manifold with the receiver.

Clause 72—A method of reprocessing a manifold for a medical waste collection system, the manifold including a housing defining a manifold volume and an outlet opening, a filter element disposed within the manifold volume, a projection joining the housing and the filter element via thermoplastic staking, and a use indicator disposed within the manifold volume, the method comprising: removing the filter basket from the manifold volume in which at least one of the housing, the filter element, and the projection is mutilated; removing the use indicator; cleaning at least one of the housing and the filter element; and inserting the filter element or another filter element into the manifold volume.

Clause 73—The method of clause 72, wherein the filter element is fused to the housing via laser welding, wherein the step of removing the filter basket from the manifold volume further comprises removing the filter basket from the manifold volume in which at least one of the housing and the filter element is mutilated at or adjacent to an interface of the laser welding.

Clause 74—The method of clauses 72 or 73, wherein the filter element or the another filter element is inserted into the manifold volume without replacing use indicator with another use indicator.

Clause 75—The method of any one of clauses 72-74, wherein the filter element or the another filter element are inserted into the manifold volume without joining or fusing the housing and the filter element.

Clause 76—The method of any one of clauses 72-75, wherein the housing further comprises a head, and a trunk including the projection and defining the outlet opening, wherein the head and the trunk are fused to one another via spin welding, the method further comprising, before the step of removing the filter element, decoupling the head from the trunk in which at least one of the head and the trunk is mutilated at or adjacent to an interface of the spin welding.

Clause 77—A method of reprocessing a manifold for a medical waste collection system, the manifold including a housing defining a manifold volume and an outlet opening, a filter element disposed within the manifold volume, a projection joining the housing and the filter element via thermoplastic staking, and a use indicator disposed within the manifold volume, the method comprising: severing the projection and at least a portion of the housing such that the filter element and the housing are no longer joined; removing the filter basket from the manifold volume; removing the use indicator; cleaning at least one of the housing and the filter element; and inserting the filter element or another filter element into the manifold volume.

Clause 78—The method of clause 77, wherein the step of severing the projection and at least a portion of the housing further comprises severing at least a portion of the housing in a plane substantially transverse to a longitudinal axis of the manifold.

Clause 79—The method of clauses 77 or 78, wherein the housing comprising a body portion extending to a distal aspect, a first leg extending proximally from the distal aspect, and a second leg spaced apart from the first leg to define a void, wherein the use indicator is disposed within the second leg, wherein the step of severing the projection and at least a portion of the housing further comprises severing at least a portion of the second leg.

Clause 80—The method of any one of clauses 77-79, wherein the filter element includes a basket having a base and at least one sidewall, wherein the step of severing the projection and at least a portion of the housing further comprises severing at least a portion of the housing at an axial position between the outlet opening and the base of the filter element.

Clause 81—The method of any one of clauses 77-80, wherein the filter element is fused to the housing via laser welding, wherein the step of removing the filter basket from the manifold volume further comprises removing the filter basket from the manifold volume in which at least one of the housing and the filter element is mutilated at or adjacent to an interface of the laser welding.

Clause 82—The method of any one of clauses 77-81, wherein the filter element or the another filter element is inserted into the manifold volume without replacing the use indicator with another use indicator.

Clause 83—The method of any one of clauses 77-82, wherein the filter element or the another filter element are inserted into the manifold volume without joining or fusing the housing and the filter element.

Clause 84—The method of any one of clauses 77-83, wherein the housing further comprises a head and a trunk comprising the projection, wherein the head and the trunk are fused to one another via spin welding, the method further comprising, before the step of removing the filter element, decoupling the head from the trunk in which at least one of the head and the trunk is mutilated at or adjacent to an interface of the spin welding.

Clause 85—A method of reprocessing a manifold for a medical waste collection system, the manifold including a housing defining a manifold volume and an outlet opening, the housing including a body portion extending to a distal aspect, a first leg extending proximally from the distal aspect, and a second leg spaced apart from the first leg to define a void, the manifold further including a filter element disposed within the manifold volume, a projection joining the housing and the filter element via thermoplastic staking, and a use indicator disposed within the second leg, the method comprising: severing at least a portion of the second leg; removing the filter basket from the manifold volume; removing the use indicator; cleaning at least one of the housing and the filter element; and inserting the filter element or another filter element into the manifold volume.

Clause 86—A method of reprocessing a manifold for a medical waste collection system, the manifold including a housing defining a manifold volume and an outlet opening, the housing including a body portion extending to a distal aspect, a first leg extending proximally from the distal aspect, and a second leg spaced apart from the first leg to define a void, the manifold further including a filter element disposed within the manifold volume, a projection joining the housing and the filter element via thermoplastic staking, the method comprising: severing at least a portion of the second leg; cleaning at least one of the housing and the filter element after the step of severing; and reattaching the severed portion of the second leg to the housing to re-enclose the manifold volume.

Clause 87—The method of clause 86, wherein the manifold includes a use indicator disposed within the second leg, the method further comprising removing the use indicator after the step of severing.

Clause 88—The method of clauses 86 or 87, wherein the step of severing at least a portion of the second leg further comprises severing at least a portion of the second leg in a plane substantially transverse to a longitudinal axis of the manifold.

Clause 89—The method of any one of clauses 86-88, wherein the step of severing at least a portion of the second leg further comprises severing at least a portion of the second leg at an axial position between the outlet opening and the base of the filter element.

Clause 90—The method of any one of clauses 86-89, wherein the filter element is fused to the housing via laser welding, wherein the step of removing the filter basket from the manifold volume further comprises removing the filter basket from the manifold volume in which at least one of the housing and the filter element is mutilated at or adjacent to an interface of the laser welding.

Clause 91—The method of clauses 86 or 90, wherein the filter element or the another filter element is inserted into the manifold volume without replacing the use indicator with another use indicator.

Clause 92—The method of any one of clauses 86, 90 and 91, wherein the filter element or the another filter element are inserted into the manifold volume without joining or fusing the housing and the filter element.

Clause 93—The method of any one of clauses 86-92, wherein the housing further comprises a head and a trunk including the projection, wherein the head and the trunk are fused to one another via spin welding, the method further comprising decoupling the head from the trunk in which at least one of the head and the trunk is mutilated at or adjacent to an interface of the spin welding.

Clause 94—A manifold for filtering medical waste received under the influence of a vacuum provided by a medical waste collection system, the manifold comprising: a housing defining a manifold volume and an outlet opening, the housing comprising at least one wall having an outer surface opposite an inner surface defining the manifold volume; a filter element disposed within the manifold volume, the filter element defining a plurality of apertures configured to filter the medical waste, and a keyway separate from the apertures; and a projection extending from the inner surface of the housing and through the keyway of the filter element, wherein the projection is joined to the filter element such that removing the filter element from the housing requires mutilation of the manifold.

Clause 95—The manifold of clause 94, wherein the projection is joined to the filter element via thermoplastic staking.

Clause 96—The manifold of clauses 94 or 95, wherein the projection and the housing are integrally formed.

Clause 97—The manifold of any one of clauses 94-96, wherein the filter element is a basket comprising a base and at least one sidewall extending from the base, wherein the keyway is disposed within the base.

Clause 98—The manifold of any one of clauses 94-97, wherein the housing further comprises a body portion extending to a distal aspect, a first leg extending proximally from the distal aspect, and a second leg spaced apart from the first leg to define a void, wherein the projection is at least partially disposed within the second leg.

Clause 99—The manifold of clause 98, wherein the filter element is a basket comprising a base and at least one sidewall extending from the base, wherein the keyway is disposed within the base, wherein the projection extends distally through the keyway from within the second leg.

Clause 100—The manifold of any one of clauses 94-99, further comprising a use indicator disposed within the manifold volume and configured to absorb liquid and/or solid within the medical waste.

Clause 101—The manifold of any one of clauses 94-100, wherein the keyway is shaped differently than the plurality of apertures.

Clause 102—The manifold of clause 101, further comprising a use indicator disposed within the second leg and configured to absorb liquid within the medical waste.

Clause 103—The manifold of any one of clauses 94-103, wherein the filter element is fused to the inner surface of the housing via laser welding such that removing the filter element from the housing requires further mutilation of the manifold.

Clause 104—The manifold of clause 103, wherein the inner surface of the housing defines a slot, wherein the filter element comprises a rib, wherein the slot and the rib are fused to one another via laser welding.

Clause 105—The manifold of any one of clauses 94-105, wherein the housing further comprises a head comprising an inlet fitting for receiving a suction tube, and a trunk comprising the projection and defining the outlet opening, wherein the head and the trunk are fused to one another via spin welding.

Clause 106—A manifold for filtering medical waste received under the influence of a vacuum provided by a medical waste collection system, the manifold comprising: a housing defining a manifold volume and an outlet opening, the housing comprising at least one wall having an outer surface opposite an inner surface defining the manifold volume; a filter element disposed within the manifold volume, the filter element comprising a plurality of apertures configured to filter the medical waste; and a use indicator disposed within the manifold volume and configured to absorb liquid and/or solid of the medical waste.

Clause 107—The manifold of clause 106, wherein the housing comprising a body portion extending to a distal aspect, a first leg extending proximally from the distal aspect, and a second leg spaced apart from the first leg to define a void, wherein the use indicator is disposed within the second leg.

Clause 108—The manifold of clauses 106 or 107, wherein the filter element further comprises a basket having a base and at least one sidewall extending from the base to define a filter volume, the basket further comprising a tray positioned external to the filter volume with the tray sized to support the use indicator.

Clause 109—The manifold of clause 108, wherein the tray extends from the base in a direction opposite a direction in which the at least one sidewall extends from the base.

Clause 110—The manifold of clauses 108 or 109, wherein the basket and the tray are integrally formed.

Clause 111—The manifold of any one of clauses 108-110, wherein each of the basket and the tray comprises the plurality of apertures.

Clause 112—The manifold of any one of clauses 108-111 wherein the at least one sidewall of the basket comprises an upper wall when the manifold is oriented for insertion into the medical waste collection system, the upper wall comprising the plurality of apertures such that a flow path is established from the filter volume to the tray through the upper wall.

Clause 113—The manifold of any one of clauses 108-112, wherein the housing comprises a projection fused to the filter element via thermoplastic staking such that removing the filter element from the housing requires mutilation of the manifold.

Clause 114—The manifold of any one of clauses 106-113, wherein the filter element is fused to the inner surface of the housing via laser welding such that removing the filter element from the housing requires mutilation of the manifold.

Clause 115—The manifold of any one of clauses 106-114, wherein the housing further comprises a head comprising an inlet fitting for receiving a suction tube, and a trunk comprising the projection and defining the outlet opening, wherein the head and the trunk are fused to one another via spin welding.

Clause 116—A manifold for filtering medical waste received under the influence of a vacuum provided by a medical waste collection system, the manifold comprising: a housing defining a manifold volume and an outlet opening, the housing comprising at least one wall having an outer surface opposite an inner surface defining the manifold volume, and a slot; a filter element disposed within the manifold volume, the filter element comprising a basket having a base, a sidewall extending from the base, a rib extending from the sidewall, and a plurality of apertures configured to filter the medical waste, wherein the rib and the slot are fused to one another such that removing the filter element from the housing requires mutilation of the manifold.

Clause 117—The manifold of clause 116, wherein the fusing is via laser welding.

Clause 118—The manifold of clauses 116 or 117, wherein the housing further comprises parallel railings extending in a proximal to distal direction to define the slot therebetween.

Clause 119—The manifold of any one of clauses 116-118, wherein the housing further comprises a body portion extending to a distal aspect, a first leg extending proximally from the distal aspect, and a second leg spaced apart from the first leg to define a void, wherein the slot is disposed within the body portion.

Clause 120—The manifold of clause 118, wherein the parallel railings are formed from laser-transparent material, and wherein the rib of the filter basket is formed from laser-absorbing material.

Clause 121—The manifold of any one of clauses 116-120, wherein the housing further comprises a projection joined to the filter element via thermoplastic staking such that removing the filter element from the housing requires mutilation of the manifold.

Clause 122—The manifold of any one of clauses 116-121, further comprising a use indicator disposed within the manifold volume and configured to absorb liquid and/or solid from the medical waste.

Clause 123—The manifold of any one of clauses 116-122, wherein the housing further comprises a head comprising an inlet fitting for receiving a suction tube, and a trunk comprising the projection and defining the outlet opening, wherein the head and the trunk are fused to one another via spin welding.

Clause 124—A manifold for filtering medical waste received under the influence of a vacuum provided by a medical waste collection system, the manifold comprising: a housing defining a manifold volume and an outlet opening;

a filter element disposed within the manifold volume, wherein the filter element is fused to the housing via laser welding such that removing the filter element from the housing requires mutilation of the manifold; and a projection extending from the housing and joined to the filter element via thermoplastic staking such that removing the filter element from the housing requires further mutilation of the manifold; and a use indicator disposed within the manifold volume and configured to absorb liquid and/or solid from the medical waste.

Clause 125—The manifold of clause 124, wherein the housing comprising a body portion extending to a distal aspect, a first leg extending proximally from the distal aspect, and a second leg spaced apart from the first leg to define a void, wherein the use indicator is disposed within the second leg and the projection is at least partially disposed within the second leg.

Clause 126—The manifold of clauses 124 or 125, where the housing is transparent.

Clause 127—The manifold of any one of clauses 124-126, wherein the use indicator defines a tortuous path.

Clause 128—The manifold of any one of clauses 124-127, wherein the use indicator is configured to absorb contaminants during clinical use of the manifold; and wherein the absorbed contaminants are visible against the use indicator.

Clause 129—The manifold of any one of clauses 124-128, wherein the use indicator has a porosity ranging from 30-70% of the total volume.

Clause 130—The manifold of any one of clauses 124-129, wherein the use indicator comprises polyethylene, polyurethane, or combinations thereof.

Clause 131—The manifold of any one of clauses 124-130, wherein the use indictor comprises one or more pores having a size ranging from 0.001 to 0.030 inches.

Clause 132—The manifold of any one of clauses 124-131, wherein the use indicator is selected from the group consisting of a foam, an open-cell foam, a closed-cell foam, and a fibrous material.

Clause 133—The manifold of any one of clauses 124-132, wherein the use indicator is hydrophilic.

Clause 134—A method of reprocessing a manifold for a medical waste collection system, the manifold including a housing defining a manifold volume and an outlet opening, the housing including a body portion extending to a distal aspect, a first leg extending proximally from the distal aspect, and a second leg spaced apart from the first leg to define a void, the manifold further including a filter element disposed within the manifold volume, a projection joining the housing and the filter element via thermoplastic staking, and a use indicator disposed within the second leg, the method comprising: milling a hole into the second leg; removing the use indicator through the milled hole; and cleaning at least one of the housing and the filter element.

Clause 135—A device for coupling a suction tube to a medical waste collection system, wherein the medical waste collection system includes a receiver defining an opening into which the manifold is configured to be inserted in a proximal direction and removed in a distal direction opposite the proximal direction, the manifold comprising: a first housing portion; a second housing portion coupled to the first housing portion with the device defining an adapter opening and a void space through which a portion of the suction tube is configured to be disposed; an arm extending outwardly from one of the first and second housing portions, the arm comprising a proximally-directed surface; a lock element extending outwardly from one of the first and second housing portions, the lock element comprising a distally-directed surface positioned distal to the proximally-directed surface of the arm; and a spine extending outwardly from one of the first and second housing portions, the spine comprising a proximally-directed surface positioned proximal to the distally-directed surface of the lock element and distal to the proximally-directed surface of the arm.

Clause 136—The device of clause 135, further comprising a catch disposed on one of the first and second housing portions, the catch comprising a distally-directed surface positioned proximal to the proximally-directed surface of the arm.

Clause 137—The device of clause 136, wherein at least one of the first and second housing portions define a rim spaced apart by from the catch by a void and positioned below the catch when the manifold is oriented for insertion into the opening of the receiver.

Clause 138—The device of clause 136, wherein the catch is disposed on the second housing portion and the spine is disposed on the first housing portion.

Clause 139—The device of any one of clauses 135-138, further comprising a tube adapter comprising an inlet port configured to be coupled to the suction tube, and a rim defining an outlet opening in fluid communication with the inlet port, wherein the tube adapter is coupled to at least one of the first and second housing portions such that the inlet port is disposed within the void space.

Clause 140—The device of clause 139, further comprising a seal coupled to the rim, the seal comprising a seal body configured to selectively cover the outlet opening.

Clause 141—The device of any one of clauses 135-140, wherein at least one of the first and second housing portions define a distal aperture through which the suction tube is configured to extend from within the void space.

Clause 142—A device for coupling a suction tube to a medical waste collection system, wherein the medical waste collection system includes a receiver defining an opening into which the device is configured to be inserted in a proximal direction and removed in a distal direction opposite the proximal direction, the device comprising: a housing defining a void space through which a portion of the suction tube is configured to be disposed; an arm comprising a proximally-directed surface; a lock element comprising a distally-directed surface positioned distal to the proximally-directed surface of the arm; a spine comprising a proximally-directed surface positioned proximal to the distally-directed surface of the lock element and distal to the proximally-directed surface of the arm; and a tube adapter comprising an inlet port configured to be coupled to the suction tube, and a rim defining an outlet opening in fluid communication with the inlet port, wherein the tube adapter is coupled to the housing such that the inlet port is disposed within the void space.

Clause 143—The device of clause 8, further comprising a catch comprising a distally-directed surface positioned proximal to the proximally-directed surface of the arm.

Clause 144—The device of clause 8, wherein the rim and the catch are spaced apart by a void, and wherein the rim is positioned below the catch when the device is oriented for insertion into the opening of the receiver.

Clause 145—A device for a medical waste collection system, including a receiver defining an opening into which the device is configured to be inserted in a proximal direction and removed in a distal direction opposite the proximal direction, the device comprising: a housing portion defining a void space; an inlet fitting disposed within the void space; a suction tube configured to be coupled to the inlet fitting such that a portion of the suction tube is disposed within the void space; an arm comprising a proximally-directed surface; a lock element comprising a distally-directed surface positioned distal to the proximally-directed surface of the arm; and a spine comprising a proximally-directed surface positioned proximal to the distally-directed surface of the lock element and distal to the proximally-directed surface of the arm.

Clause 146—The device of clause 145, further comprising a tube adapter comprising an inlet port with the suction tube coupled to the tube adapter, and a rim defining an outlet opening in fluid communication with the inlet port, wherein the tube adapter is coupled to the housing such that the inlet port is disposed within the void space.

Clause 147—The device of clauses 145 or 146, wherein at least one of the first housing portion and the second housing portion comprises an inlet port configured to be coupled to the suction tube, and rim defining an outlet opening in fluid communication with the inlet port.

Clause 148—The device of clause 148, wherein at least one of the first housing portion and the second housing portion defines a fluid volume between and in communication with the inlet port and the outlet opening, wherein the fluid volume is not in fluid communication with the void space when the suction tube is coupled to the inlet port.

Clause 149—The device of any one of clauses 146-148, wherein the tube adapter defines a fluid volume separate from the void space when the suction tube is coupled to the inlet port.

Clause 150—The device of clause 149, wherein the housing defines a distal aperture through which the suction tube extends from within the void space.

Clause 151—The device of clause 145, wherein the housing comprises an adapter frame defining an adapter opening, wherein the tube adapter is coupled to the adapter frame and extends through the adapter opening.

Clause 152—A device for coupling a suction tube to a medical waste collection system, wherein the medical waste collection system includes a receiver defining an opening into which the device is configured to be inserted in a proximal direction and removed in a distal direction opposite the proximal direction, the device comprising: a housing defining a void space through which the suction tube is disposed, the housing comprising an inlet port configured to be coupled to the suction tube, rim defining an outlet opening in fluid communication with the inlet port, and the housing defining a channel within the void space for providing fluid communication between the inlet port and the outlet opening, wherein the channel is not in fluid communication with the void space; an arm comprising a proximally-directed surface; a lock element comprising a distally-directed surface positioned distal to the proximally-directed surface of the arm; and a spine comprising a proximally-directed surface positioned proximal to the distally-directed surface of the lock element and distal to the proximally-directed surface of the arm.

Clause 153—The device of clause 150, wherein at housing defines a fluid volume between and in communication with the inlet port and the outlet opening, wherein the fluid volume is not in fluid communication with the void space when the suction tube is coupled to the inlet port.

Clause 154—The device of any one of clauses 135-153, further comprising a catch disposed on the housing, the catch comprising a distally-directed surface positioned proximal to the proximally-directed surface of the arm.

Clause 155—The device of clause 154, wherein the rim and the catch are spaced apart by a void, and wherein the rim is positioned below the catch when the device is oriented for insertion into the opening of the receiver.

Clause 156—The device of any one of clauses 135-155, wherein the housing is formed through additive manufacturing.

Clause 157—The device of any one of clauses 135-156, wherein the first and second housing portions are pivotably coupled to one another.

Clause 158—The device of clause 146, wherein the tube adapter comprises a retention feature, and wherein the first and second housing portions are pivotably coupled to one another to cooperatively engage the retention feature and restrict movement of the tube adapter relative to the first and second housing portions.

Clause 159—The device of clause 158, wherein the first and second housing portions are configured to move the device between an open configuration in which the void space is accessible, and a closed configuration in which the void space is inaccessible.

Clause 160—The device of clause 159, wherein the tube adapter is removably coupled to one of the first and second housing portions and is removable from the void space when the device is in an open configuration.

Clause 161—The device of clause 160, wherein the first and second housing portions comprising retaining features that cooperative to retain the tube adapter when the device is in the closed configuration.

Clause 162—The device of any one of clauses 134-147 and 154-161, further comprising a filter element configured to be coupled in-line with suction tube and disposed within the void space.

Clause 163—The device of any one of clauses 134-147 and 154-161, further comprising a filter element configured to be coupled in-line with suction tube and disposed external and distal to the device.

Clause 164—The device of any one of clauses 140-163, further comprising a seal coupled to the rim, the seal comprising a seal body configured to selectively cover the outlet opening.

Clause 165—A manifold for coupling a suction tube to a medical waste collection system, wherein the medical waste collection system includes a receiver defining an opening into which the manifold is configured to be inserted in a proximal direction and removed in a distal direction opposite the proximal direction, the manifold comprising: a first housing portion defining a first channel and comprising an inlet fitting configured to receive the suction tube; a second housing portion defining a second channel and an adapter opening in fluid communication with the second channel, the second housing portion removably coupled to the first housing portion to establish fluid communication between the first and second channels; a rim defining the adapter opening; a seal coupled to the rim; an inlet fitting for coupling to the suction tube; an arm comprising a proximally-directed surface; a lock element comprising a distally-directed surface positioned distal to the proximally-directed surface of the arm; a spine comprising a proximally-directed surface positioned proximal to the distally-directed surface of the lock element and distal to the proximally-directed surface of the arm, wherein the first and second housing portions and configured to be sealed the interface between the first and second channels when the first and second housing portions are removably coupled to one another.

Clause 166—The manifold of clause 165, further including a cartridge seal coupled to one of the first and second housing portions.

Clause 167—The manifold of clauses 165 or 166, further comprising a filter element disposed within the first channel.

Clause 168—The manifold of any one of clauses 165-167, wherein the arm, the lock element, and the spine extends outwardly from the second housing portion.

Clause 169—The manifold of any one of clauses 165-168, further comprising a catch comprising a distally-directed surface positioned proximal to the proximally-directed surface of the arm, wherein the rim and the catch are spaced apart by a void, and wherein the rim is positioned below the catch when the manifold is oriented for insertion into the opening of the receiver.

Clause 170—The manifold of clause 169, wherein the catch is disposed on the second housing portion.

Clause 171—A manifold for coupling a suction tube to a medical waste collection system, wherein the medical waste collection system includes a receiver defining an opening into which the manifold is configured to be inserted in a proximal direction and removed in a distal direction opposite the proximal direction, and a suction fitting that is tubular and defines a suction inlet the manifold comprising: a housing comprising a rim defining an adapter opening, the housing defining a void space through which the suction tube is configured to be disposed; an arm comprising a proximally-directed surface; a lock element comprising a distally-directed surface positioned distal to the proximally-directed surface of the arm; a spine comprising a proximally-directed surface positioned proximal to the distally-directed surface of the lock element and distal to the proximally-directed surface of the arm; and a tube adapter coupled to the housing and comprising an inlet port disposed within the void space and configured to be coupled to the suction tube, and a seal in fluid communication with the inlet port, the seal comprising a face sealing surface configured to abut and sealingly engage configured to extend within the tubular suction fitting.

Clause 172—The manifold of clause 171, wherein the seal further comprises a flange coupled to the face sealing surface and extending around and spaced apart from the outlet fitting to define an annular gap configured to receive the suction fitting.

Clause 173—The manifold of clauses 171 or 172, wherein the outlet fitting is non-circular in shape.

Clause 174—The manifold of any one of clauses 171-173, wherein the arm, the lock element, and the spine extends outwardly from the housing.

Clause 175—The manifold of any one of clauses 171-174, wherein the tube adapter is removably coupled to the housing.

Clause 176—The manifold of any one of clauses 171-175, wherein the housing further defines an aperture in communication with the void space the aperture sized to permit insertion of the tube adapter into the void space with the manifold inserted into the medical waste collection system.

Clause 177—The manifold of any one of clauses 171-176, further comprising a catch comprising a distally-directed surface positioned proximal to the proximally-directed surface of the arm, wherein the rim and the catch are spaced apart by a void, and wherein the rim is positioned below the catch when the manifold is oriented for insertion into the opening of the receiver.

Clause 178—The manifold of any one of clauses 1-52, 69-71, 94-133, 179-182, 192-204 and 208-227, and the device of any one of clauses 135-163 and 165-167, wherein the housing is at formed from polypropylene, polypropylene copolymer (PPCO), polycarbonate, Teflon perfluoroalkoxy alkanes (PFA), fluorinated ethylene propylene (FEP), or ethylene tetrafluoroethylene (ETFE), or other material capable of withstanding temperature for autoclaving.

Clause 179—A method of coupling a suction tube and a manifold with a medical waste collection system, wherein the manifold includes a housing defining a void space, and a tube adapter including a seal, wherein the medical waste collection system includes a receiver defining an opening, and a suction fitting defining a suction inlet, the method comprising the steps of: inserting the housing of the manifold into the opening of the receiver to establish fluid communication between the void space and the suction inlet; inserting the tube adapter into the void space of the housing; and coupling the seal of the tube adapter with the suction fitting, wherein fluid communication is established between the medical waste collection system and the suction tube coupled to the tube adapter and the void space is no longer in fluid communication with the suction inlet.

Clause 180—The method of clause 179, wherein the tube adapter is inserted into the housing after the step of inserting the housing into the receiver.

Clause 181—The method of clauses 179 or 180, wherein the tube adapter further includes an inlet fitting, the method further comprising removably coupling the suction tube to the inlet fitting prior to the step of inserting the tube adapter into the housing.

Clause 182—The method of any one of clauses 179-181, wherein the housing further defines an aperture in communication with the void space, the method further comprising directing the tube adapter through the aperture with the manifold inserted into the medical waste collection system.

Clause 183—A method of reprocessing a manifold for a medical waste collection system, the manifold including a housing defining a void space, and a tube adapter including a seal, wherein the medical waste collection system includes a receiver defining an opening, and a suction fitting defining a suction inlet, the method comprising the steps of: removing the housing from the opening such that suction is broken between the seal of the manifold and the suction fitting of the receiver; decoupling the tube adapter and the seal from the housing; cleaning the housing; coupling a second tube adapter and a second seal to the housing; and inserting the housing into the opening such that suction is established between the second seal of the second tube adapter and the suction fitting of the receiver.

Clause 184—The method of clause 183, further comprising removably coupling the second seal to the tube adapter before the step of inserting the housing into the opening.

Clause 185—The method of clauses 183 or 184, wherein the step of decoupling the tube adapter and the seal from the housing further comprising removing the tube adapter from the void space of the housing.

Clause 186—The method of any one of clauses 183-185, further comprising cleaning the tube adapter the step of decoupling the tube adapter and the seal from the housing.

Clause 187—The method of any one of clauses 183-186, wherein the step of cleaning the housing further comprises autoclaving the housing.

Clause 188—A medical waste collection system for collecting waste material through a suction line during a medical procedure and for coupling to a docking station having an off-load pump and a docking controller to operate the off-load pump to transfer waste material to the docking station, the waste collection cart comprising: a chassis configured to be coupled to the docking station; a waste container coupled to the chassis, the waste container configured to be in fluid communication with the suction line to collect the waste material during the medical procedure, and the waste container configured to be in fluid communication with the docking station when the chassis is coupled to the docking station; a receiver coupled to the waste container and defining an opening into which a manifold is configured to be inserted in a proximal direction and removed in a distal direction, the receiver comprising a sensor configured to output a signal based on a presence of the manifold in the receiver; a controller configured to generate an off-load signal to the docking controller based on whether the chassis is coupled to the docking station and the signal output by the sensor, the off-load signal operative to cause the docking controller to operate the off-load pump of the docking station to draw waste from the waste container to the docking station Clause 189—The medical waste collection system of clause 188, wherein the receiver further comprises a sled assembly movably coupled to the housing, wherein the sled assembly is configured to be engaged by the manifold during insertion of the manifold into the receiver and to be moved in the proximal direction, wherein the output signal is further indicative of a position of the sled assembly.

Clause 190—The medical waste collection system of clause 188, wherein the output signal is further indicative of whether the manifold is inserted into the receiver to a fully inserted operative position, wherein the controller is further configured to prevent operation of the off-load pump based on the output signal when the manifold is not inserted into the receiver to the full inserted operative position.

Clause 191—A method of controlling an off-load pump of a docking station for a medical waste collection cart, the medical waste collection cart including a receiver coupled to a waste container and receiver defining an opening into which a manifold is configured to be inserted in proximal direction and removed in a distal direction, the method comprising: sensing whether a waste collection manifold is present in the receiver of the waste collection cart; and controlling the off-load pump of the docking station based whether the waste collection manifold is present in the receiver of the waste collection cart.

Clause 192—The method of clause 191, wherein the receiver further comprises a sled assembly movably to the housing and configured to be engaged by the manifold during insertion of the manifold during insertion of the manifold into the receiver, wherein the step of sensing whether the waste collection manifold is present in the receiver of the waste collection cart is further defined as sensing a position of the sled assembly.

Clause 192—A manifold for filtering medical waste received under the influence of a vacuum provided by a medical waste collection system having a receiver defining an opening into which the manifold is configured to be removably inserted, the manifold comprising: a housing defining a manifold volume and an outlet opening in fluid communication with the manifold volume, the housing comprising a rim defining the outlet opening; a seal shaped to the outlet opening; and a filter element disposed within the manifold volume, the filter element comprising a basket, and a seal retaining element coupled to the basket, wherein the seal retaining element of the filter element supports the seal in sealing engagement with the rim.

Clause 193—The manifold of clause 192, wherein the basket comprises a base wall and sidewalls extending distally from the base wall to define a filter volume, wherein the seal retaining element extends proximally from the base wall.

Clause 194—The manifold of clauses 192 or 193, wherein the retaining element is a tubular structure comprising a rim configured to engage a groove of the seal.

Clause 195—The manifold of clause 194, wherein the seal is configured to be compressed between the rim of the sealing retaining member and the rim of the of housing.

Clause 196—The manifold of any one of clauses 192-195, wherein the housing comprises a body portion extending to a distal aspect, a first leg extending proximally from the distal aspect, and a second leg spaced apart from the first leg to define a void, wherein the basket is disposed within the body portion and the seal retaining element is disposed within the first leg.

Clause 197—The manifold of clause 196, wherein an annular gap is defined between the sealing retaining element and an inner surface of the first leg, wherein the seal comprises an outer seal rim that is resilient and has a thickness greater than the annular gap such that the outer seal rim is compressed between the sealing retaining element and the first leg.

Clause 198—A manifold for filtering medical waste received under the influence of a vacuum provided by a medical waste collection system having a receiver defining an opening into which the manifold is configured to be removably inserted, the manifold comprising: a housing defining a manifold volume and an outlet opening in fluid communication with the manifold volume, the housing comprising a rim defining the outlet opening; a seal shaped and positioned to block egress of fluid through the outlet opening; and a filter element engaging disposed within the manifold volume and contacting the seal to retain the seal in a position suitable to block egress of fluid through the outlet opening.

Clause 199—The manifold of clause 198, wherein the seal is configured to be compressed against an inner surface of the rim of the of housing by the filter element.

Clause 200—The manifold of clauses 198 or 199, wherein the seal further comprises an outer seal rim and an inner seal rim defining a groove therebetween, wherein the filter element comprises a rim disposed within the groove.

Clause 201—The manifold of any one of clauses 198-200, wherein the housing comprises a body portion extending to a distal aspect, a first leg extending proximally from the distal aspect, and a second leg spaced apart from the first leg to define a void, wherein the basket is disposed within the body portion and the seal retaining element is disposed within the first leg.

Clause 201—A manifold for filtering medical waste received under the influence of a vacuum provided by a medical waste collection system having a receiver defining an opening into which the manifold is configured to be removably inserted, the manifold comprising: a housing defining a manifold volume and an outlet opening in fluid communication with the manifold volume; a seal shaped to the outlet opening; and a filter element disposed within the manifold volume, the filter element comprising a basket, and a seal retaining element coupled to the basket, wherein the seal is coupled to the seal retaining element and positioned to block egress of fluid through the outlet opening.

Clause 202—The manifold of clause 201, wherein the seal further comprises an outer seal rim and an inner seal rim defining a groove therebetween, wherein the seal retaining element comprises a rim disposed within the groove to couple to the seal and the seal retaining element.

Clause 203—The manifold of clause 202, wherein the outer seal rim is configured to be compressed between the housing and the seal retaining element.

Clause 204—The manifold of any one of clauses 201-203, wherein the housing comprises a rim defining the outlet opening, wherein the seal is configured to be compressed between the rim of the seal retaining element and the rim of the housing.

Clause 205—A method of assembling a manifold for filtering medical waste received under the influence of a vacuum provided by a medical waste collection system, the manifold including a housing defining a manifold volume and an outlet opening, the housing including a head and a trunk, a filter element, and a seal, the method comprising: coupling the seal to the filter element; inserting the filter element and the seal into the manifold volume such that the seal contacts the housing; and coupling the head to the trunk to fix a position of the filter element to retain the seal in a position suitable to block egress of fluid through the outlet opening.

Clause 206—The method of clause 205, wherein the housing includes a rim defining the outlet opening, wherein the step of inserting the filter element further comprises positioning the filter element such that the seal is compressed between the filter element and an inner surface of the rim.

Clause 207—The method of clauses 205 or 206, wherein the filter element includes a basket and a seal retaining element coupled to the basket, wherein the step of coupling the seal to the filter element further comprises coupling the seal to the seal retaining element via interference engagement.

Clause 208—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising a body portion extending to a distal aspect, a first leg extending proximally from the distal aspect, and a second leg spaced apart from the first leg to define a void, wherein the first leg comprises a rim defining the outlet opening; a filter element disposed within the manifold volume; an arm extending outwardly from one of the body portion and the first leg, the arm comprising a proximally-directed surface; a lock element extending outwardly from one of the body portion and the first leg, the lock element comprising a distally-directed surface positioned distal to the proximally-directed surface of the arm; and a spine extending outwardly from one of the body portion and the first leg, the spine comprising a proximally-directed surface positioned proximal to the distally-directed surface of the lock element and distal to the proximally-directed surface of the arm.

Clause 209—The manifold of clause 208, further comprising a radiofrequency identification (RFID) tag at least partially positioned on the second leg. Clause 208—The manifold of clause 1, wherein the rim is positioned below the second leg when the manifold is oriented for insertion into the opening of the receiver.

Clause 210—The manifold of clause 208 or 209, wherein the second leg extends proximally from the distal aspect.

Clause 211—The manifold of any one of clauses 208-210, wherein the second leg includes a cavity defining a portion of the manifold volume.

Clause 212—The manifold of any one of clauses 208-211, wherein the housing comprises an upper wall, a lower wall, and opposing sides each extending between the upper and lower walls when the manifold is oriented for insertion into the opening of the receiver, wherein the spine extends downwardly from the lower wall.

Clause 213—The manifold of clause 212, wherein the arm and the lock element each extend laterally from one of the opposing sides.

Clause 214—The manifold of clause 212, wherein the arm comprises a pair of arms each extending laterally from a respective one of the opposing sides, wherein laterally-directed surfaces of the pair of arms cooperate to define a width that is larger than a width of the rim.

Clause 215—The manifold of any one of clauses 208-214, wherein the proximally-directed surface of the spine comprises a ramped surface tapering towards the housing in a proximal direction.

Clause 216—The manifold of any one of clauses 208-215, wherein the rim has a width larger than a height to define the outlet opening as being non-circular.

Clause 217—The manifold of clause 216, further comprising a seal coupled to the rim and comprising a seal body shaped to cover the non-circular outlet opening.

Clause 218—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising an upper wall, a lower wall, opposing sides each extending between the upper and lower walls when the manifold is oriented for insertion into the opening of the receiver, a first leg comprising at least a portion of the lower wall and at least a portion of the opposing sides, and a second leg spaced apart from the first leg to define a void; a filter element disposed within the manifold volume; an arm extending laterally from one of the opposing sides, the arm comprising a proximally-directed surface; a lock element extending laterally from one of the opposing sides, the lock element comprising a distally-directed surface positioned distal to the proximally-directed surface of the arm; and a spine extending downwardly from the lower wall, the spine comprising a proximally-directed surface positioned proximal to the distally-directed surface of the lock element and distal to the proximally-directed surface of the arm.

Clause 219—The manifold of clause 218, further comprising a radiofrequency identification (RFID) tag at least partially positioned on the upper wall.

Clause 220—The manifold of clauses 218 or 219, wherein the first leg comprises a rim having a width larger than a height to define the outlet opening that is non-circular.

Clause 221—The manifold of any one of clauses 218-220, wherein the arm comprises a pair of arms each extending laterally from a respective one of the opposing sides, wherein laterally-directed surfaces of the pair of arms cooperate to define a width of the manifold that is greater than the width of the rim.

Clause 222—The manifold of any one of clauses 218-221, wherein the lock element further comprises a pair of lock elements each extending laterally from a respective one of the opposing sides.

Clause 223—A manifold for filtering medical waste received under the influence of a vacuum provided by a medical waste collection system, wherein the medical waste collection system includes a receiver defining an opening into which the manifold is configured to be inserted in a proximal direction and removed in a distal direction opposite the proximal direction, the manifold comprising: a housing defining a manifold volume and an outlet opening in fluid communication with the manifold volume, the housing comprising a body portion extending to a distal aspect, a first leg extending proximally from the distal aspect, and a second leg spaced apart from the first leg to define a void; a filter element disposed within the manifold volume; an arm extending outwardly from one of the body portion and the first leg, the arm comprising a proximally-directed surface; a lock element extending outwardly from one of the body portion and the first leg, the lock element comprising a distally-directed surface positioned distal to the proximally-directed surface of the arm; and a spine extending outwardly from one of the body portion and the first leg, the spine having a ramped surface positioned distal to the proximally-directed surface of the arm and proximal to the distally-directed surface of the lock element.

Clause 224—The manifold of clause 223, wherein the second leg extends proximally from the distal aspect, the manifold further comprising a radiofrequency identification (RFID) tag at least partially positioned on an upper wall defining the second leg.

Clause 225—The manifold of clauses 223 or 224, wherein the first leg comprises a rim defining the outlet opening, wherein the rim has a width larger than a height to define the outlet opening as being non-circular.

Clause 226—The manifold of clause 225, wherein the arm comprises a pair of arms each extending laterally from a respective one of opposing sides of one the body portion and the first leg, wherein laterally-directed surfaces of the pair of arms cooperate to define a width that is larger than the width of the rim.

Clause 227—The manifold of clauses 225 or 226, further comprising a seal coupled to the rim and comprising a seal body shaped to cover the non-circular outlet opening.

Clause 228—A manifold for a medical waste collection system, wherein the medical waste collection system includes a receiver defining an opening into which the manifold is configured to be inserted, the manifold including: a housing defining a manifold volume and an outlet opening in fluid communication with the manifold volume, the housing including a body portion, a first leg extending proximally from the body portion, and a second leg spaced apart from the first leg to define a void; a seal including a seal body, an outer seal rim coupled to the seal, an inner seal rim to define a groove sized to be coupled to the rim with interference engagement, a tongue extending from the outer seal rim and configured to resiliently flex inwardly in interference engagement with an inner surface of the first leg to facilitate maintaining the interference engagement between the seal and the rim.

Clause 229—The manifold of clause 229, wherein a proximal-most surface of the seal is positioned distal to the rim such that the seal is recessed within the first leg.

Clause 230—The manifold of clauses 229 or 230, wherein the tongue is two tongues positioned opposite the seal body.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A medical waste collection system for collecting medical waste material through a manifold during a medical procedure, the medical waste collection system comprising:
   a waste container;
   a vacuum source configured to provide a vacuum on said waste container;
   a receiver coupled to said waste container and comprising:
      a housing comprising an opening into which the manifold is configured to be inserted, said housing further comprising a receiver outlet;
      an inlet mechanism coupled to said housing so as to be movable in proximal and distal directions, wherein said inlet mechanism comprises a suction inlet, and a suction outlet in fluid communication with said suction inlet; and
      a sled assembly movably coupled to said housing and operably coupled to said inlet mechanism, wherein said sled assembly is configured to be moved in a proximal direction during insertion of the manifold into said receiver in the proximal direction to facilitate said inlet mechanism moving correspondingly in the distal direction to establish fluid communication between said suction outlet and said receiver outlet.

2. The medical waste collection system of claim 1, wherein said sled assembly is configured to be moved in a distal direction opposite the proximal direction during removal of the manifold from said receiver to facilitate said inlet mechanism moving correspondingly in the proximal direction to break fluid communication between said suction outlet and said receiver outlet.

3. The medical waste collection system of claim 1, further comprising a transfer gear operatively coupling said sled assembly and said inlet mechanism to facilitate the respective corresponding movements of said sled assembly and said inlet mechanism in the proximal and distal directions.

4. The medical waste collection system of claim 2, wherein said receiver further comprises a claw coupled to said sled assembly, wherein said claw is configured to selectively engage the manifold facilitate movement of said sled assembly in the distal direction during removal of the manifold from said receiver.

5. The medical waste collection system of claim 1, wherein said receiver further comprises a sled lock assembly comprising a latch, and a biasing element coupled to said latch and configured to bias said latch to a locked configuration in which said latch selectively engages said sled assembly to prevent movement of said sled assembly in the proximal direction.

6. The medical waste collection system of claim 1, further comprising a controller in communication with said vacuum source, wherein said receiver further comprises a sensor in communication with said controller and configured to output a signal indicative of a position of said sled assembly in the proximal and distal directions, wherein said controller is configured to control said vacuum source based on the signal from said sensor.

7. The medical waste collection system of claim 6, further comprising a magnet disposed on said sled assembly and configured to be detected by said sensor.

8. The medical waste collection system of claim 6, wherein the signal is indicative of whether said manifold is inserted into said receiver to a fully inserted operative position, wherein said controller is configured to prevent operation of said vacuum source based on the signal from said sensor when said manifold is not inserted into said receiver to said fully inserted operative position.

9. The medical waste collection system of claim 1, wherein said receiver further comprises a first barrier pivotably coupled to said housing, and a first biasing element coupled to said first barrier configured to bias said first barrier towards a closed position to selectively cover at least a portion of said opening of said receiver.

10. The medical waste collection system of claim 9, wherein said receiver further comprises a second barrier pivotably coupled to said sled assembly and positioned proximal to said first barrier, and a second biasing element coupled to said second barrier configured to bias said second barrier towards a closed position.

11. The medical waste collection system of claim 10, wherein movement of said inlet mechanism in the distal direction facilitates moving said second barrier from the closed position to an open position in which said suction inlet of said inlet mechanism is exposed to the manifold being inserted.

12. The medical waste collection system of claim 1, wherein said receiver further comprises a locking assembly comprising a locking member having an engagement surface, a release member coupled to said locking member, and a biasing element biasing said locking assembly to a locked configuration in which said engagement surface engages the manifold in a fully inserted operative position to prevent distal movement of the manifold and said sled assembly.

13. The medical waste collection system of claim 1, wherein said locking assembly further comprises an actuator coupled to said release member and configured to receive an input from a user to move said locking assembly from the locked configuration to an unlocked configuration in which said engagement surface disengages from the manifold to permit the movement of the manifold and said sled assembly in the distal direction.

14. The medical waste collection system of claim 1, wherein said inlet mechanism further comprises a first support element spaced apart from said suction fitting and configured to facilitate that the manifold being inserted to a proper insertion depth within said receiver.

15. The medical waste collection system of claim 14, wherein said inlet mechanism further comprises a second support element spaced apart from said suction fitting and positioned opposite said first support element.

\* \* \* \* \*